US012715880B2

(12) United States Patent
Deligny et al.

(10) Patent No.: US 12,715,880 B2
(45) Date of Patent: Aug. 25, 2026

(54) MACROCYCLIC DIAMINE DERIVATIVES AS ENT INHIBITORS FOR THE TREATMENT OF CANCERS, AND COMBINATION THEREOF WITH ADENOSINE RECEPTOR ANTAGONISTS

(71) Applicant: ITEOS BELGIUM SA, Gosselies (BE)

(72) Inventors: Michael Deligny, Rhode-Saint-Genese (BE); Stefano Crosignani, Vevey (CH); Erica Joke Katelijne Heleen Houthuys, Enghien (BE); Michael Rowley, Chelmsford (GB)

(73) Assignee: ITEOS BELGIUM SA, Gosselies (BE)

( * ) Notice: Subject to any disclaimer, the term of this patent is extended or adjusted under 35 U.S.C. 154(b) by 812 days.

(21) Appl. No.: 17/917,462

(22) PCT Filed: Apr. 7, 2021

(86) PCT No.: PCT/EP2021/059096

§ 371 (c)(1),
(2) Date: Oct. 6, 2022

(87) PCT Pub. No.: WO2021/204896

PCT Pub. Date: Oct. 14, 2021

(65) Prior Publication Data

US 2023/0203058 A1 Jun. 29, 2023

Related U.S. Application Data

(60) Provisional application No. 63/006,629, filed on Apr. 7, 2020.

(51) Int. Cl.

| | |
|---|---|
| *C07D 498/08* | (2006.01) |
| *A61K 31/395* | (2006.01) |

(Continued)

(52) U.S. Cl.

CPC .......... *C07D 498/08* (2013.01); *A61K 31/395* (2013.01); *A61K 31/551* (2013.01);

(Continued)

(58) Field of Classification Search

CPC .. C07D 498/08; C07D 273/08; C07D 487/08; C07D 487/18; A61K 31/395; A61K 31/551; A61K 45/06; A61P 35/00

See application file for complete search history.

(56) References Cited

U.S. PATENT DOCUMENTS

| | | |
|---|---|---|
| 3,074,928 A | 1/1963 | Roch et al. |
| 4,997,645 A | 3/1991 | Suzuki et al. |

(Continued)

FOREIGN PATENT DOCUMENTS

| | | |
|---|---|---|
| CN | 101855224 A | 10/2010 |
| CN | 110300589 A | 10/2019 |

(Continued)

OTHER PUBLICATIONS

Playa, H. et. al. Bioorg. & Med. Chem. Lett. 2014, 24, 5801-5804 (Year: 2014).*

(Continued)

*Primary Examiner* — Clinton A Brooks
*Assistant Examiner* — Kendall Nicole Heitmeier
(74) *Attorney, Agent, or Firm* — McNeill PLLC

(57) ABSTRACT

The present invention relates to macrocyclic diamine derivatives of formula I, including pharmaceutically acceptable salts and solvates thereof. Compounds of the invention are inhibitors of ENT family transporter, especially of ENT1, and are useful as therapeutic compounds for the treatment of cancers. The invention also relates to the combined use of the macrocyclic diamine derivatives with an adenosine receptor antagonist, for the treatment of cancers.

(Continued)

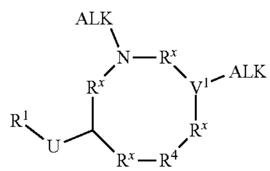

(I)

6 Claims, 4 Drawing Sheets

(51) Int. Cl.

| | |
|---|---|
| *A61K 31/439* | (2006.01) |
| *A61K 31/4995* | (2006.01) |
| *A61K 31/519* | (2006.01) |
| *A61K 31/551* | (2006.01) |
| *A61K 45/06* | (2006.01) |
| *A61P 35/00* | (2006.01) |
| *C07D 273/08* | (2006.01) |
| *C07D 487/08* | (2006.01) |
| *C07D 487/18* | (2006.01) |
| *C07D 491/08* | (2006.01) |
| *C07D 498/18* | (2006.01) |

(52) U.S. Cl.

CPC .............. *A61K 45/06* (2013.01); *A61P 35/00* (2018.01); *C07D 273/08* (2013.01); *C07D 487/08* (2013.01); *C07D 487/18* (2013.01)

(56) References Cited

U.S. PATENT DOCUMENTS

| | | | |
|---|---|---|---|
| 5,457,194 | A | 10/1995 | Luly et al. |
| 6,664,252 | B2 | 12/2003 | Castelhano et al. |
| 8,263,592 | B2 | 9/2012 | Bosmans et al. |
| 10,766,904 | B2 | 9/2020 | Strohbach et al. |
| 10,995,101 | B2 | 5/2021 | Crosignani et al. |
| 11,376,255 | B2 | 7/2022 | Crosignani et al. |
| 11,427,594 | B2 | 8/2022 | Crosignani |
| 2002/0099061 | A1 | 7/2002 | Neustadt et al. |
| 2002/0147175 | A1 | 10/2002 | Shepard et al. |
| 2005/0059683 | A1 | 3/2005 | Zablocki et al. |
| 2005/0239795 | A1 | 10/2005 | Neustadt et al. |
| 2009/0047243 | A1 | 2/2009 | Rickles et al. |
| 2009/0253732 | A1 | 10/2009 | Gregory et al. |
| 2014/0073581 | A1 | 3/2014 | Liu et al. |
| 2014/0341902 | A1 | 11/2014 | Maecker et al. |
| 2017/0088613 | A1 | 3/2017 | Grogan et al. |
| 2018/0055844 | A1 | 3/2018 | Muller et al. |
| 2019/0276473 | A1 | 9/2019 | Crosignani et al. |
| 2020/0102319 | A1 | 4/2020 | Crosignani |
| 2021/0198281 | A1 | 7/2021 | Crosignani et al. |
| 2021/0338672 | A1 | 11/2021 | Crosignani et al. |

FOREIGN PATENT DOCUMENTS

| | | | | |
|---|---|---|---|---|
| EA | 021565 | B1 | 7/2015 | |
| IN | 274489 | | 1/2011 | |
| JP | 63-316722 | | 12/1988 | |
| JP | 2188526 | | 7/1990 | |
| JP | 2017-509687 | | 4/2017 | |
| RU | 2373210 | C2 | 11/2009 | |
| WO | 9417803 | A1 | 8/1994 | |
| WO | 2000015231 | A1 | 3/2000 | |
| WO | 2003050241 | A2 | 6/2003 | |
| WO | 2003095457 | A1 | 11/2003 | |
| WO | 2004092171 | A2 | 10/2004 | |
| WO | 2004094431 | A2 | 11/2004 | |
| WO | 2007140181 | A2 | 12/2007 | |
| WO | 2009011897 | A1 | 1/2009 | |
| WO | 2009156737 | A1 | 12/2009 | |
| WO | 2011095626 | A2 | 8/2011 | |
| WO | 2011112687 | A2 | 9/2011 | |
| WO | 2011121418 | A1 | 10/2011 | |
| WO | 2012038980 | A2 | 3/2012 | |
| WO | 2012055015 | A1 | 5/2012 | |
| WO | 2012135084 | A1 | 10/2012 | |
| WO | 2013132376 | A1 | 9/2013 | |
| WO | 2015150555 | A1 | 10/2015 | |
| WO | 2015173764 | A1 | 11/2015 | |
| WO | 2017112917 | A1 | 6/2017 | |
| WO | WO-2017136717 | A1 * | 8/2017 | .............. A61P 43/00 |
| WO | 2018013918 | A2 | 1/2018 | |
| WO | 2018136700 | A1 | 7/2018 | |
| WO | 2018160704 | A1 | 9/2018 | |
| WO | 2018178338 | A1 | 10/2018 | |
| WO | 2018187484 | A1 | 10/2018 | |
| WO | 2019023504 | A1 | 1/2019 | |
| WO | 2019123482 | A1 | 6/2019 | |
| WO | 2019213184 | A1 | 11/2019 | |
| WO | 2020053263 | A1 | 3/2020 | |
| WO | 2020065036 | A1 | 4/2020 | |
| WO | 2020069439 | A1 | 4/2020 | |
| WO | 2020144178 | A1 | 7/2020 | |
| WO | 2020205527 | A1 | 10/2020 | |
| WO | 2020261219 | A1 | 12/2020 | |
| WO | 2021077070 | A1 | 4/2021 | |
| WO | 2021170797 | A1 | 9/2021 | |
| WO | 2021204896 | A1 | 10/2021 | |
| WO | 2022178135 | A1 | 8/2022 | |
| WO | 2023278603 | A2 | 1/2023 | |
| WO | 2023056910 | A1 | 4/2023 | |
| WO | 2023059739 | A1 | 4/2023 | |
| WO | 2023059817 | A1 | 4/2023 | |
| WO | 2023156506 | A1 | 8/2023 | |
| WO | 2024040036 | A2 | 2/2024 | |
| WO | 2024194391 | A1 | 9/2024 | |
| WO | 2024194392 | A1 | 9/2024 | |

OTHER PUBLICATIONS

International Search Report and Written Opinion from PCT/IB2025/050979, mailed Apr. 9, 2025, 13 pages.

Alogheli, "Computational Studies of Macrocycles and Molecular Modeling of Hepatitis C Virus NS3 Protease Inhibitors," Digital Comprehensive Summaries of Uppsala Dissertations from the Faculty of Pharmacy 247, Uppsala Universitet, 2018, pp. 1-174.

Guo et al., "Rapamycin-inspired macrocycles with new target specificity," Nat Chem., 2019, 11(3):254-263.

International Search Report and Written Opinion in PCT/EP2021/059096 dated Jul. 2, 2021, Applicant: iTeos Belgium SA, 12 pages.

Wright et al., "Structures of human ENT1 in complex with adenosine reuptake inhibitors," Nat. Struct. & Mol. Biol., 2019, 26:599-606.

International Search Report and Written Opinion received in International Application No. PCT/IB2024/053563, dated Nov. 5, 2024 (12 pages).

International Search Report and Written Opinion received in PCT/IB2024/062579, mailed on Mar. 24, 2025, 16 pages.

Mullen, Nicholas J. et al., "ENT1 blockade by CNX-774 overcomes resistance to DHODH inhibition in pancreatic cancer", Cancer Lett. 2023; 552:215981, 27 pages.

Rehan, Shahid et al., "Current Progress on Equilibrative Nucleoside Transporter Function and Inhibitor Design", SLAS Discovery, 2019, vol. 24(10) 953-968.

Sanders, Theodore J. et al., "Inhibition of equilibrative nucleoside transporter 1 relieves intracellular adenosine-mediated immune suppression", Apr. 5, 2024, Retrieved from the Internet:URL:https://investors.iteostherapeutics.com/static-files/675677d1-f157-4b4f-98a7-c63289dae65b.

Sonigo, Gabrielle et al., "Involvement of the CD39/CD73/adenosine pathway in T-cell proliferation and NK cell-mediated antibody-dependent cell cytotoxicity in Sezary syndrome", Blood, 2022, 139(17): 2712-2716.

(56) References Cited

OTHER PUBLICATIONS

Tol, Jolien et al., "Chemotherapy, Bevacizumab, and Cetuximab in Metastatic Colorectal Cancer", The New England Journal of Medicine, 2009, 360(6): 563-572.
Ueda, Kumiko et al., "Cellular Uptake of Decitabine by Equilibrative Nucleoside Transporters in HCT116 Cells", Biol. Pharm. Bull. 38, 1113-1119 (2015).
Passer, Brent J. et al., "Identification of the ENT1 Antagonists Dipyridamole and Dilazep as Amplifiers of Oncolytic Herpes Simplex Virus-1 Replication", Cancer Res; 70(10): 3890-5; 2010.
Apolonio et al.. "Oncolytic virus therapy in cancer: A current review", World Journal of Virology, vol. 10, No. 5, (2021), pp. 229-256.
Beten et al., "Interaction between dipyridamole and Eudragit S," Intl J of Pharmaceutics, 1992, 88(1-3): 31-37.
Cattaneo, Marco, "The platelet P2Y12 receptor for adenosine diphosphate: congenital and drug-induced defects", Blood, 2011, 117: 2102-2112.
Curtin et al., "Resistance-Modifying Agents of Pyrimido [5,4-d]pyrimidine Modulators of Antitumor Drug Activity. Synthesis and Structure-Activity Relationships for Nucleoside Transport Inhibition and Binding to alpha 1-Acid Glycoprotein," J Med Chem, 2004, 47(20):4905-4922.
Ibba, Giovanni V. et al., "Cardiovascular effects of a single high dose of dilazep by oral route", Int J Cardiol, 1986, vol. 11(3): abstract; retrieved from internet: https://www.sciencedirect.com/science/article/abs/pii/0167527386900380?via%3Dihub.
International Search Report and Written Opinion in PCT/EP2021/054821, dated Mar. 12, 2021, Applicant: iTeos Belgium SA, 12 pages.
Lin et al., "Synthesis, Flow Cytometric Evaluation, Identification of Highly Potent Dipyridamole Analogues as Equilibrative Nucleoside Transporter 1 Inhibitors," J Med Chem, 2007, 50(16): 3906-3920.
Stahl et al., "Usage Frequency of Acids and Bases for Forming Drug Salts," Handbook of Pharmaceutical Salts—Properties, Selection, and Use, Jan. 2002, pp. 329-350.
Wang et al., "Dipyridamole analogs as pharmacological inhibitors of equilibrative nucleoside transporters. Identification of novel potent and selective inhibitors of the adenosine transporter function of human equilibrative nucleoside transporter 4 (hENT4)," Biochemical Pharmacology, 2013, 86(11): 1531-1540.
International Search Report and Written Opinion received in PCT/IB2024/053562, dated Jul. 22, 2024, 13 pages.
International Search Report and Written Opinion from PCT/IB2024/061280, mailed Feb. 13, 2025, 13 pages.
Ohkubo, Satoko et al., "Adenosine uptake-dependent C6 cell growth inhibition", European Journal of Pharmacology (2007), 577: 35-43.
Munoz-Gutierrez et al., "HQSAR and moleular docking studies of furanyl derivatives as adenosine A2A receptor antagonists," Med. Chem Res., 2016, 25:1316-1328.
Nakagawa H, et al., "Basis for dosing time-dependent change in the anti-tumor effect of imatinib in mice", Nov. 15, 2006, vol. 72, No. 10, p. 1237-1245.
Ohta and Sitkovsky: "Role of G-protein-coupled adenosine receptors in downregulation of inflammation and protection from tissue damage," Nature (2001) 414:916-920.
Ohta, A., "A Metabolic Immune Checkpoint: Adenosine in Tumor Microenvironment", Frontiers in Immunology, Mar. 29, 2016, vol. 7, Article 109: pp. 1-11.
Parkinson et al., "Molecular Biology of Nucleoside Transporters and their Distributions and Functions in the Brain," Current Topics in Medicinal Chemistry, 2011, 11:948-972.
PCT International Search Report and Written Opinion, PCT Application No. PCT/EP2018/058301, Apr. 10, 2018, 10 pages.
Pinna A., "Adenosine A2A Receptor Antagonists in Parkinson's Disease: Progress in Clinical Trials from the Newly Approved Istradefylline to Drugs in Early Development and Those Already Discontinued", CNS Drugs, May 2014, vol. 28, Issue 5: pp. 455-474.
Riebel et al., "Expanding the set of rhodococcal Baeyer-Villiger monooxygenases by high-throughput cloning, expression and substrate cleaning," Appl Microbiol Biotechnol, 2012, 95(6): 1479-1489.
Segala et al., "Controlling the Dissociation of Ligands from the Adenosine A2A Receptor through Modulation of Salt Bridge Strength," J. Med Chem., 2016, 59(13):6470-6479.
Shryock JC and Belardinelli L: "Adenosine and adenosine receptors in the cardiovascular system: biochemistry, physiology, and pharmacology," Am J Cardiol (1997) 79(12):2-10.
Stagg J and Smyth MJ: "Extracellular adenosine triphosphate and adenosine in cancer," Oncogene (2010) 2:5346-5358.
Stephen B. Willingham, et al., "A2AR Antagonism with CPI-444 Induces Antitumor Responses and Augments Efficacy to Anti-PD-(L)1 and Anti-CTLA-4 in Preclinical Models", Cancer Immunology Research, vol. 6, No. 10, Oct. 21, 2018, p. 1136-1149.
STN Chemical Structure Search Results dated May 12, 2020 (31 pages).
STN Chemical Structure Search Results dated May 12, 2020 (41 pages).
Tran et al, "Survival comparison between glioblastoma multiforme and other incurable cancers," J Clin Neuroscience, 2010, 17:417-421.
Vijayan D et al: "Targeting immunosuppressive adenosine in cancer," Nature Reviews Cancer (2017) 17:709-724.
Wang et al., "Silence of MCL-1 upstream signaling by shRNA abrogates multiple myeloma growth," Experimental Hematology & Oncology, 2014, 3:27, 7 pages.
West, Solid State Chemistry and its Applications, Wiley, New York, 1988, p. 358.
Willingham et al., "Targeting the A2AR in cancer; early lessons from the clinic," Curr Opin Pharm, 2020, 53:126-133.
Tang et al., "Inhibition of human equilibrative nucleoside transporters by 4-((4-(2-fluorophenyl)piperazin-1-yl)methyl)-6-imino-N-(naphthalen-2-yl)-1,3,5-triazin-2-amine," Eur J Pharma, 2016, 791:544-551.
Hilfiker et al., Polymorphism in the Pharmaceutical Industry, Chapter 1: Relevance of Solid State Properties for Pharmaceutical Products, Wiley-VCH, Weinheim, 2006, 19 pages.
International Search Report and Written Opinion received in PCT/EP2024/057525, dated Jul. 8, 2024, 17 pages.
International Search Report and Written Opinion received in PCT/EP2024/057527, dated Jul. 8, 2024, 17 pages.
Allard, B., et al., "Immunosuppressive activities of adenosine in cancer.", Curr. Opin. Pharmacol., Aug. 2016, vol. 29: pp. 7-16.
Anderson CM et al: "Distribution of Equilibrative, Nitrobenzylthioinosine-Sensitive Nucleoside Transporters (ENT1) in Brain," Neurochem (1999) 73:867-873.
Andre B. Da Fonseca Antunes, et al., "Gelucire 44/14 based immediate release formulations for poorly water-soluble drugs", Drug Development and Industrial Pharmacy,vol. 39, No. 5, May 1, 2013, p. 791-798.
Antonioli L et al: "Immunity, inflammation and cancer: a leading role for adenosine," Nature Reviews Cancer (2013) 13:842-857.
Barbara Cacciari, et al., "A2A Adenosine Receptor Antagonists as Therapeutic Candidates: Are They Still an Interesting Challenge?", Mini Reviews in Medicinal Chemistry,vol. 18, No. 14, Jul. 9, 2018, p. 1168-1174.
Blay J et al: "The extracellular fluid of solid carcinomas contains immunosuppressive concentrations of adenosine," Cancer Res (1997) 57:2602-2605.
Bong et al., "Baeyer-Villiger Monooxygenase-Mediated Synthesis of Esomeprazole as an Alternative for Kagan Sulfoxidation," J. Org. Chem., 2018, 83(14): 7453-7458.
Bonnal RJP et al: "De novo transcriptome profiling of highly purified human lymphocytes primary cells," Nature (2015) 2:150051.
CAS Registry No. 2246607-08-7, Thiazolo[5,4-e][1,2,4]triazolo[1,5-c]pyrimidin-2(3H)-one, 5-amino-3-[2-[4-[2,4-difluoro-5-[2-[(S)-methylsulfinyl]ethoxy]phenyl]-1-piperazinyl]ethyl]-8-(2-furanyl)-, entered Oct. 25, 2018, 1 page.
CAS Registry No. 2411004-22-1, Thiazolo[5,4-e][1,2,4]triazolo[1,5-c]pyrimidin-2(3H)-one, 5-amino-3-[2-[4-[2,4-difluoro-5-[2-[(S)-

(56) References Cited

OTHER PUBLICATIONS methylsulfinyl]ethoxy]phenyl]-1-piperazinyl]ethyl]-8-(2-furanyl)-, hydrochloride (1:1) submitted Feb. 29, 2020, 1 page.
Cekic C and Linden J: "Purinergic regulation of the immune system", Nature Reviews | Immunology (2016) 16:177-192.
Conglian Yang, et al., "Recent Advances in the Application of Vitamin E TPGS for Drug Delivery", Theranostics,vol. 8, No. 2, Jan. 1, 2018, p. 464-485.
Dirks, "Brain Tumor Stem Cells: Bringing Order to the Chaos of Brain Cancer," J Clin Oncology, 2008, 26 (17):2916-2924 (abstract only).
Domingues et al., "Melanoma Treatment in Review," ImmunoTargets and Therapy, 2018, 7:35-49.
Fallah-Mehrjardi et al., "Pharmacological targeting of immune checkpoint A2aR improves function of anti-CD19 CAR T cells in vitro," Immunology Letters, 2020, 223:44-52.
Maczka et al., "Biotechnological Methods of Sulfoxidation: Yesterday, Today, Tomorrow," Catalysts, 2018, 8(12): 624, 27 pages.
File History of U.S. Appl. No. 16/354,022, filed Mar. 14, 2019, Inventors: Stefano Crosignani et al., Title: 2-Oxo-Thiazole Derivatives as A2A Inhibitors and Compounds for Use in the Treatment of Cancers.
Lopez-Lazaro, "The migration ability of stem cells can explain the existence of cancer of unknown primary site. Rethinking metastasis. ," Oncoscience, 2015, 2(5): 467-475.
File History of U.S. Appl. No. 16/584,596, filed Sep. 26, 2019, Inventors: Stefano Crosignani et al., Title: Non Brain Penetrant A2A Inhibitors and Methods For Use in the Treatment of Cancer.
Leroy X., "Discovery and Pharmacological Characterization of an A2A Receptor Antagonists for Immune-Oncology Development," Basic & Clinical Pharmacology & Toxicology, Aug. 2018, vol. 123, Suppl. 2, Abstract No. RT030, 1 page.
File History of U.S. Appl. No. 16/993,897, filed Aug. 14, 2020, Inventors: Stefano Crosignani et al., Title: 2-Oxo-Thiazole Derivatives as A2A Inhibitors and Compounds for Use in the Treatment of Cancers.
File History of U.S. Appl. No. 17/015,850, filed Sep. 9, 2020, Inventors: Stefano Crosignani et al.
File History of U.S. Appl. No. 17/281,156, filed Mar. 29, 2021, Inventors: Stefano Crosignani et al.
File History of U.S. Appl. No. 17/518,075, filed Nov. 3, 2021, Inventors: Stefano Crosignani et al.
File History of U.S. Appl. No. 17/829,919, filed Jun. 1, 2022, Inventors: Stefano Crosignani et al.
File History of U.S. Appl. No. 17/867,229, filed Jul. 18, 2022, Inventor: Stefano Crosignani.
File History of U.S. Appl. No. 17/919,115, filed Oct. 14, 2022, Inventors: Olivier de Henau et al.
File History of U.S. Appl. No. 17/949,595, filed Sep. 21, 2022, Inventors: Stefano Crosignani et al.
File History of U.S. Appl. No. 17/949,597, filed Sep. 21, 2022, Inventors: Stefano Crosignani et al.
File History of U.S. Appl. No. 18/034,449, filed Apr. 28, 2023, Inventors: Xuecheng Jiao et al.
File History of U.S. Appl. No. 18/277,256, filed Aug. 15, 2023, Inventors: Chiara Martinoli et al., available on Patent Center.
Fong et al., "Adenosine 2A Receptor Blockage as an Immunotherapy for Treatment-Refractory Renal Cell Cancer," Cancer Discovery, 2019, 10(1): 40-53.
Gengyang Yuan, et al., "Fluorinated Adenosine A 2A Receptor Antagonists Inspired by Preladenant as Potential Cancer Immunotherapeutics", International Journal of Medicinal Chemistry,vol. 2017, Jan. 1, 2017, p. 1-8.
Gonzalo et al., "Oxidations catalyzed by phenylacetone monooxygenase from Thermobifida fusca," Tetrahedron Asymmetry, 2005, 16(18): 3077-3083.
Griffith DA and Jarvis SM: "Nucleoside and nucleobase transport systems of mammalian cells," Biochim Biophys Acta (1996) 1286:153-181.
Hatfield Stephen M, et al., "A2A adenosine receptor antagonists to weaken the hypoxia-HIF-1[alpha] driven immunosuppression and improve immunotherapies of cancer", Current Opinion in Pharmacology, Elsevier Science Publishers, NL,vol. 29, Aug. 17, 2016, p. 90-96.
Hauser, R.A., et al., "Preladenant as an Adjunctive Therapy With Levodopa in Parkinson Disease: Two Randomized Clinical Trials and Lessons Learned", JAMA Neurol., Dec. 2015, vol. 72, Issue 12: pp. 1491-1500.
Hodgson, R. A., et al., "Characterization of the Potent and Highly Selective A2A Receptor Antagonists Preladenant and SCH 412348 [7-[2-[4-2,4-Difluorophenyl]-1-piperazinyl]ethyl]-2-(2-furanyl)-7H-pyrazolo[4,3-e][1,2,4]triazolo[1,5-c] pyrimidin-5-amine] in Rodent Models of Movement Disorders and Depression", The Journal of Pharmacology and Experimental Therapeutics, Jul. 2009, vol. 330, Issue 1: pp. 294-303.
Houthuys Erica, et al., "Abstract LB-291: EOS100850, an insurmountable and non-brain penetrant A2A receptor antagonist, inhibits adenosine-mediated T cell suppression, demonstrates anti-tumor activity and exhibits best-in class characteristics", Cancer Research, Apr. 14-18, 2018, Retrieved from the Internet: URL:https://cancerres.aacrjournals.org/content/78/13_Supplement/LB-291.
International Search Report and Written Opinion for PCT/CN2021/127308, dated Mar. 14, 2022, Applicant: iTeos Belgium SA, 15 pages.
International Search Report and Written Opinion for PCT/EP2019/074208 mailed Jan. 17, 2020.
International Search Report and Written Opinion for PCT/EP2019/076244 mailed Jan. 8, 2020.
International Search Report and Written Opinion for PCT/EP2021/059996, dated Jul. 8, 2021, Applicant: iTeos Belgium SA, 9 pages.
International Search Report and Written Opinion for PCT/US2022/016808, dated Jun. 13, 2022, Applicant: iTeos Belgium SA, 12 pages.
International Search Report and Written Opinion in PCT/US2022/045923 dated Jan. 18, 2023, Applicant: iTeos Belgium SA, 9 pages.
Kuznetzova, "Brackets in Text of Legal Document as a Linguistic and Cognitive Phenomenom," Russian Philology, 2015, 3:37-43 (english abstract only).
File History of U.S. Appl. No. 17/281,156, filed Mar. 29, 2021, Inventors: Stefano Crosignani et al., available on Patent Center.
File History of U.S. Appl. No. 17/895,667, filed Aug. 25, 2022, Inventors: Michael Deligny et al., available on Patent Center.
International Search Report and Written Opinion in PCT/CN2022/123711, dated Jan. 11, 2023, Applicant: iTeos Belgium SA, 13 pages.
International Search Report and Written Opinion in PCT/US2022/045808, dated Jan. 5, 2023, Applicant: iTeos Belgium SA, 12 pages.
Playa et al., Dilazep analogues for the study of equilibrative nucleoside transporters 1 and 2 (ENT1 and ENT2), Bioorganic & Medicinal Chemical Letters, 2014, 24(24):5801-5804.
Bookser et al., "Adenosine Kinase Inhibitors. 4. 6,8-Disubstituted Purine Nucleoside Derivatives. Synthesis, Conformation, and Enzyme Inhibition," J. Med. Chem., 2005, 48:3389-3399.
File History of U.S. Appl. No. 18/612,120, filed Mar. 21, 2024, Inventors: Ron Lawrence et al., available on Patent Center.
File History of U.S. Appl. No. 18/616,553, filed Mar. 26, 2024, Inventors: Michael Deligny et al., available on Patent Center.
File History of U.S. Appl. No. 18/624,336, filed Apr. 2, 2024, Inventors: Michael Deligny et al., available on Patent Center.
File History of U.S. Appl. No. 18/618,211, filed Mar. 27, 2024, Inventors: Marcel de Matas et al., available on Patent Center.
Hocek et al., "Cytostatic 6-Arylpurine Nucleosides II. + Synthesis of Sugar Modified Derivatives: 9-(2-deoxy-beta-D-erythro-pentofuranosyl)-, 9-(5-deoxy-beta-D-ribofuranosyl)- and 9-(2,3-Dihydroxypropyl)-6-phenylpurines," Collect. Czech. Chem. Commun., 2000, 65(11):1683-1697.
International Search Report and Written Opinion in PCT/IB2023/063020, dated May 17, 2024, Applicant: iTeos Belgium SA, 20 pages.
International Search Report and Written Opinion in PCT/US2023/072187, dated Feb. 21, 2024, Applicant: iTeos Belgium SA, 14 pages.

(56) References Cited

OTHER PUBLICATIONS

STN Caplus Online, American Chemical Society, Jan. 1, 2012, Database Accession No. 2012:1789448, 1 page.
Vlachodimou et al., "Affinity, binding kinetics and functional characterization of draflazine analogues for human equilibrative nucleoside transporter 1 (SLC29A1)," Biochemical Pharmacology, 2020, 172:113747, 11 pages.
Zhu et al., "Constrained NBMPR analogue synthesis, pharmacophore mapping and 3D-QSAR modeling of equilibrative nucleoside transporter 1 (ENT1) inhibitory activity," Bioorganic & Medicinal Chemistry, 2008, 16:3848-3865.
Jouan et al., "Differential Inhibition of Equilibrative Nucleoside Transporter 1 (ENT1) Activity by Tyrosine Kinase Inhibitors," Eur J Drug Metab Pharmacokinet. 46(5):625-635 (2021).
Werner, Doris, International Search Report and Written Opinion issued in International Application No. PCT/IB2025/063078; mailed Mar. 23, 2026, 14 pages.
Weiss, Marie-France, PCT International Search Report and Written Opinion from PCT/IB2025/058239, mailed Dec. 2, 2025, 11 pages.
Hilfiker, Rolf et al., "Relevance of Solid-state Properties for Pharmaceutical Products", Polymorphism in the Pharmaceutical Industry, 2006, pp. 1-19.
Guo et al. "Binding Kinetics of ZM241385 Derivatives at the Human Adenosine A2A Receptor," Chem Med Chem 2014, 9:752-761.
Gerlach "Einfluss von Pyrimidopyrimidin- und Pteridin-Derivaten auf Phosphat- und Adenosin-Permeabilitaet Menschlicher Erythrocyten," Arzneimittel Forschung, 1965, 15(5): 558-563 (previously cited).

* cited by examiner

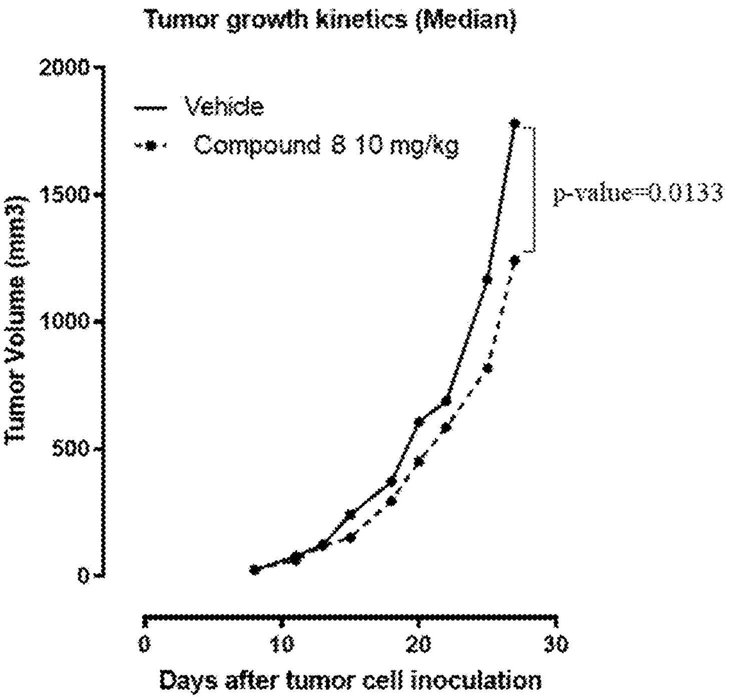
FIG. 4A
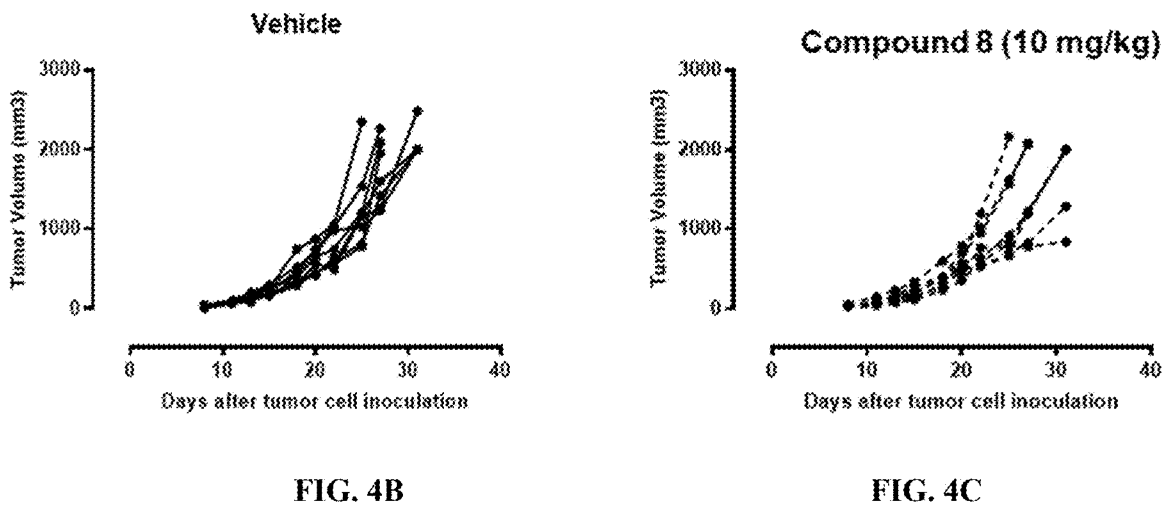
FIG. 4B
FIG. 4C

MACROCYCLIC DIAMINE DERIVATIVES AS ENT INHIBITORS FOR THE TREATMENT OF CANCERS, AND COMBINATION THEREOF WITH ADENOSINE RECEPTOR ANTAGONISTS

FIELD

The present invention relates to macrocyclic diamine derivatives, including pharmaceutically acceptable salts and solvates thereof. Compounds of the invention are inhibitors of ENT family transporter, especially of ENT1, and are useful as therapeutic compounds, especially in the treatment of cancers. The invention also relates to the combined use of the macrocyclic diamine derivatives of the invention with an adenosine receptor antagonist, for the treatment of cancers.

BACKGROUND

The equilibrative nucleoside transporter (ENT) family, also known as SLC29, is a group of plasmalemmal transport proteins which transport nucleoside substrates into cells. There are four known ENTs, designated ENT1, ENT2, ENT3, and ENT4.

One of the endogenous substrates for ENTs is adenosine, a potent physiological and pharmacological regulator of numerous functions. Cellular signaling by adenosine occurs through four known G-protein-coupled adenosine receptors A1, A2A, A2B, and A3. By influencing the concentration of adenosine available to these receptors, ENTs fulfil important regulatory roles in different physiological processes, such as modulation of coronary blood flow, inflammation, and neurotransmission (Griffith D A and Jarvis S M, Biochim Biophys Acta, 1996, 1286, 153-181; Shryock J C and Belardinelli L, Am J Cardiol, 1997, 79(12A), 2-10; Anderson C M et al., J Neurochem, 1999, 73, 867-873).

Adenosine is also a potent immunosuppressive metabolite that is often found elevated in the extracellular tumor microenvironment (TME) (Blay J et al., Cancer Res, 1997, 57, 2602-2605). Extracellular adenosine is generated mainly by the conversion of ATP by the ectonucleotidases CD39 and CD73 (Stagg J and Smyth M J, Oncogene, 2010, 2, 5346-5358). Adenosine activates four G-protein-coupled receptor subtypes (A1, A2A, A2B, and A3). In particular, activation of the A2A receptor is believed to be the main driver of innate and adaptive immune cell suppression leading to suppression of antitumor immune responses (Ohta and Sitkovsky, Nature, 2001, 414, 916-920) (Stagg and Smyth, Oncogene, 2010, 2, 5346-5358) (Antonioli L et al., Nature Reviews Cancer, 2013, 13, 842-857) (Cekic C and Linden J, Nature Reviews, Immunology, 2016, 16, 177-192) (Allard B et al., Curr Op Pharmacol, 2016, 29, 7-16) (Vijayan D et al., Nature Reviews Cancer, 2017, 17, 709-724).

The Applicant previously evidenced in PCT/EP2019/076244 that adenosine as well as ATP profoundly suppress T cell proliferation and cytokine secretion (IL-2), and strongly reduce T cell viability. Adenosine- and ATP-mediated suppression of T cell viability and proliferation were successfully restored by using ENTs inhibitors. Moreover, the use of an ENT inhibitor in combination with an adenosine receptor antagonist enabled to restore not only adenosine- and ATP-mediated suppression of T cell viability and proliferation, but also restored T cell cytokine secretion. These results showed that ENTs inhibitors either alone or in combination with an adenosine receptor antagonist may be useful for the treatment of cancers.

A variety of drugs such as dilazep, dipyridamole, and draflazine interact with ENTs and alter adenosine levels, and were developed for their cardioprotective or vasodilatory effects.

Currently, two non-selective ENT1 inhibitors (dilazep and dipyridamole) are on the market (Vlachodimou et al., BioChemical Pharmacology, 2020, 172, 113747). However, their binding kinetics are unknown; moreover, there is still a need for more potent ENTs inhibitors, and especially ENT1 inhibitors to be used for the treatment of cancers, either alone or in combination with an adenosine receptor antagonist.

Hence, this study focused on finding new and improved ENT1 inhibitors. For that purpose, the Applicant herein provides the macrocyclic diamine derivatives of formula I and II detailed below.

SUMMARY

This invention thus relates to a compound of formula I:

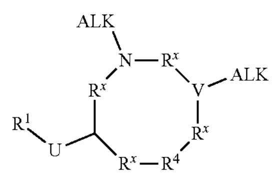

(I)

or a pharmaceutically acceptable salt or solvate thereof, wherein $R^x$, $R^1$, $R^4$, U, V, and ALK are hereafter defined.

This invention also relates to a compound of formula II:

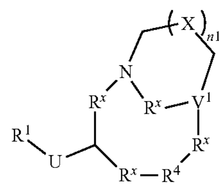

(II)

or a pharmaceutically acceptable salt or solvate thereof, wherein $R^x$, $R^1$, $R^4$, U, V, X, and $n^1$ are hereafter defined.

According to one embodiment, the compound of the invention is of formula IIa or IIa1 as defined hereafter. Preferably, the compound of the invention is selected from the compounds listed in Table 1 hereafter.

In some embodiments, the compound according to the invention comprises one chiral center.

In some embodiments, the compound according to the invention is racemic mixture containing 'R' isomer and 'S' isomer.

In some embodiments, the compound according to the invention is 'R' isomer.

In some embodiments, the compound according to the invention is 'S' isomer.

In some embodiments, the compound according to the invention comprises more than one chiral center. In some embodiments, each chiral center comprises the same configuration. In some embodiments, each chiral center comprises "R" or "S" configurations independently.

The present invention also relates to a pharmaceutical composition comprising a compound of formula I or formula II according to the invention and at least one pharmaceutically acceptable excipient.

In one embodiment, the pharmaceutical composition according to the invention, further comprises an adenosine receptor antagonist. In one embodiment, the adenosine receptor antagonist is an A2A or A2B receptor antagonist.

In one embodiment, the adenosine receptor antagonist is selected from:

5-bromo-2,6-di-(1H-pyrazol-1-yl)pyrimidin-4-amine;

(S)-7-(5-methylfuran-2-yl)-3-((6-(([tetrahydrofuran-3-yl]oxy)methyl)pyridin-2-yl)methyl)-3H-[1,2,3]triazolo[4,5-d]pyrimidin-5-amine;

6-(2-chloro-6-methylpyridin-4-yl)-5-(4-fluorophenyl)-1,2,4-triazin-3-amine;

3-(2-amino-6-(1-((6-(2-hydroxypropan-2-yl)pyridin-2-yl)methyl)-1H-1,2,3-triazol-4-yl)pyrimidin-4-yl)-2-methylbenzonitrile;

2-(2-furanyl)-7-(2-(4-(4-(2-methoxyethoxy)phenyl)-1-piperazinyl)ethyl)-7H-pyrazolo(4,3-e)(1,2,4)triazolo(1,5-c)pyrimidine-5-amine;

3-(4-amino-3-methylbenzyl)-7-(2-furyl)-3H-(1,2,3)triazolo(4,5-d)pyrimidine-5-amine; and 4-hydroxy-N-(4-methoxy-7-morpholinobenzo[d]thiazol-2-yl)-4-methylpiperidine-1-carboxamide.

In another embodiment, the adenosine receptor antagonist is the adenosine receptor antagonist is a compound of Formula (III):

(III)

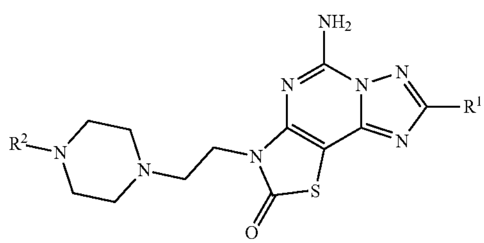

or a pharmaceutically acceptable salt or solvate thereof, wherein $R^1$ and $R^2$ are as defined hereafter.

The invention further relates to a method of inhibiting ENT1 in a patient need thereof, comprising: administering to said patient an effective amount of a compound of formula I or formula II according to the invention.

The invention also relates to method of treating cancer in a patient need thereof, comprising: administering to said patient an effective amount of a compound of formula I or II according to the invention.

The invention is also directed to a method of treating cancer in a patient need thereof, comprising: administering to said patient a combination of a compound of formula I or II according to the invention and an adenosine receptor antagonist. In one embodiment, the compound of formula I or II according to the invention is administered prior to, concomitant with, or subsequent to administration of the adenosine receptor antagonist. In one embodiment, the adenosine receptor antagonist is an A2A or A2B receptor antagonist. In one embodiment, the adenosine receptor antagonist is selected among those listed above.

The invention further relates to a kit of parts comprising: (a) a first part comprising an effective amount of a compound of formula I or II according to the invention; and (b) a second part comprising an effective amount of an adenosine receptor antagonist.

In one embodiment, in the kit of parts, the adenosine receptor antagonist is an A2A or A2B receptor antagonist, and is preferably selected among those listed above.

BRIEF DESCRIPTION OF THE DRAWINGS

FIG. 4 consists of three graphs: A, B, and C depicting the evolution of to assess the anti-tumor efficacy of compound Compound 8 in syngeneic fibrosarcoma model.

DETAILED DESCRIPTION

Figure 1A:
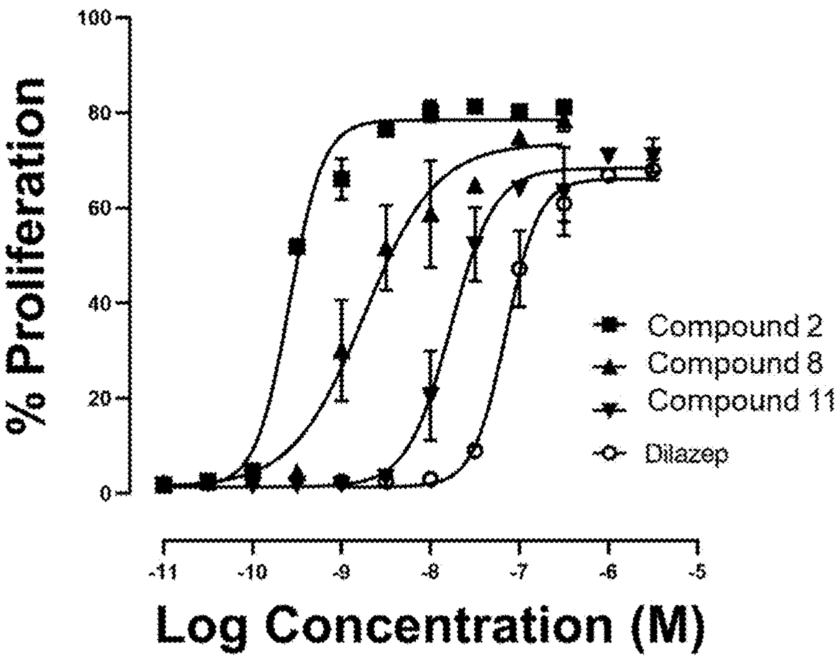
FIG. 1A depicts a graph of log concentration (M) versus percent proliferation. Purified human T cells were activated with anti-CD3/CD28 dynabeads in the presence of ATP (100 μM) as a source of adenosine for 96 h and then proliferation was assessed by CFSE dilution.

It is to be understood that both the foregoing general description and the following detailed description are exemplary and explanatory only and are not restrictive of the invention, as claimed. Herein, the use of the singular includes the plural unless specifically stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. Where permitted, all patents, applications, published applications and other publications, gene accession numbers and associated sequence information obtainable through databases such as National Center for Biotechnology Information (NCBI) and other data referred to throughout in the disclosure are incorporated by reference in their entirety for any purpose. Any conflict between the teachings of these patents and publications and this specification shall be resolved in favor of the latter.

Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art. Standard techniques may be used for chemical synthesis, and chemical analysis. As appropriate, procedures involving the use of commercially available kits and reagents are generally carried out in accordance with manufacturer-defined protocols and conditions unless otherwise noted.

For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

Unless otherwise indicated, the following terms have the following meanings:

As used herein, the singular forms "a," "an," and "the" include the plural referents unless the context clearly indicates otherwise. The terms "include," "such as," and the like are intended to convey inclusion without limitation, unless otherwise specifically indicated.

As used herein, the term "comprising" also specifically includes embodiments "consisting of" and "consisting essentially of" the recited elements, unless specifically indicated otherwise.

The term "about" indicates and encompasses an indicated value and a range above and below that value. In certain embodiments, the term "about" indicates the designated value±10%, ±5%, or ±1%. In certain embodiments, where applicable, the term "about" indicates the designated value(s)±one standard deviation of that value(s).

The term "aldehyde" refers to a group —CHO.

The term "alkenyl" refers to unsaturated hydrocarbyl group, which may be linear or branched, comprising one or more carbon-carbon double bonds. Suitable alkenyl groups comprise between 2 and 6 carbon atoms, preferably between 2 and 4 carbon atoms, still more preferably between 2 and 3 carbon atoms. Examples of alkenyl groups are ethenyl, 2-propenyl, 2-butenyl, 3-butenyl, 2-pentenyl and its isomers, 2-hexenyl and its isomers, 2,4-pentadienyl and the like.

The term "alkenylcarbonyl" refers to a group —(C═O)-alkenyl wherein alkenyl is as herein defined.

The term "alkenylcarbonylamino" refers to a group —NH—(C═O)-alkenyl wherein alkenyl is as herein defined.

The term "alkoxy" refers to a group —O-alkyl wherein alkyl is as herein defined.

The term "ALK" or "Alk" or "alk" refers to an alkyl group (hydrocarbyl radical of formula $C_nH_{2n+1}$ wherein n is a number greater than or equal to 1) or an alkyl group substituted by, for example, one to four substituents, such as, halo, trifluoromethyl, trifluoromethoxy, hydroxy, alkoxy, cycloalkoxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. SO2NH2), substituted sulfonamido, nitro, cyano, carboxy, carbamyl (e.g. CONH2), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl. In some embodiments, ALK is optionally substituted $C_1$-$C_8$ alkyl.

In some embodiments, an alkyl group is substituted by OH, OAlk, $CF_3$, $NR_2$.

Generally, alkyl groups of this invention comprise from 1 to 8 carbon atoms, more preferably, alkyl groups of this invention comprise from 1 to 6 carbon atoms. Alkyl groups may be linear or branched. Suitable alkyl groups include methyl, ethyl, propyl, butyl, pentyl, hexyl, heptyl and octyl.

The term "alkylaminoalkyl" refers to a group -alkyl-NH-alkyl wherein alkyl is as herein defined.

The term "alkylaminoalkylaminocarbonyl" refers to a group —(C═O)—NH-alkyl-NH-alkyl wherein alkyl is as herein defined.

The term "(alkylaminoalkyl)(alkyl)aminocarbonyl" refers to a group —(C═O)—$NR^1R^2$ wherein $R^1$ is an alkyl group and $R^2$ is a -alkyl-NH-alkyl group, wherein alkyl is as herein defined.

The term "alkylaminoalkylcarbonyl" refers to a group —(C═O)-alkyl-NH-alkyl wherein alkyl is as herein defined.

The term "alkylcarbonyl" refers to a group —(C═O)-alkyl wherein alkyl is as herein defined.

The term "alkylcarbonylamine" refers to a group —NH—(C═O)-alkyl wherein alkyl is as herein defined.

The term "alkylcarbonyloxyalkyl" refers to a group -alkyl-O—(C═O)-alkyl wherein alkyl is as herein defined.

The term "alkylheteroaryl" refers to any heteroaryl substituted by an alkyl group wherein alkyl is as herein defined.

The term "alkyloxyalkyl" refers to a group -alkyl-O-alkyl wherein alkyl is as herein defined.

The term "alkyloxycarbonyl" refers to a group —(C═O)—O-alkyl wherein alkyl is as herein defined.

The term "alkylsulfonyl" refers to a group —$SO_2$-alkyl wherein alkyl is as herein defined.

The term "alkylsulfonylaminoalkyl" refers to a group -alkyl-NH—$SO_2$-alkyl wherein alkyl is as herein defined.

The term "alkylsulfonealkyl" refers to a group -alkyl-$SO_2$-alkyl wherein alkyl is as herein defined.

The term "alkylsulfonimidoyl" refers to a group —S(═O)(═NH)-alkyl wherein alkyl is as herein defined.

The term "alkylsulfoxide" refers to a group —(S═O)-alkyl wherein alkyl is as herein defined.

The term "alkylsulfoxidealkyl" refers to a group -alkyl-SO-alkyl wherein alkyl is as herein defined.

The term "alkylene," as used herein, refers to an alkyl group, as defined above, wherein one of the alkyl group's hydrogen atoms has been replaced with a bond. Alkylene group possess two points of attachment. Non-limiting examples of alkylene groups include $—CH_2—$, $—CH_2CH_2—$, $—CH_2CH_2CH_2—$, $—CH_2CH_2CH_2CH_2—$, $—CH(CH_3)CH_2CH_2—$, $—CH(CH_3)—$ and $CH_2CH(CH_3)CH_2—$. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is $—CH_2—$. In one embodiment, at least one hydrogen atom of an alkylene group is substituted by a substituent such as halo, trifluoromethyl, trifluoromethoxy, hydroxy, alkoxy, cycloalkoxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. SO2NH2), substituted sulfonamido, nitro, cyano, carboxy, carbamyl (e.g. CONH2), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl. In another embodiment, at least one hydrogen atom of an alkylene group is substituted by OH, OAlk, $CF_3$, $NR_2$.

The term "alkyne" refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkyl groups. Non-limiting examples of alkynyl groups are ethynyl, 2-propynyl, 2-butynyl, 3-butynyl, 2-pentynyl and its isomers, 2-hexynyl and its isomers and the like.

The term "alkynealkyl" refers to a group -alkyl-alkyne wherein alkyl and alkyne are as herein defined.

The term "amino" refers to a group $—NH_2$.

The term "aminoalkyl" refers to a group $-alkyl-NH_2$ wherein alkyl is as herein defined.

The term "aminoalkylaminocarbonyl" refers to a group $—(C═O)—NH-alkyl-NH_2$ wherein alkyl is as herein defined.

The term "aminoalkylcarbonylamino" refers to a group $—NH—(C═O)-alkyl-NH_2$ wherein alkyl is as herein defined.

The term "aminocarbonyl" or "aminocarboxy" refers to a group $—(C═O)—NH_2$.

The term "(aminocarbonylalkyl)(alkyl)amino" refers to a group $—NR^1R^2$ wherein $R^1$ is an alkyl group and $R^2$ is a $-alkyl-(C═O)—NH_2$ group, wherein alkyl is as herein defined.

The term "aminocarbonylalkylamino" refers to a group $—NH-alkyl-(C═O)—NH_2$ wherein alkyl is as herein defined.

The term "aminosulfonyl" refers to a group $—SO_2—NH_2$.

The term "aryl" refers to a polyunsaturated, aromatic hydrocarbyl group having a single ring (i.e. phenyl) or multiple aromatic rings fused together (e.g. naphtyl), typically containing 5 to 12 atoms; preferably 5 to 10; more preferably the aryl is a 5- or 6-membered aryl. Non-limiting examples of aryl comprise phenyl, naphthalenyl.

The term "arylalkyl" refers to a group -alkyl-aryl wherein alkyl and aryl are as herein defined.

The term "aryloxyalkyl" refers to a group -alkyl-O-aryl wherein alkyl and aryl are as herein defined.

The term "carbonyl" refers to a group —(C═O)—.

The term "carbonylamino" refers to a group —NH—(C═O)—.

The term "cyano" refers to a group —CN.

The term "cyano" refers to a group -alkyl-CN.═ wherein alkyl is as herein defined.

The term "cycloalkyl" refers to a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms; still more preferably more preferably the cycloalkyl is a 5- or 6-membered cycloalkyl. Examples of cycloalkyl groups include but are not limited to cyclopropyl, cyclobutyl, cyclopentyl, cyclohexyl.

The term "cycloalkyloxy" refers to a group —O-cycloalkyl wherein cycloalkyl is as herein defined.

The term "dialkylamino" refers to a group $—NR^1R^2$ wherein $R^1$ and $R^2$ are both independently alkyl group as herein defined.

The term "dialkylaminoalkyl" refers to a group $-alkyl-NR^1R^2$ wherein $R^1$ and $R^2$ are both independently alkyl group, as herein defined.

The term "dialkylaminoalkylaminocarbonyl" refers to a group $—(C═O)—NH-alkyl-NR^1R^2$ wherein $R^1$ and $R^2$ are both alkyl group, as herein defined.

The term "dialkylaminoalkylcarbonyl" refers to a group $—(C═O)-alkyl-NR^1R^2$ wherein $R^1$ and $R^2$ are both alkyl group, as herein defined.

The term "dihydroxyalkyl" refers to a group alkyl is as herein defined substituted by two hydroxyl (—OH) groups.

The term "halo" or "halogen" refers to fluoro, chloro, bromo, or iodo.

The term "haloalkyl" refers to an alkyl group in which one or more hydrogen atom is replace by a halogen atom.

The term "haloalkyloxy" refers to a group —O-haloalkyl wherein alkyl is as herein defined.

The term "heteroaryl" refers to an aryl group as herein defined wherein at least one carbon atom is replaced with a heteroatom. In other words, it refers to 5 to 12 carbon-atom aromatic single rings or ring systems containing 2 rings which are fused together, typically containing 5 to 6 atoms; in which one or more carbon atoms is replaced by oxygen, nitrogen and/or sulfur atoms where the nitrogen and sulfur heteroatoms may optionally be oxidized and the nitrogen heteroatoms may optionally be quaternized. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, pyridinyl, pyridazinyl, pyrimidinyl and pyrazinyl.

The term "heteroarylalkyl" refers to a group -alkyl-heteroaryl wherein alkyl and heteroaryl are as herein defined.

The term “heterocyclyl” or “heterocycle” refers to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Preferably the heterocyclyl is a 5- or 6-membered heterocyclyl. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include piperidinyl, piperazinyl, azetidinyl, azocanyl, diazepanyl, diazocanyl, morpholin-4-yl, oxazepanyl, pyrrolidinyl, thiomorpholin-4-yl, tetrahydrofuranyl, tetrahydropyranyl, aziridinyl, oxiranyl, thiiranyl, 2-imidazolinyl, pyrazolidinyl imidazolidinyl, isoxazolinyl, oxazolidinyl, isoxazolidinyl, thiazolidinyl, isothiazolidinyl, succinimidyl, 3H-indolyl, indolinyl, isoindolinyl, 2H-pyrrolyl, 1-pyrrolinyl, 2-pyrrolinyl, 3-pyrrolinyl, 4H-quinolizinyl, 2-oxopiperazinyl, homopiperazinyl, 2-pyrazolinyl, 3-pyrazolinyl, tetrahydro-2H-pyranyl, 2H-pyranyl, 4H-pyranyl, 3,4-dihydro-2H-pyranyl, oxetanyl, thietanyl, 3-dioxolanyl, 1,4-dioxanyl, 2,5-dioximidazolidinyl, 2-oxopiperidinyl, 2-oxopyrrolodinyl, indolinyl, tetrahydrothiophenyl, tetrahydroquinolinyl, tetrahydroisoquinolinyl, 1-oxido-1-thiomorpholin-4-yl, 1-dioxido-1-thiomorpholin-4-yl, 1,3-dioxolanyl, 1,4-oxathianyl, 1,4-dithianyl, 1,3,5-trioxanyl, 1H-pyrrolizinyl, tetrahydro-1,1-dioxothiophenyl, N-formylpiperazinyl, dihydrotriazolopyrazine, dihydroimidazopyrazine, hexahydropyrrolopyrrole, hexahydropyrrolopyrazine.

The term “heterocyclylalkyl” refers to a group -alkyl-heterocyclyl wherein alkyl and heterocyclyl are as herein defined.

The term “heterocyclylalkylaminocarbonyl” refers to a group —(C═O)—NH-alkyl-heterocyclyl, wherein alkyl and heterocyclyl are as herein defined.

The term “(heterocyclyl)(alkyl)aminoalkyl” refers to a group -alkyl-$NR^1R^2$ wherein $R^1$ is an alkyl group and $R^2$ is a heterocyclyl group, wherein alkyl and heterocyclyl are as herein defined.

The term “heterocyclylalkyloxyalkyl” refers to a group -alkyl-O-alkyl-heterocyclyl wherein alkyl and heterocyclyl are as herein defined.

The term “heterocyclylcarbonyl” refers to a group —(C═O)-heterocyclyl wherein heterocyclyl is as herein defined.

The term “heterocyclyloxy” to a group —O-heterocyclyl wherein heterocyclyl is as herein defined.

The term “heterocyclylsulfonyl” refers to a group —$SO_2$-heterocyclyl wherein heterocyclyl is as herein defined.

The term “hydroxy” or “hydroxyl” refers to a group —OH.

The term “hydroxyalkyl” refers to a group -alkyl-OH wherein alkyl is as herein defined.

The term “hydroxyalkylaminoalkyl” refers to a group -alkyl-NH-alkyl-OH wherein alkyl is as herein defined.

The term “hydroxycarbonyl” refers to a group —C(═O)—OH wherein carbonyl is as herein defined. In other words, “hydroxycarbonyl” corresponds to a carboxylic acid group.

The term “oxo” refers to a ═O substituent.

The term “sulfonylamino” refers to a group —NH—$SO_2$.

The term “intermediate” or “intermediate compound” refers to a compound which is produced in the course of a chemical synthesis, which is not itself the final product, but is used in further reactions which produce the final product. There may be many different intermediate compounds between the starting material and end product in the course of a complex synthesis.

The term “about”, preceding a figure encompasses plus or minus 10%, or less, of the value of said figure. It is to be understood that the value to which the term “about” refers is itself also specifically, and preferably, disclosed.

The term “administration”, or a variant thereof (e.g. “administering”), means providing the active agent or active ingredient, alone or as part of a pharmaceutically acceptable composition, to the patient in whom/which the condition, symptom, or disease is to be treated or prevented.

The term “antagonist” refers to a natural or synthetic compound which binds to the protein and blocks the biological activation of the protein, and thereby the action of the said protein. The protein may be a receptor, i.e. a protein molecule that receives chemical signals from outside a cell. Consequently, “an adenosine receptor antagonist” includes any chemical entity that, upon administration to a patient, results in inhibition or down-regulation of a biological activity associated with activation of an adenosine receptor in the patient, including any of the downstream biological effects otherwise resulting from the binding to an adenosine receptor of its natural ligand. Such adenosine receptor antagonists include any agent that can block activation of an adenosine receptor or any of the downstream biological effects of an adenosine receptor activation.

The term “inhibitor” refers to a natural or synthetic compound that has a biological effect to inhibit or significantly reduce or down-regulate the expression of a gene and/or a protein or that has a biological effect to inhibit or significantly reduce the biological activity of a protein. Consequently, an “ENT inhibitor” or «inhibitor of an ENT family transporter” refers to a compound that has a biological effect to inhibit or significantly reduce or down-regulate the biological activity of ENT family transporter.

The term “chemotherapy” refers to a type of cancer treatment that uses one or more anti-cancer drugs (chemotherapeutic agents) as part of a standardized chemotherapy regimen. Chemotherapy may be given with a curative intent or it may aim to prolong life or to reduce symptoms. Chemotherapeutic agents are for example selected from anticancer alkylating agents, anticancer antimetabolites, anticancer antibiotics, plant-derived anticancer agents, anticancer platinum coordination compounds and any combination thereof.

The term “hormone therapy” refers to the use of hormones in medical treatment. In one embodiment, the hormone therapy is oncologic hormone therapy.

The term “human” refers to a subject of both genders and at any stage of development (i.e. neonate, infant, juvenile, adolescent, adult).

The term “patient” refers to a mammal, more preferably a human, who/which is awaiting the receipt of, or is receiving medical care or is/will be the object of a medical procedure.

The term “immunotherapy” refers to a therapy aiming at inducing and/or enhancing an immune response towards a specific target, for example towards cancer cells. Immunotherapy may involve the use of checkpoint inhibitors, checkpoint agonists (also called T-cell agonists), IDO inhibitors, PI3K inhibitors, adenosine receptor inhibitors, adenosineproducing enzymes inhibitors, adoptive transfer, therapeutic vaccines, and combinations thereof.

The expression "pharmaceutically acceptable" refers to the ingredients of a pharmaceutical composition are compatible with each other and not deleterious to the subject to which it is administered.

The expression "pharmaceutically acceptable carrier, diluent, excipient and/or adjuvant" refers to a substance that does not produce an adverse, allergic or other untoward reaction when administered to an animal, preferably a human. It includes any and all inactive substance such as for example solvents, cosolvents, antioxidants, surfactants, stabilizing agents, emulsifying agents, buffering agents, pH modifying agents, preserving agents (or preservating agents), antibacterial and antifungal agents, isotonifiers, granulating agents or binders, lubricants, disintegrants, glidants, diluents or fillers, adsorbents, dispersing agents, suspending agents, coating agents, bulking agents, release agents, absorption delaying agents, sweetening agents, flavoring agents and the like. For human administration, preparations should meet sterility, pyrogenicity, general safety and purity standards as required by regulatory offices, such as, e.g., FDA Office or EMA.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "prodrug" as used herein means the pharmacologically acceptable derivatives of compounds of Formula (I), such as for example esters or amides, whose in vivo biotransformation product generates the biologically active drug. Prodrugs are generally characterized by increased bio-availability and are readily metabolized into biologically active compounds in vivo.

The term "radiation therapy" refers to a method of treatment of cancer employing various radiations such as X-ray, gamma-ray, neutron ray, electron beam, proton beam and radiation sources. It is used as part of cancer treatment to control or kill malignant cells. Radiation therapy may be curative in a number of types of cancer if they are localized to one area of the body. It may also be used as part of adjuvant therapy, to prevent tumor recurrence after surgery to remove a primary malignant tumor. The three main divisions of radiation therapy are: external beam radiation therapy (EBRT or XRT); brachytherapy or sealed source radiation therapy; and systemic radioisotope therapy (RIT) or unsealed source radiotherapy.

The terms "therapeutically effective amount" or "effective amount" or "therapeutically effective dose" refer to the amount or dose of active ingredient that is aimed at, without causing significant negative or adverse side effects to the subject, (1) delaying or preventing the onset of a cancer in the subject; (2) reducing the severity or incidence of a cancer; (3) slowing down or stopping the progression, aggravation, or deterioration of one or more symptoms of a cancer affecting the subject; (4) bringing about ameliorations of the symptoms of a cancer affecting the subject; or (5) curing a cancer affecting the subject. A therapeutically effective amount may be administered prior to the onset of a cancer for a prophylactic or preventive action. Alternatively, or additionally, a therapeutically effective amount may be administered after initiation of a cancer for a therapeutic action.

The terms "treating" or "treatment" refer to therapeutic treatment; wherein the object is to prevent or slow down the targeted pathologic condition or disease. A subject or mammal is successfully "treated" for a disease or affection or condition if, after receiving the treatment according to the present invention, the subject or mammal shows observable and/or measurable reduction in or absence of one or more of the following: reduction of the number of cancer cells; and/or relief to some extent, for one or more of the symptoms associated with the specific disease or condition; reduced morbidity and mortality, and improvement in quality of life issues. The above parameters for assessing successful treatment and improvement in the disease are readily measurable by routine procedures familiar to a physician.

The term "stem cell transplant" refers to a procedure in which a patient receives healthy blood-forming cells (stem cells) to replace their own that have been destroyed by disease or by the radiation or high doses of anticancer drugs that are given as part of the procedure. The healthy stem cells may come from the blood or bone marrow of the patient, from a donor, or from the umbilical cord blood of a newborn baby. A stem cell transplant may be autologous (using a patient's own stem cells that were collected and saved before treatment), allogeneic (using stem cells donated by someone who is not an identical twin), or syngeneic (using stem cells donated by an identical twin).

The term "subject" refers to a mammal, preferably a human. In one embodiment, the subject is diagnosed with a cancer. In one embodiment, the subject is a patient, preferably a human patient, who/which is awaiting the receipt of, or is receiving, medical care or was/is/will be the subject of a medical procedure or is monitored for the development or progression of a disease, such as a cancer. In one embodiment, the subject is a human patient who is treated and/or monitored for the development or progression of a cancer. In one embodiment, the subject is a male. In another embodiment, the subject is a female. In one embodiment, the subject is an adult. In another embodiment, the subject is a child.

Compounds—ENT Inhibitors

The invention thus provides macrocyclic diamine derivatives, which may be useful as ENT inhibitors. In one embodiment, the invention thus provides compounds of formula I:

(I)

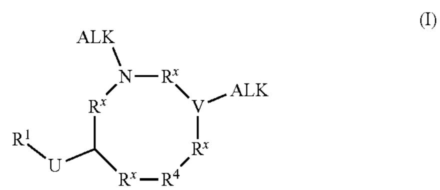

or a pharmaceutically acceptable salt or solvate thereof wherein $R^1$ is selected from the group consisting of

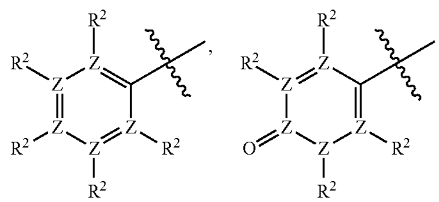

-continued

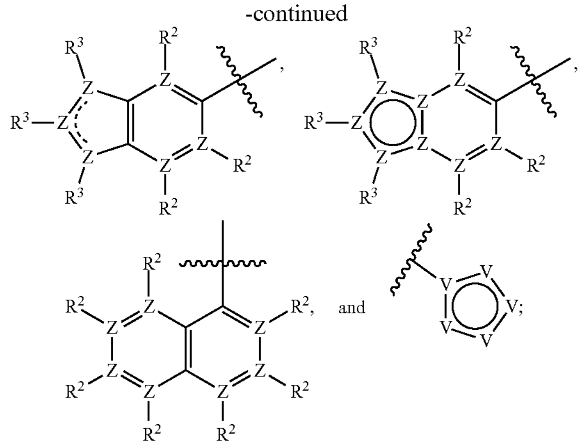

each $R^2$ is independently selected from the group consisting of absent, halogen, —$NHR^3$, —$OR^3$, —$R^3$, —C(O)$R^3$, —$CO_2R^3$, C(O)N$(R^3)_2$, —$CH_2C(O)N(R^3)_2$, —$S(O)_2R^3$, and —CN;

or two instances of $R^2$ are taken together with the atoms on which they are attached to form a heterocylyl or heteroaryl ring;

each $R^3$ is independently selected from absent, —H, oxo, ALK, phenyl, heterocylyl, and heteroaryl;

$R^4$ is selected from the group consisting of

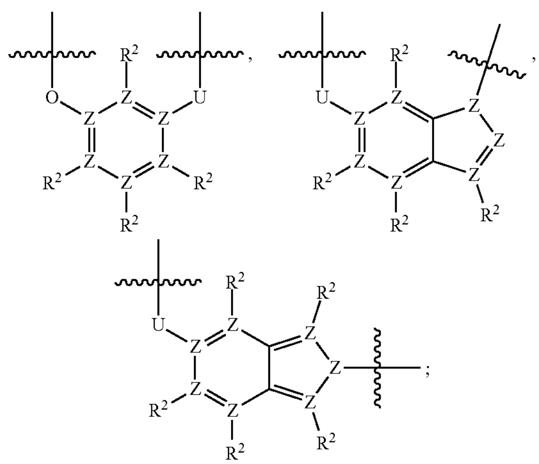

and

U is selected from the group consisting of —C(O)—, alkylene, —O—, —N$(R^3)$—, —C(O)O—, —C(O)N$(R^3)$—, and

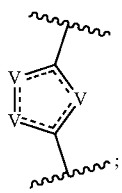

each $R^x$ is independently selected from alkylene;

each V is independently selected from —C$(R^3)$—, —N$(R^3)$—, —N—, and —O—; and Z is C or N;

wherein ALK is unsubstituted alkyl or substituted alkyl, or two instances of ALK may be joined together with their intervening atoms to form a cycloalkyl or heterocyclyl ring.

In one embodiment, the invention thus provides compounds of formula I, wherein $R^1$ is

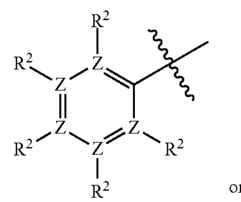

or

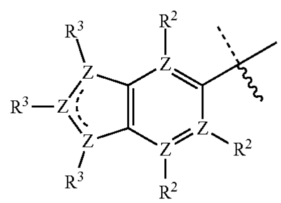

each $R^2$ is independently selected from the group consisting of halogen, —$OR^3$, —$R^3$, —$CO_2R^3$, C(O)N$(R^3)_2$, —$CH_2C(O)N(R^3)_2$, and —CN;

each $R^3$ is independently —H or ALK;

$R^4$ is

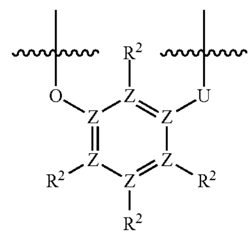

U is selected from the group consisting of —C(O)—, alkylene, —O—, —N$(R^3)$—, —C(O)O—, —C(O)N$(R^3)$—, and

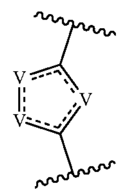

each $R^x$ is independently selected from alkylene;

each V is independently selected from —C$(R^3)$—, —N$(R^3)$, —N—, —O—; and

Z is C; or when $R^2$ is absent, Z is N.

In another embodiment, the invention also provides compounds of formula II:

(II)

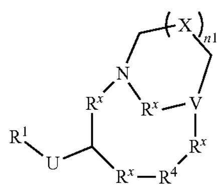

or a pharmaceutically acceptable salt or solvate thereof; wherein $R^1$ is selected from the group consisting of ALK, cycloalkyl, heterocylyl,

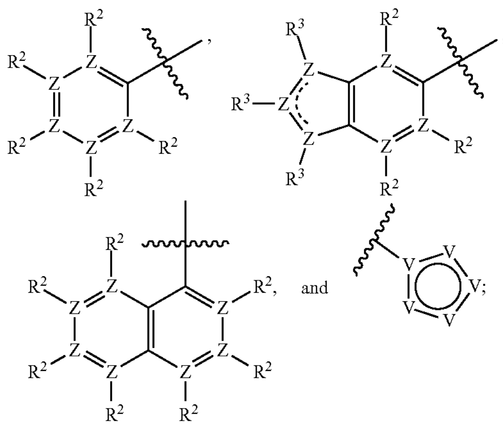

each $R^2$ is independently selected from the group consisting of absent, halogen, —$OR^3$, —$R^3$, —$CO_2R^3$, $C(O)N(R^3)_2$, —$CH_2C(O)N(R^3)_2$, —$S(O)_2R^3$, and —CN;

or two instances of $R^2$ are taken together with the atoms on which they are attached to form a heterocylyl or heteroaryl ring;

each $R^3$ is independently selected from absent, —H, ALK, phenyl, and heteroaryl;

$R^4$ is selected from the group consisting of

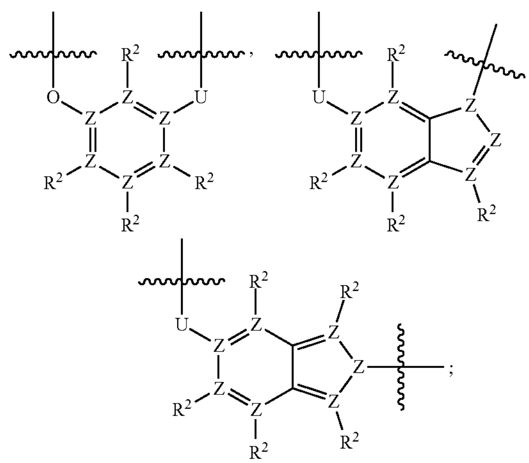

X is selected from the group consisting of —$CH_2$—, —CHF—, —$CF_2$—;

each U is independently selected from the group consisting of —O—, —$N(R^3)$—, —C(O)O—, —$C(O)N(R^3)$—,

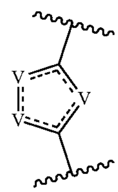

—C(O)—, —O—N═C(H)— and alkylene;

each $R^x$ is independently selected from alkylene;

each V is independently selected from —$C(R^3)$—, —$N(R^3)$—, —N═, —O—; Z is C or N; and n is a number of 0 or 1;

wherein ALK is unsubstituted alkyl or substituted alkyl, or two instances of ALK may be joined together with their intervening atoms to form a cycloalkyl or heterocyclyl ring.

In another embodiment, the invention also provides compounds of formula II, wherein $R^1$ is

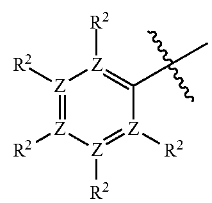

or

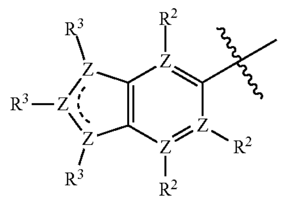

each $R^2$ is independently selected from the group consisting of halogen, —$OR^3$, —$R^3$, —$CO_2R^3$, $C(O)N(R^3)_2$, —$CH_2C(O)N(R^3)_2$, and —CN;

each $R^3$ is independently —H or ALK;

$R^4$ is

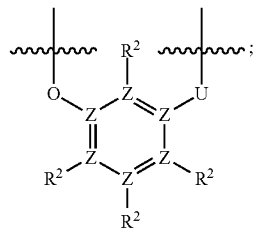

X is selected from the group consisting of —$CH_2$—, —CHF—, —$CF_2$—;

each U is insentiently selected from the group consisting of —O—, —$N(R^3)$—, —C(O)O—, —$C(O)N(R^3)$—,

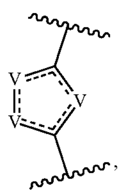

—C(O)—, and alkylene;

each $R^x$ is independently selected from alkylene;

each V is independently selected from —C($R^3$)—, —N($R^3$)—, —N═, and —O—;

each Z is independently C; or $R^2$ is absent and Z═N; and $n^1$ is a number of 0 or 1.

In one embodiment, compounds of formula II are of formula IIa:

(IIa)

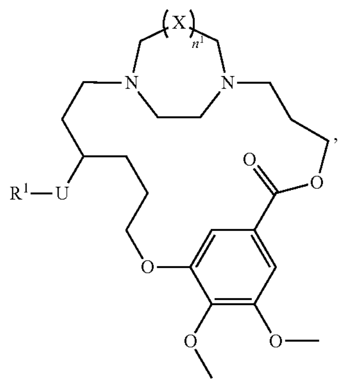

or a pharmaceutically acceptable salt or solvate thereof, wherein X is $CH_2$, CHF, or $CF_2$; and $R^1$, U, and $n^1$ are defined herein.

$R^1$ is

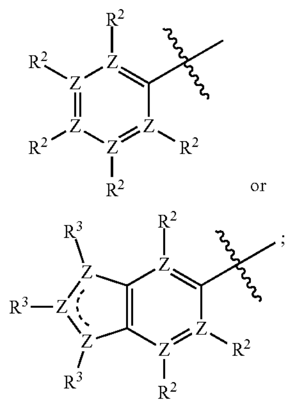

each $R^2$ is independently selected from the group consisting of halogen, —$OR^3$, —$R^3$, —$CO_2R^3$, C(O)N($R^3$)$_2$, —$CH_2$C(O)N($R^3$)$_2$, and —CN;

each $R^3$ is independently —H or ALK;

$R^4$ is

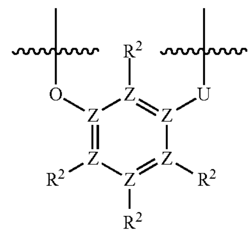

X is selected from the group consisting of —$CH_2$—, —CHF—, —$CF_2$—;

each U is insentiently selected from the group consisting of —O—, —N($R^3$)—, —C(O)O—, —C(O)N($R^3$)—,

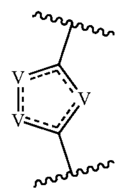

—C(O)—, and alkylene;

each $R^x$ is independently selected from alkylene;

each V is independently selected from —C($R^3$)—, —N($R^3$)—, —N═, and —O—;

each Z is independently C; or $R^2$ is absent and Z═N; and $n^1$ is a number of 0 or 1.

In one embodiment, compounds of formula IIa are of formula Hal:

(IIa1)

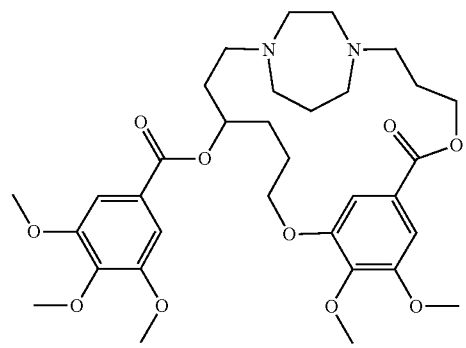

or a pharmaceutically acceptable salt or solvate thereof

In some embodiments, compounds of formula II are of formula IIb:

(IIb)

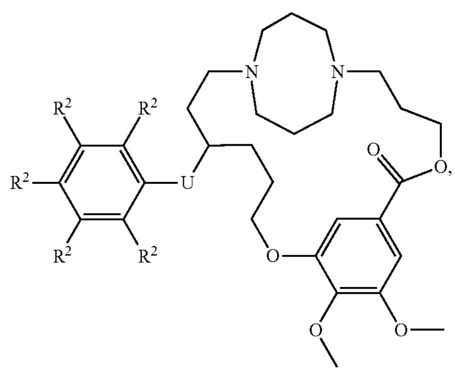

or a pharmaceutically acceptable salt or solvate thereof, wherein $R^2$ and U are defined herein.

In some embodiments, $R^1$ is selected from the group consisting of

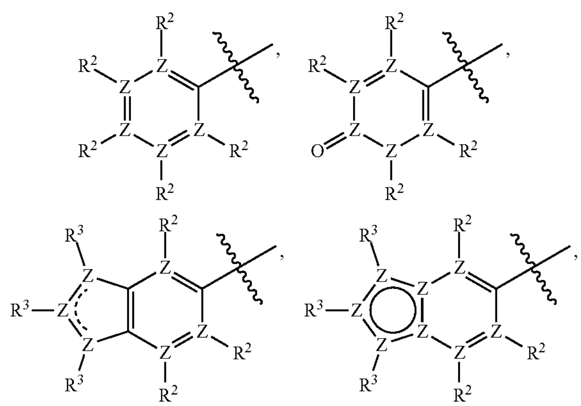

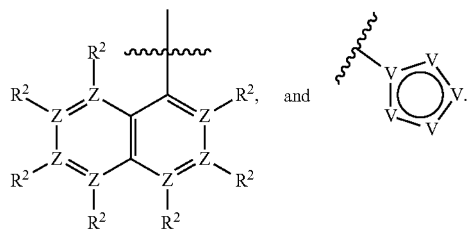

In some embodiments, $R^1$ is selected from the group consisting of

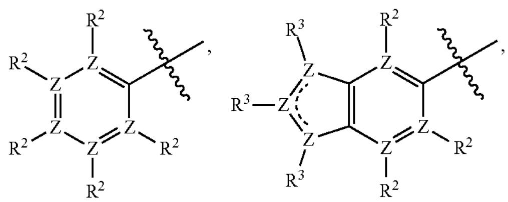

-continued

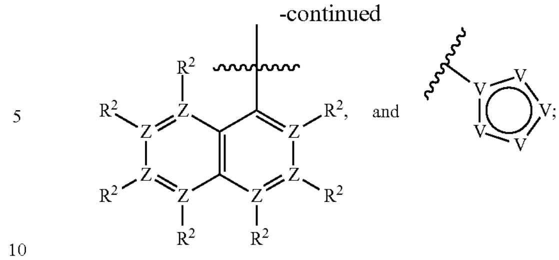

In some embodiments, $R^1$ is

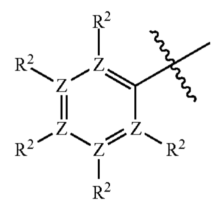

In some embodiments, $R^1$ is

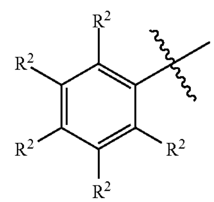

In some embodiments, In some embodiments, each $R^2$ is independently selected from the group consisting of absent, halogen, —$OR^3$, —$R^3$, —$CO_2R^3$, $C(O)N(R^3)_2$, —$CH_2C(O)N(R^3)_2$, —$S(O)_2R^3$, and —CN; or two instances of $R^2$ are taken together with the atoms on which they are attached to form a heterocylyl or heteroaryl ring;

In some embodiments, each $R^2$ is independently selected from the group consisting of absent, halogen, —$OR^3$, —$R^3$, —$CO_2R^3$, $C(O)N(R^3)_2$, —$CH_2C(O)N(R^3)_2$, —$S(O)_2R^3$, and —CN.

In some embodiments, each $R^2$ is independently selected from the group consisting of absent, halogen, —$OR^3$, and —$R^3$.

In some embodiments, each $R^2$ is independently selected from the group consisting of absent, halogen, —$OR^3$, and hydrogen.

In some embodiments, each $R^3$ is independently selected from absent, —H, ALK, phenyl, and heteroaryl.

In some embodiments, each $R^3$ is independently selected from —H and methyl.

In some embodiments, $R^4$ is selected from the group consisting of

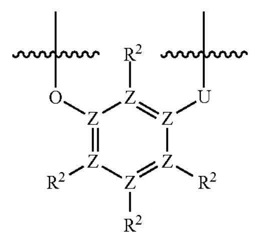

-continued

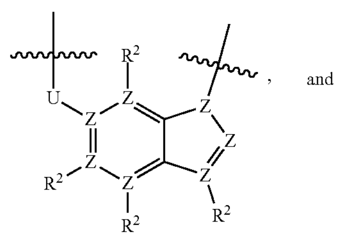

, and

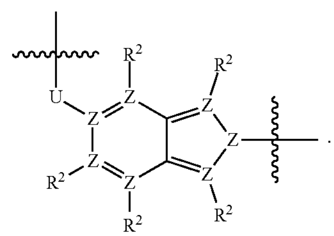

In some embodiments, $R^4$ is selected from the group consisting of

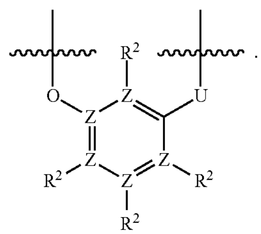

In some embodiments, U is selected from the group consisting of —C(O)—, alkylene, —O—, —N($R^3$)—, —C(O)O—, —C(O)N($R^3$)—, and

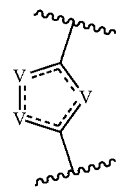

In some embodiments, each $R^x$ is independently selected from alkylene.

In some embodiments, each V is independently selected from —C($R^3$)—, —N($R^3$)—, —N—, and —O—.

In some embodiments, Z is C or N.

In some embodiments, macrocyclic diamine derivatives according to the invention comprises only one chiral center.

In some embodiments, macrocyclic diamine derivatives according to the invention are racemic mixture containing 'R' isomer and 'S' isomer.

In some embodiments, macrocyclic diamine derivatives according to the invention are 'R' isomer.

In some embodiments, macrocyclic diamine derivatives according to the invention are 'S' isomer.

In some embodiments, macrocyclic diamine derivatives according to the invention comprises more than one chiral center.

In some embodiments, each chiral center comprise 'R' or 'S' configurations independently. In some embodiments, each chiral center comprise the same configuration.

Particularly preferred compound structures of formula II of the invention are those listed in Table 1 hereafter.

TABLE 1a

| Compound Structures | Chemical Name |
|---|---|
| 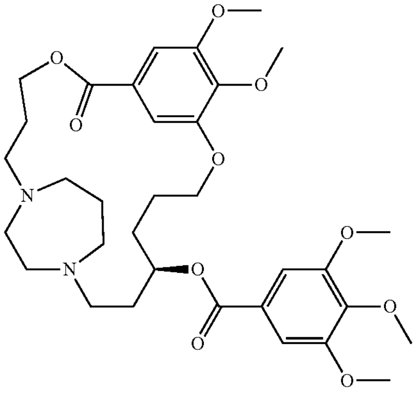 [SMILES: COc1cc(C(=O)O[C@@H]2CCCOc3cc(cc(OC)c3OC)C(=O)OCCCN3CCCN(CC2)CC3)cc(OC)c1OC] | (12R)-74,75-dimethoxy-6-oxo-5,8-dioxa-1(1,4)-diazepana-7(1,3) benzenacyclotetradecaphane-12-yl 3,4,5-trimethoxybenzoate |

TABLE 1a-continued

| Compound Structures | Chemical Name |
|---|---|
| 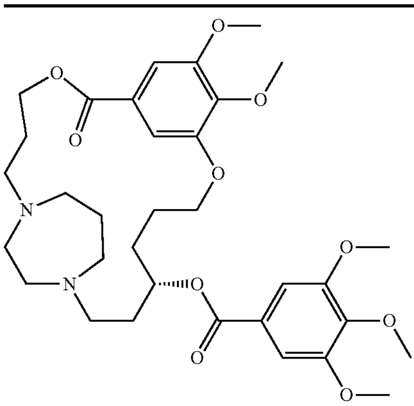 | (12S)-74,75-dimethoxy-6-oxo-5,8-dioxa-1(1,4)-diazepana-7(1,3)-benzenacyclotetradecaphane-12-yl 3,4,5-trimethoxybenzoate |
| 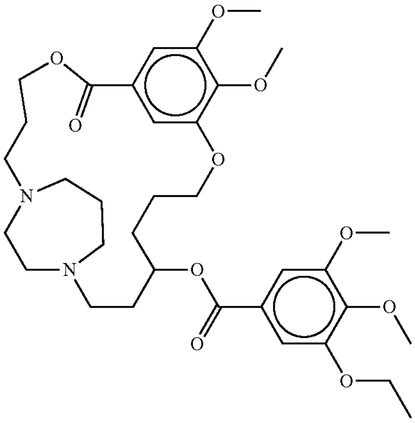 | 74,75-dimethoxy-6-oxo-5,8-dioxa-1(1,4)-diazepana-7(1,3)-benzenacyclotetradecaphane-12-yl 3-ethoxy-4,5-dimethoxybenzoate; |
| 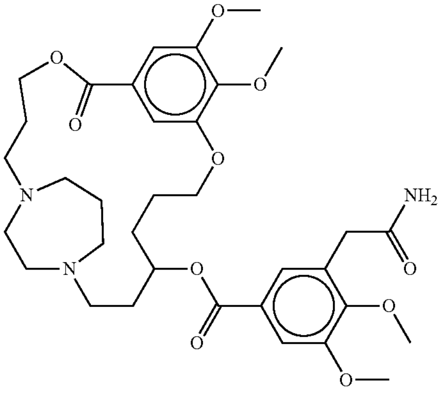 | 74,75-dimethoxy-6-oxo-5,8-dioxa-1(1,4)-diazepana-7(1,3)-benzenacyclotetradecaphane-12-yl 3-(2-amino-2-oxoethyl)-4,5-dimethoxybenzoate; |
| 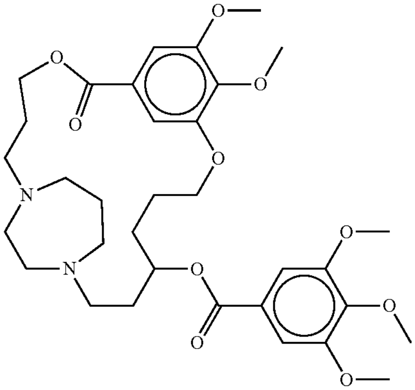 | 74,75-dimethoxy-6-oxo-5,8-dioxa-1(1,4)-diazepana-7(1,3)-benzenacyclotetradecaphane-12-yl 3,4,5 trimethoxybenzoate |

TABLE 1a-continued

| Compound Structures | Chemical Name |
| --- | --- |
| 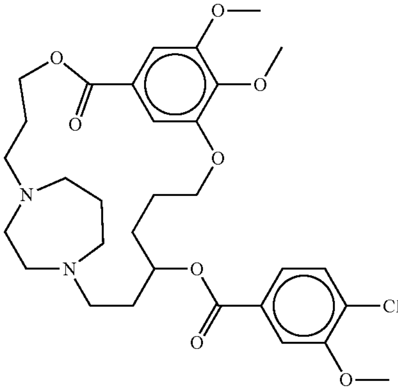 | 74,75-dimethoxy-6-oxo-5,8-dioxa-1(1,4)-diazepana-7(1,3)-benzenacyclotetradecaphane-12-yl 4-chloro-3-methoxybenzoate |
| 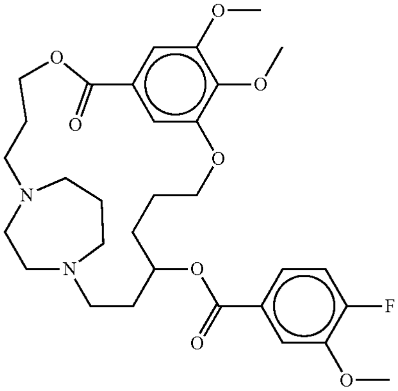 | 74,75-dimethoxy-6-oxo-5,8-dioxa-1(1,4)-diazepana-7(1,3)-benzenacyclotetradecaphane-12-yl 4-fluoro-3-methoxybenzoate |
| 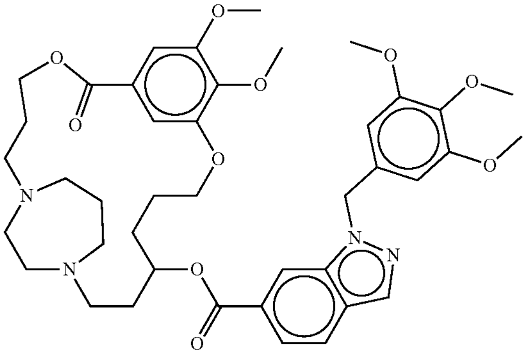 | 74,75-dimethoxy-6-oxo-5,8-dioxa-1(1,4)-diazepana-7(1,3)-benzenacyclotetradecaphane-12-yl 1-(3,4,5-trimethoxybenzyl)-1H-indazole-6-carboxylate |
| 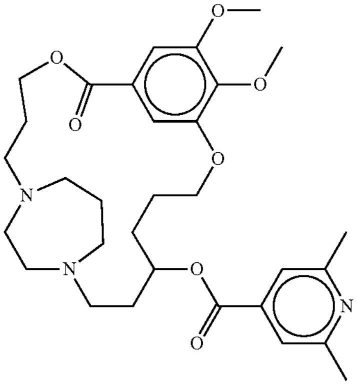 | 74,75-dimethoxy-6-oxo-5,8-dioxa-1(1,4)-diazepana-7(1,3)-benzenacyclotetradecaphane-12-yl 2,6-dimethylisonicotinate |

TABLE 1a-continued
| Compound Structures | Chemical Name |
| --- | --- |
| 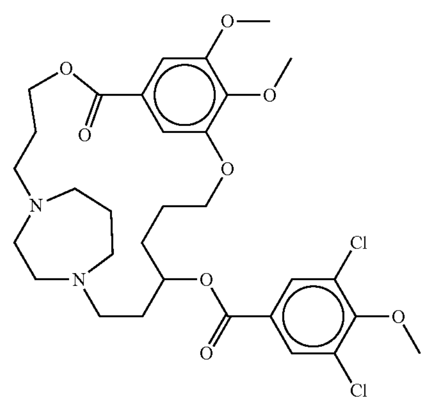 | 74,75-dimethoxy-6-oxo-5,8-dioxa-1(1,4)-diazepana-7(1,3)-benzenacyclotetradecaphane-12-yl 3,5-dichloro-4-methoxybenzoate |
| 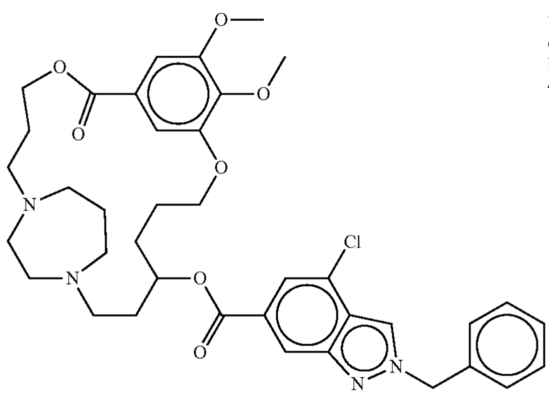 | 74,75-dimethoxy-6-oxo-5,8-dioxa-1(1,4)-diazepana-7(1,3)-benzenacyclotetradecaphane-12-yl 2-benzyl-4-chloro-2H-indazole-6-carboxylate |
| 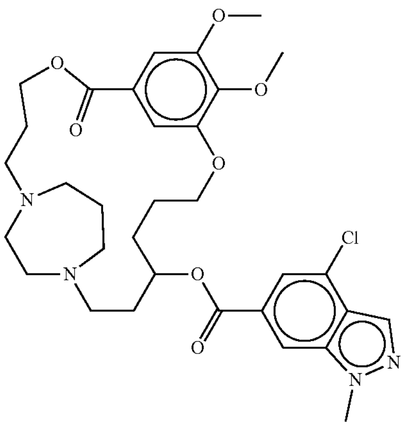 | 74,75-dimethoxy-6-oxo-5,8-dioxa-1(1,4)-diazepana-7(1,3)-benzenacyclotetradecaphane-12-yl 4-chloro-1-methyl-1H-indazole-6-carboxylate |

TABLE 1a-continued
| Compound Structures | Chemical Name |
| --- | --- |
| 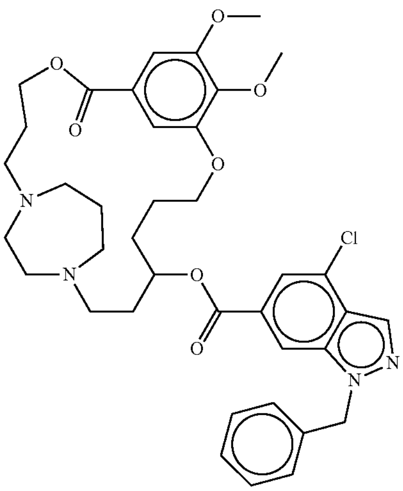 | 74,75-dimethoxy-6-oxo-5,8-dioxa-1(1,4)-diazepana-7(1,3)-benzenacyclotetradecaphane-12-yl 1-benzyl-4-chloro-1H-indazole-6-carboxylate |
| 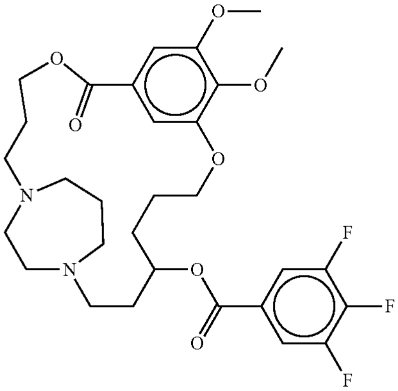 | 74,75-dimethoxy-6-oxo-5,8-dioxa-1(1,4)-diazepana-7(1,3)-benzenacyclotetradecaphane-12-yl 3,4,5-trifluorobenzoate |
| 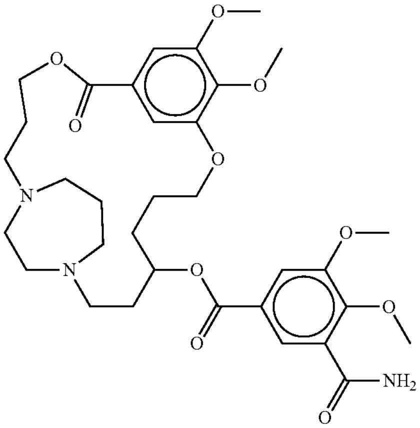 | 74,75-dimethoxy-6-oxo-5,8-dioxa-1(1,4)-diazepana-7(1,3)-benzenacyclotetradecaphane-12-yl 3-carbamoyl-4,5-dimethoxybenzoate |

TABLE 1a-continued

| Compound Structures | Chemical Name |
|---|---|
| 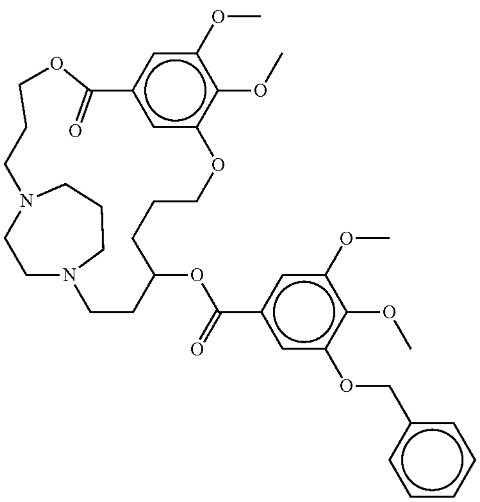 | 74,75-dimethoxy-6-oxo-5,8-dioxa-1(1,4)-diazepana-7(1,3)-benzenacyclotetradecaphane-12-yl 3-(benzyloxy)-4,5-dimethoxybenzoate |
| 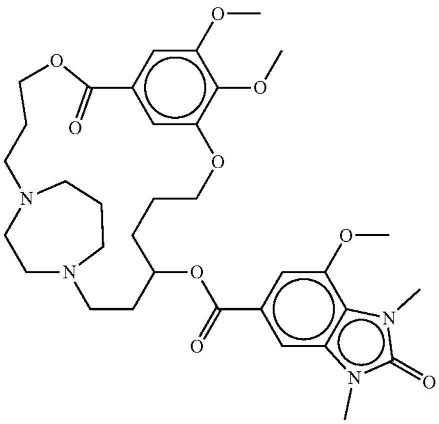 | 74,75-dimethoxy-6-oxo-5,8-dioxa-1(1,4)-diazepana-7(1,3)-benzenacyclotetradecaphane-12-yl 7-methoxy-1,3-dimethyl-2-oxo-2,3-dihydro-1H-benzo[d]imidazole-5-carboxylate |
| 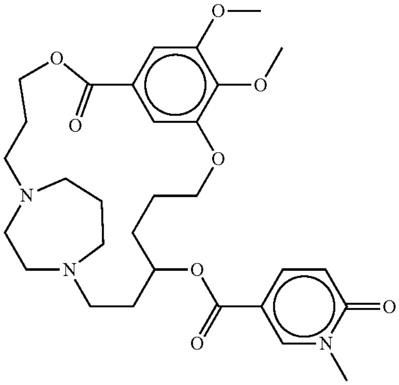 | 74,75-dimethoxy-6-oxo-5,8-dioxa-1(1,4)-diazepana-7(1,3)-benzenacyclotetradecaphane-12-yl 1-methyl-6-oxo-1,6-dihydropyridine-3-carboxylate |

TABLE 1a-continued

| Compound Structures | Chemical Name |
| --- | --- |
| 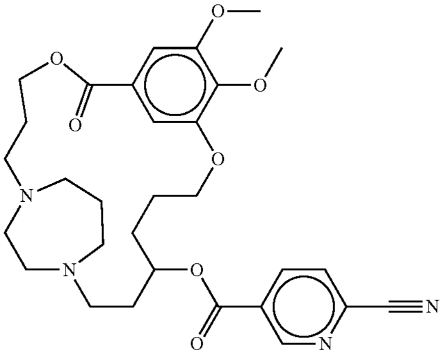 | 74,75-dimethoxy-6-oxo-5,8-dioxa-1(1,4)-diazepana-7(1,3)-benzenacyclotetradecaphane-12-yl 6-cyanonicotinate |
| 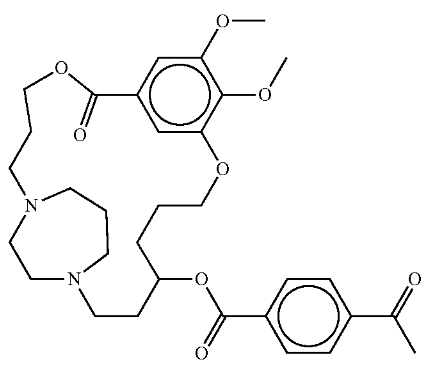 | 74,75-dimethoxy-6-oxo-5,8-dioxa-1(1,4)-diazepana-7(1,3)-benzenacyclotetradecaphane-12-yl 4-acetylbenzoate |
| 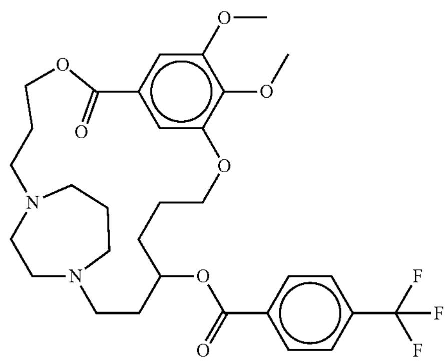 | 74,75-dimethoxy-6-oxo-5,8-dioxa-1(1,4)-diazepana-7(1,3)-benzenacyclotetradecaphane-12-yl 4-(trifluoromethyl)benzoate |
| 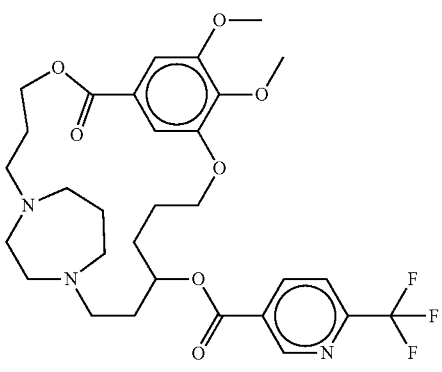 | 74,75-dimethoxy-6-oxo-5,8-dioxa-1(1,4)-diazepana-7(1,3)-benzenacyclotetradecaphane-12-yl 6-(trifluoromethyl)nicotinate |

TABLE 1a-continued

| Compound Structures | Chemical Name |
| --- | --- |
| 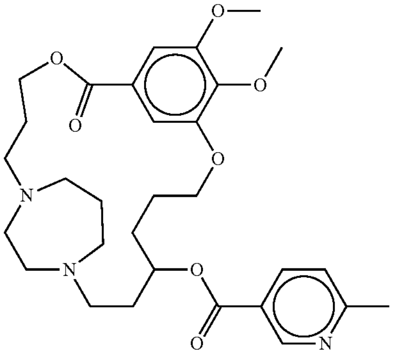 | 74,75-dimethoxy-6-oxo-5,8-dioxa-1(1,4)-diazepana-7(1,3)-benzenacyclotetradecaphane-12-yl 6-methylnicotinate |
| 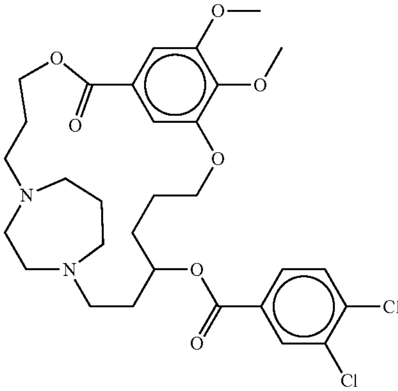 | 74,75-dimethoxy-6-oxo-5,8-dioxa-1(1,4)-diazepana-7(1,3)-benzenacyclotetradecaphane-12-yl 3,4-dichlorobenzoate |
| 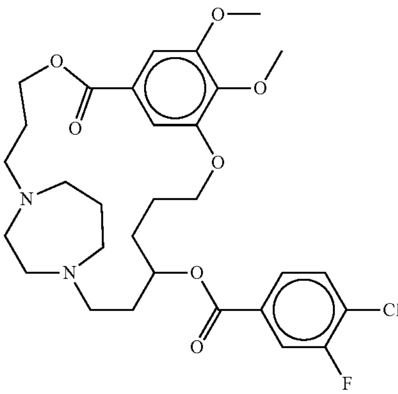 | 74,75-dimethoxy-6-oxo-5,8-dioxa-1(1,4)-diazepana-7(1,3)-benzenacyclotetradecaphane-12-yl 4-chloro-3-fluorobenzoate |
| 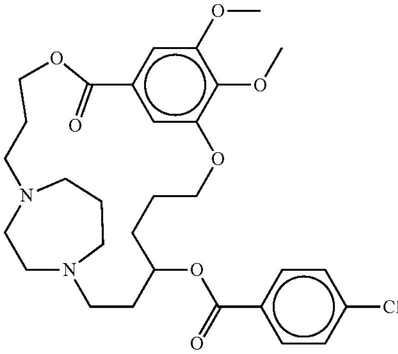 | 74,75-dimethoxy-6-oxo-5,8-dioxa-1(1,4)-diazepana-7(1,3)-benzenacyclotetradecaphane-12-yl 4-chlorobenzoate |

TABLE 1a-continued

| Compound Structures | Chemical Name |
|---|---|
| 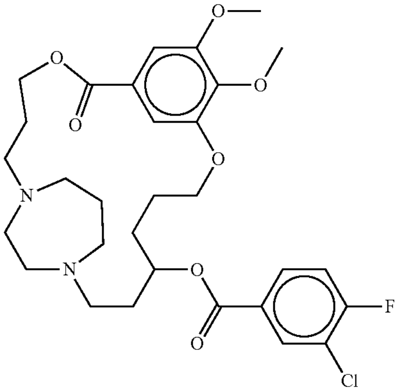 | 74,75-dimethoxy-6-oxo-5,8-dioxa-1(1,4)-diazepana-7(1,3)-benzenacyclotetradecaphane-12-yl 3-chloro-4-fluorobenzoate |
| 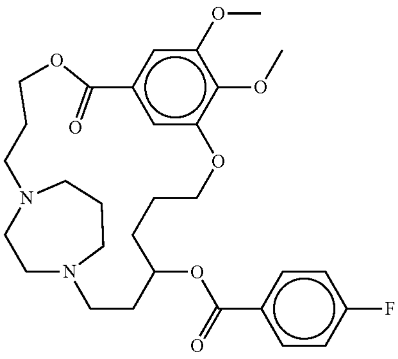 | 74,75-dimethoxy-6-oxo-5,8-dioxa-1(1,4)-diazepana-7(1,3)-benzenacyclotetradecaphane-12-yl 4-fluorobenzoate |
| 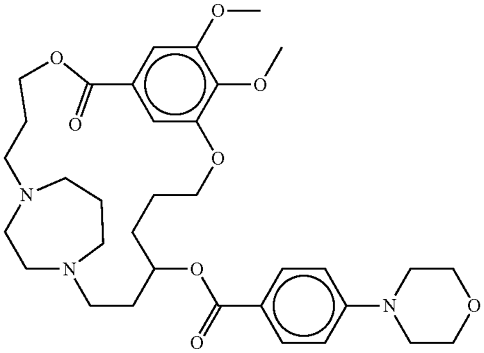 | 74,75-dimethoxy-6-oxo-5,8-dioxa-1(1,4)-diazepana-7(1,3)-benzenacyclotetradecaphane-12-yl 4-morpholinobenzoate |
| 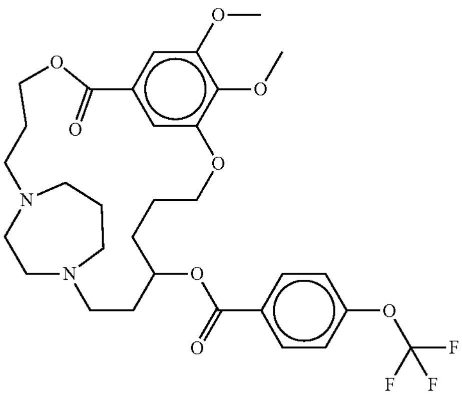 | 74,75-dimethoxy-6-oxo-5,8-dioxa-1(1,4)-diazepana-7(1,3)-benzenacyclotetradecaphane-12-yl 4-(trifluoromethoxy)benzoate |

TABLE 1a-continued

| Compound Structures | Chemical Name |
| --- | --- |
| 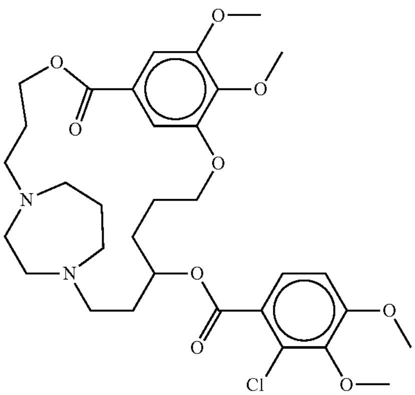 | 74,75-dimethoxy-6-oxo-5,8-dioxa-1(1,4)-diazepana-7(1,3)-benzenacyclotetradecaphane-12-yl 2-chloro-3,4-dimethoxybenzoate |
| 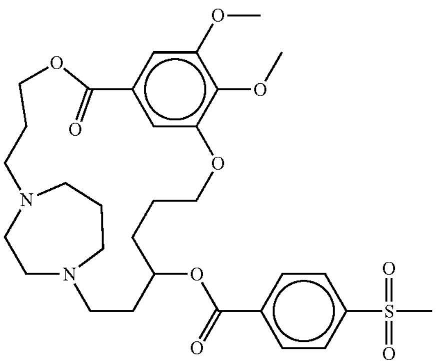 | 74,75-dimethoxy-6-oxo-5,8-dioxa-1(1,4)-diazepana-7(1,3)-benzenacyclotetradecaphane-12-yl 4-(methylsulfonyl)benzoate |
| 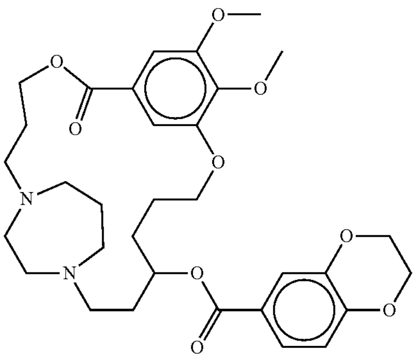 | 74,75-dimethoxy-6-oxo-5,8-dioxa-1(1,4)-diazepana-7(1,3)-benzenacyclotetradecaphane-12-yl 2,3-dihydrobenzo[b][1,4]dioxine-6-carboxylate |
| 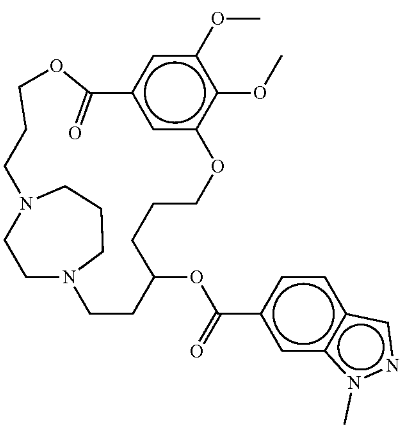 | 74,75-dimethoxy-6-oxo-5,8-dioxa-1(1,4)-diazepana-7(1,3)-benzenacyclotetradecaphane-12-yl 1-methyl-1H-indazole-6-carboxylate |

TABLE 1a-continued
| Compound Structures | Chemical Name |
| --- | --- |
| 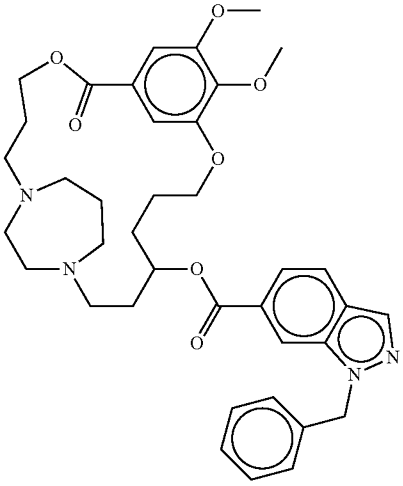 | 74,75-dimethoxy-6-oxo-5,8-dioxa-1(1,4)-diazepana-7(1,3)-benzenacyclotetradecaphane-12-yl 1-benzyl-1H-indazole-6-carboxylate |
| 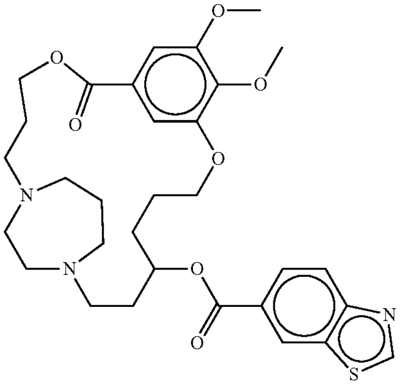 | 74,75-dimethoxy-6-oxo-5,8-dioxa-1(1,4)-diazepana-7(1,3)-benzenacyclotetradecaphane-12-yl benzo[d]thiazole-6-carboxylate |
| 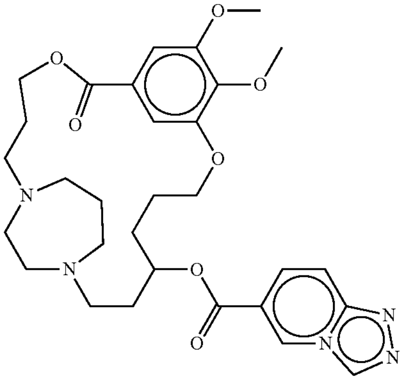 | 74,75-dimethoxy-6-oxo-5,8-dioxa-1(1,4)-diazepana-7(1,3)-benzenacyclotetradecaphane-12-yl [1,2,4]triazolo[4,3-a]pyridine-6-carboxylate |

TABLE 1a-continued

| Compound Structures | Chemical Name |
| --- | --- |
| 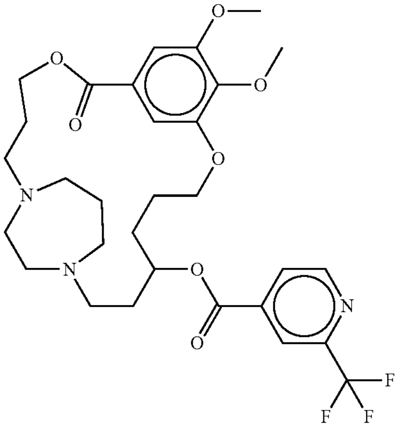 | 74,75-dimethoxy-6-oxo-5,8-dioxa-1(1,4)-diazepana-7(1,3)-benzenacyclotetradecaphane-12-yl 2-(trifluoromethyl)isonicotinate |
| 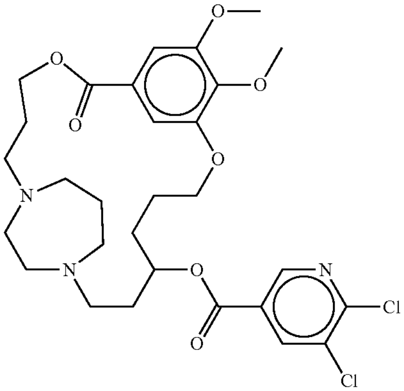 | 74,75-dimethoxy-6-oxo-5,8-dioxa-1(1,4)-diazepana-7(1,3)-benzenacyclotetradecaphane-12-yl 5,6-dichloronicotinate |
| 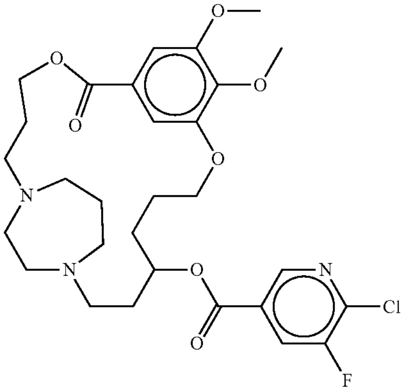 | 74,75-dimethoxy-6-oxo-5,8-dioxa-1(1,4)-diazepana-7(1,3)-benzenacyclotetradecaphane-12-yl 6-chloro-5-fluoronicotinate |
| 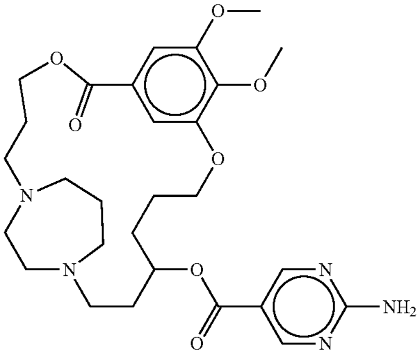 | 74,75-dimethoxy-6-oxo-5,8-dioxa-1(1,4)-diazepana-7(1,3)-benzenacyclotetradecaphane-12-yl 2-aminopyrimidine-5-carboxylate |

TABLE 1a-continued

| Compound Structures | Chemical Name |
|---|---|
| 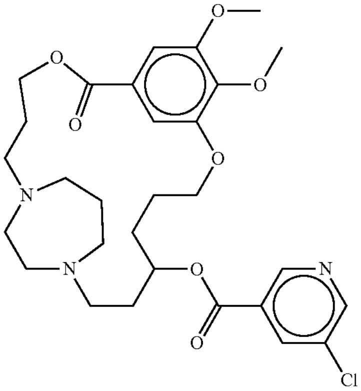 | 74,75-dimethoxy-6-oxo-5,8-dioxa-1(1,4)-diazepana-7(1,3)-benzenacyclotetradecaphane-12-yl 5-chloronicotinate |
| 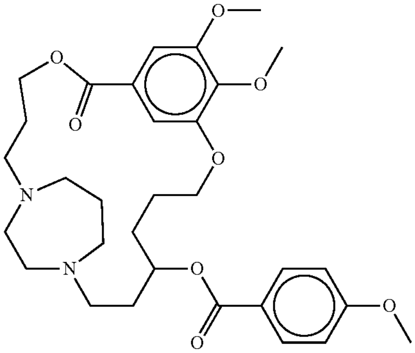 | 74,75-dimethoxy-6-oxo-5,8-dioxa-1(1,4)-diazepana-7(1,3)-benzenacyclotetradecaphane-12-yl 4-methoxybenzoate |
| 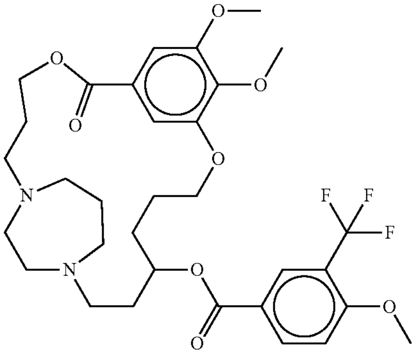 | 74,75-dimethoxy-6-oxo-5,8-dioxa-1(1,4)-diazepana-7(1,3)-benzenacyclotetradecaphane-12-yl 4-methoxy-3-(trifluoromethyl)benzoate |
| 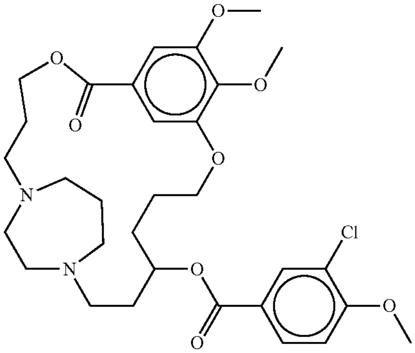 | 74,75-dimethoxy-6-oxo-5,8-dioxa-1(1,4)-diazepana-7(1,3)-benzenacyclotetradecaphane-12-yl 3-chloro-4-methoxybenzoate |

TABLE 1a-continued

| Compound Structures | Chemical Name |
|---|---|
| 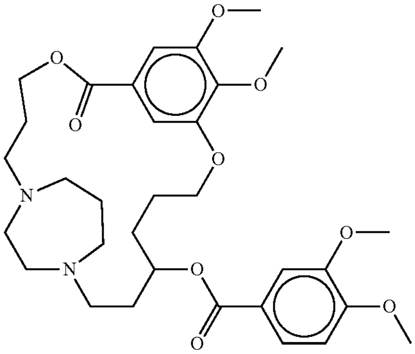 | 74,75-dimethoxy-6-oxo-5,8-dioxa-1(1,4)-diazepana-7(1,3)-benzenacyclotetradecaphane-12-yl 3,4-dimethoxybenzoate |
| 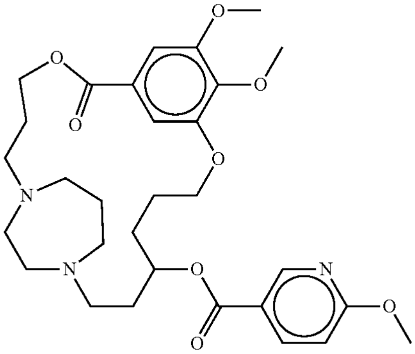 | 74,75-dimethoxy-6-oxo-5,8-dioxa-1(1,4)-diazepana-7(1,3)-benzenacyclotetradecaphane-12-yl 6-methoxynicotinate |
| 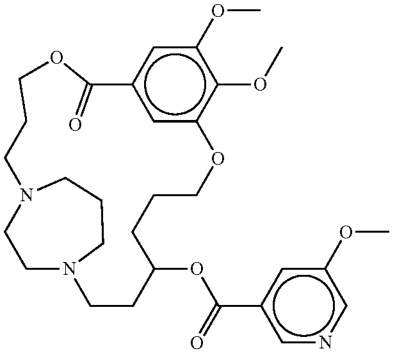 | 74,75-dimethoxy-6-oxo-5,8-dioxa-1(1,4)-diazepana-7(1,3)-benzenacyclotetradecaphane-12-yl 5-methoxynicotinate |
| 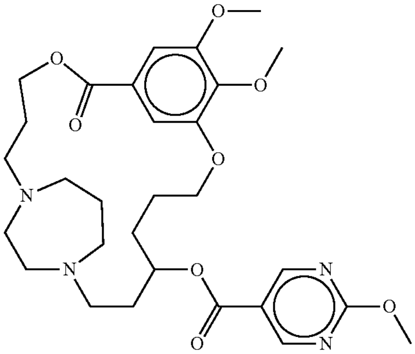 | 74,75-dimethoxy-6-oxo-5,8-dioxa-1(1,4)-diazepana-7(1,3)-benzenacyclotetradecaphane-12-yl 2-methoxypyrimidine-5-carboxylate |

TABLE 1a-continued

| Compound Structures | Chemical Name |
|---|---|
| 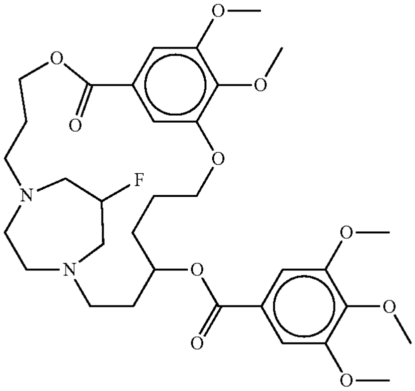 | 16-fluoro-74,75-dimethoxy-6-oxo-5,8-dioxa-1(1,4)-diazepana-7(1,3)-benzenacyclotetradecaphane-12-yl 3,4,5-trimethoxybenzoate |
| 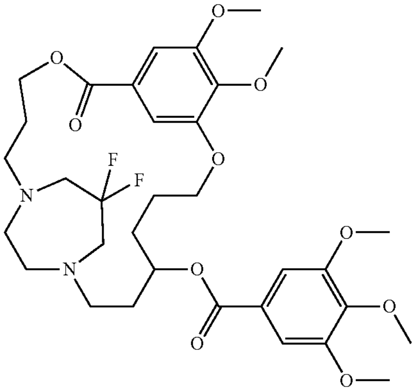 | 16,16-difluoro-74, 75-dimethoxy-6-oxo-5,8-dioxa-1(1,4)-diazepana-7(1,3)-benzenacyclotetradecaphane-12-yl 3,4,5-trimethoxybenzoate |
| 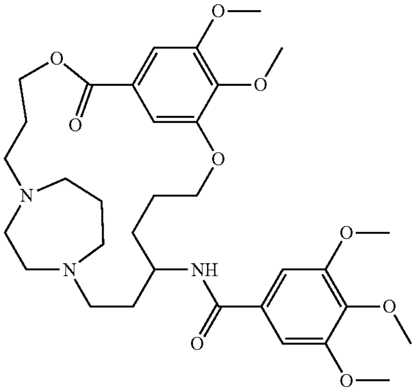 [SMILES: COc1cc(C(=O)NC2CCCOc3cc(cc(OC)c3OC)C(=O)OCCCN3CCCN(CC2)CC3)cc(OC)c1OC] | N-(74,75-dimethoxy-6-oxo-5,8-dioxa-1(1,4)-diazepana-7(1,3)-benzenacyclotetradecaphane-12-yl)-3,4,5-trimethoxybenzamide |
| 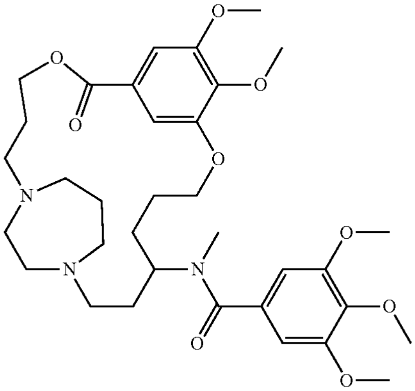 [SMILES: COc1cc(C(=O)N(C)C2CCCOc3cc(cc(OC)c3OC)C(=O)OCCCN3CCCN(CC2)CC3)cc(OC)c1OC] | N-(74,75-dimethoxy-6-oxo-5,8-dioxa-1(1,4)-diazepana-7(1,3)-benzenacyclotetradecaphane-12-yl)-3,4,5-trimethoxy-N-methylbenzamide |

TABLE 1a-continued

| Compound Structures | Chemical Name |
| --- | --- |
| 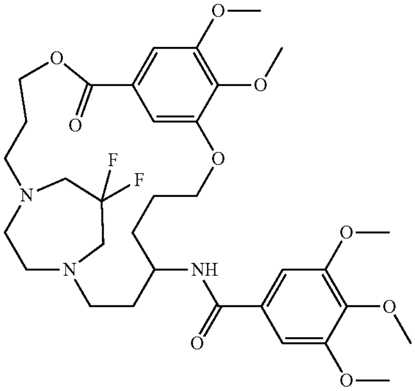 [SMILES: COc1cc(C(=O)NC2CCCOc3cc(cc(OC)c3OC)C(=O)OCCCN3CCN(CC2)CC(F)(F)C3)cc(OC)c1OC] | N-(16,16-difluoro-74, 75-dimethoxy-6-oxo-5,8-dioxa-1(1,4)-diazepana-7(1,3)-benzenacyclotetradecaphane-12-yl)-3,4,5-trimethoxybenzamide |
| 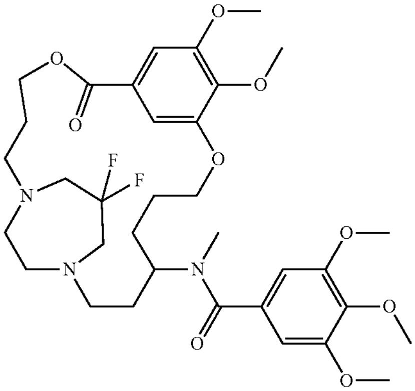 [SMILES: COc1cc(C(=O)N(C)C2CCCOc3cc(cc(OC)c3OC)C(=O)OCCCN3CCN(CC2)CC(F)(F)C3)cc(OC)c1OC] | N-(16,16-difluoro-74,75-dimethoxy-6-oxo-5,8-dioxa-1(1,4)-diazepana-7(1,3)-benzenacyclotetradecaphane-12-yl)-3,4,5-trimethoxy-N-methylbenzamide |
| 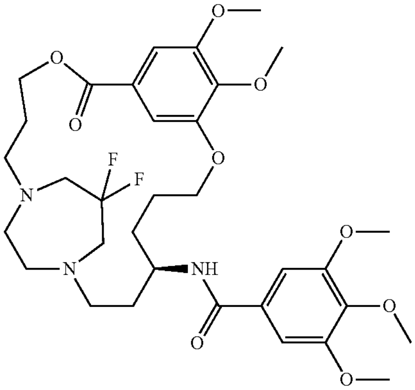 [SMILES: COc1cc(C(=O)N[C@@H]2CCCOc3cc(cc(OC)c3OC)C(=O)OCCCN3CCN(CC2)CC(F)(F)C3)cc(OC)c1OC] | N-((12R)-16,16-difluoro-74,75-dimethoxy-6-oxo-5,8-dioxa-1(1,4)-diazepana-7(1,3) benzenacyclotetradecaphane-12-yl)-3,4,5-trimethoxybenzamide |
| 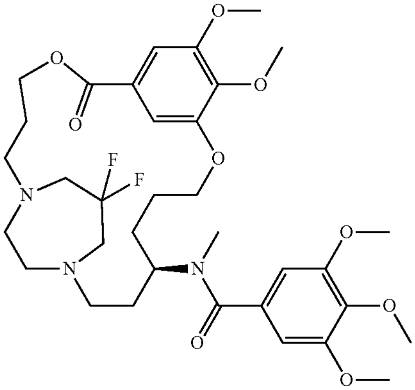 [SMILES: COc1cc(C(=O)N(C)[C@@H]2CCCOc3cc(cc(OC)c3OC)C(=O)OCCCN3CCN(CC2)CC(F)(F)C3)cc(OC)c1OC] | N-((12R)-16,16-difluoro-74,75-dimethoxy-6-oxo-5,8-dioxa-1(1,4)-diazepana-7(1,3) benzenacyclotetradecaphane-12-yl)-3,4,5-trimethoxy-N-methylbenzamide |

TABLE 1a-continued

| Compound Structures | Chemical Name |
|---|---|
| 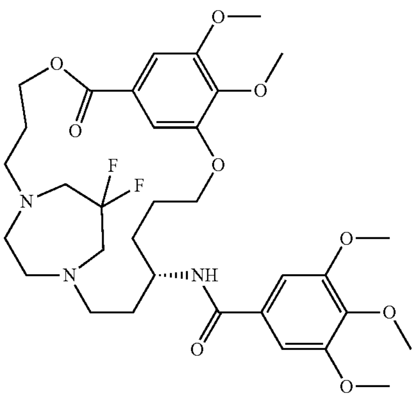 [SMILES: COc1cc(C(=O)N[C@H]2CCCOc3cc(cc(OC)c3OC)C(=O)OCCCN3CCN(CC2)CC(F)(F)C3)cc(OC)c1OC] | N-((12S)-16,16-difluoro-74,75-dimethoxy-6-oxo-5,8-dioxa-1(1,4)-diazepana-7(1,3)-benzenacyclotetradecaphane-12-yl)-3,4,5-trimethoxybenzamide |
| 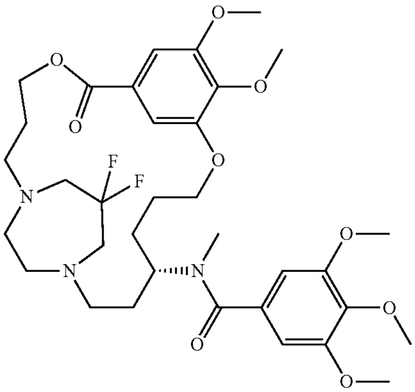 [SMILES: COc1cc(C(=O)N(C)[C@H]2CCCOc3cc(cc(OC)c3OC)C(=O)OCCCN3CCN(CC2)CC(F)(F)C3)cc(OC)c1OC] | N-((12S)-16,16-difluoro-74,75-dimethoxy-6-oxo-5,8-dioxa-1(1,4)-diazepana-7(1,3)-benzenacyclotetradecaphane-12-yl)-3,4,5-trimethoxy-N-methylbenzamide |

TABLE 1b

| Compound | STRUCTURE | Name |
|---|---|---|
| 1 | 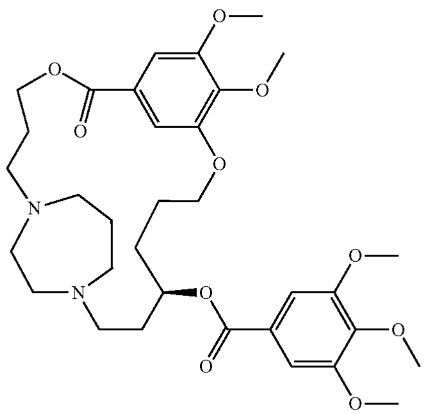 [SMILES: COc1cc(C(=O)O[C@@H]2CCCOc3cc(cc(OC)c3OC)C(=O)OCCCN3CCCN(CC2)CC3)cc(OC)c1OC] | (12R)-74,75-dimethoxy-6-oxo-5,8-dioxa-1(1,4)-diazepana-7(1,3)-benzenacyclotetradecaphane-12-yl 3,4,5-trimethoxybenzoate |

TABLE 1b-continued

| Compound | STRUCTURE | Name |
| --- | --- | --- |
| 2 | 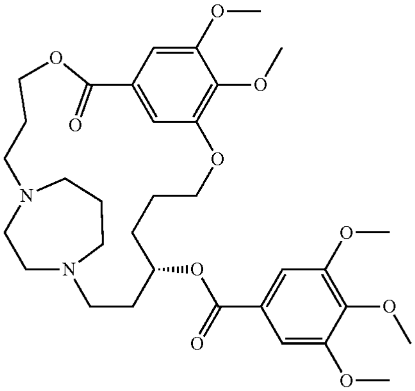 [SMILES: COc1cc(C(=O)O[C@H]2CCCOc3cc(cc(OC)c3OC)C(=O)OCCCN3CCCN(CC2)CC3)cc(OC)c1OC] | (12S)-74,75-dimethoxy-6-oxo-5,8-dioxa-1(1,4)-diazepana-7(1,3)-benzenacyclotetradecaphane-12-yl 3,4,5-trimethoxybenzoate |
| 3 | 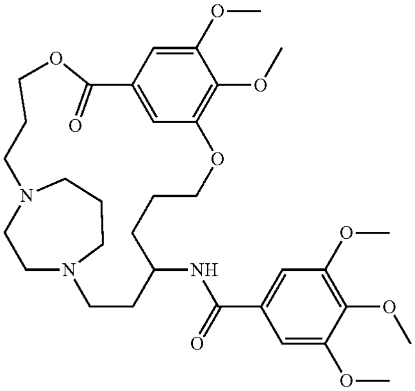 [SMILES: COc1cc(C(=O)NC2CCCOc3cc(cc(OC)c3OC)C(=O)OCCCN3CCCN(CC2)CC3)cc(OC)c1OC] | N-(74,75-dimethoxy-6-oxo-5,8-dioxa-1(1,4)-diazepana-7(1,3)-benzenacyclotetradecaphane-12-yl)-3,4,5-trimethoxybenzamide |
| 4 | 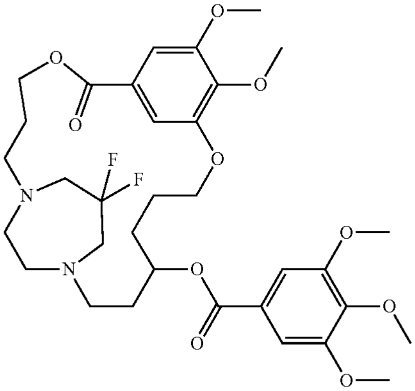 | 16,16-difluoro-74, 75-dimethoxy-6-oxo-5,8-dioxa-1(1,4)-diazepana-7(1,3)-benzenacyclotetradecaphane-12-yl 3,4,5-trimethoxybenzoate |
| 6 | 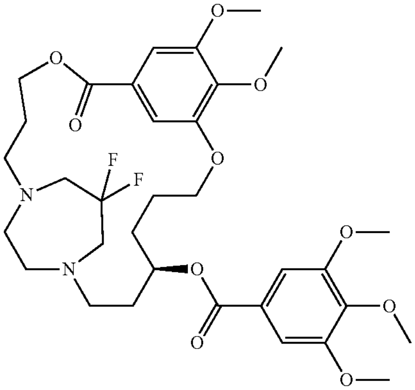 [SMILES: COc1cc(C(=O)O[C@@H]2CCCOc3cc(cc(OC)c3OC)C(=O)OCCCN3CCN(CC2)CC(F)(F)C3)cc(OC)c1OC] | (12R)-16,16-difluoro-74,75-dimethoxy-6-oxo-5,8-dioxa-1(1,4)-diazepana-7(1,3)-benzenacyclotetradecaphane-12-yl 3,4,5-trimethoxybenzoate |

TABLE 1b-continued

| Compound | STRUCTURE | Name |
|---|---|---|
| 8 | 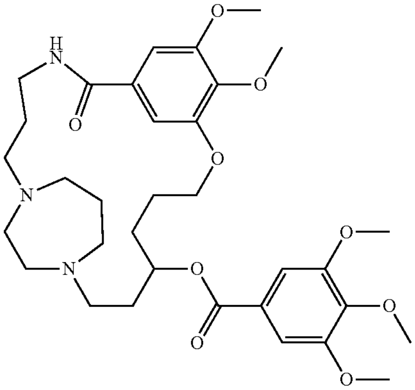 [SMILES: COc1cc(C(=O)OC2CCCOc3cc(cc(OC)c3OC)C(=O)NCCCN3CCCN(CC2)CC3)cc(OC)c1OC] | 74,75-dimethoxy-6-oxo-8-oxa-5-aza-1(1,4)-diazepana-7(1,3)-benzenacyclotetradecaphane-12-yl 3,4,5-trimethoxybenzoate |
| 9 | 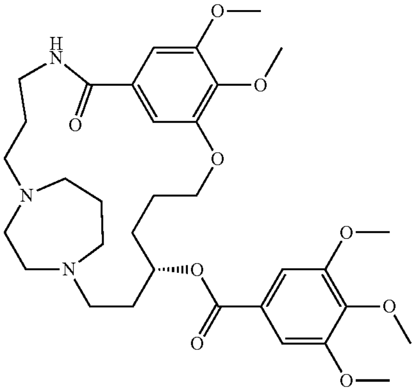 [SMILES: COc1cc(C(=O)O[C@H]2CCCOc3cc(cc(OC)c3OC)C(=O)NCCCN3CCCN(CC2)CC3)cc(OC)c1OC] | (12S)-74, 75-dimethoxy-6-oxo-8-oxa-5-aza-1(1,4)-diazepana-7(1,3)-benzenacyclotetradecaphane-12-yl 3,4,5-trimethoxybenzoate |
| 10 | 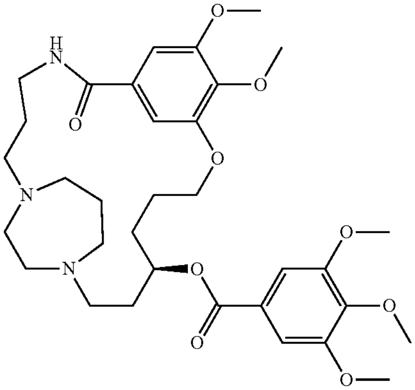 [SMILES: COc1cc(C(=O)O[C@@H]2CCCOc3cc(cc(OC)c3OC)C(=O)NCCCN3CCCN(CC2)CC3)cc(OC)c1OC] | (12R)-74,75-dimethoxy-6-oxo-8-oxa-5-aza-1(1,4)-diazepana-7(1,3)-benzenacyclotetradecaphane-12-yl 3,4,5-trimethoxybenzoate |
| 11 | 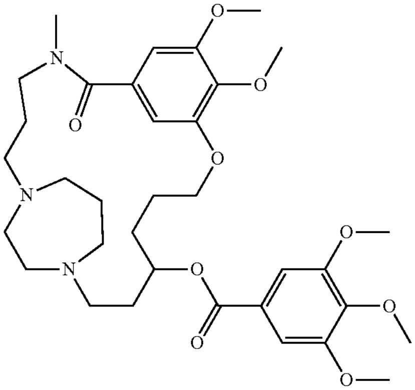 | 74,75-dimethoxy-5-methyl-6-oxo-8-oxa-5-aza-1(1,4)-diazepana-7(1,3)-benzenacyclotetradecaphane-12-yl 3,4,5-trimethoxybenzoate |

TABLE 1b-continued
| Compound STRUCTURE | Name |
|---|---|
| 12 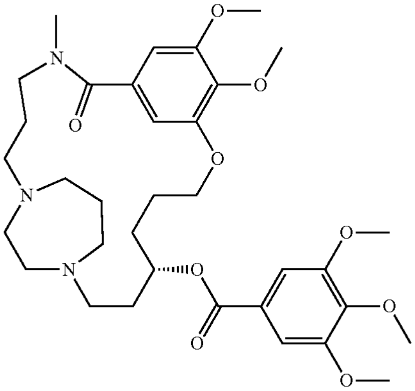 [SMILES: COc1cc(C(=O)O[C@H]2CCCOc3cc(cc(OC)c3OC)C(=O)N(C)CCCN3CCCN(CC2)CC3)cc(OC)c1OC] | (12S)-74,75-dimethoxy-5-methyl-6-oxo-8-oxa-5-aza-1(1,4)-diazepana-7(1,3)-benzenacyclotetradecaphane-12-yl 3,4,5-trimethoxybenzoate |
| 13 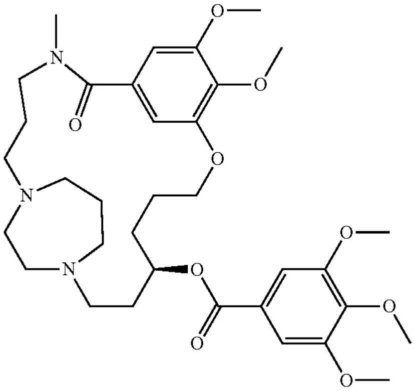 [SMILES: COc1cc(C(=O)O[C@@H]2CCCOc3cc(cc(OC)c3OC)C(=O)N(C)CCCN3CCCN(CC2)CC3)cc(OC)c1OC] | (12R)-74,75-dimethoxy-5-methyl-6-oxo-8-oxa-5-aza-1(1,4)-diazepana-7(1,3)-benzenacyclotetradecaphane-12-yl 3,4,5-trimethoxybenzoate |
| 14 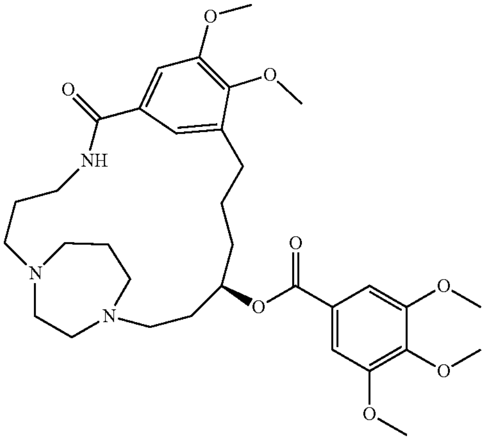 [SMILES: COc1cc2cc(c1OC)CCC[C@@H](OC(=O)c1cc(OC)c(OC)c(OC)c1)CCN1CCCN(CCCNC2=O)CC1] | (11R)-74,75-dimethoxy-6-oxo-5-aza-1(1,4)-diazepana-7(1,3)-benzenacyclotridecaphane-11-yl 3,4,5-trimethoxybenzoate |

TABLE 1b-continued
| Compound STRUCTURE | | Name |
|---|---|---|
| 15 | 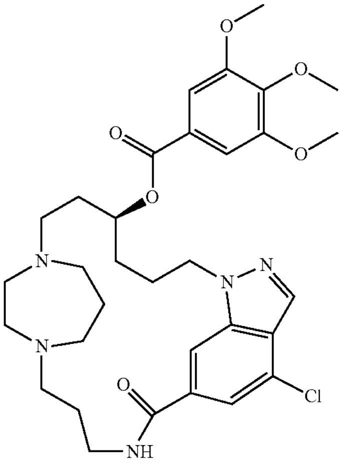 [SMILES: COc1cc(C(=O)O[C@H]2CCCn3ncc4c(Cl)cc(cc43)C(=O)NCCCN3CCCN(CC2)CC3)cc(OC)c1OC] | (10S)-14-chloro-2-oxo-11H-3-aza-1(6,1)-indazola-7(1,4)-diazepanacyclotridecaphane-10-yl 3,4,5-trimethoxybenzoate |
| 16 | 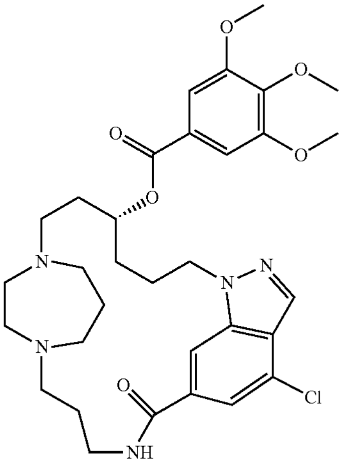 [SMILES: COc1cc(C(=O)O[C@@H]2CCCn3ncc4c(Cl)cc(cc43)C(=O)NCCCN3CCCN(CC2)CC3)cc(OC)c1OC] | (10R)-14-chloro-2-oxo-11H-3-aza-1(6,1)-indazola-7(1,4)-diazepanacyclotridecaphane-10-yl 3,4,5-trimethoxybenzoate |
| 17 | 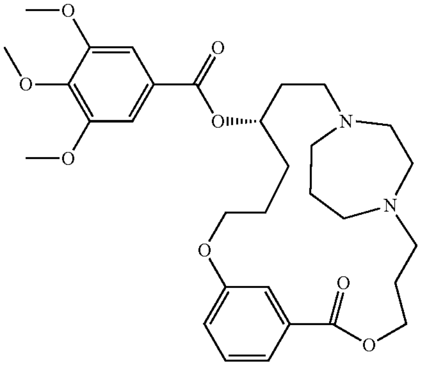 [SMILES: COc1cc(C(=O)O[C@H]2CCCOc3cccc(c3)C(=O)OCCCN3CCCN(CC2)CC3)cc(OC)c1OC] | (12S)-6-oxo-5,8-dioxa-1(1,4)-diazepana-7(1,3)-benzenacyclotetradecaphane-12-yl 3,4,5-trimethoxybenzoate |

TABLE 1b-continued
| Compound STRUCTURE | | Name |
|---|---|---|
| 18 | 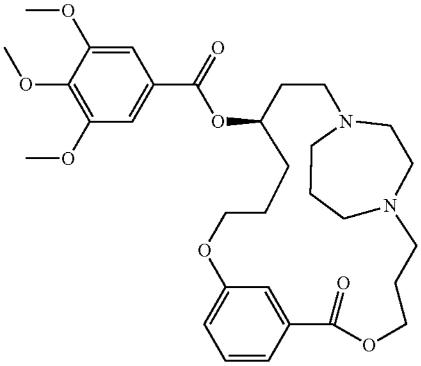 [SMILES: COc1cc(C(=O)O[C@@H]2CCCOc3cccc(c3)C(=O)OCCCN3CCCN(CC2)CC3)cc(OC)c1OC] | (12R)-6-oxo-5,8-dioxa-1(1,4)-diazepana-7(1,3)-benzenacyclotetradecaphane-12-yl 3,4,5-trimethoxybenzoate |
| 19 | 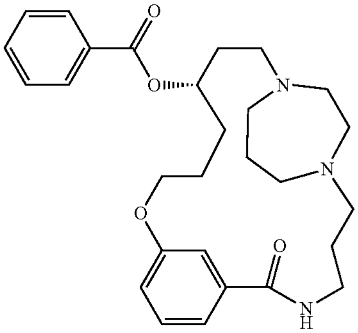 [SMILES: O=C1NCCCN2CCCN(CC[C@@H](OC(=O)c3ccccc3)CCCOc3cccc1c3)CC2] | (12S)-6-oxo-8-oxa-5-aza-1(1,4)-diazepana-7(1,3)-benzenacyclotetradecaphane-12-yl benzoate |
| 20 | 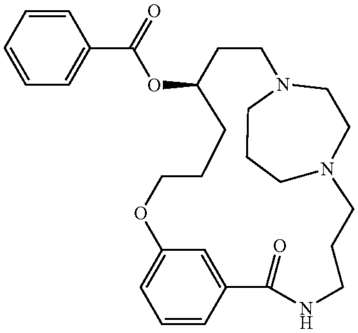 [SMILES: O=C1NCCCN2CCCN(CC[C@H](OC(=O)c3ccccc3)CCCOc3cccc1c3)CC2] | (12R)-6-oxo-8-oxa-5-aza-1(1,4)-diazepana-7(1,3)-benzenacyclotetradecaphane-12-yl benzoate |
| 21 | 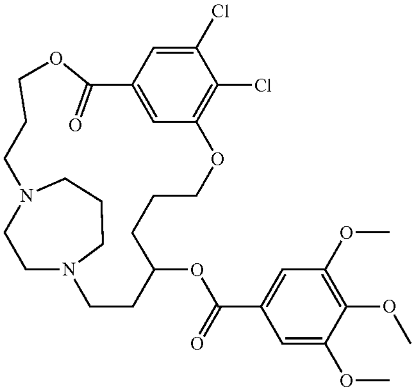 | 74,75-dichloro-6-oxo-5,8-dioxa-1(1,4)-diazepana-7(1,3)-benzenacyclotetradecaphane-12-yl 3,4,5-trimethoxybenzoate |

TABLE 1b-continued

| Compound STRUCTURE | Name |
| --- | --- |
| 22 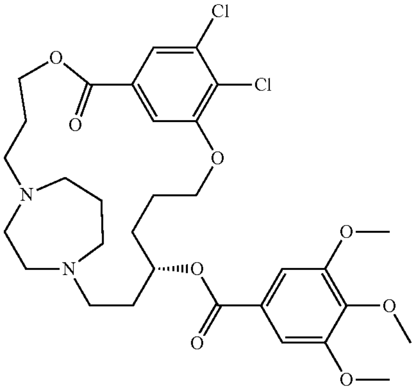 [SMILES: COc1cc(C(=O)OC2CCCOc3cc(cc(Cl)c3Cl)C(=O)OCCCN3CCCN(CC2)CC3)cc(OC)c1OC] | (12S)-74,75-dichloro-6-oxo-5,8-dioxa-1(1,4)-diazepana-7(1,3)-benzenacyclotetradecaphane-12-yl 3,4,5-trimethoxybenzoate |
| 23 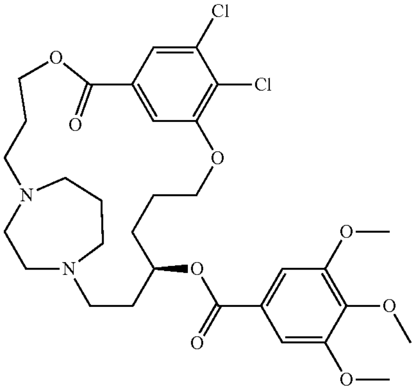 [SMILES: COc1cc(C(=O)O[C@@H]2CCCOc3cc(cc(Cl)c3Cl)C(=O)OCCCN3CCCN(CC2)CC3)cc(OC)c1OC] | (12R)-74,75-dichloro-6-oxo-5,8-dioxa-1(1,4)-diazepana-7(1,3)-benzenacyclotetradecaphane-12-yl 3,4,5-trimethoxybenzoate |
| 24 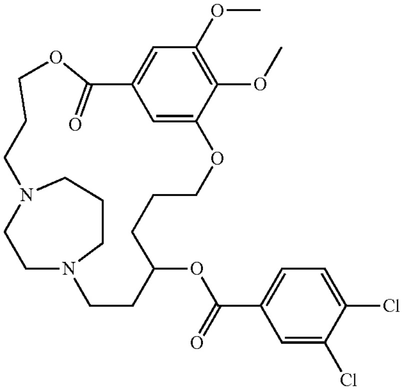 [SMILES: COc1cc2cc(c1OC)OCCCC(OC(=O)c1ccc(Cl)c(Cl)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3,4-dichlorobenzoate |
| 25 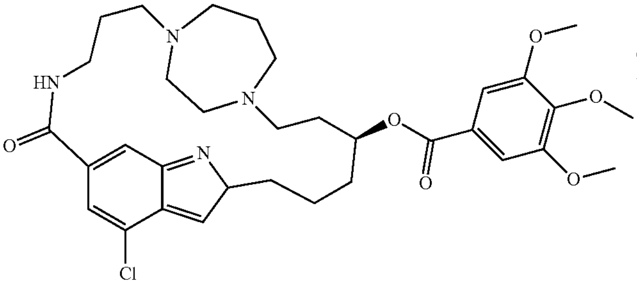 [SMILES: COc1cc(C(=O)O[C@H]2CCCC3C=c4c(Cl)cc(cc4=N3)C(=O)NCCCN3CCCN(CC2)CC3)cc(OC)c1OC] | (11Z,16E, 10S)-14-chloro-2-oxo-12H-3-aza-1(6,2)-indazola-7(1,4)-diazepanacyclotridecaphane-10-yl 3,4,5-trimethoxybenzoate |

TABLE 1b-continued

| Compound | STRUCTURE | Name |
| --- | --- | --- |
| 26 | 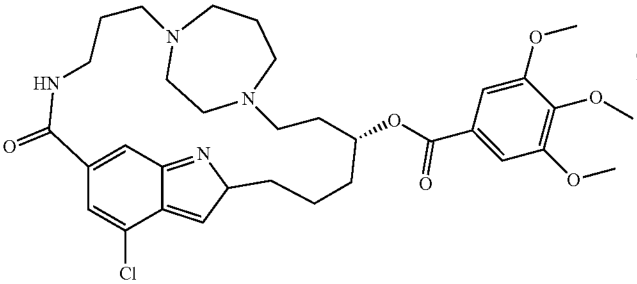 [SMILES: COc1cc(C(=O)O[C@@H]2CCCC3C=c4c(Cl)cc(cc4=N3)C(=O)NCCCN3CCCN(CC2)CC3)cc(OC)c1OC] | (11Z,16E,10R)-14-chloro-2-oxo-12H-3-aza-1(6,2)-indazola-7(1,4)-diazepanacyclotridecaphane-10-yl 3,4,5-trimethoxybenzoate |
| 27 | 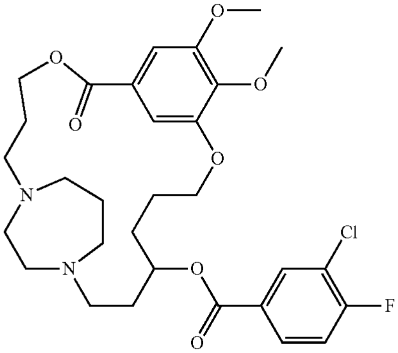 [SMILES: COc1cc2cc(c1OC)OCCCC(OC(=O)c1ccc(F)c(Cl)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-chloro-4-fluorobenzoate |
| 28 | 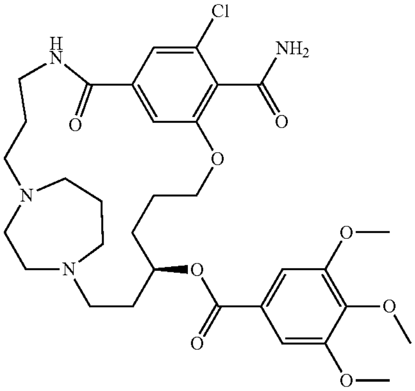 [SMILES: COc1cc(C(=O)O[C@@H]2CCCOc3cc(cc(Cl)c3C(N)=O)C(=O)NCCCN3CCCN(CC2)CC3)cc(OC)c1OC] | (12R)-74-carbamoyl-75-chloro-6-oxo-8-oxa-5-aza-1(1,4)-diazepana-7(1,3)-benzenacyclotetradecaphane-12-yl 3,4,5-trimethoxybenzoate |
| 29 | 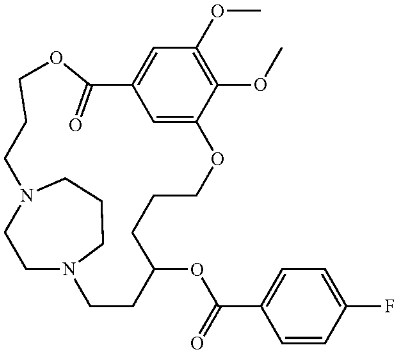 [SMILES: COc1cc2cc(c1OC)OCCCC(OC(=O)c1ccc(F)cc1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-fluorobenzoate |

TABLE 1b-continued

| Compound STRUCTURE | | Name |
|---|---|---|
| 30 | 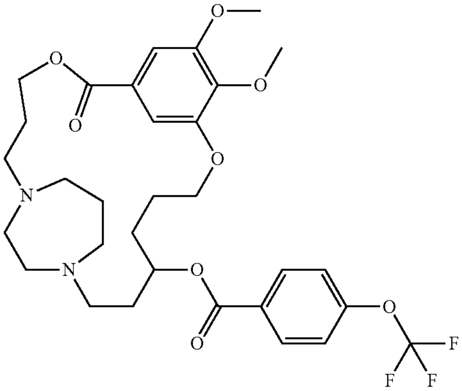 [SMILES: COc1cc2cc(c1OC)OCCCC(OC(=O)c1ccc(OC(F)(F)F)cc1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-(trifluoromethoxy)benzoate |
| 31 | 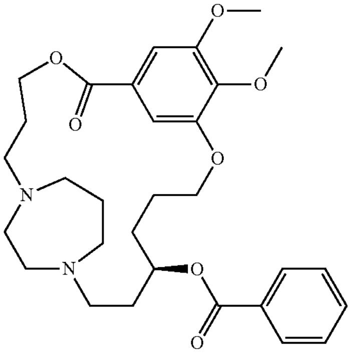 [SMILES: COc1cc2cc(c1OC)OCCC[C@@H](OC(=O)c1ccccc1)CCN1CCCN(CCCOC2=O)CC1] | (12R)-74, 75-dimethoxy-6-oxo-5,8-dioxa-1(1,4)-diazepana-7(1,3)-benzenacyclotetradecaphane-12-yl benzoate |
| 32 | 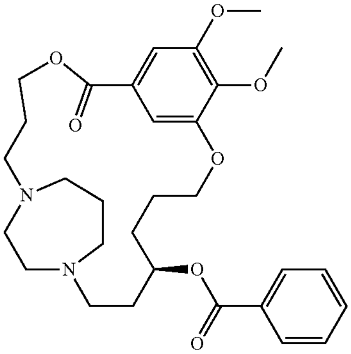 [SMILES: COc1cc2cc(c1OC)OCCC[C@@H](OC(=O)c1ccccc1)CCN1CCCN(CCCOC2=O)CC1] | (12R)-74,75-dimethoxy-6-oxo-5,8-dioxa-1(1,4)-diazepana-7(1,3)-benzenacyclotetradecaphane-12-yl benzoate |
| 33 | 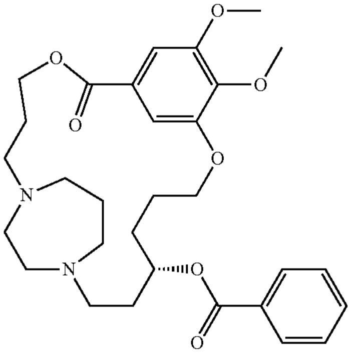 | (12S)-74,75-dimethoxy-6-oxo-5,8-dioxa-1(1,4)-diazepana-7(1,3)-benzenacyclotetradecaphane-12-yl benzoate |

TABLE 1b-continued

| Compound STRUCTURE | | Name |
|---|---|---|
| 34 | 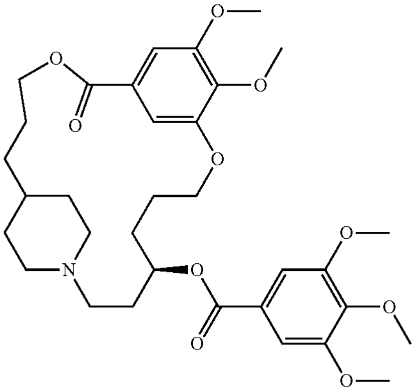 [SMILES: COc1cc(C(=O)O[C@@H]2CCCOc3cc(cc(OC)c3OC)C(=O)OCCCC3CCN(CC3)CC2)cc(OC)c1OC] | (R)-74,75-dimethoxy-6-oxo-5,8-dioxa-1(4,1)-piperidina-7(1,3)-benzenacyclotetradecaphane-12-yl 3,4,5-trimethoxybenzoate |
| 35 | 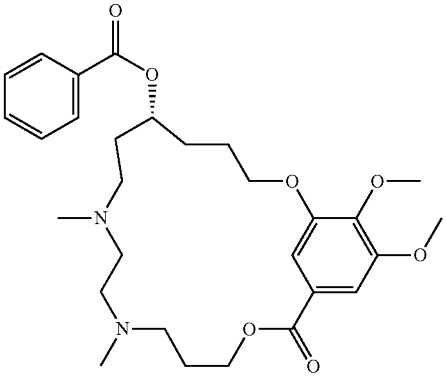 [SMILES: COc1cc2cc(c1OC)OCCC[C@@H](OC(=O)c1ccccc1)CCN(C)CCN(C)CCCOC2=O] | (R)-15,16-dimethoxy-9,12-dimethyl-17-oxo-2,16-dioxa-9,12-diaza-1(1,3)-benzenacycloheptadecaphane-6-yl benzoate |
| 36 | 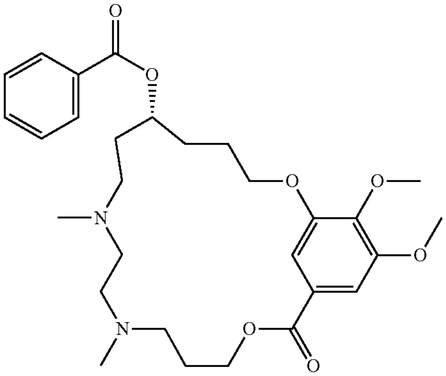 [SMILES: COc1cc2cc(c1OC)OCCC[C@@H](OC(=O)c1ccccc1)CCN(C)CCN(C)CCCOC2=O] | (R)-15,16-dimethoxy-9,12-dimethyl-17-oxo-2,16-dioxa-9,12-diaza-1(1,3)-benzenacycloheptadecaphane-6-yl benzoate |
| 37 | 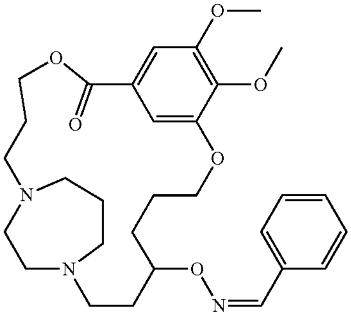 [SMILES: COc1cc2cc(c1OC)OCCCC(O/N=C\c1ccccc1)CCN1CCCN(CCCOC2=O)CC1] | (Z)-benzaldehyde O-(74,75-dimethoxy-6-oxo-5,8-dioxa-1(1,4)-diazepana-7(1,3)-benzenacyclotetradecaphane-12-yl) oxime |

TABLE 1b-continued

| Compound STRUCTURE | | Name |
|---|---|---|
| 38 | 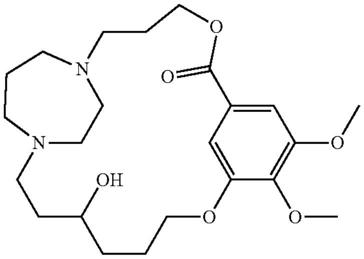 | 12-hydroxy-74,75-dimethoxy-5,8-dioxa-1(1,4)-diazepana-7(1,3)-benzenacyclotetradecaphan-6-one |
| 39 | 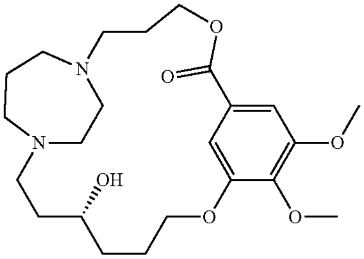 [SMILES: COc1cc2cc(c1OC)OCCC[C@@H](O)CCN1CCCN(CCCOC2=O)CC1] | (12R)-12-hydroxy-74,75-dimethoxy-5,8-dioxa-1(1,4)-diazepana-7(1,3)-benzenacyclotetradecaphan-6-one |
| 40 | 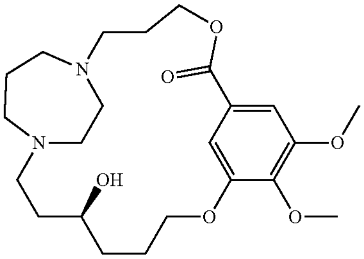 [SMILES: COc1cc2cc(c1OC)OCCC[C@H](O)CCN1CCCN(CCCOC2=O)CC1] | (12S)-12-hydroxy-74,75-dimethoxy-5,8-dioxa-1(1,4)-diazepana-7(1,3)-benzenacyclotetradecaphan-6-one |
| 41 | 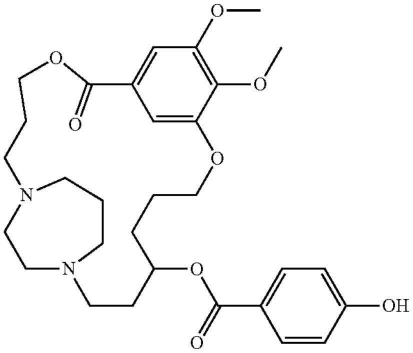 [SMILES: COc1cc2cc(c1OC)OCCCC(OC(=O)c1ccc(O)cc1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-hydroxybenzoate |
| 43 | 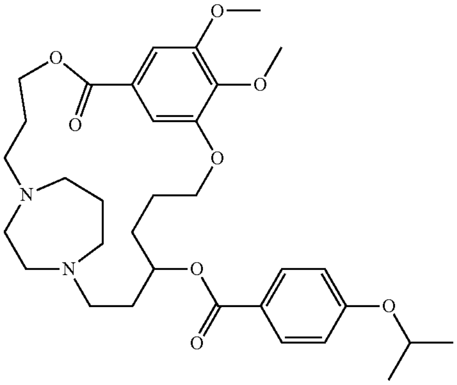 [SMILES: COc1cc2cc(c1OC)OCCCC(OC(=O)c1ccc(OC(C)C)cc1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-isopropoxybenzoate |

TABLE 1b-continued

| Compound STRUCTURE | | Name |
|---|---|---|
| 44 | 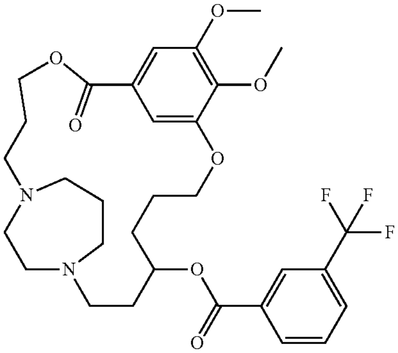 [SMILES: COc1cc2cc(c1OC)OCCCC(OC(=O)c1cccc(C(F)(F)F)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-(trifluoromethyl)benzoate |
| 45 | 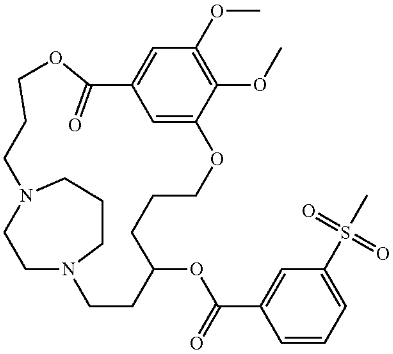 [SMILES: COc1cc2cc(c1OC)OCCCC(OC(=O)c1cccc(S(C)(=O)=O)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-(methylsulfonyl)benzoate |
| 46 | 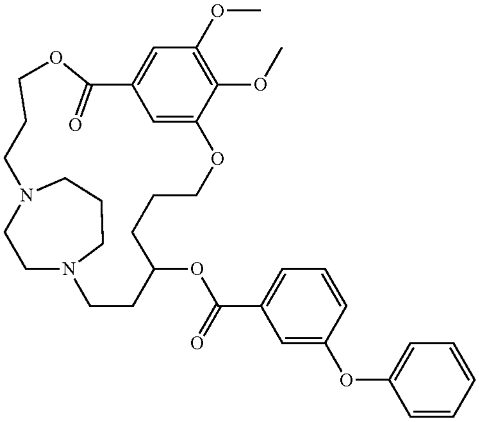 [SMILES: COc1cc2cc(c1OC)OCCCC(OC(=O)c1cccc(Oc3ccccc3)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-phenoxybenzoate |
| 47 | 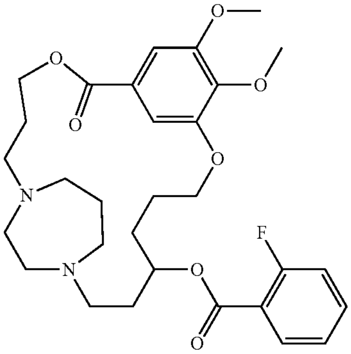 [SMILES: COc1cc2cc(c1OC)OCCCC(OC(=O)c1ccccc1F)CCN1CCCN(CCCOC2=O)CC1] | 74,75-dimethoxy-6-oxo-5,8-dioxa-1(1,4)-diazepana-7(1,3)-benzenacyclotetradecaphane-12-yl 2-fluorobenzoate |

TABLE 1b-continued

| Compound STRUCTURE | | Name |
|---|---|---|
| 48 | 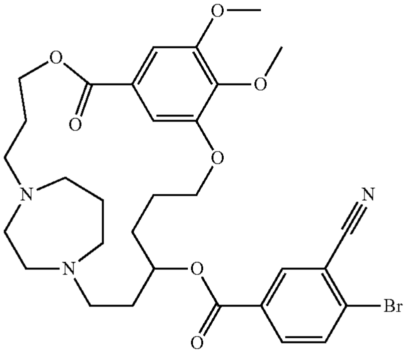 [SMILES: COc1cc2cc(c1OC)OCCCC(OC(=O)c1ccc(Br)c(C#N)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-bromo-3-cyanobenzoate |
| 49 | 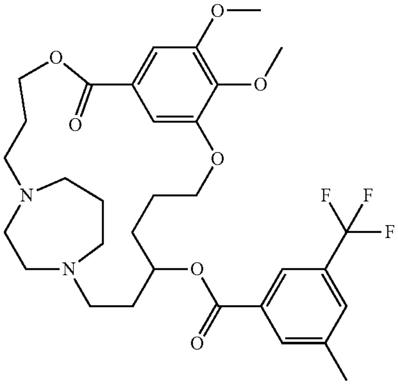 [SMILES: COc1cc2cc(c1OC)OCCCC(OC(=O)c1cc(C)cc(C(F)(F)F)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-methyl-5-(trifluoromethyl)benzoate |
| 50 | 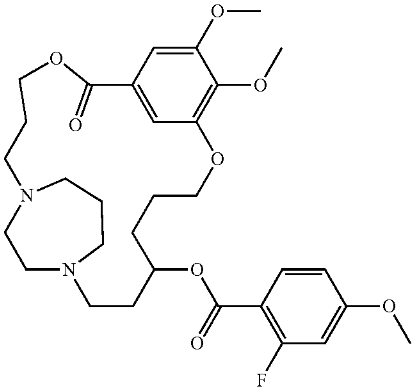 [SMILES: COc1ccc(C(=O)OC2CCCOc3cc(cc(OC)c3OC)C(=O)OCCCN3CCCN(CC2)CC3)c(F)c1] | 74,75-dimethoxy-6-oxo-5,8-dioxa-1(1,4)-diazepana-7(1,3)-benzenacyclotetradecaphane-12-yl 2-fluoro-4-methoxybenzoate |
| 51 | 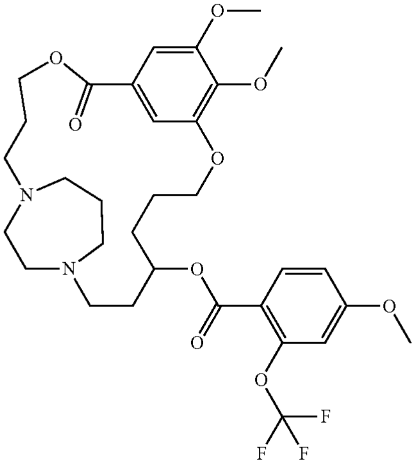 [SMILES: COc1ccc(C(=O)OC2CCCOc3cc(cc(OC)c3OC)C(=O)OCCCN3CCCN(CC2)CC3)c(OC(F)(F)F)c1] | 74,75-dimethoxy-6-oxo-5,8-dioxa-1(1,4)-diazepana-7(1,3)-benzenacyclotetradecaphane-12-yl 4-methoxy-2-(trifluoromethoxy)benzoate |

TABLE 1b-continued

| Compound STRUCTURE | Name |
|---|---|
| 52 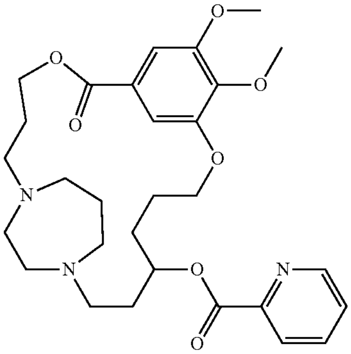 | 74,75-dimethoxy-6-oxo-5,8-dioxa-1(1,4)-diazepana-7(1,3)-benzenacyclotetradecaphane-12-yl picolinate |
| 53 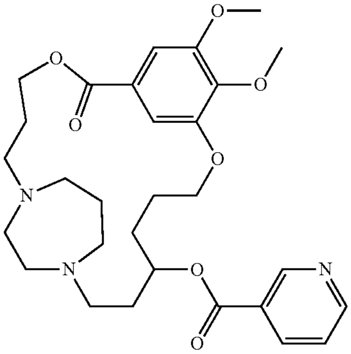 [SMILES: COc1cc2cc(c1OC)OCCCC(OC(=O)c1cccnc1)CCN1CCCN(CCCOC2=O)CC1] | 74,75-dimethoxy-6-oxo-5,8-dioxa-1(1,4)-diazepana-7(1,3)-benzenacyclotetradecaphane-12-yl nicotinate |
| 54 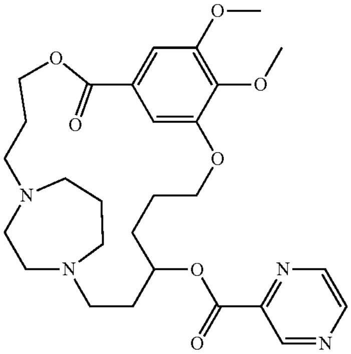 [SMILES: COc1cc2cc(c1OC)OCCCC(OC(=O)c1cnccn1)CCN1CCCN(CCCOC2=O)CC1] | 74,75-dimethoxy-6-oxo-5,8-dioxa-1(1,4)-diazepana-7(1,3)-benzenacyclotetradecaphane-12-yl pyrazine-2-carboxylate |
| 55 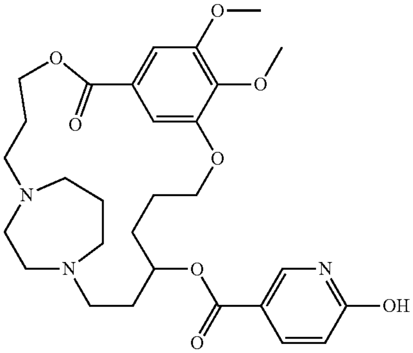 | 74,75-dimethoxy-6-oxo-5,8-dioxa-1(1,4)-diazepana-7(1,3)-benzenacyclotetradecaphane-12-yl 6-hydroxynicotinate |

TABLE 1b-continued

| Compound | STRUCTURE | Name |
|---|---|---|
| 56 | 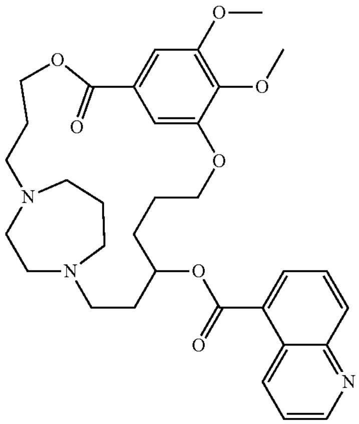 [SMILES: COc1cc2cc(c1OC)OCCCC(OC(=O)c1cccc3ncccc13)CCN1CCCN(CCCOC2=O)CC1] | 74,75-dimethoxy-6-oxo-5,8-dioxa-1(1,4)-diazepana-7(1,3)-benzenacyclotetradecaphane-12-yl quinoline-5-carboxylate |
| 57 | 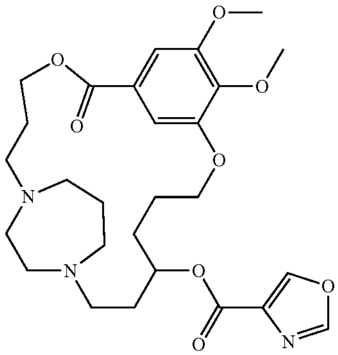 [SMILES: COc1cc2cc(c1OC)OCCCC(OC(=O)c1cocn1)CCN1CCCN(CCCOC2=O)CC1] | 74,75-dimethoxy-6-oxo-5,8-dioxa-1(1,4)-diazepana-7(1,3)-benzenacyclotetradecaphane-12-yl oxazole-4-carboxylate |
| 58 | 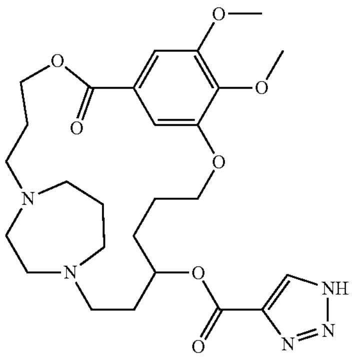 [SMILES: COc1cc2cc(c1OC)OCCCC(OC(=O)c1c[nH]nn1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 1H-1,2,3-triazole-4-carboxylate |
| 59 | 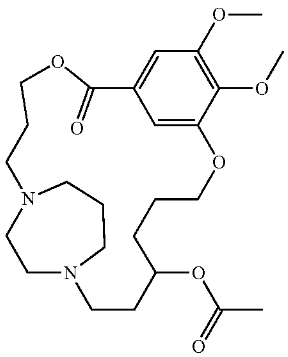 [SMILES: COc1cc2cc(c1OC)OCCCC(OC(C)=O)CCN1CCCN(CCCOC2=O)CC1] | 74,75-dimethoxy-6-oxo-5,8-dioxa-1(1,4)-diazepana-7(1,3)-benzenacyclotetradecaphane-12-yl acetate |

TABLE 1b-continued

| Compound STRUCTURE | | Name |
| --- | --- | --- |
| 60 | 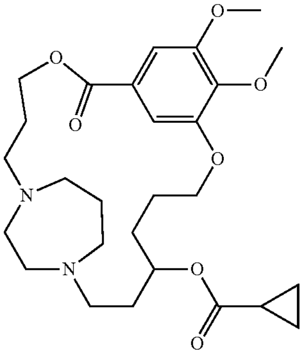 [SMILES: COc1cc2cc(c1OC)OCCCC(OC(=O)C1CC1)CCN1CCCN(CCCOC2=O)CC1] | 74,75-dimethoxy-6-oxo-5,8-dioxa-1(1,4)-diazepana-7(1,3)-benzenacyclotetradecaphane-12-yl cyclopropanecarboxylate |
| 61 | 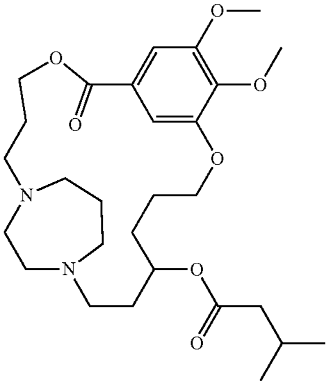 [SMILES: COc1cc2cc(c1OC)OCCCC(OC(=O)CC(C)C)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-methylbutanoate |
| 62 | 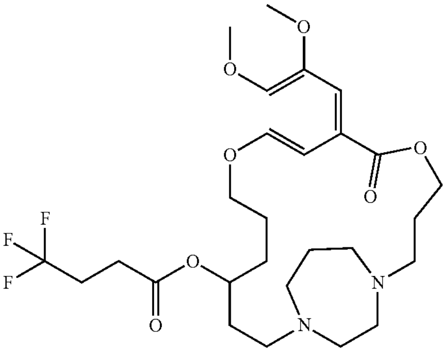 [SMILES: CO/C=C(/C=C1\C=C\OCCCC(OC(=O)CCC(F)(F)F)CCN2CCCN(CCCOC1=O)CC2)OC] | 74,75-dimethoxy-6-oxo-5,8-dioxa-1(1,4)-diazepana-7(1,3)-benzenacyclotetradecaphane-12-yl 4,4,4-trifluorobutanoate |
| 63 | 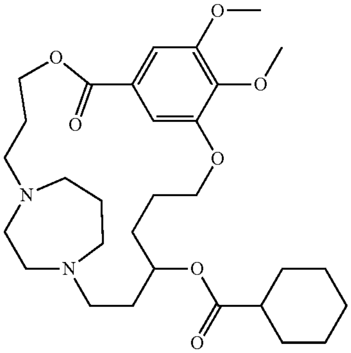 [SMILES: COc1cc2cc(c1OC)OCCCC(OC(=O)C1CCCCC1)CCN1CCCN(CCCOC2=O)CC1] | 74,75-dimethoxy-6-oxo-5,8-dioxa-1(1,4)-diazepana-7(1,3)-benzenacyclotetradecaphane-12-yl cyclohexanecarboxylate |

TABLE 1b-continued

| Compound STRUCTURE | | Name |
|---|---|---|
| 64 | 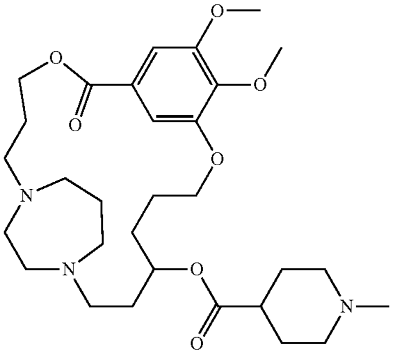 [SMILES: COc1cc2cc(c1OC)OCCCC(OC(=O)C1CCN(C)CC1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 1-methylpiperidine-4-carboxylate |
| 65 | 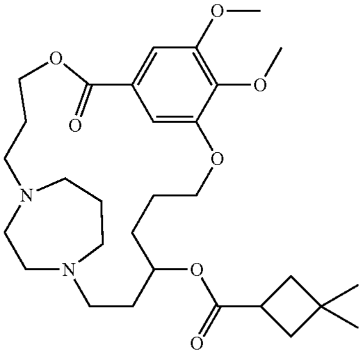 [SMILES: COc1cc2cc(c1OC)OCCCC(OC(=O)C1CC(C)(C)C1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3,3-dimethylcyclobutane-1-carboxylate |
| 66 | 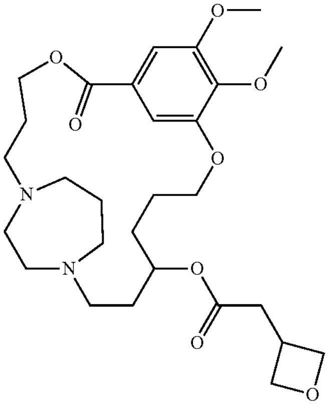 [SMILES: COc1cc2cc(c1OC)OCCCC(OC(=O)CC1COC1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 2-(oxetan-3-yl)acetate |
| 67 | 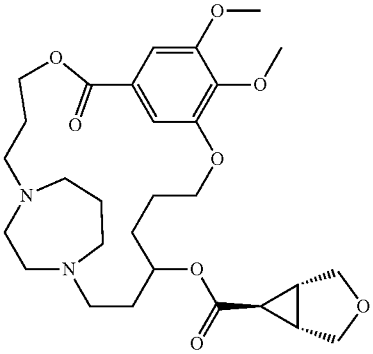 [SMILES: COc1cc2cc(c1OC)OCCCC(OC(=O)[C@H]1[C@@H]3COC[C@@H]31)CCN1CCCN(CCCOC2=O)CC1] | 74,75-dimethoxy-6-oxo-5,8-dioxa-1(1,4)-diazepana-7(1,3)-benzenacyclotetradecaphane-12-yl (1R,5S,6r)-3-oxabicyclo[3.1.0] hexane-6-carboxylate |

TABLE 1b-continued

| Compound STRUCTURE | Name |
|---|---|
| 68 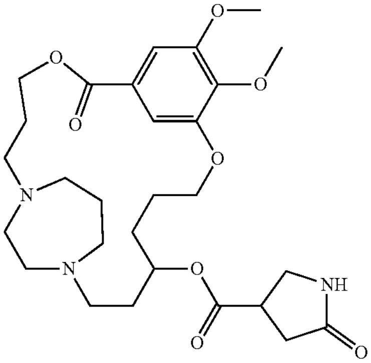 [SMILES: COc1cc2cc(c1OC)OCCCC(OC(=O)C1CNC(=O)C1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 5-oxopyrrolidine-3-carboxylate |
| 69 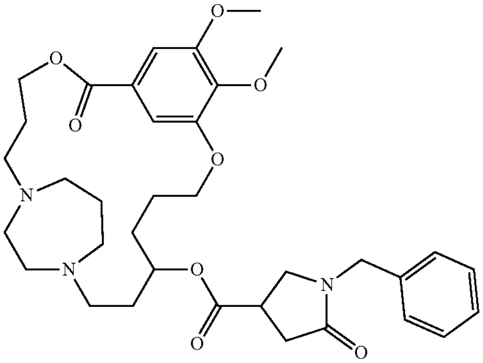 [SMILES: COc1cc2cc(c1OC)OCCCC(OC(=O)C1CC(=O)N(Cc3ccccc3)C1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 1-benzyl-5-oxopyrrolidine-3-carboxylate |
| 70 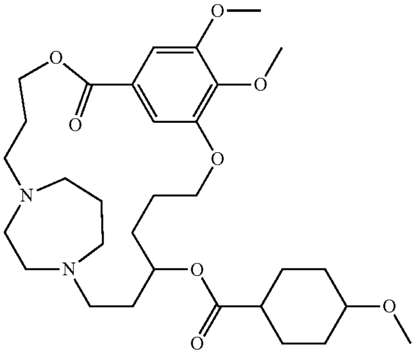 [SMILES: COc1cc2cc(c1OC)OCCCC(OC(=O)C1CCC(OC)CC1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-methoxycyclohexane-1-carboxylate |
| 71 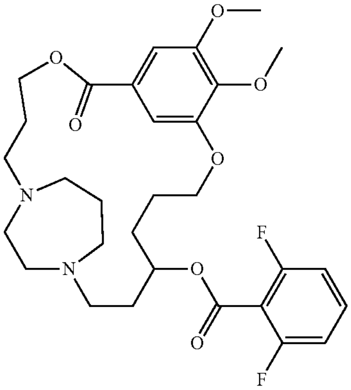 [SMILES: COc1cc2cc(c1OC)OCCCC(OC(=O)c1c(F)cccc1F)CCN1CCCN(CCCOC2=O)CC1] | 74,75-dimethoxy-6-oxo-5,8-dioxa-1(1,4)-diazepana-7(1,3)-benzenacyclotetradecaphane-12-yl 2,6-difluorobenzoate |

TABLE 1b-continued

| Compound STRUCTURE | | Name |
|---|---|---|
| 73 | 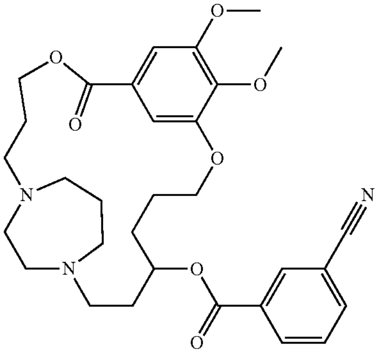 [SMILES: COc1cc2cc(c1OC)OCCCC(OC(=O)c1cccc(C#N)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-cyanobenzoate |
| 74 | 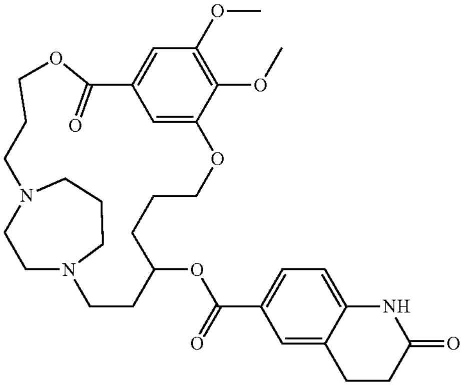 [SMILES: COc1cc2cc(c1OC)OCCCC(OC(=O)c1ccc3c(c1)CCC(=O)N3)CCN1CCCN(CCCOC2=O)CC1] | 74,75-dimethoxy-6-oxo-5,8-dioxa-1(1,4)-diazepana-7(1,3)-benzenacyclotetradecaphane-12-yl 2-oxo-1,2,3,4-tetrahydroquinoline-6-carboxylate |
| 75 | 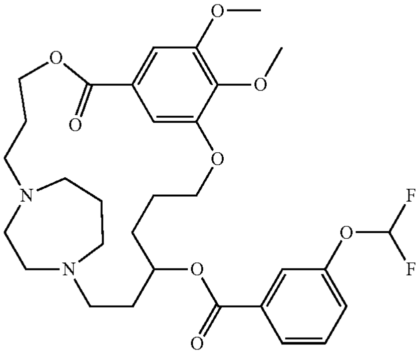 [SMILES: COc1cc2cc(c1OC)OCCCC(OC(=O)c1cccc(OC(F)F)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-(difluoromethoxy)benzoate |
| 76 | 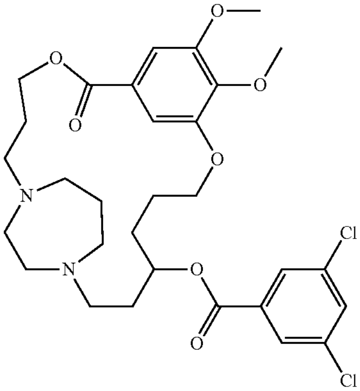 [SMILES: COc1cc2cc(c1OC)OCCCC(OC(=O)c1cc(Cl)cc(Cl)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3,5-dichlorobenzoate |

TABLE 1b-continued

| Compound STRUCTURE | Name |
| --- | --- |
| 78 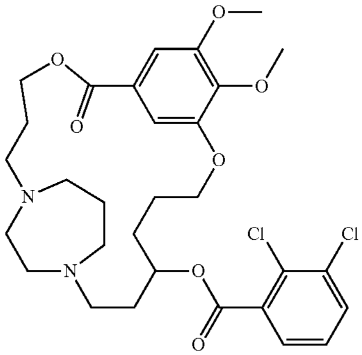 [SMILES: COc1cc2cc(c1OC)OCCCC(OC(=O)c1cccc(Cl)c1Cl)CCN1CCCN(CCCOC2=O)CC1] | 74,75-dimethoxy-6-oxo-5,8-dioxa-1(1,4)-diazepana-7(1,3)-benzenacyclotetradecaphane-12-yl 2,3-dichlorobenzoate |
| 79 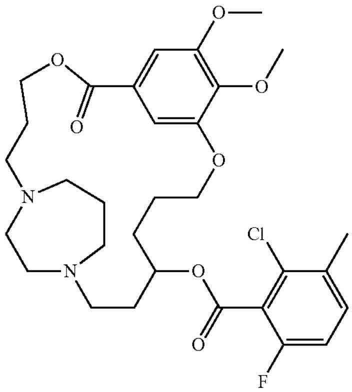 [SMILES: COc1cc2cc(c1OC)OCCCC(OC(=O)c1c(F)ccc(C)c1Cl)CCN1CCCN(CCCOC2=O)CC1] | 74,75-dimethoxy-6-oxo-5,8-dioxa-1(1,4)-diazepana-7(1,3)-benzenacyclotetradecaphane-12-yl 2-chloro-6-fluoro-3-methylbenzoate |
| 80 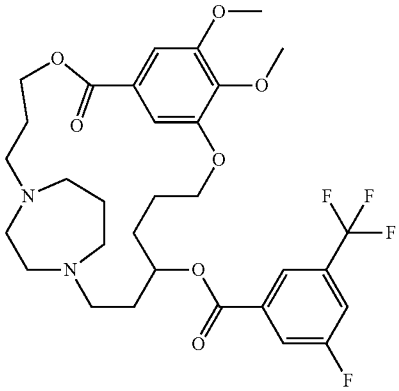 [SMILES: COc1cc2cc(c1OC)OCCCC(OC(=O)c1cc(F)cc(C(F)(F)F)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-fluoro-5-(trifluoromethyl)benzoate |
| 81 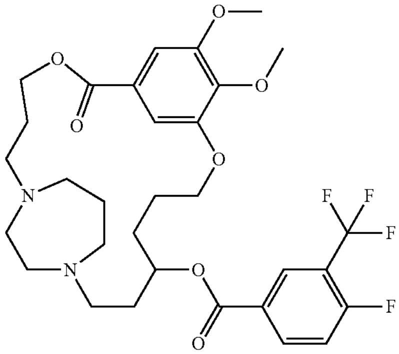 [SMILES: COc1cc2cc(c1OC)OCCCC(OC(=O)c1ccc(F)c(C(F)(F)F)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-fluoro-3-(trifluoromethyl)benzoate |

TABLE 1b-continued

| Compound STRUCTURE | | Name |
|---|---|---|
| 82 | 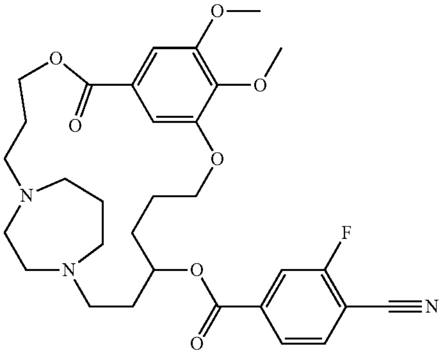 [SMILES: COc1cc2cc(c1OC)OCCCC(OC(=O)c1ccc(C#N)c(F)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-cyano-3-fluorobenzoate |
| 83 | 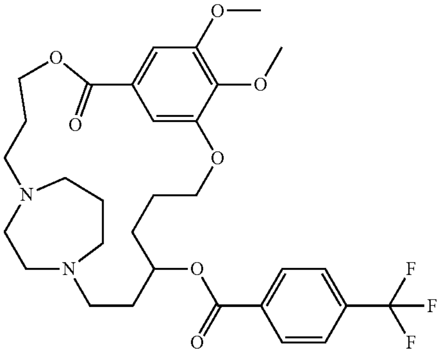 [SMILES: COc1cc2cc(c1OC)OCCCC(OC(=O)c1ccc(C(F)(F)F)cc1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-(trifluoromethyl)benzoate |
| 84 | 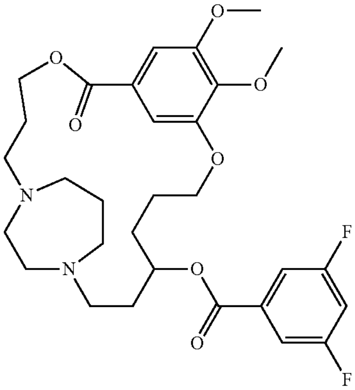 [SMILES: COc1cc2cc(c1OC)OCCCC(OC(=O)c1cc(F)cc(F)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3,5-difluorobenzoate |
| 85 | 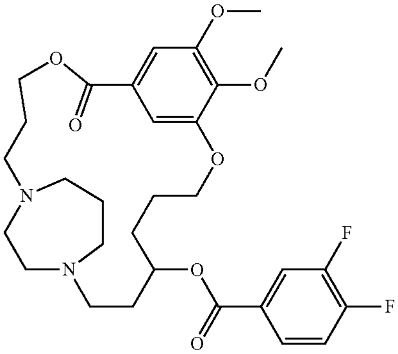 [SMILES: COc1cc2cc(c1OC)OCCCC(OC(=O)c1ccc(F)c(F)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3,4-difluorobenzoate |

TABLE 1b-continued

| Compound STRUCTURE | Name |
| --- | --- |
| 86 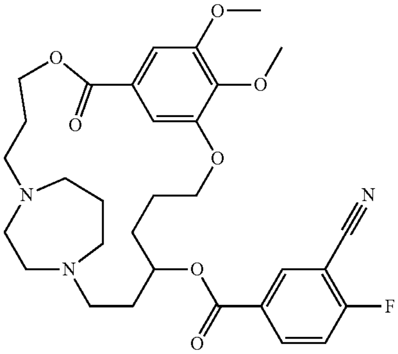 [SMILES: COc1cc2cc(c1OC)OCCCC(OC(=O)c1ccc(F)c(C#N)c1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-cyano-4-fluorobenzoate |
| 87 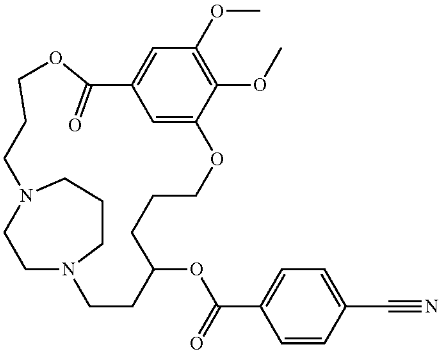 [SMILES: COc1cc2cc(c1OC)OCCCC(OC(=O)c1ccc(C#N)cc1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-cyanobenzoate |
| 89 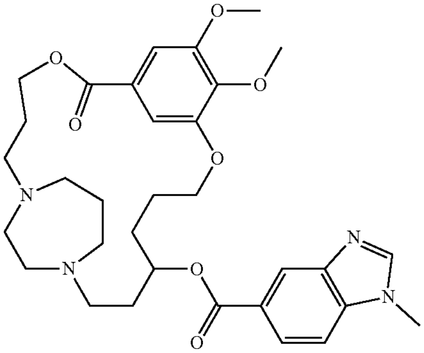 [SMILES: COc1cc2cc(c1OC)OCCCC(OC(=O)c1ccc3c(c1)ncn3C)CCN1CCCN(CCCOC2=O)CC1] | 74,75-dimethoxy-6-oxo-5,8-dioxa-1(1,4)-diazepana-7(1,3)-benzenacyclotetradecaphane-12-yl 1-methyl-1H-benzo[d]imidazole-5-carboxylate |
| 90 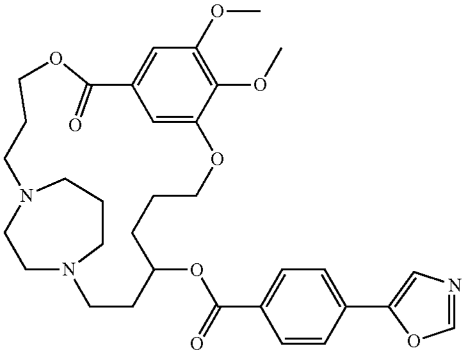 [SMILES: COc1cc2cc(c1OC)OCCCC(OC(=O)c1ccc(-c3cnco3)cc1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-(oxazol-5-yl)benzoate |

TABLE 1b-continued

| Compound | STRUCTURE | Name |
|---|---|---|
| 91 | 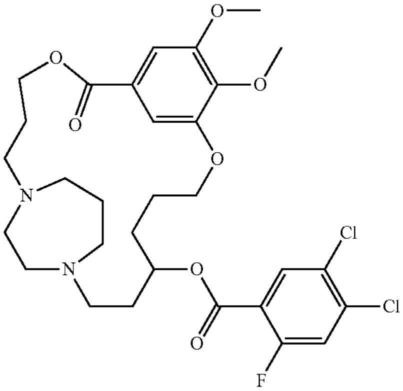 [SMILES: COc1cc2cc(c1OC)OCCCC(OC(=O)c1cc(Cl)c(Cl)cc1F)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4,5-dichloro-2-fluorobenzoate |
| 92 | 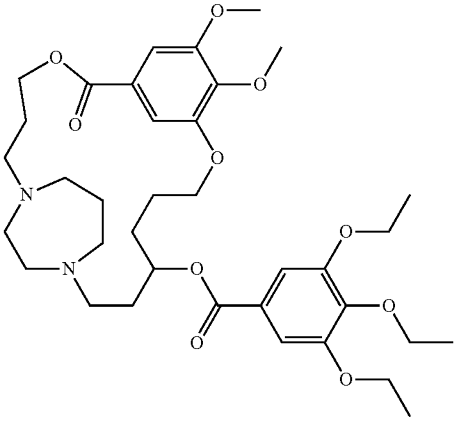 [SMILES: CCOc1cc(C(=O)OC2CCCOc3cc(cc(OC)c3OC)C(=O)OCCCN3CCCN(CC2)CC3)cc(OCC)c1OCC] | 74,75-dimethoxy-6-oxo-5,8-dioxa-1(1,4)-diazepana-7(1,3)-benzenacyclotetradecaphane-12-yl 3,4,5-triethoxybenzoate |
| 93 | 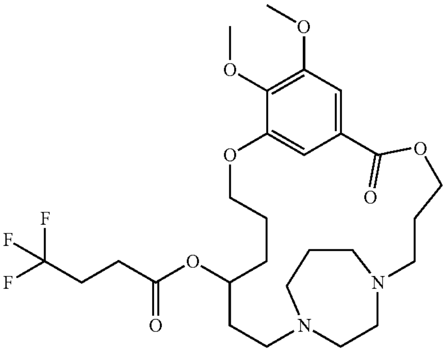 | 74,75-dimethoxy-6-oxo-5,8-dioxa-1(1,4)-diazepana-7(1,3)-benzenacyclotetradecaphane-12-yl 3-methoxypropanoate |
| 94 | 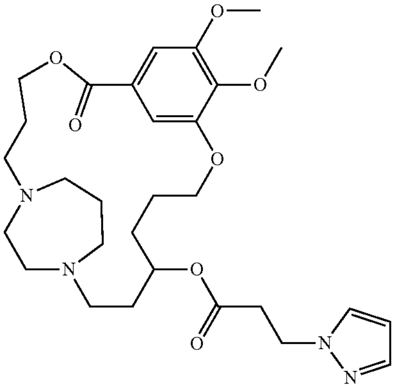 [SMILES: COc1cc2cc(c1OC)OCCCC(OC(=O)CCn1cccn1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-(1H-pyrazol-1-yl)propanoate |

TABLE 1b-continued

| Compound STRUCTURE | | Name |
| --- | --- | --- |
| 95 | 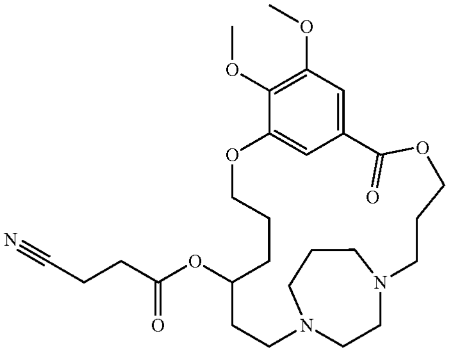 [SMILES: COc1cc2cc(c1OC)OCCCC(OC(=O)CCC#N)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-cyanopropanoate |
| 96 | 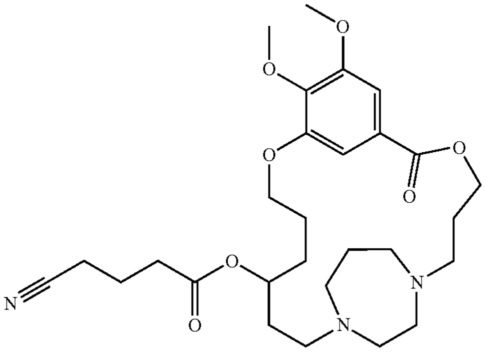 [SMILES: COc1cc2cc(c1OC)OCCCC(OC(=O)CCCC#N)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-cyanobutanoate |
| 97 | 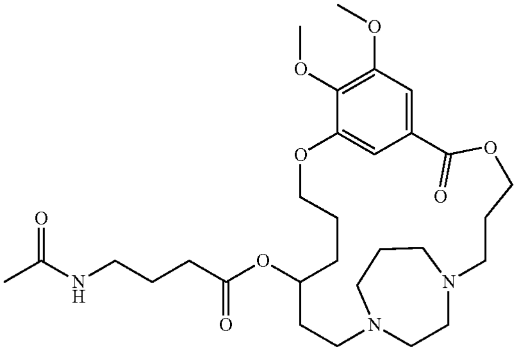 [SMILES: COc1cc2cc(c1OC)OCCCC(OC(=O)CCCNC(C)=O)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-acetamidobutanoate |
| 98 | 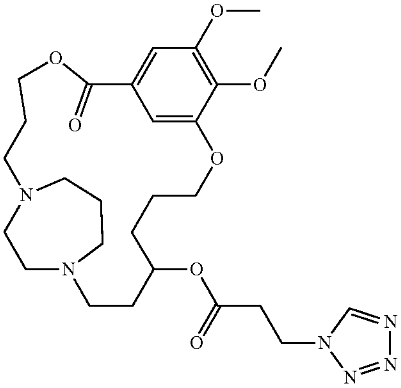 [SMILES: COc1cc2cc(c1OC)OCCCC(OC(=O)CCn1cnnn1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-(1H-tetrazol-1-yl)propanoate |

TABLE 1b-continued

| Compound | STRUCTURE | Name |
| --- | --- | --- |
| 99 | 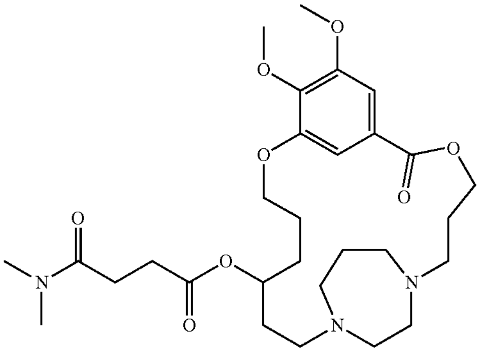 [SMILES: COc1cc2cc(c1OC)OCCCC(OC(=O)CCC(=O)N(C)C)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-(dimethylamino)-4-oxobutanoate |
| 100 | 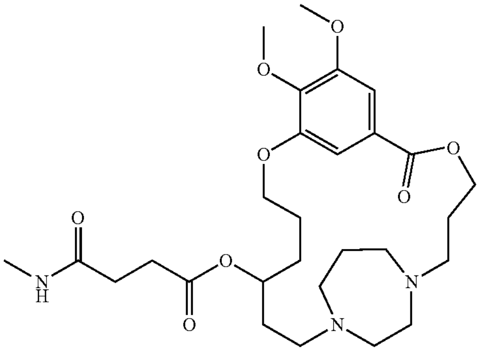 [SMILES: CNC(=O)CCC(=O)OC1CCCOc2cc(cc(OC)c2OC)C(=O)OCCCN2CCCN(CC1)CC2] | 74,75-dimethoxy-6-oxo-5,8-dioxa-1(1,4)-diazepana-7(1,3)-benzenacyclotetradecaphane-12-yl 3-acetamidopropanoate |
| 101 | 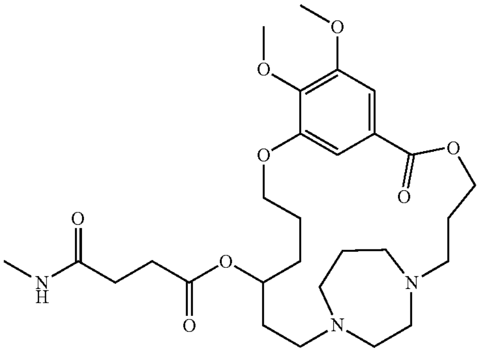 [SMILES: CNC(=O)CCC(=O)OC1CCCOc2cc(cc(OC)c2OC)C(=O)OCCCN2CCCN(CC1)CC2] | 74,75-dimethoxy-6-oxo-5,8-dioxa-1(1,4)-diazepana-7(1,3)-benzenacyclotetradecaphane-12-yl 4-(methylamino)-4-oxobutanoate |
| 102 | 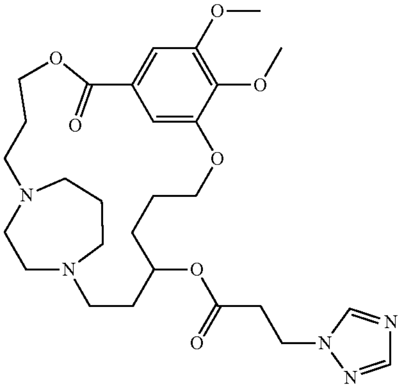 [SMILES: COc1cc2cc(c1OC)OCCCC(OC(=O)CCn1cncn1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-(1H-1,2,4-triazol-1-yl)propanoate |

TABLE 1b-continued

| Compound | STRUCTURE | Name |
|---|---|---|
| 103 | 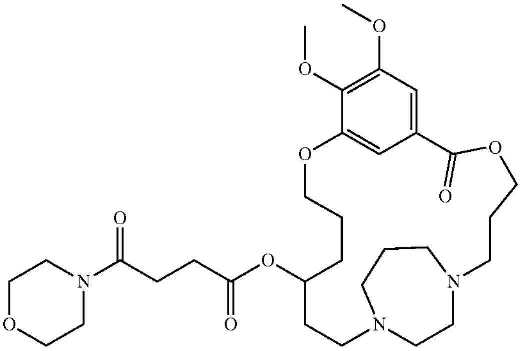 [SMILES: COc1cc2cc(c1OC)OCCCC(OC(=O)CCC(=O)N1CCOCC1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-morpholino-4-oxobutanoate |
| 104 | 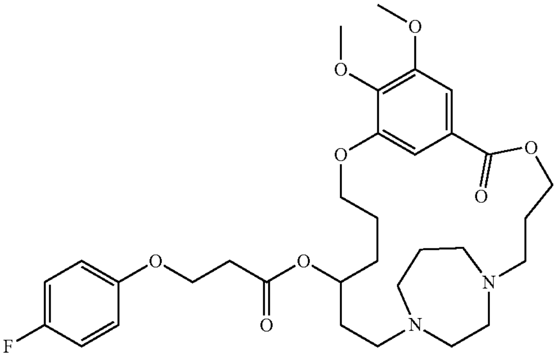 [SMILES: COc1cc2cc(c1OC)OCCCC(OC(=O)CCOc1ccc(F)cc1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-(4-fluorophenoxy)propanoate |
| 105 | 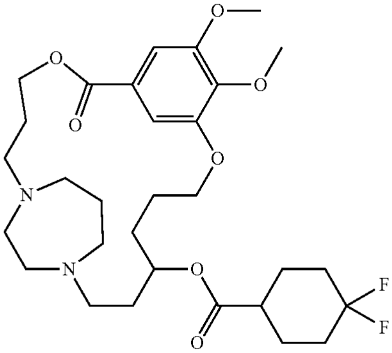 [SMILES: COc1cc2cc(c1OC)OCCCC(OC(=O)C1CCC(F)(F)CC1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4,4-difluorocyclohexane-1-carboxylate |
| 106 | 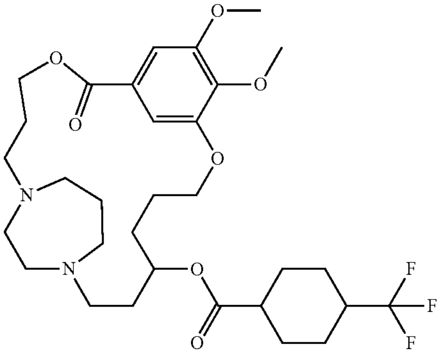 [SMILES: COc1cc2cc(c1OC)OCCCC(OC(=O)C1CCC(C(F)(F)F)CC1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 4-(trifluoromethyl)cyclohexane-1-carboxylate |

TABLE 1b-continued

| Compound STRUCTURE | | Name |
|---|---|---|
| 107 | 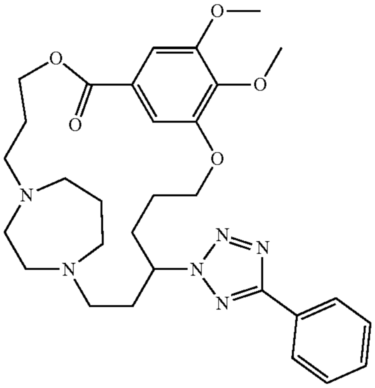 [SMILES: COc1cc2cc(c1OC)OCCCC(n1nnc(-c3ccccc3)n1)CCN1CCCN(CCCOC2=O)CC1] | 74,75-dimethoxy-12-(5-phenyl-2H-tetrazol-2-yl)-5,8-dioxa-1(1,4)-diazepana-7(1,3)-benzenacyclotetradecaphan-6-one |
| 108 | 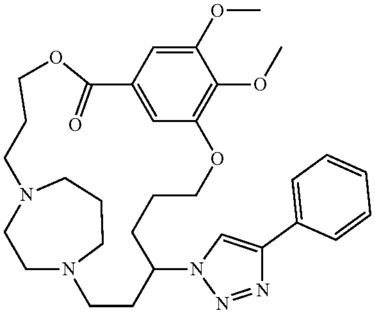 [SMILES: COc1cc2cc(c1OC)OCCCC(n1cc(-c3ccccc3)nn1)CCN1CCCN(CCCOC2=O)CC1] | 74,75-dimethoxy-12-(4-phenyl-1H-1,2,3-triazol-1-yl)-5,8-dioxa-1(1,4)-diazepana-7(1,3)-benzenacyclotetradecaphan-6-one |
| 110 | 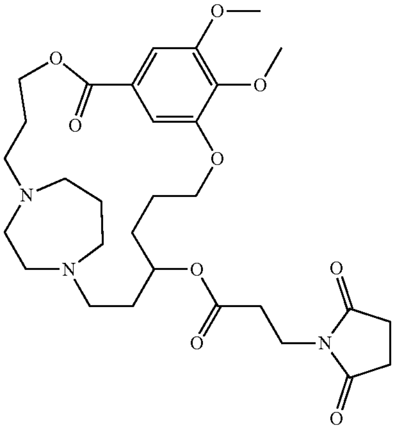 [SMILES: COc1cc2cc(c1OC)OCCCC(OC(=O)CCN1C(=O)CCC1=O)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-(2,5-dioxopyrrolidin-1-yl)propanoate |
| 111 | 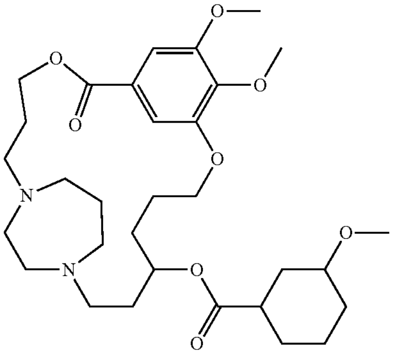 [SMILES: COc1cc2cc(c1OC)OCCCC(OC(=O)C1CCCC(OC)C1)CCN1CCCN(CCCOC2=O)CC1] | 74,75-dimethoxy-6-oxo-5,8-dioxa-1(1,4)-diazepana-7(1,3)-benzenacyclotetradecaphane-12-yl 3-methoxycyclohexane-1-carboxylate |

TABLE 1b-continued
| Compound | STRUCTURE | Name |
|---|---|---|
| 113 | 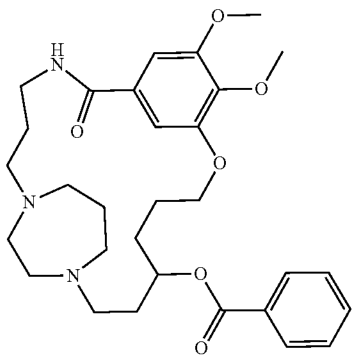 [SMILES: COc1cc2cc(c1OC)OCCCC(OC(=O)c1ccccc1)CCN1CCCN(CCCNC2=O)CC1] | 74,75-dimethoxy-6-oxo-8-oxa-5-aza-1(1,4)-diazepana-7(1,3)-benzenacyclotetradecaphane-12-yl benzoate |
| 114 | 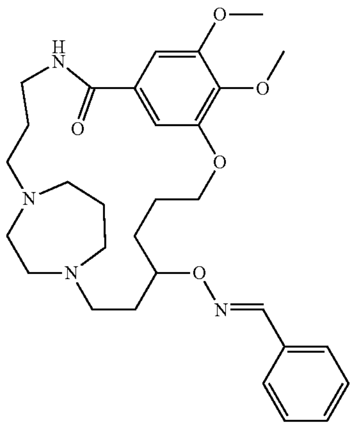 | (E)-benzaldehyde O-(74,75-dimethoxy-6-oxo-8-oxa-5-aza-1(1,4)-diazepana-7(1,3)-benzenacyclotetradecaphane-12-yl) oxime |
| 115 | 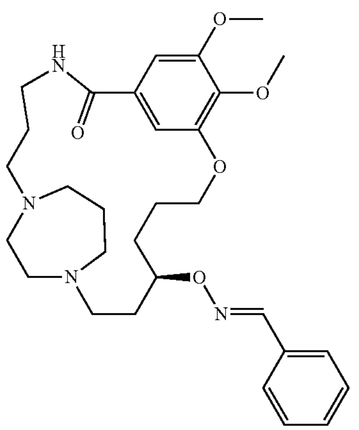 [SMILES: COc1cc2cc(c1OC)OCCC[C@@H](O/N=C/c1ccccc1)CCN1CCCN(CCCNC2=O)CC1] | (E)-benzaldehyde O-((12R)-74,75-dimethoxy-6-oxo-8-oxa-5-aza-1(1,4)-diazepana-7(1,3)-benzenacyclotetradecaphane-12-yl) oxime |

TABLE 1b-continued

| Compound STRUCTURE | Name |
| --- | --- |
| 116 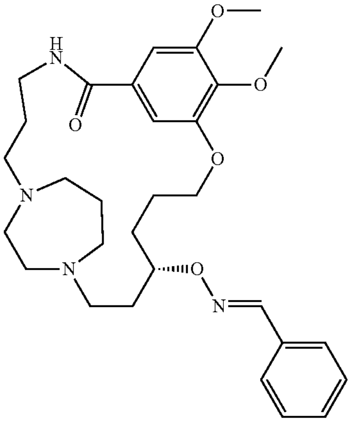 | (E)-benzaldehyde O-((12S)-74,75-dimethoxy-6-oxo-8-oxa-5-aza-1(1,4)-diazepana-7(1,3)-benzenacyclotetradecaphane-12-yl) oxime |
| 117 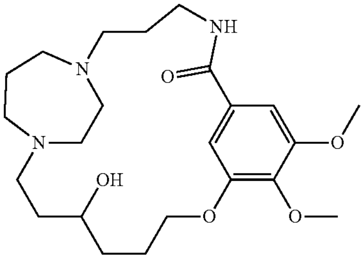 [SMILES: COc1cc2cc(c1OC)OCCCC(O)CCN1CCCN(CCCNC2=O)CC1] | 12-hydroxy-74,75-dimethoxy-8-oxa-5-aza-1(1,4)-diazepana-7(1,3)-benzenacyclotetradecaphan-6-one |
| 118 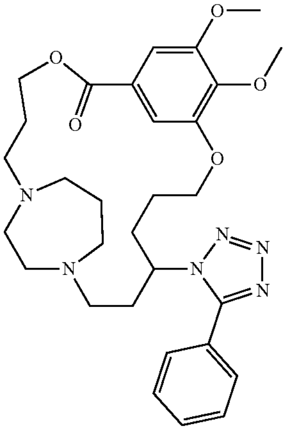 [SMILES: COc1cc2cc(c1OC)OCCCC(n1nnnc1-c1ccccc1)CCN1CCCN(CCCOC2=O)CC1] | 74,75-dimethoxy-12-(5-phenyl-1H-tetrazol-1-yl)-5,8-dioxa-1(1,4)-diazepana-7(1,3)-benzenacyclotetradecaphan-6-one |
| 119 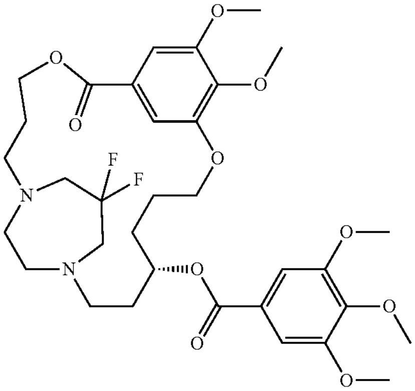 [SMILES: COc1cc(C(=O)O[C@H]2CCCOc3cc(cc(OC)c3OC)C(=O)OCCCN3CCN(CC2)CC(F)(F)C3)cc(OC)c1OC] | (12S)-16,16-difluoro-74,75-dimethoxy-6-oxo-5,8-dioxa-1(1,4)-diazepana-7(1,3)-benzenacyclotetradecaphane-12-yl 3,4,5-trimethoxybenzoate |

TABLE 1b-continued
| Compound STRUCTURE | | Name |
|---|---|---|
| 120 | 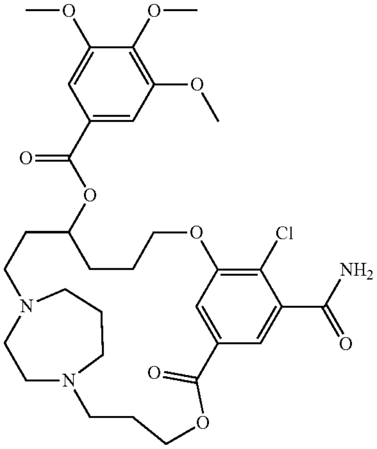 [SMILES: COc1cc(C(=O)OC2CCCOc3cc(cc(C(N)=O)c3Cl)C(=O)OCCCN3CCCN(CC2)CC3)cc(OC)c1OC] | 75-carbamoyl-74-chloro-6-oxo-5,8-dioxa-1(1,4)-diazepana-7(1,3)-benzenacyclotetradecaphane-12-yl 3,4,5-trimethoxybenzoate |
| 121 | 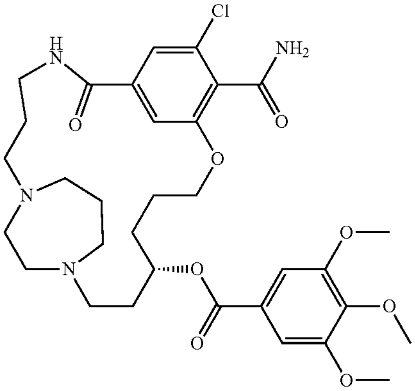 [SMILES: COc1cc(C(=O)O[C@H]2CCCOc3cc(cc(Cl)c3C(N)=O)C(=O)NCCCN3CCCN(CC2)CC3)cc(OC)c1OC] | (12S)-74-carbamoyl-75-chloro-6-oxo-8-oxa-5-aza-1(1,4)-diazepana-7(1,3)-benzenacyclotetradecaphane-12-yl 3,4,5-trimethoxybenzoate |
| 122 | 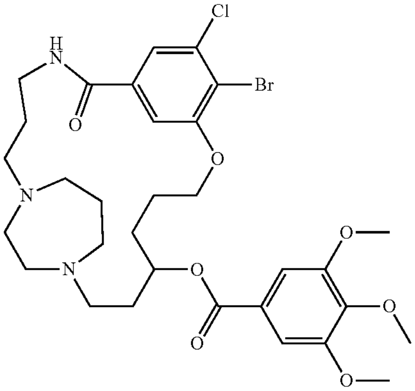 | 74-bromo-75-chloro-6-oxo-8-oxa-5-aza-1(1,4)-diazepana-7(1,3)-benzenacyclotetradecaphane-12-yl 3,4,5-trimethoxybenzoate |

TABLE 1b-continued

| Compound STRUCTURE | Name |
|---|---|
| 123 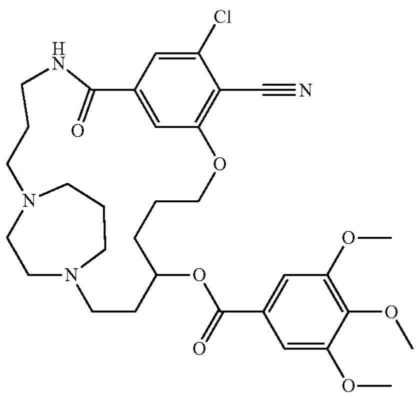 [SMILES: COc1cc(C(=O)OC2CCCOc3cc(cc(Cl)c3C#N)C(=O)NCCCN3CCCN(CC2)CC3)cc(OC)c1OC] | 75-chloro-74-cyano-6-oxo-8-oxa-5-aza-1(1,4)-diazepana-7(1,3)-benzenacyclotetradecaphane-12-yl 3,4,5-trimethoxybenzoate |
| 124 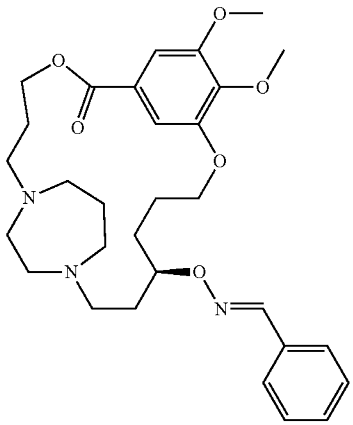 [SMILES: COc1cc2cc(c1OC)OCCC[C@@H](O/N=C/c1ccccc1)CCN1CCCN(CCCOC2=O)CC1] | 74,75-dimethoxy-12-(5-phenyl-1H-tetrazol-1-yl)-5,8-dioxa-1(1,4)-diazepana-7(1,3)-benzenacyclotetradecaphan-6-one |
| 125 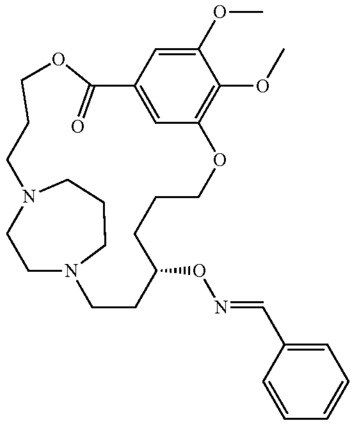 [SMILES: COc1cc2cc(c1OC)OCCC[C@H](O/N=C/c1ccccc1)CCN1CCCN(CCCOC2=O)CC1] | 74,75-dimethoxy-12-(5-phenyl-1H-tetrazol-1-yl)-5,8-dioxa-1(1,4)-diazepana-7(1,3)-benzenacyclotetradecaphan-6-one |

The compounds of Table 1 were named using ChemBioDraw® Ultra version 12.0 (PerkinElmer).

In one embodiment, the present invention also relates to salts, solvates, enantiomers, isomers (including optical, geometric and tautomeric isomers), polymorphs, multi-component complexes, liquid crystals, prodrugs of compounds of formula I or II and subformula thereof, and to isotopically-labeled compounds of formula I or II and subformula thereof.

In one embodiment, the present invention relates to enantiomers and isomers (including optical, geometric and tautomeric isomers) of compounds of formula I and subformula thereof. Indeed, the compounds of formula I or II and subformula thereof may contain an asymmetric center and thus may exist as different stereoisomeric forms. Accordingly, the present invention includes all possible stereoisomers and includes not only racemic compounds but the individual enantiomers and their non-racemic mixtures as well. When a compound is desired as a single enantiomer, such may be obtained by stereospecific synthesis, by resolution of the final product or any convenient Intermediate compound, or by chiral chromatographic methods as each are known in the art. Resolution of the final product, an Intermediate compound, or a starting material may be performed by any suitable method known in the art.

In one embodiment, the present invention also relates to salts of compounds of formula I or II and subformula thereof. Especially, the compounds of the invention may be in the form of pharmaceutically acceptable salts. Pharmaceutically acceptable salts of the compounds of formula I or II ate, ammonium salt, aspartate, benzoate, besylate, benzenesulfonate, bicarbonate/carbonate, bisulphate/sulphate, bitartrate, borate, calcium edetate, camsylate, citrate, clavulanate, cyclamate, dihydrochloride, edetate, edisylate, estolate, esylate, formate, fumarate, gluceptate, gluconate, glucuronate, glutamate, glycollylarsanilate, hexafluorophosphate, hexylresorcinate, hibenzate, hydrabamine, hydrochloride/chloride, hydrobromide/bromide, hydroiodide/iodide, hydroxynaphthoate, isethionate, isothionate, lactate, lactobionate, laurate, malate, maleate, malonate, mandelate, mesylate, methylbromide, N-methylglucamine, methylnitrate, methylsulphate, mucate, panoate, naphthylate, 2-napsylate, nicotinate, nitrate, oleate, orotate, oxalate, palmitate, pamoate, pantothenate, phosphate/hydrogen phosphate/dihydrogen phosphate, polygalacturonate, pyroglutamate, saccharate, salicylate, stearate, subacetate, succinate, tannate, tartrate, teoclate, tosylate, triethiodide, trifluoroacetate, valerate and xinofoate salts. Preferred pharmaceutically acceptable acid addition salts include hydrochloride/chloride, hydrobromide/bromide, bisulphate/sulphate, nitrate, citrate, tosylate, esylate and acetate. Suitable base salts are formed from bases which form non-toxic salts. Examples include the aluminum, ammonia, arginine, benzathine, N-benzylphenethyl-amine, calcium, chloroprocaine, choline, N,N'-dibenzylethylene-diamine, diethanolamine, diethylamine, 2-(diethylamino)ethanol, diolamine, ethanolamine, ethylenediamine, glycine, lithium, lysine, magnesium, meglumine, N-methyl-glutamine, morpholine, 4-(2-hydroxyethyl)morpholine, olamine, ornithine, piperazine, potassium, procaine, sodium, tetramethylammonium hydroxide, tris(hydroxymethyl)aminomethane, tromethamine and zinc salts. Hemisalts of acids and bases may also be formed, for example, hemisulphate and hemicalcium salts. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of formula I or II and subformula thereof may be prepared by one or more of these methods:

(i) by reacting the compound of formula I or II with the desired acid;

(ii) by reacting the compound of formula I or II with the desired base;

(iii) by removing an acid- or base-labile protecting group from a suitable precursor of the compound of formula I or II or by ring-opening a suitable cyclic precursor, for example, a lactone or lactam, using the desired acid; or (iv) by converting one salt of the compound of formula I or II to another by reaction with an appropriate acid or by means of a suitable ion exchange column.

All these reactions are typically carried out in solution. The salt may precipitate from solution and be collected by filtration or may be recovered by evaporation of the solvent. The degree of ionization in the salt may vary from completely ionized to almost non-ionized.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of formula I or II above.

In one embodiment, the present invention also relates to solvates of compounds of formula I or II and subformula thereof. The compounds of the invention may be in the form of pharmaceutically acceptable solvates. Pharmaceutically acceptable solvates of the compounds of formula I or II and subformula thereof contains stoichiometric or sub-stoichiometric amounts of one or more pharmaceutically acceptable solvent molecule such as ethanol or water. The term "hydrate" refers to when the said solvent is water.

In one embodiment, the present invention also relates to prodrugs of compounds of formula I or II and subformula thereof. For example, in the case of an alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

Process of Manufacturing

The compounds of formula I or II can be prepared by different ways with reactions known by one skilled in the art.

The invention also provides a process of manufacturing of compounds of formula I:

(I)

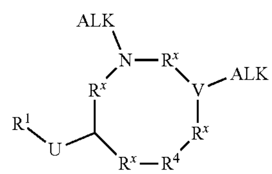

or a pharmaceutically acceptable salt or solvate thereof, wherein $R^x$, $R^1$, $R^4$, U, V, and ALK are hereafter defined.

The invention also provides a process of manufacturing of compounds of formula II:

(II)

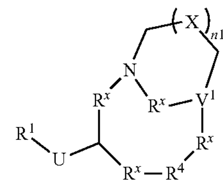

or a pharmaceutically acceptable salt or solvate thereof, wherein $R^x$, $R^1$, $R^4$, X, U, V, and $n^1$ are hereafter defined.

Uses

The invention is further directed to the use of the compounds of the invention, or pharmaceutically acceptable salts and solvates thereof, as inhibitors of ENT family transporters. Accordingly, in a particularly preferred embodiment, the invention relates to the use of compounds of formula I or II and subformula in particular those of Table 1 above, or pharmaceutically acceptable salts and solvates thereof, as inhibitors of ENT family transporters.

In one embodiment, the compounds of the invention are inhibitors of ENT1, ENT2, ENT3 and/or ENT4. In one embodiment, the compounds of the invention are inhibitors of ENT1 and ENT2. In one embodiment, the compounds of the invention are inhibitors of ENT1, preferably selective inhibitors of ENT1. In one embodiment, the compounds of the invention are inhibitors selective of ENT1, with respect to other ENT family transporters, especially with respect to ENT2 and ENT4.

The invention also provides a method for inhibiting ENT family transporters, especially ENT1, in a patient, preferably a warm-blooded animal, and even more preferably a human, in need thereof, which comprises administering to said patient an effective amount of a compound of the invention, or a pharmaceutically acceptable salt and solvate thereof.

The invention is further directed to the use of the compounds of the invention as a medicament, i.e. for medical use. Thus, in one embodiment, the invention provides the use of the compounds of the invention for the manufacturing of a medicament. Especially, the invention provides the use of the compounds of the invention for the manufacturing of a medicament.

Especially, the invention provides the compounds of the invention, for use in the treatment and/or prevention of proliferative disorders, including cancers. Thus, in one embodiment, the invention provides the use of the compounds of the invention for the manufacture of a medicament for treating and/or preventing cancer. The invention also provides a method of treatment of cancer, which comprises administering to a mammal species in need thereof a therapeutically effective amount of a compound of the invention.

The invention also provides for a method for delaying in patient the onset of cancer comprising the administration of a pharmaceutically effective amount of a compound of the invention to a patient in need thereof.

Various cancers are known in the art. Cancers that can be treated using the methods of the invention include solid cancers and non-solid cancers, especially benign and malignant solid tumors and benign and malignant non-solid tumors. The cancer may be metastatic or non-metastatic. The cancer may be may be familial or sporadic.

In one embodiment, the cancer to be treated according to the present invention is a solid cancer. As used herein, the term "solid cancer" encompasses any cancer (also referred to as malignancy) that forms a discrete tumor mass, as opposed to cancers (or malignancies) that diffusely infiltrate a tissue without forming a mass.

Examples of solid tumors include, but are not limited to: biliary tract cancer, brain cancer (including glioblastomas and medulloblastomas), breast cancer, carcinoid, cervical cancer, choriocarcinoma, colon cancer, colorectal cancer, endometrial cancer, esophageal cancer, gastric cancer, glioma, head and neck cancer, intraepithelial neoplasms (including Bowen's disease and Paget's disease), liver cancer, lung cancer, neuroblastomas, oral cancer (including squamous cell carcinoma), ovarian cancer (including those arising from epithelial cells, stromal cells, germ cells and mesenchymal cells), pancreatic cancer, prostate cancer, rectal cancer, renal cancer (including adenocarcinoma and Wilms tumor), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumors (seminomas, and non-seminomas such as teratomas and choriocarcinomas), stromal tumors, germ cell tumors, thyroid cancer (including thyroid adenocarcinoma and medullary carcinoma) and urothelial cancer.

In another embodiment, the cancer to be treated according to the present invention is a non-solid cancer. Examples of non-solid tumors include but are not limited to hematological neoplasms. As used herein, a hematologic neoplasm is a term of art which includes lymphoid disorders, myeloid disorders, and AIDS associated leukemias.

Lymphoid disorders include but are not limited to acute lymphocytic leukemia and chronic lymphoproliferative disorders (e.g., lymphomas, myelomas, and chronic lymphoid leukemias). Lymphomas include, for example, Hodgkin's disease, non-Hodgkin's lymphoma lymphomas, and lymphocytic lymphomas). Chronic lymphoid leukemias include, for example, T cell chronic lymphoid leukemias and B cell chronic lymphoid leukemias.

In a specific embodiment, the cancer is selected from breast, carcinoid, cervical, colorectal, endometrial, glioma, head and neck, liver, lung, melanoma, ovarian, pancreatic, prostate, renal, gastric, thyroid and urothelial cancers.

In a specific embodiment, the cancer is breast cancer. In a specific embodiment, the cancer is carcinoid cancer. In a specific embodiment, the cancer is cervical cancer. In a specific embodiment, the cancer is colorectal cancer. In a specific embodiment, the cancer is endometrial cancer. In a specific embodiment, the cancer is glioma. In a specific embodiment, the cancer is head and neck cancer. In a specific embodiment, the cancer is liver cancer. In a specific embodiment, the cancer is lung cancer. In a specific embodiment, the cancer is melanoma. In a specific embodiment, the cancer is ovarian cancer. In a specific embodiment, the cancer is pancreatic cancer. In a specific embodiment, the cancer is prostate cancer. In a specific embodiment, the cancer is renal cancer. In a specific embodiment, the cancer is gastric cancer. In a specific embodiment, the cancer is thyroid cancer. In a specific embodiment, the cancer is urothelial cancer.

In another specific embodiment, the cancer is selected from the group consisting of: leukemia and multiple myeloma.

Preferably, the patient is a warm-blooded animal, more preferably a human.

In one embodiment, the cancer to be treated according to the present invention is a solid cancer. As used herein, the term "solid cancer" encompasses any cancer (also referred to as malignancy) that forms a discrete tumor mass, as opposed to cancers (or malignancies) that diffusely infiltrate a tissue without forming a mass.

Examples of solid tumors include, but are not limited to: biliary tract cancer, brain cancer (including glioblastomas and medulloblastomas), breast cancer, carcinoid, cervical cancer, choriocarcinoma, colon cancer, colorectal cancer, endometrial cancer, esophageal cancer, gastric cancer, glioma, head and neck cancer, intraepithelial neoplasms (including Bowen's disease and Paget's disease), liver cancer, lung cancer, neuroblastomas, oral cancer (including squamous cell carcinoma), ovarian cancer (including those arising from epithelial cells, stromal cells, germ cells and mesenchymal cells), pancreatic cancer, prostate cancer, rectal cancer, renal cancer (including adenocarcinoma and Wilms tumor), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumors (seminomas, and non-seminomas such as teratomas and choriocarcinomas), stromal tumors, germ cell tumors, thyroid cancer (including thyroid adenocarcinoma and medullary carcinoma) and urothelial cancer.

In another embodiment, the cancer to be treated according to the present invention is a non-solid cancer. Examples of non-solid tumors include but are not limited to hematological neoplasms. As used herein, a hematologic neoplasm is a term of art which includes lymphoid disorders, myeloid disorders, and AIDS associated leukemias.

Lymphoid disorders include but are not limited to acute lymphocytic leukemia and chronic lymphoproliferative disorders (e.g., lymphomas, myelomas, and chronic lymphoid leukemias). Lymphomas include, for example, Hodgkin's disease, non-Hodgkin's lymphoma lymphomas, and lymphocytic lymphomas). Chronic lymphoid leukemias include, for example, T cell chronic lymphoid leukemias and B cell chronic lymphoid leukemias.

In a specific embodiment, the cancer is selected from breast, carcinoid, cervical, colorectal, endometrial, glioma, head and neck, liver, lung, melanoma, ovarian, pancreatic, prostate, renal, gastric, thyroid and urothelial cancers.

In a specific embodiment, the cancer is breast cancer. In a specific embodiment, the cancer is carcinoid cancer. In a specific embodiment, the cancer is cervical cancer. In a specific embodiment, the cancer is colorectal cancer. In a specific embodiment, the cancer is endometrial cancer. In a specific embodiment, the cancer is glioma. In a specific embodiment, the cancer is head and neck cancer. In a specific embodiment, the cancer is liver cancer. In a specific embodiment, the cancer is lung cancer. In a specific embodiment, the cancer is melanoma. In a specific embodiment, the cancer is ovarian cancer. In a specific embodiment, the cancer is pancreatic cancer. In a specific embodiment, the cancer is prostate cancer. In a specific embodiment, the cancer is renal cancer. In a specific embodiment, the cancer is gastric cancer. In a specific embodiment, the cancer is thyroid cancer. In a specific embodiment, the cancer is urothelial cancer.

In another specific embodiment, the cancer is selected from the group consisting of: leukemia and multiple myeloma.

Preferably, the patient is a warm-blooded animal, more preferably a human.

In one embodiment, the subject receiving the ENT inhibitor of the invention is treated with an additional therapeutic agent in combination with the ENT inhibitor of the invention, or has received the additional therapeutic agent within about fourteen days of administration of the ENT inhibitor of the invention. In one embodiment, the additional therapeutic agent comprises an adenosine receptor antagonist.

In one embodiment, the subject has previously received at least one prior therapeutic treatment, and has progressed subsequent to the administration of the at least one prior therapeutic treatment and prior to administration of the ENT inhibitor of the invention. In one embodiment, the prior therapeutic treatment is selected from the group consisting of chemotherapy, immunotherapy, radiation therapy, stem cell transplant, hormone therapy, and surgery.

In one embodiment, ENT inhibitor of the invention is administered prior to, concomitant with, or subsequent to administration of the additional therapeutic agent, such as an adenosine receptor antagonist.

The invention also provides pharmaceutical compositions comprising a compound of formula I or II and subformula thereof, or a pharmaceutically acceptable salt and solvate thereof, and at least one pharmaceutically acceptable carrier, diluent, excipient and/or adjuvant.

Another object of this invention is a medicament comprising at least one compound of the invention, or a pharmaceutically acceptable salt and solvate thereof, as active ingredient.

Generally, for pharmaceutical use, the compounds of the invention may be formulated as a pharmaceutical preparation comprising at least one compound of the invention and at least one pharmaceutically acceptable carrier, diluent, excipient and/or adjuvant, and optionally one or more further pharmaceutically active compounds. Details regarding the presence of further pharmaceutically active compounds are provided hereafter.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Depending on the condition to be prevented or treated and the route of administration, the active compound of the invention may be administered as a single daily dose, divided over one or more daily doses, or essentially continuously, e.g. using a drip infusion.

Formulations

Combined Use with Adenosine Receptor Antagonist

The invention further relates to the combined use of an ENT inhibitor of the invention, of formula I or II or a subformula thereof, as defined above, with an adenosine receptor antagonist.

The invention thus relates to a combination comprising: an effective amount of an ENT inhibitor of the invention, of formula I or II a subformula thereof, as defined above; and (b) an effective amount of an adenosine receptor antagonist.

In the context of the present invention the term "combination" preferably means a combined occurrence of the ENT inhibitor and of an A2AR antagonist. Therefore, the combination of the invention may occur either as one composition, comprising all the components in one and the same mixture (e.g. a pharmaceutical composition), or may occur as a kit of parts, wherein the different components form different parts of such a kit of parts. The administration of the ENT inhibitor and of the A2AR antagonist may occur either simultaneously or timely staggered, with similar or different timing of administration (i.e. similar or different numbers of administration of each component), either at the same site of administration or at different sites of administration, under similar of different dosage form.

The invention further relates to a method of treating cancer, comprising: administering, to a patient in need thereof, a combination of an adenosine receptor antagonist and the ENT inhibitor of the invention.

Above embodiments relative to the ENT inhibitors of the invention also apply to the combination of the invention. Especially, in one embodiment, in the combination of the invention, the ENT inhibitor may be of formula I or II of the subformula defined above.

As a second component, the combination of the invention includes at least one adenosine receptor antagonist.

As defined above, "adenosine receptor antagonist" refers to a compound that, upon administration to a patient, results in inhibition or down-regulation of a biological activity associated with activation of an adenosine receptor in the patient, including any of the downstream biological effects otherwise resulting from the binding to an adenosine receptor of its natural ligand. Such adenosine receptor antagonists include any agent that can block activation of an adenosine receptor or any of the downstream biological effects of an adenosine receptor activation.

Adenosine receptors (or P1 receptors) are a class of purinergic G protein-coupled receptors with adenosine as endogenous ligand. There are four known types of adenosine receptors in humans: A1, A2A, A2B and A3; each is encoded by a different gene (ADOARA1, ADORA2A, ADORA2B, and ADORA3 respectively).

In one embodiment, the adenosine receptor antagonist is an antagonist of A1 receptor, A2A receptor, A2B receptor, A3 receptor or of a combination thereof.

In one embodiment, the adenosine receptor antagonist is an antagonist of A2A receptor, A2B receptor or of a combination thereof. In one embodiment, the adenosine receptor antagonist is an A2A or A2B receptor antagonist.

In one embodiment, the adenosine receptor antagonist is an antagonist of A2A receptor (A2AR antagonist). In one embodiment, the adenosine receptor antagonist is an antagonist of A2B receptor (A2BR antagonist).

In one embodiment, the adenosine receptor antagonist is an antagonist which is selective of A2A receptor with respect to other adenosine receptors. In one embodiment, the adenosine receptor antagonist is an antagonist which is selective of A2A receptor with respect to A2B receptor.

In one embodiment, the adenosine receptor antagonist is an antagonist which is selective of A2B receptor with respect to other adenosine receptors. In one embodiment, the adenosine receptor antagonist is an antagonist which is selective of A2B receptor with respect to A2A receptor.

In a specific embodiment, the combination of the invention comprises at least one A2A receptor antagonist as herein defined and at least one ENT inhibitor of formula I or II as defined above.

A2A Receptor Antagonist

In one embodiment, the combination of the invention includes at least one A2AR antagonist.

An "A2AR antagonist" refers to a compound that, upon administration to a patient, results in inhibition or down-regulation of a biological activity associated with activation of A2A receptor in the patient, including any of the downstream biological effects otherwise resulting from the binding to A2A receptor of its natural ligand. Such A2AR antagonists include any agent that can block activation of A2A receptor or any of the downstream biological effects of A2A receptor activation.

Examples of A2AR antagonists include: Preladenant (SCH-420,814), Vipadenant (BIIB-014), Tozadenant (SYK-115), ATL-444, Istradefylline (KW-6002), MSX-3, SCH-58261, SCH-412,348, SCH-442,416, ST-1535, Caffeine, VER-6623, VER-6947, VER-7835, ZM-241,385, theophylline. It also includes A2AR antagonists disclosed in WO2018/178338, WO2011/121418, WO2009/156737, WO2011/095626 or WO2018/136700, the content of which is herein incorporated by reference.

In one embodiment, the A2AR antagonist is a thiocarbamate derivative, especially a thiocarbamate derivative as those disclosed in WO2018/178338. More preferably the A2AR antagonist is a thiocarbamate derivative of formula (III) as described below.

Thus, in a specific embodiment, the invention provides a combination comprising:

an ENT inhibitor according to the invention, of formula I or II or a subformula thereof, as defined above; and (b) an A2AR antagonist being a thiocarbamate derivative of Formula (III) according to WO2018/178338:

(III)

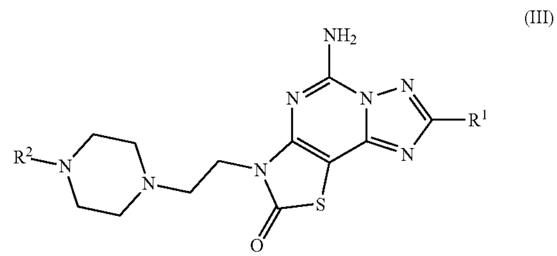

or a pharmaceutically acceptable salt or solvate thereof, wherein $R^1$ and $R^2$ are as defined below.

In a preferred embodiment, the A2AR antagonist is thus a compound of Formula (III), or a pharmaceutically acceptable salt or solvate thereof, wherein:

$R^1$ represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro); preferably $R^1$ represents 5-membered heteroaryl; more preferably $R^1$ represents furyl;

$R^2$ represents 6-membered aryl or 6-membered heteroaryl;

wherein heteroaryl or aryl groups are optionally substituted by one or more substituent selected from halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino and alkylsulfonealkyl;

said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl alkylsulfonyl and alkylsulfonealkyl;

or the heteroaryl or aryl groups are optionally substituted with two substituents that form together with the atoms to which they are attached a 5- or 6-membered aryl ring, a 5- or 6-membered heteroaryl ring, a 5- or 6-membered cycloalkyl ring or a 5- or 6-membered heterocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In one embodiment, preferred A2AR antagonists of Formula (III) are of Formula (IIIa):

(IIIa)

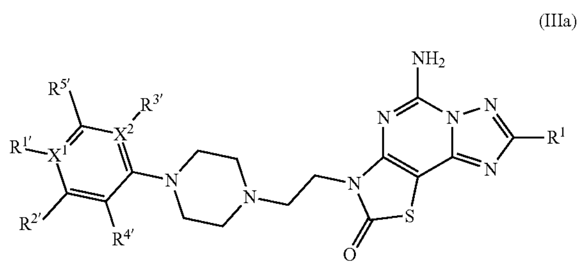

or a pharmaceutically acceptable salt or solvate thereof, wherein:

$R^1$ represents 5- or 6-membered heteroaryl or 5- or 6-membered aryl, wherein heteroaryl or aryl groups are optionally substituted by one or more substituent selected from C1-C6 alkyl (preferably methyl) and halo (preferably fluoro or chloro); preferably $R^1$ represents 5-membered heteroaryl; more preferably $R^1$ represents furyl;

$X^1$ and $X^2$ represent each independently C or N;

$R^{1'}$ is absent when $X^1$ is N; or when $X^1$ is C, $R^{1'}$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino or alkylsulfonealkyl;

said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

$R^{2'}$ represents H, halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino, or alkylsulfonealkyl;

said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

or $R^{1'}$ and $R^{2'}$ form together with the atoms to which they are attached a 5- or 6-membered aryl ring, a 5- or 6-membered heteroaryl ring, a 5- or 6-membered cycloalkyl ring or a 5- or 6-membered heterocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl;

$R^{3'}$ is absent when $X^2$ is N; or when $X^2$ is C, $R^{3'}$ represents H or halo, preferably H or F;

$R^{4'}$ represents H or halo, preferably H or F; and $R^{5'}$ represents H or halo, preferably H or F.

In one embodiment, preferred A2AR antagonists of Formula (IIIa) are those of Formula (IIIa-1):

(IIIa-1)

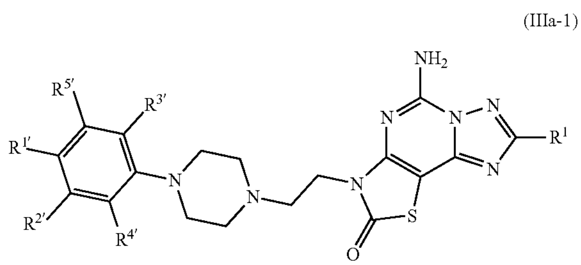

or a pharmaceutically acceptable salt or solvate thereof, wherein $R^1$, $R^{1'}$, $R^{2'}$, $R^{3'}$, $R^{4'}$ and $R^{5'}$ are as defined in Formula (IIIa).

In one embodiment, preferred A2AR antagonists of Formula (IIIa-1) are those of Formula (IIIa-1a):

(IIIa-1a)

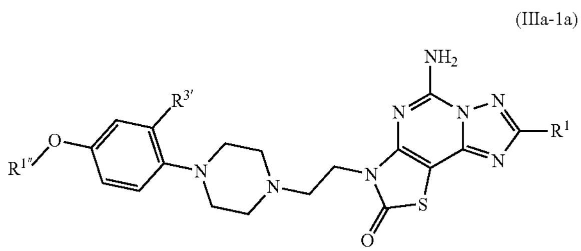

or a pharmaceutically acceptable salt or solvate thereof, wherein:

$R^1$ and $R^{3'}$ are as defined in Formula (IIIa); and $R^{1''}$ represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In one embodiment, preferred A2AR antagonists of Formula (IIIa-1) are those of Formula (IIIa-1b):

(IIIa-1b)

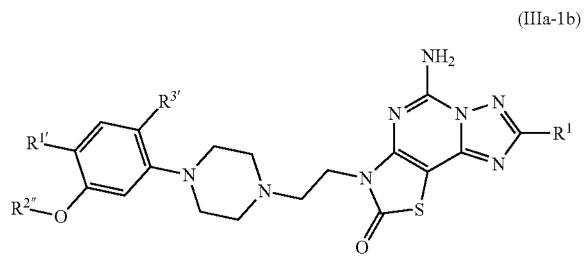

or a pharmaceutically acceptable salt or solvate thereof, wherein:

$R^1$ and $R^{3'}$ are as defined in Formula (IIIa);

$R^{1'}$ represents H or halo, preferably H or F; and $R^{2''}$ represents an alkyl or heterocyclyl group substituted by one or more group selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

In one embodiment, preferred A2AR antagonists of Formula (IIIa-1) are those of Formula (IIIa-1c) or (IIIa-1d):

(IIIa-1c)

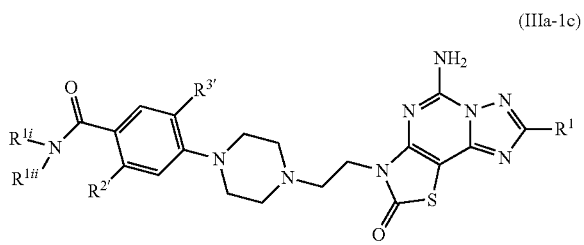

(IIIa-1d)

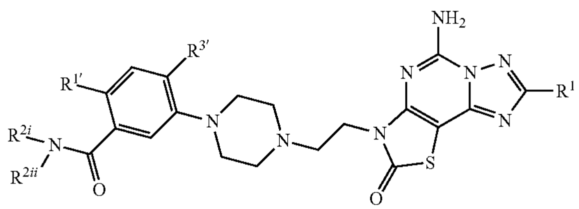

or a pharmaceutically acceptable salt or solvate thereof, wherein:

$R^1$ and $R^{3'}$ are as defined in Formula (IIIa);

$R^{1'}$ represents H or halo, preferably H or F;

$R^{2'}$ represents H or halo, preferably H or F;

$R^{1i}$ and $R^{1ii}$ represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl; and $R^{2i}$ and $R^{2ii}$ represent each independently hydrogen, hydroxy, alkyl, alkenyl, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkynealkyl, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxidealkyl or alkylsulfonealkyl.

In one embodiment, preferred A2AR antagonists of Formula (IIIa) are those of Formulae (IIIa-2) or (IIIa-3):

(IIIa-2)

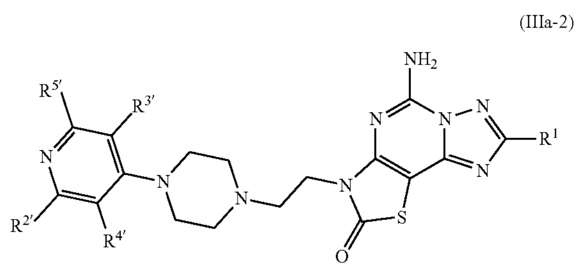

(IIIa-3)

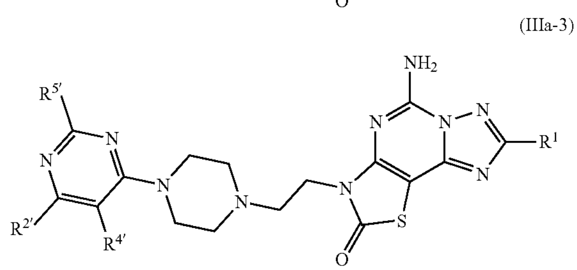

or a pharmaceutically acceptable salt or solvate thereof, wherein $R^1$, $R^{2'}$, $R^{3'}$, $R^{4'}$ and $R^{5'}$ are as defined in Formula (IIIa).

Particularly preferred A2AR antagonists of Formula (III) are those listed hereafter:

3-(2-(4-(4-((1H-1,2,3-triazolo-4yl)methoxy-2fluorophenyl) piperazine-1-yl)ethyl)-5-amino-(8-(furan-2-yl)thiazolo[5,4-e][1,2,4]triazolo[1,5-c]pyrimidine-2(3H)-one 5-((4-(4-(2-(5-amino-8-(furan-2-yl)-2-oxothiazolo [5,4-e][1,2,4]triazolo[1,5-c]pyrimidin-3(2H)- yl)ethyl)piperazin-1-yl)-3-fluorophenoxy)methyl)-1,3,4-oxadiazol-2(3H)-one 5-amino-3-(2-(4-(3-fluoropyridin-4-yl)piperazin-1-yl) ethyl)-8-(furan-2-yl)thiazolo[5,4-e][1,2,4]triazolo[1,5-c]pyrimidin-2(3H)-one 2-(5-(4-(2-(5-amino-8-(furan-2-yl)-2-oxothiazolo[5,4-e][1,2,4]triazolo [1,5-c]pyrimidin-3(2H)- yl)ethyl)piperazin-1-yl)-2,4-difluorophenoxy)acetamide (S)-5-amino-3-(2-(4-(2-fluoro-4-(2-(methylsulfinyl)ethoxy) phenyl)piperazin-1-yl)ethyl)-8-(furan-2-yl)thiazolo[5,4-e][1,2,4]triazolo[1,5-c]pyrimidin-2(3H)-one (R)-5-amino-3-(2-(4-(2-fluoro-4-(2-(methylsulfinyl)ethoxy) phenyl)-piperazin-1-yl)ethyl)-8-(furan-2-yl)thiazolo[5,4-e][1,2,4]triazolo[1,5-c]pyrimidin-2(3H)-one (R,S)-5-amino-3-(2-(4-(2,4-difluoro-5-(2-(methylsulfinyl) ethoxy)phenyl)piperazin-1-yl)ethyl)-8-(furan-2-yl)thiazolo[5,4-e][1,2,4]triazolo[1,5-c]pyrimidin-2(3H)-one (+)-5-amino-3-(2-(4-(2,4-difluoro-5-(2-(methylsulfinyl) ethoxy)phenyl)piperazin-1-yl)ethyl)-8-(furan-2-yl)thiazolo[5,4-e][1,2,4]triazolo[1,5-c]pyrimidin-2(3H)-one (−)-5-amino-3-(2-(4-(2,4-difluoro-5-(2-(methylsulfinyl) ethoxy)phenyl)piperazin-1-yl)ethyl)-8-(furan-2-yl)thiazolo[5,4-e][1,2,4]triazolo[1,5-c]pyrimidin-2(3H)-one 5-amino-8-(furan-2-yl)-3-(2-(4-(4-(2-hydroxyethoxy) phenyl)piperazin-1-yl)ethyl)thiazolo[5,4-e][1,2,4]triazolo[1,5-c]pyrimidin-2(3H)-one 2-(4-(4-(2-(5-amino-8-(furan-2-yl)-2-oxothiazolo [5,4-e][1,2,4]triazolo[1,5-c]pyrimidin-3(2H)- yl)ethyl)piperazin-1-yl)phenoxy)acetic acid 2-(4-(4-(2-(5-amino-8-(furan-2-yl)-2-oxothiazolo [5,4-e][1,2,4]triazolo[1,5-c]pyrimidin-3(2H)- yl)ethyl)piperazin-1-yl)phenoxy)acetamide 5-amino-3-(2-(4-(4-(2,3-dihydroxypropoxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(4-(2-aminoethoxy)phenyl)piperazin-1-yl) ethyl)-8-(furan-2-yl)thiazolo[5,4-e]triazolo[1,5-c]pyrimidin-2(3H)-one 4-(4-(2-(5-amino-8-(furan-2-yl)-2-oxothiazolo[5,4-e][1,2,4] triazolo[1,5-c]pyrimidin-3(2H)-yl) ethyl)piperazin-1-yl) benzamide 4-(4-(2-(5-amino-8-(furan-2-yl)-2-oxothiazolo[5,4-e][1,2,4] triazolo[1,5-c]pyrimidin-3(2H)- yl)ethyl)piperazin-1-yl)-N-methylbenzamide 5-amino-8-(furan-2-yl)-3-(2-(4-(4-(2-morpholinoethoxy) phenyl)piperazin-1-yl)ethyl)thiazolo[5,4-e][1,2,4]triazolo[1,5-c]pyrimidin-2(3H)-one 5-amino-3-(2-(4-(4-(2-(dimethylamino)ethoxy)phenyl)piperazin-1-yl)ethyl)-8-(furan-2-yl)thiazolo[5,4-e][1,2,4]triazolo[1,5-c]pyrimidin-2(3H)-one 4-(4-(2-(5-amino-8-(furan-2-yl)-2-oxothiazolo[5,4-e][1,2,4] triazolo[1,5-c]pyrimidin-3(2H)- yl)ethyl)piperazin-1-yl) benzenesulfonamide 4-(4-(2-(5-amino-8-(furan-2-yl)-2-oxothiazolo[5,4-e][1,2,4] triazolo[1,5-c]pyrimidin-3(2H)-yl)ethyl) piperazin-1-yl)-N-methylbenzenesulfonamide 5-amino-8-(furan-2-yl)-3-(2-(4-(4-(methylsulfonyl) phenyl) piperazin-1-yl)ethyl)thiazolo[5,4-e][1,2,4]triazolo[1,5-c] pyrimidin-2(3H)-one 5-amino-8-(furan-2-yl)-3-(2-(4-(4-(methylsulfinyl) phenyl) piperazin-1-yl)ethyl)thiazolo[5,4-e][1,2,4]triazolo[1,5-c] pyrimidin-2(3H)-one 3-(4-(2-(5-amino-8-(furan-2-yl)-2-oxothiazolo[5,4-e][1,2,4] triazolo[1,5-c]pyrimidin-3(2H)- yl)ethyl)piperazin-1-yl) benzamide 5-amino-8-(furan-2-yl)-3-(2-(4-(3-(2-hydroxyethoxy) phenyl)piperazin-1-yl)ethyl)thiazolo[5,4-e][1,2,4]triazolo[1,5-c]pyrimidin-2(3H)-one 5-amino-3-(2-(4-(2-fluoro-4-(2-oxo-2-(piperazin-1-yl) ethoxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(piperidin-4-ylmethoxy) phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(piperazine-1-carbonyl) phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(2-(piperazin-1-yl)ethoxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(piperazin-1-ylsulfonyl)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(methylsulfonyl)phenyl) piperazin-1-yl)ethyl)-8-(furan-2-yl)thiazolo[5,4-e][1,2,4]triazolo[1,5-c]pyrimidin-2(3H)-one 4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-N-(2-aminoethyl)-3-fluorobenzamide 4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-3-fluoro-N-(2-(methylamino)ethyl) benzamide 4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-N-(2-(dimethylamino)ethyl)-3-fluorobenzamide 4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-3-fluoro-N-(2-hydroxyethyl)benzamide 4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-N-(2,3-dihydroxypropyl)-3-fluorobenzamide 2-(4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-3-fluorophenoxy)acetic acid 2-(4-(4-(2-(5-amino-8-(furan-2-yl)-2-oxothiazolo [5,4-e][1,2,4]triazolo[1,5-c]pyrimidin-3(2H)- yl)ethyl) piperazin-1-yl)-3,5-difluorophenoxy) acetic acid 2-(4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-3-fluorophenoxy)propanoic acid (S)-2-(4-(4-(2-(5-amino-8-(furan-2-yl)-2-oxothiazolo [5,4-e][1,2,4]triazolo[1,5-c]pyrimidin-3(2H)-yl)ethyl)piperazin-1-yl)-3-fluorophenoxy)propanoic acid 2-(4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-3-fluorophenoxy)-2-methylpropanoic acid 3-(4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-3-fluorophenyl)propanoic acid 4-(4-(4-(2-(5-amino-8-(furan-2-yl)-2-oxothiazolo [5,4-e][1,2,4]triazolo[1,5-c]pyrimidin-3(2H)- yl)ethyl)piperazin-1-yl)-3-fluorophenoxy)butanoic acid 2-(3-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-2,6-difluorophenoxy) acetic acid 2-(5-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-2,4-difluorophenoxy) acetic acid 4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-3-fluorobenzoic acid 2-((2-(4-(4-(2-(5-amino-8-(furan-2-yl)-2-oxothiazolo [5,4-e][1,2,4]triazolo[1,5-c]pyrimidin-3(2H)-yl)ethyl)piperazin-1-yl)-3-fluorophenoxy)ethyl) amino)acetamide 2-((2-(4-(4-(2-(5-amino-8-(furan-2-yl)-2-oxothiazolo [5,4-e][1,2,4]triazolo[1,5-c]pyrimidin-3(2H)-yl)ethyl)piperazin-1-yl)-3-fluorophenoxy)ethyl)(methyl)amino)acetamide 5-amino-3-(2-(4-(2-fluoro-4-(piperidin-4-yloxy) phenyl) piperazin-1-yl) ethyl)-8-(furan-2-yl) thiazolo[5,4-e][1,2,4]triazolo[1,5-c]pyrimidin-2(3H)-one 5-amino-3-(2-(4-(2-fluoro-4-(pyrrolidin-3-yloxy)phenyl) piperazin-1-yl)ethyl)-8-(furan-2-yl)thiazolo[5,4-e][1,2,4]triazolo[1,5-c]pyrimidin-2(3H)-one 3-(2-(4-(4-((1H-1,2,4-triazol-3-yl)methoxy)-2-fluorophenyl)piperazin-1-yl)ethyl)-5-amino-8-(furan-2-yl)thiazolo[5,4-e][1,2,4]triazolo[1,5-c]pyrimidin-2(3H)-one 2-(4-(4-(2-(5-amino-8-(furan-2-yl)-2-oxothiazolo [5,4-e][1,2,4]triazolo[1,5-c]pyrimidin-3(2H)- yl)ethyl)piperazin-1-yl)-3-fluorophenoxy)-N-(2-(methylamino)ethyl) acetamide 2-(4-(4-(2-(5-amino-8-(furan-2-yl)-2-oxothiazolo [5,4-e][1,2,4]triazolo[1,5-c]pyrimidin-3(2H)-yl) ethyl)piperazin-1-yl)-3-fluorophenoxy)-N-(2-(dimethylamino)ethyl) acetamide 2-(4-(4-(2-(5-amino-8-(furan-2-yl)-2-oxothiazolo [5,4-e][1,2,4]triazolo[1,5-c]pyrimidin-3(2H)- yl)ethyl)piperazin-1-yl)-3-fluorophenoxy)-N-(2-aminoethyl)acetamide (R)-2-(4-(4-(2-(5-amino-8-(furan-2-yl)-2-oxothiazolo [5,4-e][1,2,4]triazolo[1,5-c]pyrimidin-3(2H)-yl)ethyl)piperazin-1-yl)-3-fluorophenoxy)propanoic acid 2-(4-(4-(2-(5-amino-8-(furan-2-yl)-2-oxothiazolo [5,4-e][1,2,4]triazolo[1,5-c]pyrimidin-3(2H)-yl) ethyl)piperazin-1-yl)-3-fluorophenoxy)acetamide 4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-3-fluoro-N-methyl-N-(2-(methylamino)ethyl) benzamide 4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-N-(2-(dimethylamino)ethyl)-3-fluoro-N-methylbenzamide (R)-4-(4-(2-(5-amino-8-(furan-2-yl)-2-oxothiazolo [5,4-e][1,2,4]triazolo[1,5-c]pyrimidin-3(2H)-yl) ethyl)piperazin-1-yl)-N-(1-(dimethylamino) propan-2-yl)-3-fluorobenzamide 2-(4-(4-(2-(5-amino-8-(furan-2-yl)-2-oxothiazolo [5,4-e][1,2,4]triazolo[1,5-c]pyrimidin-3(2H)-yl) ethyl)piperazin-1-yl)-3-fluorophenoxy)-N-methyl-N-(2-(methylamino) ethyl) acetamide 2-(5-(4-(2-(5-amino-8-(furan-2-yl)-2-oxothiazolo [5,4-e][1,2,4]triazolo[1,5-c]pyrimidin-3(2H)- yl)ethyl)piperazin-1-yl)-2,4-difluorophenoxy)-2-methylpropanoic acid (S)-2-(5-(4-(2-(5-amino-8-(furan-2-yl)-2-oxothiazolo [5,4-e][1,2,4]triazolo[1,5-c]pyrimidin-3(2H)-yl)ethyl)piperazin-1-yl)-2,4-difluorophenoxy) propanoic acid (R)-2-(5-(4-(2-(5-amino-8-(furan-2-yl)-2-oxothiazolo [5,4-e][1,2,4]triazolo[1,5-c]pyrimidin-3(2H)-yl)ethyl)piperazin-1-yl)-2,4-difluorophenoxy) propanoic acid 2-(5-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-2,4-difluorophenoxy)-N-(2-(methylamino)ethyl) acetamide 2-(5-(4-(2-(5-amino-8-(furan-2-yl)-2-oxothiazolo [5,4-e][1,2,4]triazolo[1,5-c]pyrimidin-3(2H)- yl)ethyl)piperazin-1-yl)-2,4-difluorophenoxy)-N-(2-(dimethylamino)ethyl) acetamide 5-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-N-(2-(dimethylamino)ethyl)-2,4-difluoro-N-methylbenzamide 4-(5-(4-(2-(5-amino-8-(furan-2-yl)-2-oxothiazolo [5,4-e][1,2,4]triazolo[1,5-c]pyrimidin-3(2H)- yl)ethyl)piperazin-1-yl)-2,4-difluorophenoxy) butanoic acid 3-(2-(4-(5-((1H-tetrazol-5-yl)methoxy)-2,4-difluorophenyl) piperazin-1-yl)ethyl)-5-amino-8-(furan-2-yl)thiazolo[5,4-e][1,2,4]triazolo[1,5-c]pyrimidin-2(3H)-one 5-amino-3-(2-(4-(2-fluoro-4-((1-methyl-1H-1,2,4-triazol-3-yl)methoxy) phenyl)piperazin-1-yl)ethyl)-8-(furan-2-yl) thiazolo[5,4-e][1,2,4]triazolo[1,5-c]pyrimidin-2(3H)-one 5-amino-3-(2-(4-(2,4-difluoro-5-((1-methyl-1H-1,2,4-triazol-3-yl) methoxy)phenyl)piperazin-1-yl)ethyl)-8-(furan-2-yl)thiazolo[5,4-e][1,2,4]triazolo[1,5-c]pyrimidin-2(3H)-one 4-(4-(2-(5-amino-8-(furan-2-yl)-2-oxothiazolo[5,4-e][1,2,4] triazolo[1,5-c]pyrimidin-3(2H)-yl) ethyl)piperazin-1-yl)-3-fluoro-N-(2-(methyl (oxetan-3-yl)amino)ethyl) benzamide 4-(4-(2-(5-amino-8-(furan-2-yl)-2-oxothiazolo[5,4-e][1,2,4] triazolo[1,5-c]pyrimidin-3(2H)- yl)ethyl)piperazin-1-yl)-3-fluoro-N-(2-((2-hydroxyethyl)amino)ethyl)benzamide 2-amino-N-(2-(4-(4-(2-(5-amino-8-(furan-2-yl)-2-oxothiazolo[5,4-e][1,2,4]triazolo[1,5-c]pyrimidin-3(2H)-yl) ethyl)piperazin-1-yl)-3-fluorophenoxy)ethyl) acetamide (S)-2-amino-N-(2-(4-(4-(2-(5-amino-8-(furan-2-yl)-2-oxothiazolo[5,4-e][1,2,4]triazolo[1,5-c]pyrimidin-3(2H)-yl)ethyl)piperazin-1-yl)-3-fluorophenoxy)ethyl)-3-methylbutanamide ethyl 2-(5-(4-(2-(5-amino-8-(furan-2-yl)-2-oxothiazolo[5,4-e][1,2,4]triazolo[1,5-c]pyrimidin-3(2H)-yl) ethyl)piperazin-1-yl)-2,4-difluorophenoxy) acetate 2-(5-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-2,4-difluorophenoxy) acetonitrile 5-amino-8-(furan-2-yl)-3-(2-(4-(pyridin-4-yl) piperazin-1-yl)ethyl)thiazolo[5,4-e][1,2,4]triazolo[1,5-c]pyrimidin-2(3H)-one 5-amino-8-(furan-2-yl)-3-(2-(4-(pyrimidin-4-yl)piperazin-1-yl)ethyl)thiazolo[5,4-e][1,2,4]triazolo[1,5-c]pyrimidin-2(3H)-one 5-amino-3-(2-(4-(2,4-difluoro-5-(2-(methylsulfonyl) ethoxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(2-(methylsulfonyl)ethoxy) phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(6-fluoro-2-oxoindolin-5-yl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(S-methylsulfonimidoyl)phenyl)piperazin-1-yl)ethyl)-8-(furan-2-yl)thiazolo[5,4-e][1,2,4]triazolo[1,5-c]pyrimidin-2(3H)-one 5-(4-(2-(5-amino-8-(furan-2-yl)-2-oxothiazolo[5,4-e][1,2,4] triazolo[1,5-c]pyrimidin-3(2H)- yl)ethyl)piperazin-1-yl)-N-(2-(dimethylamino)ethyl)-2,4-difluorobenzamide 5-amino-3-(2-(4-(5-fluoro-2-methylpyridin-4-yl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(((3R,4R)-4-hydroxytetrahydrofuran-3-yl)oxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(((3S,4S)-4-hydroxytetrahydrofuran-3-yl)oxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(2-hydroxy-2-methylpropoxy) phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(2-hydroxypropan-2-yl)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(3,3,3-trifluoro-2-hydroxypropoxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-5-(2-hydroxyethoxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2,4-difluoro-5-(morpholin-2-ylmethoxy) phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2,4-difluoro-5-(morpholin-3-ylmethoxy) phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2,4-difluoro-5-(((3S,4S)-4-fluoropyrrolidin-3-yl)oxy)phenyl)piperazin-1-yl)ethyl)-8-(furan-2-yl) thiazolo[5,4-e][1,2,4]triazolo[1,5-c]pyrimidin-2(3H)-one 5-amino-3-(2-(4-(2,4-difluoro-5-(((3S,4S)-4-fluoropyrrolidin-3-yl)oxy)phenyl)piperazin-1-yl)ethyl)-8-(furan-2-yl) thiazolo[5,4-e][1,2,4]triazolo[1,5-c]pyrimidin-2(3H)-one 5-amino-3-(2-(4-(2,4-difluoro-5-(((3R,4S)-4-fluoropyrrolidin-3-yl)oxy)phenyl)piperazin-1-yl)ethyl)-8-(furan-2-yl) thiazolo[5,4-e][1,2,4]triazolo[1,5-c]pyrimidin-2(3H)-one 5-amino-3-(2-(4-(2,4-difluoro-5-(((3S,4R)-4-fluoropyrrolidin-3-yl)oxy)phenyl)piperazin-1-yl)ethyl)-8-(furan-2-yl) thiazolo[5,4-e][1,2,4]triazolo[1,5-c]pyrimidin-2(3H)-one (S)-5-amino-3-(2-(4-(2,4-difluoro-5-((2-oxopyrrolidin-3-yl) oxy)phenyl)piperazin-1-yl)ethyl)-8-(furan-2-yl)thiazolo [5,4-e][1,2,4]triazolo[1,5-c]pyrimidin-2(3H)-one (R)-5-amino-3-(2-(4-(2,4-difluoro-5-((2-oxopyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one 2-(5-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-2,4-difluorophenoxy)-N-(2-morpholinoethyl)acetamide 5-(4-(2-(5-amino-8-(furan-2-yl)-2-oxothiazolo[5,4-e][1,2,4] triazolo[1,5-c]pyrimidin-3(2H)- yl)ethyl)piperazin-1-yl)-2,4-difluoro-N-(morpholin-3-ylmethyl)benzamide 5-amino-3-(2-(4-(2-fluoro-4-(morpholin-3-ylmethoxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(morpholin-2-ylmethoxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(((3R,4R)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(((3S,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(((3R,4S)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(((3S,4R)-4-fluoropyrrolidin-3-yl)oxy)phenyl)piperazin-1-yl)ethyl)-8-(furan-2-yl)thiazolo[5,4-e][1,2,4]triazolo[1,5-c]pyrimidin-2(3H)-one 2-(4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-3-fluorophenoxy)-N-(2-morpholinoethyl)acetamide 4-(4-(2-(5-amino-8-(furan-2-yl)-2-oxothiazolo[5,4-e][1,2,4] triazolo[1,5-c]pyrimidin-3(2H)- yl)ethyl)piperazin-1-yl)-3-fluoro-N-(2-morpholinoethyl)benzamide 4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-3-fluoro-N-(morpholin-3-ylmethyl)benzamide 5-amino-3-(2-(4-(4-(azetidin-3-yloxy)phenyl)piperazin-1-yl)ethyl)-8-(furan-2-yl)thiazolo[5,4-e][1,2,4]triazolo[1,5-c]pyrimidin-2(3H)-one (S)-5-amino-3-(2-(4-(2,4-difluoro-5-(methylsulfinyl)phenyl)piperazin-1-yl)ethyl)-8-(furan-2-yl)thiazolo[5,4-e][1,2,4]triazolo[1,5-c]pyrimidin-2(3H)-one (R)-5-amino-3-(2-(4-(2,4-difluoro-5-(methylsulfinyl)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2,4-difluoro-5-(((1s,4s)-1-oxidotetrahydro-2H-thiopyran-4-yl)oxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2,4-difluoro-5-(((1r,4r)-1-oxidotetrahydro-2H-thiopyran-4-yl)oxy)phenyl)piperazin-1-yl)ethyl)-8-(furan-2-yl)thiazolo[5,4-e][1,2,4]triazolo[1,5-c]pyrimidin-2(3H)-one (S)-5-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-2,4-difluoro-N-(2-(methylsulfinyl)ethyl)benzamide (R)-5-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-2,4-difluoro-N-(2-(methylsulfinyl)ethyl)benzamide (S)-5-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-2,4-difluoro-N-methyl-N-(2-(methylsulfinyl)ethyl)benzamide (R)-5-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-2,4-difluoro-N-methyl-N-(2-(methylsulfinyl)ethyl)benzamide 5-amino-3-(2-(4-(2,4-difluoro-5-(1-oxidothiomorpholine-4-carbonyl)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2,4-difluoro-5-(1-oxidothiomorpholino)phenyl)piperazin-1-yl)ethyl)-8-(furan-2-yl)thiazolo[5,4-e][1,2,4]triazolo[1,5-c]pyrimidin-2(3H)-one (R)-5-amino-3-(2-(4-(2-fluoro-4-(methylsulfinyl)phenyl)piperazin-1-yl)ethyl)-8-(furan-2-yl)thiazolo[5,4-e][1,2,4]triazolo[1,5-c]pyrimidin-2(3H)-one (S)-5-amino-3-(2-(4-(2-fluoro-4-(methylsulfinyl)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(((1s,4s)-1-oxidotetrahydro-2H-thiopyran-4-yl)oxy)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(((1r,4r)-1-oxidotetrahydro-2H-thiopyran-4-yl)oxy)phenyl)piperazin-1-yl)ethyl)-8-(furan-2-yl)thiazolo[5,4-e][1,2,4]triazolo[1,5-c]pyrimidin-2(3H)-one (S)-4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-3-fluoro-N-(2-(methylsulfinyl)ethyl)benzamide (R)-4-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-3-fluoro-N-(2-(methylsulfinyl)ethyl)benzamide 5-amino-3-(2-(4-(2-fluoro-4-(1-oxidothiomorpholine-4-carbonyl)phenyl)piperazin-1-yl)ethyl)-8-(furan-2-yl)thiazolo[5,4-e][1,2,4]triazolo[1,5-c]pyrimidin-2(3H)-one 5-amino-3-(2-(4-(2-fluoro-4-(1-oxidothiomorpholino)phenyl)piperazin-1-yl)ethyl)-8-(furan-2-yl)thiazolo[5,4-e][1,2,4]triazolo[1,5-c]pyrimidin-2(3H)-one (S)-5-amino-3-(2-(4-(5-(2,3-dihydroxypropoxy)-2,4-difluorophenyl)piperazin-1-yl)ethyl)-8-(furan-2-yl)thiazolo[5,4-e][1,2,4]triazolo[1,5-c]pyrimidin-2(3H)-one (R)-5-amino-3-(2-(4-(5-(2,3-dihydroxypropoxy)-2,4-difluorophenyl)piperazin-1-yl)ethyl)-8-(furan-2-yl)thiazolo[5,4-e][1,2,4]triazolo[1,5-c]pyrimidin-2(3H)-one (S)-5-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-N-(2,3-dihydroxypropyl)-2,4-difluorobenzamide (R)-5-(4-(2-(5-amino-8-(furan-2-yl)-2-oxothiazolo[5,4-e][1,2,4]triazolo[1,5-c]pyrimidin-3(2H)- yl)ethyl)piperazin-1-yl)-N-(2,3-dihydroxypropyl)-2,4-difluorobenzamide 5-amino-3-(2-(4-(4-(azetidin-3-yloxy)-2-fluorophenyl)piperazin-1-yl)ethyl)-8-(furan-2-yl)thiazolo[5,4-e][1,2,4]triazolo[1,5-c]pyrimidin-2(3H)-one 5-amino-3-(2-(4-(5-(azetidin-3-yloxy)-2,4-difluorophenyl)piperazin-1-yl)ethyl)-8-(furan-2-yl)thiazolo[5,4-e][1,2,4]triazolo[1,5-c]pyrimidin-2(3H)-one (S)-5-amino-3-(2-(4-(2,4-difluoro-5-(3-(methylsulfinyl)propoxy)phenyl)piperazin-1-yl)ethyl)-8-(furan-2-yl)thiazolo[5,4-e][1,2,4]triazolo[1,5-c]pyrimidin-2(3H)-one In one embodiment, the A2AR antagonist of Formula (III) is selected from:

(R,S)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one (compound 7);

(+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one (compound 8a) and (−)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one (compound 8b).

In a specific embodiment, the A2AR antagonist of Formula (III) is selected from:

(R,S)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one (compound 7); and (+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one (compound 8a).

In preferred embodiment, the A2AR antagonist of Formula (III) is (+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one (compound 8a).

In another preferred embodiment, the A2AR antagonist of Formula (III) is (−)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one (compound 8b).

The embodiments relative to salts, solvates, enantiomers, isomers (including optical, geometric and tautomeric isomers), polymorphs, multi-component complexes, liquid crystals, prodrugs and isotopically-labeled ENT inhibitors of the invention also apply to the A2AR antagonists Formula (III) and subformula thereof detailed above In another embodiment, the A2AR antagonist is an A2AR antagonist disclosed in WO2011/121418. Especially, the A2AR antagonist is the compound of example 1 of WO2011/121418, namely 5-bromo-2,6-di-(1H-pyrazol-1-yl)pyrimidin-4-amine, also known as NIR178:

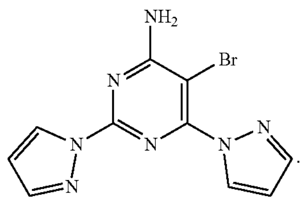 [SMILES: Nc1nc(-n2cccn2)nc(-n2cccn2)c1Br]

In another embodiment, the A2AR antagonist is an A2AR antagonist disclosed in WO2009/156737. Especially, the A2AR antagonist is the compound of example 1S of WO2009/156737, namely (S)-7-(5-methylfuran-2-yl)-3-((6-((([tetrahydrofuran-3-yl]oxy)methyl)pyridin-2-yl)methyl)-3H-[1,2,3]triazolo[4,5-d]pyrimidin-5-amine, also known as CPI-444:

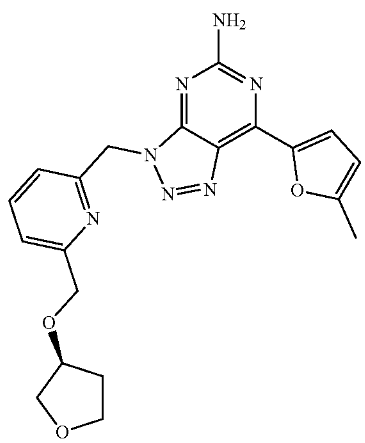 [SMILES: Cc1ccc(-c2nc(N)nc3c2nnn3Cc2cccc(CO[C@H]3CCOC3)n2)o1]

In another embodiment, the A2AR antagonist is an A2AR antagonist disclosed in WO2011/095626. Especially, the A2AR antagonist is the compound (cxiv) of WO2011/095626, namely 6-(2-chloro-6-methylpyridin-4-yl)-5-(4-fluorophenyl)-1,2,4-triazin-3-amine, also known as AZD4635:

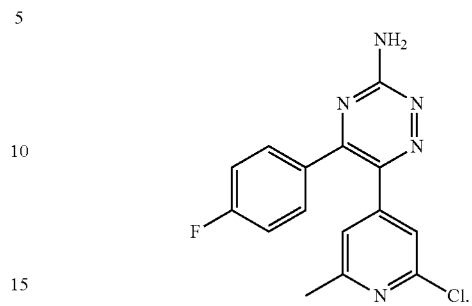

In another embodiment, the A2AR antagonist is an A2AR antagonist disclosed in WO2018/136700. Especially, the A2AR antagonist is the compound of example 1 of WO2018/136700, namely 3-(2-amino-6-(1-((6-(2-hydroxypropan-2-yl)pyridin-2-yl)methyl)-1H-1,2,3-triazol-4-yl)pyrimidin-4-yl)-2-methylbenzonitrile, also known as AB928:

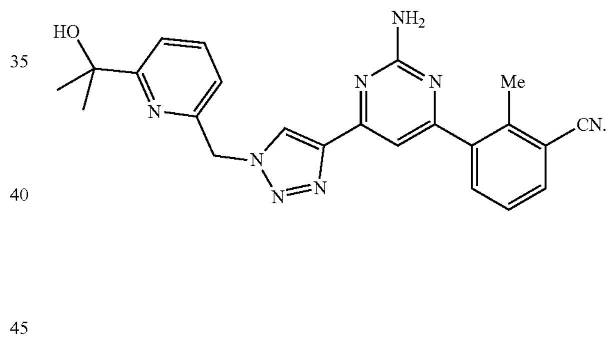

In another embodiment, the A2AR antagonist is Preladenant (SCH-420,814), namely 2-(2-furanyl)-7-(2-(4-(4-(2-methoxyethoxy)phenyl)-1-piperazinyl)ethyl)-7H-pyrazolo(4,3-e)(1,2,4)triazolo(1,5-c)pyrimidine-5-amine:

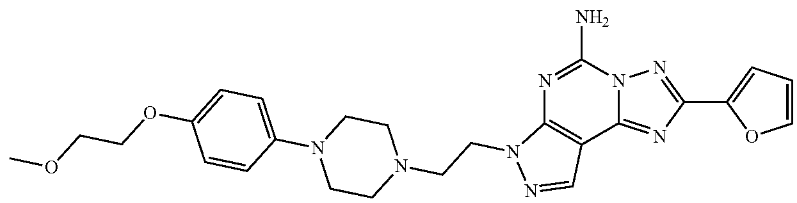

In another embodiment, the A2AR antagonist is Vipadenant (BIIB-014), namely 3-(4-amino-3-methylbenzyl)-7-(2-furyl)-3H-(1,2,3)triazolo(4,5-d)pyrimidine-5-amine:

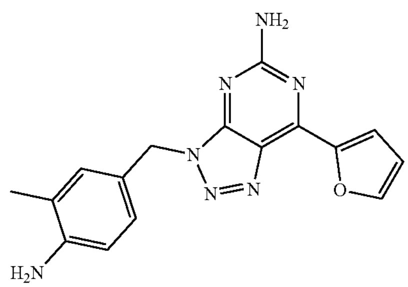

In another embodiment, the A2AR antagonist is Tozadenant (SYK-115), namely 4-hydroxy-N-(4-methoxy-7-morpholinobenzo[d]thiazol-2-yl)-4-methylpiperidine-1-carboxamide:

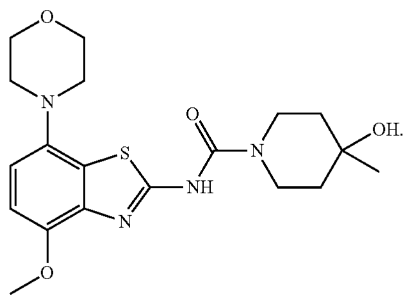 [SMILES: COc1ccc(N2CCOCC2)c2sc(NC(=O)N3CCC(C)(O)CC3)nc12]

Thus, in one embodiment, the adenosine receptor antagonist is selected from:

5-bromo-2,6-di-(1H-pyrazol-1-yl)pyrimidin-4-amine;
(S)-7-(5-methylfuran-2-yl)-3-((6-(([tetrahydrofuran-3-yl]oxy)methyl)pyridin-2-yl)methyl)-3H-[1,2,3]triazolo[4,5-d]pyrimidin-5-amine;
6-(2-chloro-6-methylpyridin-4-yl)-5-(4-fluorophenyl)-1,2,4-triazin-3-amine;
3-(2-amino-6-(1-((6-(2-hydroxypropan-2-yl)pyridin-2-yl)methyl)-1H-1,2,3-triazol-4-yl)pyrimidin-4-yl)-2-methylbenzonitrile;
2-(2-furanyl)-7-(2-(4-(4-(2-methoxyethoxy)phenyl)-1-piperazinyl)ethyl)-7H-pyrazolo(4,3-e)(1,2,4)triazolo(1,5-c)pyrimidine-5-amine;
3-(4-amino-3-methylbenzyl)-7-(2-furyl)-3H-(1,2,3)triazolo(4,5-d)pyrimidine-5-amine; and
4-hydroxy-N-(4-methoxy-7-morpholinobenzo[d]thiazol-2-yl)-4-methylpiperidine-1-carboxamide.

In one embodiment, the adenosine receptor antagonist is 5-bromo-2,6-di-(1H-pyrazol-1-yl)pyrimidin-4-amine. In one embodiment, the adenosine receptor antagonist is (S)-7-(5-methylfuran-2-yl)-3-((6-(([tetrahydrofuran-3-yl]oxy)methyl)pyridin-2-yl)methyl)-3H-[1,2,3]triazolo[4,5-d]pyrimidin-5-amine. In one embodiment, the adenosine receptor antagonist is 6-(2-chloro-6-methylpyridin-4-yl)-5-(4-fluorophenyl)-1,2,4-triazin-3-amine. In one embodiment, the adenosine receptor antagonist is 3-(2-amino-6-(1-((6-(2-hydroxypropan-2-yl)pyridin-2-yl)methyl)-1H-1,2,3-triazol-4-yl)pyrimidin-4-yl)-2-methylbenzonitrile.

A2B Receptor Antagonist

In one embodiment, the combination of the invention includes at least one A2BR antagonist.

An "A2BR antagonist" refers to a compound that, upon administration to a patient, results in inhibition or down-regulation of a biological activity associated with activation of A2B receptor in the patient, including any of the downstream biological effects otherwise resulting from the binding to A2B receptor of its natural ligand. Such A2BR antagonists include any agent that can block activation of A2B receptor or any of the downstream biological effects of A2B receptor activation.

Examples of A2BR antagonists include: Vipadenant (BIIB-014), CVT-6883, MRS-1706, MRS-1754, PSB-603, PSB-0788, PSB-1115, OSIP-339,391, ATL-801, theophylline, Caffeine, Specific Combinations In one embodiment, the combination of the invention comprises:

(a) an effective amount of an ENT inhibitor of the invention, of formula I or II or a subformula thereof, and
(b) an effective amount of an adenosine receptor antagonist, preferably an A2AR antagonist, preferably selected from:

(+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one;
(−)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one;
5-bromo-2,6-di-(1H-pyrazol-1-yl)pyrimidin-4-amine;
(S)-7-(5-methylfuran-2-yl)-3-((6-(([tetrahydrofuran-3-yl]oxy)methyl)pyridin-2-yl)methyl)-3H-[1,2,3]triazolo [4,5-d]pyrimidin-5-amine;
6-(2-chloro-6-methylpyridin-4-yl)-5-(4-fluorophenyl)-1,2,4-triazin-3-amine;
3-(2-amino-6-(1-((6-(2-hydroxypropan-2-yl)pyridin-2-yl)methyl)-1H-1,2,3-triazol-4-yl)pyrimidin-4-yl)-2-methylbenzonitrile;
and pharmaceutically acceptable salts thereof.

In one embodiment, the combination of the invention comprises:

(a) an effective amount of an ENT inhibitor of the invention, of formula I or II or a subformula thereof, and
(b) an effective amount of (+)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one as A2AR antagonist.

In one embodiment, the combination of the invention comprises:

(a) an effective amount of an ENT inhibitor of the invention, of formula I or II or a subformula thereof, and
(b) an effective amount of (−)-5-amino-3-(2-(4-(2,4-difluoro-5-(2-(methylsulfinyl)ethoxy)phenyl)piperazin-1-yl)ethyl)-8-(furan-2-yl)thiazolo[5,4-e][1,2,4]triazolo[1,5-c]pyrimidin-2(3H)-one as A2AR antagonist.

Combined Formulation and Kit of Parts

The invention further provides a combined formulation, comprising the combination of the invention. Especially, the invention provides a combined formulation, comprising: an effective amount of an adenosine receptor antagonist in combination with an effective amount of an ENT inhibitor of the invention, as defined above, along with a pharmaceutically acceptable excipient.

The invention further relates to a combined pharmaceutical composition comprising the combination of the invention. In one embodiment, the pharmaceutical composition comprises:

(a) an effective amount of an ENT inhibitor of the invention, of formula I or II or a subformula thereof, as defined above; (b) an effective amount of an adenosine receptor antagonist; and (c) at least one pharmaceutically acceptable carrier, diluent, excipient and/or adjuvant.

The specific embodiments relative to the adenosine receptor antagonists and to the ENT inhibitor of the invention recited above also apply in the context of the combined formulation and pharmaceutical composition of the invention.

In a preferred embodiment, the invention provides a combined pharmaceutical composition comprising: (a) an effective amount of an ENT inhibitor of the invention, of formula I or II or a subformula thereof, as defined above; (b) an effective amount an A2AR antagonist being a thiocarbamate derivative, more preferably a thiocarbamate derivative of Formula (III)

(III)

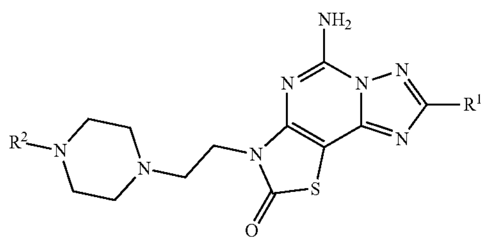

or a pharmaceutically acceptable salt or solvate thereof, as defined above; and (c) at least one pharmaceutically acceptable carrier, diluent, excipient and/or adjuvant.

In one embodiment, the combined formulation or the pharmaceutical composition of the invention further comprises an additional therapeutic agent.

The at least one pharmaceutically acceptable carrier, diluent, excipient and/or adjuvant for use in the preparation of the administration forms will be clear to the skilled person; reference is made to the latest edition of Remington's Pharmaceutical Sciences. The specific embodiments relative to formulations comprising an ENT inhibitor of the invention also apply in the context of the combined formulation and pharmaceutical composition of the invention.

The invention further relates to a kit of parts comprising the combination of the invention. In one embodiment, the kit of parts of the invention comprises:

(a) a first part comprising an effective amount of an ENT inhibitor of the invention, of formula I or II or a subformula thereof, as defined above; and (b) a second part comprising an effective amount of an adenosine receptor antagonist.

Above embodiments relative to the ENT inhibitor of the invention and adenosine receptor antagonists also apply to the kit of parts of the invention.

In a preferred embodiment, the invention provides a kit of parts comprising:

(a) a first part comprising an effective amount of an ENT inhibitor of the invention, of formula I or II or a subformula thereof, as defined above; and (b) a second part comprising an effective amount an A2AR antagonist being a thiocarbamate derivative, more preferably a thiocarbamate derivative of Formula (III)

(III)

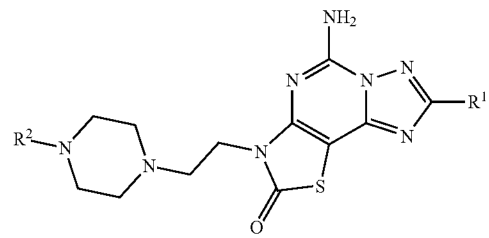

or a pharmaceutically acceptable salt or solvate thereof, as defined above.

Depending on the ENT inhibitor and adenosine receptor antagonist, the first and second parts of the kit may be under the form of pharmaceutical compositions. Excipients, dosage form and administration route of such pharmaceutical compositions will be clear to the skilled person (reference is made to the latest edition of Remington's Pharmaceutical Sciences), and especially may be those listed above with regards to the pharmaceutical compositions of the invention.

In one embodiment, the kit of parts of the invention further comprises an additional therapeutic agent.

In the context of the present invention, the administration of the ENT inhibitor and the adenosine receptor antagonist may occur either simultaneously or timely staggered, either at the same site of administration or at different sites of administration, under similar or different dosage forms as further outlined below.

In one embodiment, the ENT inhibitor is administered prior to, concomitant with, or subsequent to administration of an adenosine receptor antagonist. To ensure that the separate mechanisms elicited by the ENT inhibitor and the adenosine receptor antagonist are not negatively influenced by each other, the adenosine receptor antagonist and the ENT inhibitor may be administered separated in time (in a time-staggered manner), i.e. sequentially, and/or are administered at different administration sites. This means that the adenosine receptor antagonist may be administrated e.g. prior, concurrent or subsequent to the ENT inhibitor, or vice versa. Alternatively, or additionally, the adenosine receptor antagonist and the ENT inhibitor may be administered at different administration sites, or at the same administration site, preferably, when administered in a time staggered manner.

In one embodiment, the adenosine receptor antagonist is to be administered prior to and/or concomitantly with an ENT inhibitor. In one embodiment, the adenosine receptor antagonist is to be administered prior to the day or on the same day that the ENT inhibitor is administered. In another embodiment, the ENT inhibitor is to be administered prior to and/or concomitantly with an adenosine receptor antagonist. In one embodiment, the ENT inhibitor is to be administered prior to the day or on the same day that the adenosine receptor antagonist is administered. In one embodiment, the adenosine receptor antagonist is to be administered prior to and/or concomitantly with an ENT inhibitor and continuously thereafter. In another embodiment, the ENT inhibitor is to be administered prior to and/or concomitantly with an adenosine receptor antagonist and continuously thereafter.

Depending on the condition to be prevented or treated and the form of administration, the ENT inhibitor and the adenosine receptor antagonist may be administered as a single daily dose, divided over one or more daily doses.

It will be understood that the total daily usage of adenosine receptor antagonist and ENT inhibitor will be decided by the attending physician within the scope of sound medical judgment. The specific dose for any particular subject will depend upon a variety of factors such as the cancer to be treated; the age, body weight, general health, sex and diet of the patient; and like factors well-known in the medical arts.

Another object of this invention is the use of the combination as a medicament, i.e. for medical use. Thus, in one embodiment, the invention provides the use of the combination of the invention for the manufacturing of a medicament. Especially, the invention provides the use of the combined pharmaceutical composition of the invention or the kit of the invention for the manufacturing of a medicament.

Especially, the invention provides the combination, the combined pharmaceutical composition or the kit of parts of the invention, for use in the treatment and/or prevention of cancer. The invention further provides the use of the combination, combined pharmaceutical composition or kit of parts of the invention for the manufacture of a medicament for treating and/or preventing cancer. The invention further provides a method of treating of cancer, which comprises administering to a mammal species in need thereof a therapeutically effective amount of the combination, combined pharmaceutical composition or kit of parts of the invention.

Especially, the invention provides a method of treating cancer, comprising: administering, to a patient in need thereof, a combination of an adenosine receptor antagonist and an ENT inhibitor. The specific embodiments relative to the adenosine receptor antagonists and ENT inhibitors recited above also applies in the context of the methods of treatment of the invention.

The invention also provides for a method for delaying in patient the onset of cancer comprising the administration of a pharmaceutically effective amount of the combination, combined pharmaceutical composition or kit of parts of the invention to a patient in need thereof.

ENUMERATED EMBODIMENTS

1. A compound of formula I:

(I)

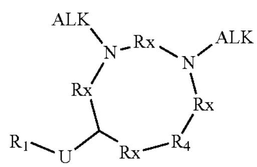

or a pharmaceutically acceptable salt or solvate thereof; wherein $R^1$ is

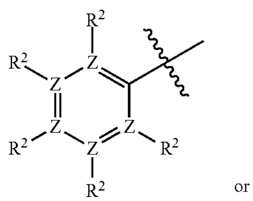

or

-continued

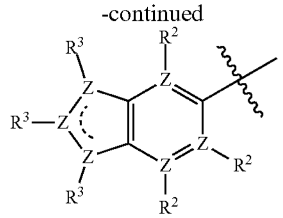

each $R^2$ is independently selected from the group consisting of halogen, —$OR^3$, —$R^3$, —$CO_2R^3$, $C(O)N(R^3)_2$, —$CH_2C(O)N(R^3)_2$, and —CN;

each $R^3$ is independently —H or ALK;

$R^4$ is

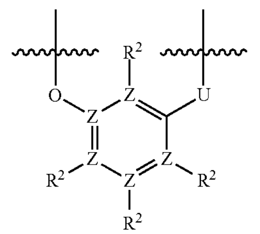

U is selected from the group consisting of —C(O)—, alkylene, —O—, —$N(R^3)$—, —C(O)O—, —C(O)N($R^3$)—, and;

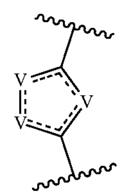

each $R^x$ is independently selected from alkylene, each V is independently selected from —$C(R^3)$—, —$N(R^3)$, —N—, —O—; and Z is C; or when $R^2$ is absent, Z is N.

2. A compound of formula II:

(II)

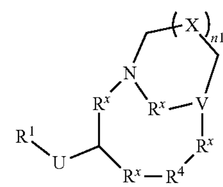

or a pharmaceutically acceptable salt or solvate thereof, wherein $R^1$ is

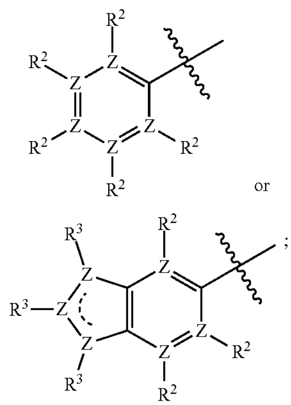

each $R^2$ is independently selected from the group consisting of halogen, $—OR^3$, $—R^3$, $—CO_2R^3$, $C(O)N(R^3)_2$, $—CH_2C(O)N(R^3)_2$, and —CN;

each $R^3$ is independently —H or ALK;

$R^4$ is

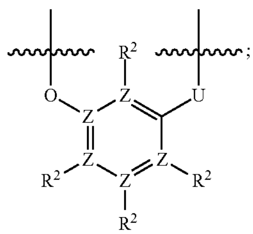

X is selected from the group consisting of $—CH_2—$, —CHF—, $—CF_2—$;

each U is independently selected from the group consisting of —O—, $—N(R^3)—$, —C(O)O—, $—C(O)N(R^3)—$,

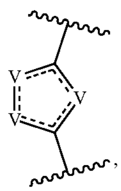

—C(O)—, and alkylene;

each $R^x$ is independently selected from alkylene;

each V is independently selected from $—C(R^3)—$, $—N(R^3)—$, —N═, and —O—;

each Z is independently C; or $R^2$ is absent and Z═N; and $n^1$ is a number of 0 or 1.

3. The compound according to enumerated embodiment 2, of formula IIa:

(IIa)

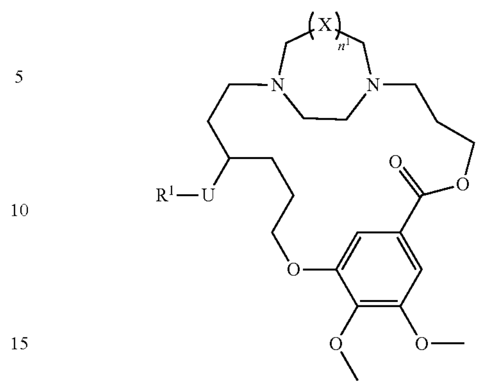

or a pharmaceutically acceptable salt or solvate thereof, wherein

R is

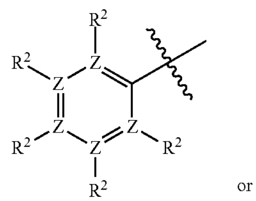

or

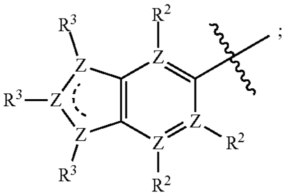

each $R^2$ is independently selected from the group consisting of halogen, $—OR^3$, $—R^3$, $—CO_2R^3$, $C(O)N(R^3)_2$, $—CH_2C(O)N(R^3)_2$, and —CN;

each $R^3$ is independently —H or ALK;

$R^4$ is

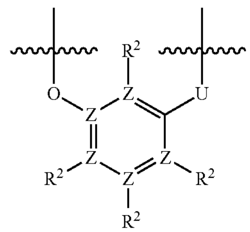

X is selected from the group consisting of $—CH_2—$, —CHF—, $—CF_2—$;

each U is insentiently selected from the group consisting of —O—, $—N(R^3)—$, —C(O)O—, $—C(O)N(R^3)—$,

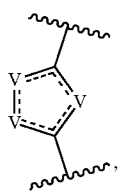

—C(O)—, and alkylene;

each $R^x$ is independently selected from alkylene;

each V is independently selected from —C($R^3$)—, —N($R^3$)—, —N═, and —O—;

each Z is independently C; or $R^2$ is absent and Z═N; and $n^1$ is a number of 0 or 1.

4. The compound according to enumerated embodiment 2, of formula IIa1:

(IIa1)

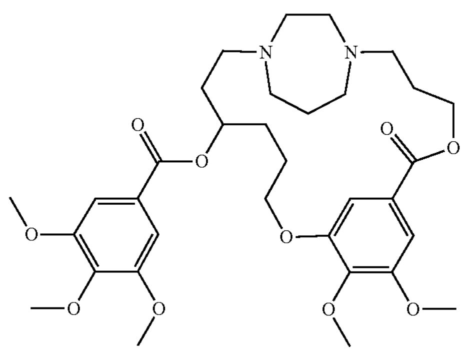

or a pharmaceutically acceptable salt or solvate thereof.

5. The compound according to any one of the enumerated embodiments 2-4, selected from the group consisting of:

(12R)-74,75-dimethoxy-6-oxo-5,8-dioxa-1(1,4)-diazepana-7(1,3) benzenacyclotetradecaphane-12-yl 3,4,5-trimethoxybenzoate;

(12S)-74,75-dimethoxy-6-oxo-5,8-dioxa-1(1,4)-diazepana-7(1,3)-benzenacyclotetradecaphane-12-yl 3,4,5-trimethoxybenzoate;

74,75-dimethoxy-6-oxo-5,8-dioxa-1(1,4)-diazepana-7(1,3)-benzenacyclotetradecaphane-12-yl 3-ethoxy-4,5-dimethoxybenzoate;

74,75-dimethoxy-6-oxo-5,8-dioxa-1(1,4)-diazepana-7(1,3)-benzenacyclotetradecaphane-12-yl 3-(2-amino-2-oxoethyl)-4,5-dimethoxybenzoate;

74,75-dimethoxy-6-oxo-5,8-dioxa-1(1,4)-diazepana-7(1,3)-benzenacyclotetradecaphane-12-yl 3,4,5-trimethoxybenzoate;

74,75-dimethoxy-6-oxo-5,8-dioxa-1(1,4)-diazepana-7(1,3)-benzenacyclotetradecaphane-12-yl 4-chloro-3-methoxybenzoate;

74,75-dimethoxy-6-oxo-5,8-dioxa-1(1,4)-diazepana-7(1,3)-benzenacyclotetradecaphane-12-yl 4-fluoro-3-methoxybenzoate;

74,75-dimethoxy-6-oxo-5,8-dioxa-1(1,4)-diazepana-7(1,3)-benzenacyclotetradecaphane-12-yl 1-(3,4,5-trimethoxybenzyl)-1H-indazole-6-carboxylate;

74,75-dimethoxy-6-oxo-5,8-dioxa-1(1,4)-diazepana-7(1,3)-benzenacyclotetradecaphane-12-yl 2,6-dimethylisonicotinate;

74,75-dimethoxy-6-oxo-5,8-dioxa-1(1,4)-diazepana-7(1,3)-benzenacyclotetradecaphane-12-yl 3,5-dichloro-4-methoxybenzoate;

74,75-dimethoxy-6-oxo-5,8-dioxa-1(1,4)-diazepana-7(1,3)-benzenacyclotetradecaphane-12-yl 2-benzyl-4-chloro-2H-indazole-6-carboxylate;

74,75-dimethoxy-6-oxo-5,8-dioxa-1(1,4)-diazepana-7(1,3)-benzenacyclotetradecaphane-12-yl 4-chloro-1-methyl-1H-indazole-6-carboxylate;

74,75-dimethoxy-6-oxo-5,8-dioxa-1(1,4)-diazepana-7(1,3)-benzenacyclotetradecaphane-12-yl 1-benzyl-4-chloro-1H-indazole-6-carboxylate;

74,75-dimethoxy-6-oxo-5,8-dioxa-1(1,4)-diazepana-7(1,3)-benzenacyclotetradecaphane-12-yl 3,4,5-trifluorobenzoate;

74,75-dimethoxy-6-oxo-5,8-dioxa-1(1,4)-diazepana-7(1,3)-benzenacyclotetradecaphane-12-yl 3-carbamoyl-4,5-dimethoxybenzoate;

74,75-dimethoxy-6-oxo-5,8-dioxa-1(1,4)-diazepana-7(1,3)-benzenacyclotetradecaphane-12-yl 3-(benzyloxy)-4,5-dimethoxybenzoate;

74,75-dimethoxy-6-oxo-5,8-dioxa-1(1,4)-diazepana-7(1,3)-benzenacyclotetradecaphane-12-yl 7-methoxy-1,3-dimethyl-2-oxo-2,3-dihydro-1H-benzo[d]imidazole-5-carboxylate;

74,75-dimethoxy-6-oxo-5,8-dioxa-1(1,4)-diazepana-7(1,3)-benzenacyclotetradecaphane-12-yl 1-methyl-6-oxo-1,6-dihydropyridine-3-carboxylate;

74,75-dimethoxy-6-oxo-5,8-dioxa-1(1,4)-diazepana-7(1,3)-benzenacyclotetradecaphane-12-yl 6-cyanonicotinate;

74,75-dimethoxy-6-oxo-5,8-dioxa-1(1,4)-diazepana-7(1,3)-benzenacyclotetradecaphane-12-yl 4-acetylbenzoate;

74,75-dimethoxy-6-oxo-5,8-dioxa-1(1,4)-diazepana-7(1,3)-benzenacyclotetradecaphane-12-yl 4-(trifluoromethyl)benzoate;

74,75-dimethoxy-6-oxo-5,8-dioxa-1(1,4)-diazepana-7(1,3)-benzenacyclotetradecaphane-12-yl 6-(trifluoromethyl)nicotinate;

74,75-dimethoxy-6-oxo-5,8-dioxa-1(1,4)-diazepana-7(1,3)-benzenacyclotetradecaphane-12-yl 6-methylnicotinate;

74,75-dimethoxy-6-oxo-5,8-dioxa-1(1,4)-diazepana-7(1,3)-benzenacyclotetradecaphane-12-yl 3,4-dichlorobenzoate;

74,75-dimethoxy-6-oxo-5,8-dioxa-1(1,4)-diazepana-7(1,3)-benzenacyclotetradecaphane-12-yl 4-chloro-3-fluorobenzoate;

74,75-dimethoxy-6-oxo-5,8-dioxa-1(1,4)-diazepana-7(1,3)-benzenacyclotetradecaphane-12-yl 4-chlorobenzoate;

74,75-dimethoxy-6-oxo-5,8-dioxa-1(1,4)-diazepana-7(1,3)-benzenacyclotetradecaphane-12-yl 3-chloro-4-fluorobenzoate;

74,75-dimethoxy-6-oxo-5,8-dioxa-1(1,4)-diazepana-7(1,3)-benzenacyclotetradecaphane-12-yl 4-fluorobenzoate;

74,75-dimethoxy-6-oxo-5,8-dioxa-1(1,4)-diazepana-7(1,3)-benzenacyclotetradecaphane-12-yl 4-morpholinobenzoate;

74,75-dimethoxy-6-oxo-5,8-dioxa-1(1,4)-diazepana-7(1,3)-benzenacyclotetradecaphane-12-yl 4-(trifluoromethoxy)benzoate;

74,75-dimethoxy-6-oxo-5,8-dioxa-1(1,4)-diazepana-7(1,3)-benzenacyclotetradecaphane-12-yl 2-chloro-3,4-dimethoxybenzoate;

74,75-dimethoxy-6-oxo-5,8-dioxa-1(1,4)-diazepana-7(1,3)-benzenacyclotetradecaphane-12-yl 4-(methylsulfonyl)benzoate;

74,75-dimethoxy-6-oxo-5,8-dioxa-1(1,4)-diazepana-7(1,3)-benzenacyclotetradecaphane-12-yl 2,3-dihydrobenzo[b][1,4]dioxine-6-carboxylate;

74,75-dimethoxy-6-oxo-5,8-dioxa-1(1,4)-diazepana-7(1,3)-benzenacyclotetradecaphane-12-yl 1-methyl-1H-indazole-6-carboxylate;

74,75-dimethoxy-6-oxo-5,8-dioxa-1(1,4)-diazepana-7(1,3)-benzenacyclotetradecaphane-12-yl 1-benzyl-1H-indazole-6-carboxylate;

74,75-dimethoxy-6-oxo-5,8-dioxa-1(1,4)-diazepana-7(1,3)-benzenacyclotetradecaphane-12-yl benzo[d]thiazole-6-carboxylate; 74,75-dimethoxy-6-oxo-5,8-dioxa-1(1,4)-diazepana-7(1,3)-benzenacyclotetradecaphane-12-yl [1,2,4]triazolo[4,3-a]pyridine-6-carboxylate;

74,75-dimethoxy-6-oxo-5,8-dioxa-1(1,4)-diazepana-7(1,3)-benzenacyclotetradecaphane-12-yl 2-(trifluoromethyl)isonicotinate;

74,75-dimethoxy-6-oxo-5,8-dioxa-1(1,4)-diazepana-7(1,3)-benzenacyclotetradecaphane-12-yl 5,6-dichloronicotinate;

74,75-dimethoxy-6-oxo-5,8-dioxa-1(1,4)-diazepana-7(1,3)-benzenacyclotetradecaphane-12-yl 6-chloro-5-fluoronicotinate;

74,75-dimethoxy-6-oxo-5,8-dioxa-1(1,4)-diazepana-7(1,3)-benzenacyclotetradecaphane-12-yl 2-aminopyrimidine-5-carboxylate;

74,75-dimethoxy-6-oxo-5,8-dioxa-1(1,4)-diazepana-7(1,3)-benzenacyclotetradecaphane-12-yl 5-chloronicotinate;

74,75-dimethoxy-6-oxo-5,8-dioxa-1(1,4)-diazepana-7(1,3)-benzenacyclotetradecaphane-12-yl 4-methoxybenzoate;

74,75-dimethoxy-6-oxo-5,8-dioxa-1(1,4)-diazepana-7(1,3)-benzenacyclotetradecaphane-12-yl 4-methoxy-3-(trifluoromethyl)benzoate;

74,75-dimethoxy-6-oxo-5,8-dioxa-1(1,4)-diazepana-7(1,3)-benzenacyclotetradecaphane-12-yl 3-chloro-4-methoxybenzoate 74,75-dimethoxy-6-oxo-5,8-dioxa-1(1,4)-diazepana-7(1,3)-benzenacyclotetradecaphane-12-yl 3,4-dimethoxybenzoate;

74,75-dimethoxy-6-oxo-5,8-dioxa-1(1,4)-diazepana-7(1,3)-benzenacyclotetradecaphane-12-yl 6-methoxynicotinate;

74,75-dimethoxy-6-oxo-5,8-dioxa-1(1,4)-diazepana-7(1,3)-benzenacyclotetradecaphane-12-yl 5-methoxynicotinate;

74,75-dimethoxy-6-oxo-5,8-dioxa-1(1,4)-diazepana-7(1,3)-benzenacyclotetradecaphane-12-yl 2-methoxypyrimidine-5-carboxylate;

16-fluoro-74,75-dimethoxy-6-oxo-5,8-dioxa-1(1,4)-diazepana-7(1,3)-benzenacyclotetradecaphane-12-yl 3,4,5-trimethoxybenzoate;

16,16-difluoro-74,75-dimethoxy-6-oxo-5,8-dioxa-1(1,4)-diazepana-7(1,3)-benzenacyclotetradecaphane-12-yl 3,4,5-trimethoxybenzoate;

N-(74,75-dimethoxy-6-oxo-5,8-dioxa-1(1,4)-diazepana-7(1,3)-benzenacyclotetradecaphane-12-yl)-3,4,5-trimethoxybenzamide;

N-(74,75-dimethoxy-6-oxo-5,8-dioxa-1(1,4)-diazepana-7(1,3)-benzenacyclotetradecaphane-12-yl)-3,4,5-trimethoxy-N-methylbenzamide;

N-(16,16-difluoro-74,75-dimethoxy-6-oxo-5,8-dioxa-1(1,4)-diazepana-7(1,3)-benzenacyclotetradecaphane-12-yl)-3,4,5-trimethoxybenzamide;

N-(16,16-difluoro-74,75-dimethoxy-6-oxo-5,8-dioxa-1(1,4)-diazepana-7(1,3)-benzenacyclotetradecaphane-12-yl)-3,4,5-trimethoxy-N-methylbenzamide;

N-((12R)-16,16-difluoro-74,75-dimethoxy-6-oxo-5,8-dioxa-1(1,4)-diazepana-7(1,3) benzenacyclotetradecaphane-12-yl)-3,4,5-trimethoxybenzamide;

N-((12R)-16,16-difluoro-74,75-dimethoxy-6-oxo-5,8-dioxa-1(1,4)-diazepana-7(1,3) benzenacyclotetradecaphane-12-yl)-3,4,5-trimethoxy-N-methylbenzamide;

N-((12S)-16,16-difluoro-74,75-dimethoxy-6-oxo-5,8-dioxa-1(1,4)-diazepana-7(1,3)-benzenacyclotetradecaphane-12-yl)-3,4,5-trimethoxybenzamide;

N-((12S)-16,16-difluoro-74,75-dimethoxy-6-oxo-5,8-dioxa-1(1,4)-diazepana-7(1,3)-benzenacyclotetradecaphane-12-yl)-3,4,5-trimethoxy-N-methylbenzamide, and pharmaceutically acceptable salts or solvates thereof.

6. The compound according to any one of the enumerated embodiments preceding, wherein the compound comprises only one chiral center.

7. The compound according to enumerated embodiment 6, wherein the compound is racemic mixture containing 'R' isomer and 'S' isomer.

8. The compound according to enumerated embodiment 6, wherein the compound is 'R' isomer.

9. The compound according to enumerated embodiment 6, wherein the compound is 'S' isomer.

10. The compound according to any one of the enumerated embodiments 1-5, wherein the compound comprises more than one chiral center.

11. The compound according to enumerated embodiment 10, wherein the chiral centers comprise 'R' or 'S' configurations independently.

12. The compound according to enumerated embodiment 10, wherein the chiral centers comprise the same configuration.

13. A pharmaceutical composition comprising a compound according to any one of the enumerated embodiments preceding and at least one pharmaceutically acceptable excipient.

14. The pharmaceutical composition according to enumerated embodiment 13, further comprising an adenosine receptor antagonist.

15. The pharmaceutical composition according to enumerated embodiment 14, wherein the adenosine receptor antagonist is an A2A or A2B receptor antagonist.

16. The pharmaceutical composition according to enumerated embodiment 14, wherein the adenosine receptor antagonist is selected from:

5-bromo-2,6-di-(1H-pyrazol-1-yl)pyrimidin-4-amine;

(S)-7-(5-methylfuran-2-yl)-3-((6-(([tetrahydrofuran-3-yl]oxy)methyl)pyridin-2-yl)methyl)-3H-[1,2,3]triazolo[4,5-d]pyrimidin-5-amine;

6-(2-chloro-6-methylpyridin-4-yl)-5-(4-fluorophenyl)-1,2,4-triazin-3-amine;

3-(2-amino-6-(1-((6-(2-hydroxypropan-2-yl)pyridin-2-yl)methyl)-1H-1,2,3-triazol-4-yl)pyrimidin-4-yl)-2-methylbenzonitrile;

2-(2-furanyl)-7-(2-(4-(4-(2-methoxyethoxy)phenyl)-1-piperazinyl)ethyl)-7H-pyrazolo(4,3-e)(1,2,4)triazolo(1,5-c)pyrimidine-5-amine;

3-(4-amino-3-methylbenzyl)-7-(2-furyl)-3H-(1,2,3)triazolo(4,5-d)pyrimidine-5-amine; and 4-hydroxy-N-(4-methoxy-7-morpholinobenzo[d]thiazol-2-yl)-4-methylpiperidine-1-carboxamide.

17. The pharmaceutical composition according to enumerated embodiment 14, wherein the adenosine receptor antagonist is a compound of Formula (III):

(III)

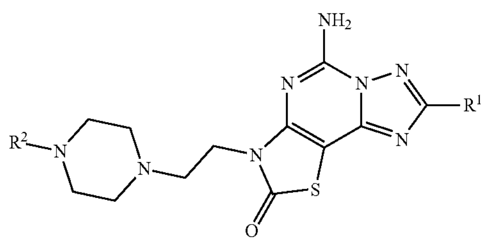

or a pharmaceutically acceptable salt or solvate thereof, wherein:

$R^1$=5- or 6-membered heteroaryl or 5- or 6-membered aryl, wherein heteroaryl or aryl groups are optionally substituted by one or more substituent selected from C1-C6 alkyl and halo;

$R^2$=6-membered aryl or 6-membered heteroaryl, wherein heteroaryl or aryl groups are optionally substituted by one or more substituent selected from halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino and alkylsulfonealkyl;

said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl alkylsulfonyl and alkylsulfonealkyl;

or the heteroaryl or aryl groups are optionally substituted with two substituents that form together with the atoms to which they are attached a 5- or 6-membered aryl ring, a 5- or 6-membered heteroaryl ring, a 5- or 6-membered cycloalkyl ring or a 5- or 6-membered heterocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

18. A method of inhibiting ENT1 in a patient need thereof, comprising: administering to said patient an effective amount of a compound according to any one of the enumerated embodiments 1 to 12.

19. A method of treating cancer in a patient need thereof, comprising: administering to said patient an effective amount of a compound according to any one of the enumerated embodiments 1 to 12.

20. A method of treating cancer in a patient need thereof, comprising: administering to said patient a combination of a compound according to any one of the enumerated embodiments 1 to 12 and an adenosine receptor antagonist.

21. The method according to enumerated embodiment 20, wherein the compound according to any one of the enumerated embodiments 1 to 12 is administered prior to, concomitant with, or subsequent to administration of the adenosine receptor antagonist.

22. The method according to any one of the enumerated embodiments 20-21, wherein the adenosine receptor antagonist is an A2A or A2B receptor antagonist.

23. The method according to enumerated embodiment 20, wherein the adenosine receptor antagonist is selected from:

5-bromo-2,6-di-(1H-pyrazol-1-yl)pyrimidin-4-amine;

(S)-7-(5-methylfuran-2-yl)-3-((6-(([tetrahydrofuran-3-yl]oxy)methyl)pyridin-2-yl)methyl)-3H-[1,2,3]triazolo[4,5-d]pyrimidin-5-amine;

6-(2-chloro-6-methylpyridin-4-yl)-5-(4-fluorophenyl)-1,2,4-triazin-3-amine;

3-(2-amino-6-(1-((6-(2-hydroxypropan-2-yl)pyridin-2-yl)methyl)-1H-1,2,3-triazol-4-yl)pyrimidin-4-yl)-2-methylbenzonitrile;

2-(2-furanyl)-7-(2-(4-(4-(2-methoxyethoxy)phenyl)-1-piperazinyl)ethyl)-7H-pyrazolo(4,3-e)(1,2,4)triazolo(1,5-c)pyrimidine-5-amine;

3-(4-amino-3-methylbenzyl)-7-(2-furyl)-3H-(1,2,3)triazolo(4,5-d)pyrimidine-5-amine; and 4-hydroxy-N-(4-methoxy-7-morpholinobenzo[d]thiazol-2-yl)-4-methylpiperidine-1-carboxamide.

24. The method according to enumerated embodiment 20, wherein the adenosine receptor antagonist is a compound of Formula (III):

(III)

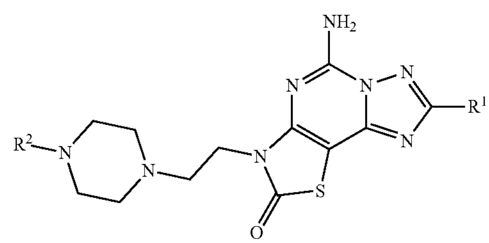

or a pharmaceutically acceptable salt or solvate thereof, wherein:

$R^1$=5- or 6-membered heteroaryl or 5- or 6-membered aryl, wherein heteroaryl or aryl groups are optionally substituted by one or more substituent selected from C1-C6 alkyl and halo;

$R^2$=6-membered aryl or 6-membered heteroaryl, wherein heteroaryl or aryl groups are optionally substituted by one or more substituent selected from halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino and alkylsulfonealkyl;

said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl) amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl) aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl alkylsulfonyl and alkylsulfonealkyl;

or the heteroaryl or aryl groups are optionally substituted with two substituents that form together with the atoms to which they are attached a 5- or 6-membered aryl ring, a 5- or 6-membered heteroaryl ring, a 5- or 6-membered cycloalkyl ring or a 5- or 6-membered heterocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

25. A kit of parts comprising:

(a) a first part comprising an effective amount of a compound according to any one of the enumerated embodiments 1 to 12; and (b) a second part comprising an effective amount of an adenosine receptor antagonist.

26. The kit of parts according to enumerated embodiment 25, wherein the adenosine receptor antagonist is an A2A or A2B receptor antagonist.

27. The kit of parts according to enumerated embodiment 25, wherein the adenosine receptor antagonist is selected from:

5-bromo-2,6-di-(1H-pyrazol-1-yl)pyrimidin-4-amine;

(S)-7-(5-methylfuran-2-yl)-3-((6-(([tetrahydrofuran-3-yl]oxy)methyl)pyridin-2-yl)methyl)-3H-[1,2,3]triazolo[4,5-d]pyrimidin-5-amine;

6-(2-chloro-6-methylpyridin-4-yl)-5-(4-fluorophenyl)-1,2,4-triazin-3-amine;

3-(2-amino-6-(1-((6-(2-hydroxypropan-2-yl)pyridin-2-yl)methyl)-1H-1,2,3-triazol-4-yl)pyrimidin-4-yl)-2-methylbenzonitrile;

2-(2-furanyl)-7-(2-(4-(4-(2-methoxyethoxy)phenyl)-1-piperazinyl)ethyl)-7H-pyrazolo(4,3-e)(1,2,4)triazolo(1,5-c)pyrimidine-5-amine;

3-(4-amino-3-methylbenzyl)-7-(2-furyl)-3H-(1,2,3)triazolo(4,5-d)pyrimidine-5-amine; and 4-hydroxy-N-(4-methoxy-7-morpholinobenzo[d]thiazol-2-yl)-4-methylpiperidine-1-carboxamide.

28. The kit of parts according to enumerated embodiment 25, wherein the adenosine receptor antagonist is a compound of Formula (III):

(III)

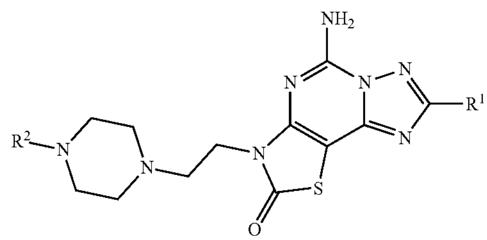

or a pharmaceutically acceptable salt or solvate thereof, wherein:

$R^1$=5- or 6-membered heteroaryl or 5- or 6-membered aryl, wherein heteroaryl or aryl groups are optionally substituted by one or more substituent selected from C1-C6 alkyl and halo;

$R^2$=6-membered aryl or 6-membered heteroaryl, wherein heteroaryl or aryl groups are optionally substituted by one or more substituent selected from halo, alkyl, heterocyclyl, alkoxy, cycloalkyloxy, heterocyclyloxy, carbonyl, alkylcarbonyl, aminocarbonyl, hydroxycarbonyl, heterocyclylcarbonyl, alkylsulfoxide, alkylsulfonyl, aminosulfonyl, heterocyclylsulfonyl, alkylsulfonimidoyl, carbonylamino, sulfonylamino and alkylsulfonealkyl;

said substituents being optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl) amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl) aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl alkylsulfonyl and alkylsulfonealkyl;

or the heteroaryl or aryl groups are optionally substituted with two substituents that form together with the atoms to which they are attached a 5- or 6-membered aryl ring, a 5- or 6-membered heteroaryl ring, a 5- or 6-membered cycloalkyl ring or a 5- or 6-membered heterocyclyl ring; optionally substituted by one or more substituent selected from oxo, halo, hydroxy, cyano, alkyl, alkenyl, aldehyde, heterocyclylalkyl, hydroxyalkyl, dihydroxyalkyl, hydroxyalkylaminoalkyl, aminoalkyl, alkylaminoalkyl, dialkylaminoalkyl, (heterocyclyl)(alkyl)aminoalkyl, heterocyclyl, heteroaryl, alkylheteroaryl, alkyne, alkoxy, amino, dialkylamino, aminoalkylcarbonylamino, aminocarbonylalkylamino, (aminocarbonylalkyl)(alkyl)amino, alkenylcarbonylamino, hydroxycarbonyl, alkyloxycarbonyl, aminocarbonyl, aminoalkylaminocarbonyl, alkylaminoalkylaminocarbonyl, dialkylaminoalkylaminocarbonyl, heterocyclylalkylaminocarbonyl, (alkylaminoalkyl)(alkyl)aminocarbonyl, alkylaminoalkylcarbonyl, dialkylaminoalkylcarbonyl, heterocyclylcarbonyl, alkenylcarbonyl, alkynylcarbonyl, alkylsulfoxide, alkylsulfoxidealkyl, alkylsulfonyl and alkylsulfonealkyl.

EXAMPLES

The present invention will be better understood with reference to the following examples. These examples are intended to representative of specific embodiments of the invention, and are not intended as limiting the scope of the invention.

The following abbreviations are used:

THF: tetrahydrofuran;
DCM: dichloromethane;
EtOAC: ethyl acetate;
ACN: acetonitrile;
TEA: triethylamine;
DIPEA: N,N-Diisopropyléthylamine;
EDCI 1-Ethyl-3-(3-diméthylaminopropyl)carbodiimide;
HAUT: (1-[Bis(dimethylamino)methylene]-1H-1,2,3-triazolo[4,5-b]pyridinium 3-oxide hexafluorophosphate;
DPPF: 1,1'-Bis(diphenylphosphino)ferrocene
HOBt: 1-Hydroxybenzotriazole;
DTAD: Di-tert-butyl azodicarboxylate;
EDC·HCl: N'-ethylcarbodiimide hydrochloride
N2: nitrogen gas;
min: minute;
hr: hour;
$Na_2SO_4$: sodium sulfate;
TLC: Thin layer chromatography;
prep-HPLC: preparative High-Pressure Liquid Chromatography;
HPLC: High Pressure Liquid Chromatography;
$SiO_2$: silica gel;
$K_2CO_3$: potassium carbonate;
LiOH: lithium hydroxide.
DCC: N,N'-Dicyclohexylcarbodiimide
DMAP: 4-Dimethylaminopyridine
DEAD: Diethyl azodicarboxylate
$PPh_3$: triphenylphosphine
TBAF: tetra-n-butylammonium fluoride
TFA: trifluoroacetic acid

I. Chemistry Examples

The MS data provided in the examples described below were obtained as follows: LCMS were recorded using Agilent 6130 or 6130B multimode (ESI+APCI).

LCMS Methods

Method A

This method was used for the LCMS analysis of intermediates. The column used for chromatography was a ZORBAX Eclipse XDB-C18 2.1*30 mm, (3.5 um particles. Detection methods are diode array (DAD). MS mode was positive electrospray ionization. MS range was 100-1000. Mobile phase A was 0.037% Trifluoroacetic acid in water, and mobile phase B was 0.018% Trifluoroacetic acid in HPLC grade acetonitrile. The gradient was 5-95% B in 2.20 min, 5% B in 0.01 min, 5-95% B (0.01-1.00 min), 95-100% B (1.00-1.80 min), 5% B in 1.81 min with a hold at 5% B for 0.39 min. The flow rate was 1.0 mL/min.

Method B

This method was used for the LCMS analysis of compounds. The column used for chromatography was a Kinetex C18 50*2.1 mm column (5 um particles). Detection methods are diode array (DAD) and evaporative light scattering (ELSD) detection as well as positive electrospray ionization. MS range was 100-1000. The gradient was 5% B in 0.40 min and 5-95% B at 0.40-3.00 min, hold on 95% B for 1.00 min, and then 95-5% B in 0.01 min, the flow rate was 1.0 ml/min. Mobile phase A was 0.037% trifluoroacetic acid in water, mobile phase B was 0.018% trifluoroacetic acid in acetonitrile.

Preparative Basic LCMS

Method Used for Purification by Prep-HPLC:

Instrument: Gilson 281 semi-preparative HPLC system
Mobile phase: A: 10 mM NH4HCO3 in H2O; B: ACN
Column: Waters Xbridge BEH C18 100*30 mm*10 um
Flow rate: 25 mL/min
Monitor wavelength: 220&254 nm

TABLE 2

| LCMS Parameters | |
|---|---|
| Time | B % |
| 0.0 | 42 |
| 8.0 | 65 |
| 8.1 | 65 |
| 8.2 | 100 |
| 10.2 | 100 |
| 10.3 | 42 |
| 11.5 | 42 |

Preparative Acid LCMS

Instrument: Gilson 281 semi-preparative HPLC system
Mobile phase: A: HCl/H2O=0.1% v/v; B: ACN
Column: Phenomenex Luna C18 100*30 mm*5 um
Flow rate: 25 mL/min
Monitor wavelength: 220 & 254 nm

| Time | B % |
|---|---|
| 0.0 | 20 |
| 9.0 | 50 |
| 9.1 | 50 |
| 9.2 | 100 |
| 11.2 | 100 |

-continued

| Time | B % |
|---|---|
| 11.3 | 20 |
| 12.5 | 20 |

Chiral SFC Method A:

Column: Chiralcel OD-3 50×4.6 mm I.D., 3 um

Mobile phase: Phase A for CO2, and Phase B for MeOH (0.05% DEA);

Gradient elution: 40% MeOH (0.05% DEA) in CO2

Flow rate: 3 mL/min; Detector: PDA

Column Temp: 35 C; Back Pressure: 100 Bar

Chiral SFC Method B:

Column: Chiralpak IC-3 50×4.6 mm I.D., 3 um

Mobile phase: A2=Heptane; B2=80% EtOH (0.05% DEA)

Flow rate: 1 mL/min

Wavelength:220 nm

Column Temp:35 C

Chiral HPLC:

CHIRAL-HPLC (Column: SB 100×4.6 mm 3.0 um, Mobile Phase, A: (60% DCM+20 mM NH3); B: MeOH; Flow Rate: 3 mL/min; Conc. of Pump B: 10%-50.0% in 3.7 min; Detection: 254 nm.

NMR Analysis

The NMR data provided in the examples described below were obtained as followed:

1H-NMR: Bruker DPX 400 MHz. Abbreviations for multiplicities observed in NMR spectra are as follows: s (singlet), d (doublet), t (triplet), q (quadruplet), m (multiplet), br (broad).

Solvents, reagents and starting materials were purchased and used as received from commercial vendors unless otherwise specified.

Example I.1. Synthesis of Intermediate Compounds

Intermediate Compound 1:

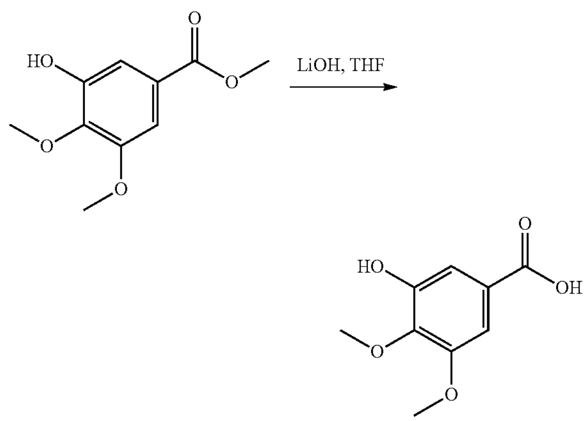

To a solution of methyl 3-hydroxy-4,5-dimethoxybenzoate (0.5 g, 2.35 mmol) in tetrahydrofuran (9 mL) and methanol (3 mL) were added LiOH·H2O (495 mg, 11.75 mmol) at 25° C. The resulting mixture was stirred at 25° C. for 16 hr. The solvent was removed and the residue dissolved in water (5 mL). The aqueous phase was acidified with HCl (3 N) to pH=4. The aqueous phase was extracted with ethyl acetate (4×5 mL). The combined organic phase was washed with brine, dried over Na2SO4, filtered and concentrated under reduced pressure to give the intermediate compound 1 (480 mg, crude) as white solid.

1H NMR (400 MHz, CDCl3-d) δ 12.71 (s, 1H), 9.52 (s, 1H), 7.08 (s, 1H), 7.02 (s, 1H), 3.77 (s, 3H), 3.70 (s, 3H).

Intermediate Compound 2:

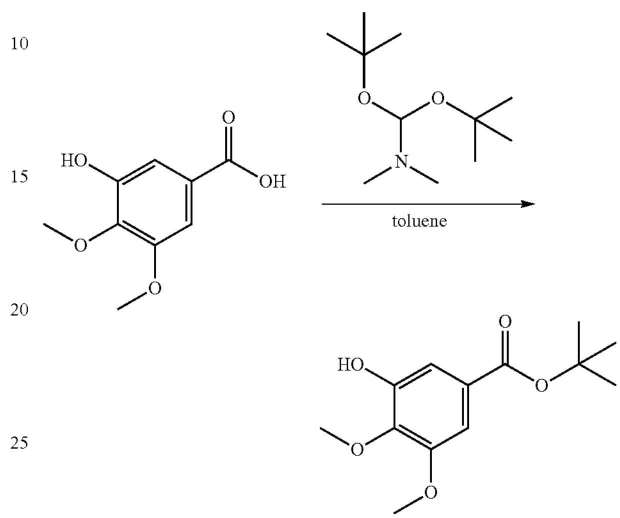

To a solution of intermediate compound 1 (480 mg, 2.4 mmol) in toluene (8 mL) was added 1,1-di-tert-butoxy-N,N-dimethylmethanamine (1.97 g, 9.6 mmol) at 20° C. The mixture was stirred at 85° C. for 1 hr. At rt, the reaction mixture was poured into water (20 mL) and extracted with ethyl acetate (3×5 mL). The combined organic phase was washed with brine (10 mL), dried over Na2SO4, filtered and concentrated under reduced pressure. The residue was purified by column on silica gel (petroleum ether/ethyl acetate=100/0 to 90/10) to give the intermediate compound 2 (300 mg, yield 63%) as white solid.

1H NMR (CDCl3-d) δ 7.26 (d, J=1.8 Hz, 1H), 7.19-7.16 (m, 1H), 5.84-5.80 (m, 1H), 3.98-3.94 (m, 3H), 3.93-3.89 (m, 3H), 1.60-1.57 (m, 9H)

Intermediate Compound 3:

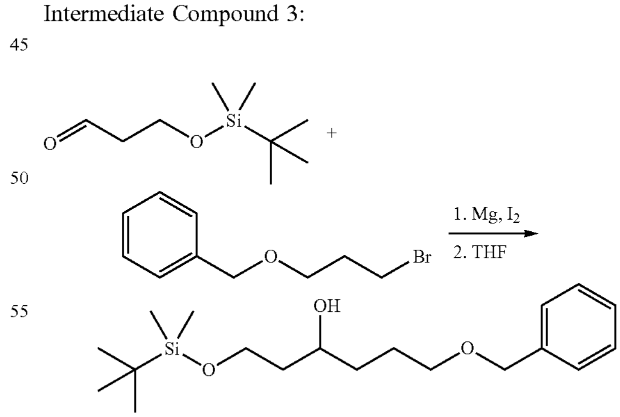

A Grignard reagent was prepared by the following procedure:

To a mixture of Mg (1.41 g, 58.1 mmol) and 12 (80.2 mg, 315.8 umol) in tetrahydrofuran (40 mL) was added a solution of ((3-bromopropoxy)methyl)benzene (11.1 g, 48.4 mmol) in tetrahydrofuran (30 mL). The reaction mixture was stirred at 25° C. for 1 hr. The inner temperature was raised up from 25° C. to 65° C. The Mg was almost consumed and the inner temperature was cooled from 65° C. to 25° C. The remained Mg was filtered to give a yellow tetrahydrofuran solution which was used directly for next step. To a solution of intermediate compound 63 (11.0 g, 58.4 mmol) in tetrahydrofuran (50 mL) was added the Grignard reagent (70 mL tetrahydrofuran solution) at 0° C. Then the reaction mixture was warmed up to 25° C. and stirred for 16 hr. The reaction was poured into aqueous solution of NH4Cl (200 mL). The mixture was extracted with ethyl acetate (2×50 mL). The combined organic phase was washed with brine (50 mL), dried over Na2SO4, the suspension was filtered was concentrated under reduced pressure. The residue was purified by column on silica gel (petroleum ether/ethyl acetate=100:0 to 90:10) to give intermediate compound 3 (4.24 g, yield 26%) as colorless oil.

1H NMR (400 MHz CDCl3-d) δ ppm 7.26-7.18 (m, 5H), 4.44 (s, 2H), 3.83-3.79 (m, 3H), 3.43 (s, 3H), 1.64-1.47 (m, 6H), 0.82 (s, 9H), 0.00 (s, 6H).

Intermediate Compound 4:

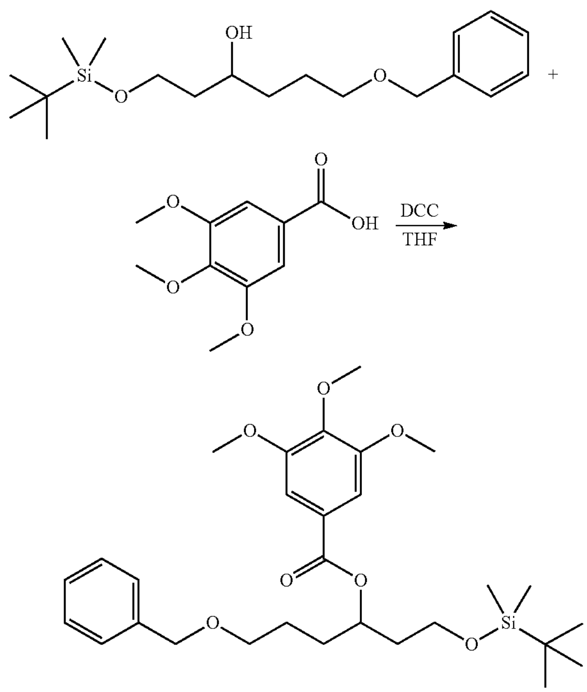

To a solution of intermediate compound 3 (4.94 g, 14.6 mmol) and intermediate compound 2 (3.72 g, 17.5 mmol) in tetrahydrofuran (100 mL) were added DCC (4.52 g, 21.9 mmol) and DMAP (2.67 g, 21.9 mmol) at 20° C. The mixture was stirred at 20° C. for 16 hr. The reaction mixture was filtered and the filtrate was concentrated under reduced pressure. The residue was purified by column on silica gel (petroleum ether/ethyl acetate=100/0 to 90/10) to give intermediate compound 4 (4.9 g, yield 63%) as colorless oil.

1H NMR (400 MHz, CDCl3-d) δ=7.36-7.25 (m, 7H), 5.31-5.17 (m, 1H), 4.50-4.44 (m, 2H), 3.92-3.85 (m, 8H), 3.73-3.65 (m, 2H), 3.52-3.43 (m, 2H), 2.01-1.61 (m, 6H), 0.90-0.81 (m, 10H), 0.09-0.03 (m, 6H).

Intermediate Compound 5:

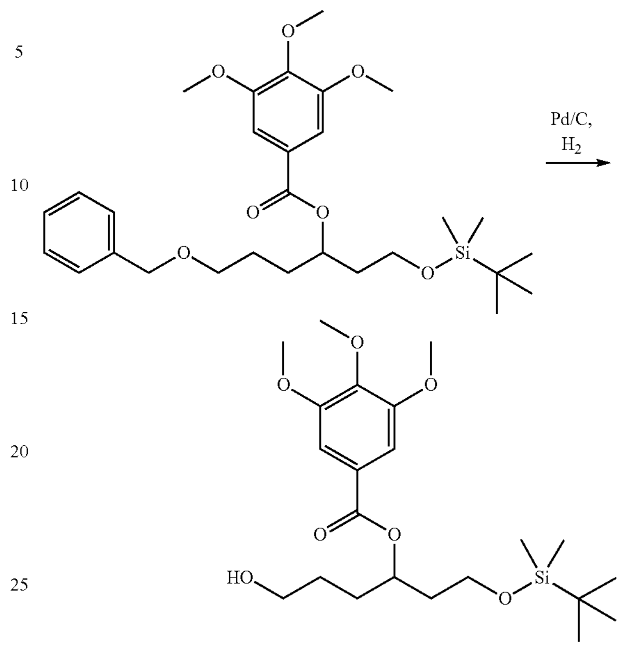

To a solution of Pd/C (150 mg, 10% purity) in methanol (20 mL) was added intermediate compound 4 (1.4 g, 2.63 mmol) at 20° C. The mixture was purged and degassed with H2 for 3 times and stirred at 20° C. for 3 hr under H2 (15 psi). The reaction mixture was filtered and the filtrate was concentrated under reduced pressure to give intermediate compound 5 (800 mg, yield 61%) as colorless oil.

1H NMR (400 MHz, CDCl3-d) δ ppm 7.28-7.25 (m, 2H), 5.30-5.20 (m, 1H), 3.91-3.86 (m, 9H), 3.73-3.62 (m, 4H), 2.03-1.84 (m, 2H), 1.84-1.74 (m, 2H), 1.68-1.59 (m, 2H), 1.45-1.37 (m, 1H), 0.86-0.84 (m, 9H), 0.03--0.02 (m, 6H)

Intermediate Compound 6:

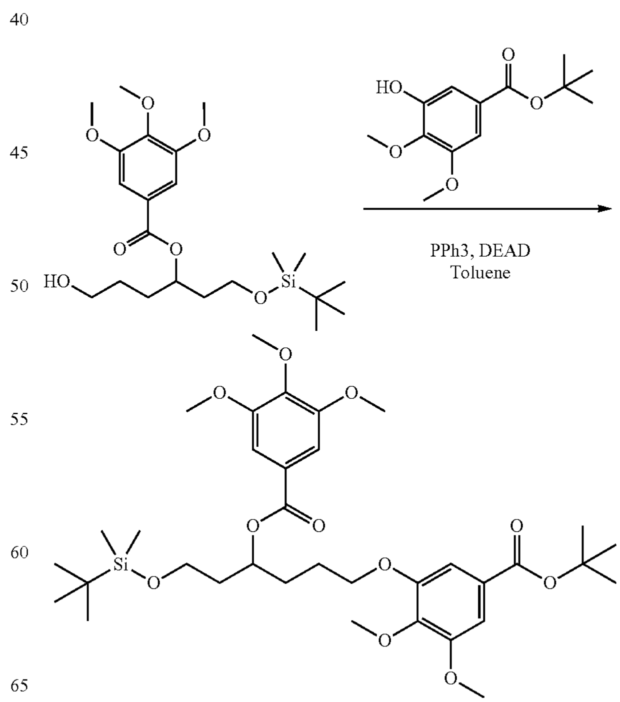

To a solution of intermediate compound 5 (700 mg, 1.58 mmol) and intermediate 2 (442.36 mg, 1.74 mmol) in toluene (8 mL) was added triphenylphosphine (705.18 mg, 2.69 mmol, 1.7 eq). Then DEAD (479.7 mg, 2.37 mmol) was added at 0° C. After the addition the mixture was stirred at 115° C. for 6 hr. The solvent was removed and the crude was purified by prep-TLC (eluted with petroleum ether/ethyl acetate=2/1) to give the intermediate compound 6 (603 mg, yield 56%) as colorless oil.

1H NMR (CDCl3-d 400 MHz) δ ppm 7.26-7.22 (m, 4H), 7.21-7.17 (m, 2H), 7.16-7.13 (m, 1H), 5.34-5.28 (m, 1H), 4.07-4.00 (m, 2H), 3.96-3.91 (m, 4H), 3.91-3.83 (m, 18H), 3.74-3.65 (m, 2H), 2.04-1.78 (m, 6H), 1.58-1.54 (m, 20H), 0.94-0.78 (m, 9H), 0.04-−0.04 (m, 6H)

Intermediate Compound 7:

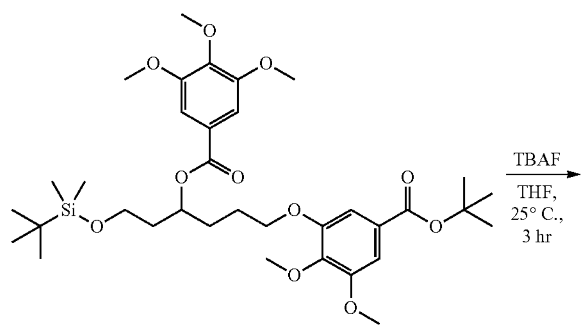

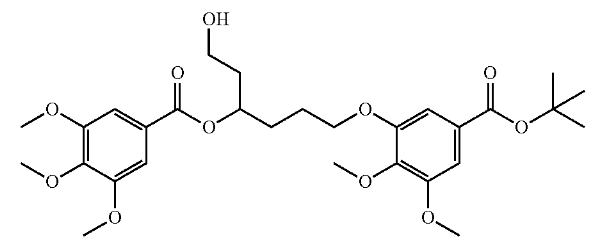

To a solution of intermediate compound 6 (440 mg, 648.13 umol, 1 eq) in tetrahydrofuran (5 mL) was added tetrabutylammonium fluoride (972.19 uL, 1 M, 1.5 eq) at 25° C. The mixture was stirred at 25° C. for 3 hr. The reaction was quenched with water (20 mL) slowly at 0° C., extracted with ethyl acetate (2×10 mL). The combined organic layers were washed with brine (20 mL), dried over Na2SO4, filtered and concentrated under reduced pressure. The residue was purified by silica gel column (SiO2, petroleum ether/ethyl acetate=20/1 to 0/1) to give the intermediate compound 7 (250 mg, yield 68%) as colorless oil.

LCMS (ESI position ion) m/z: 587.2 (M+Na)+ (calculated: 564.2)

Intermediate Compound 8:

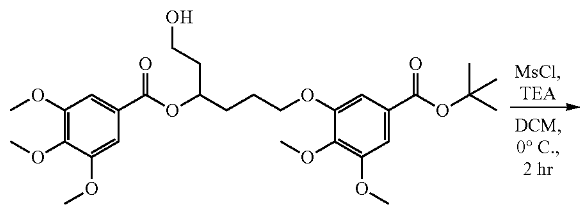

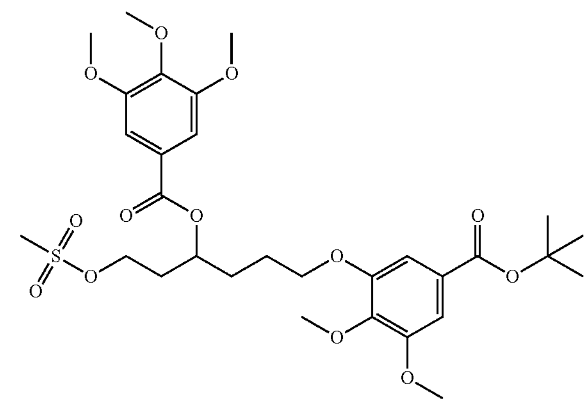

To a mixture of intermediate compound 7 (250 mg, 442.78 umol) in dichloromethane (3 mL) was added triethylamine (89.61 mg, 885.55 umol) and methanesulfonyl chloride (76.08 mg, 664.16 umol) at 0° C. Then the mixture was stirred at 0° C. and for 2 hr. The reaction mixture was quenched with water (10 mL) slowly at 0° C., extracted with ethyl acetate (3×5 mL). The combined organic layers were washed with brine (10 mL), dried over Na2SO4, filtered and concentrated under reduced pressure. The residue was purified by prep-TLC (SiO2, petroleum ether/ethyl acetate=1/1) to give the intermediate compound 8 (210 mg, yield 74%) as colorless oil.

LCMS (ESI position ion) m/z: 665.2 (M+Na)+ (calculated: 642.2).

1H NMR (400 MHz, CDCl3-d) δ ppm 7.22 (s, 2H), 7.16 (d, J=1.8 Hz, 1H), 7.15-7.13 (m, 1H), 5.31 (br t, J=5.9 Hz, 1H), 4.32-4.20 (m, 2H), 4.01 (br d, J=6.5 Hz, 2H), 3.84 (s, 9H), 3.82 (s, 3H), 3.81-3.79 (s, 3H), 2.93-2.90 (s, 3H), 2.17-2.10 (m, 2H), 1.93-1.80 (m, 4H), 1.51 (s, 9H).

Intermediate Compound 9:

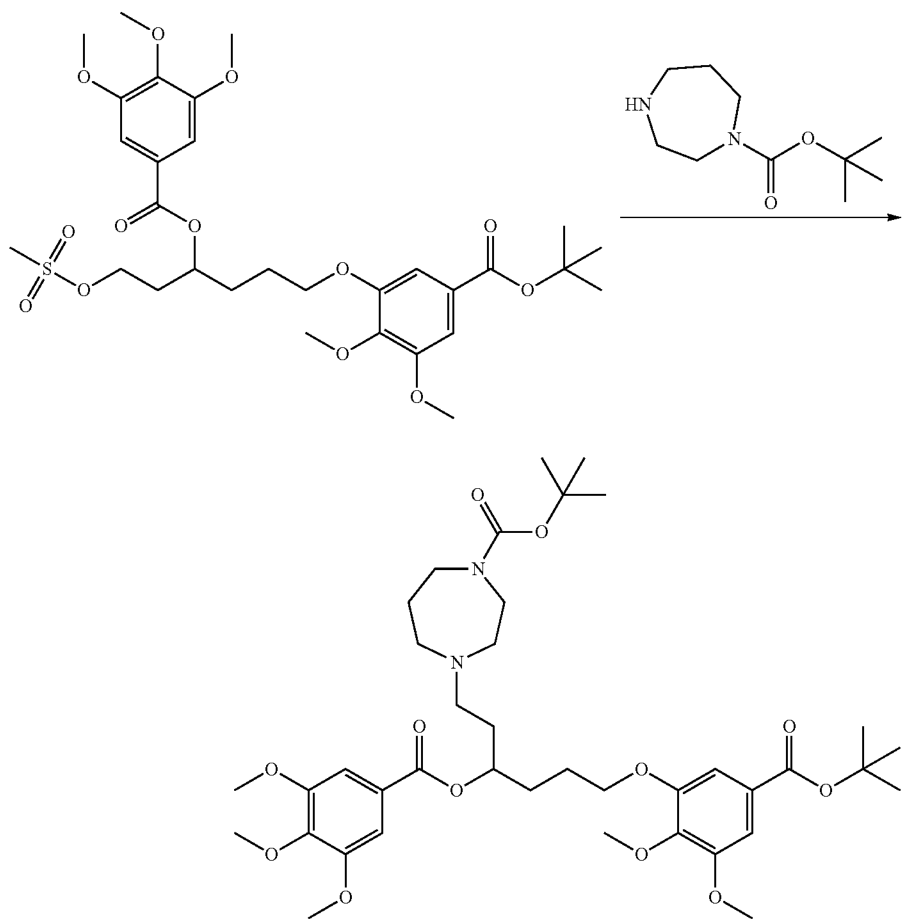

To a solution of intermediate compound 8 (210 mg, 326.74 umol) in acetonitrile (2 mL) was added tert-butyl 1,4-diazepane-1-carboxylate (65.44 mg, 326.74 umol), potassium iodide (54.24 mg, 326.74 umol) and K2CO3 (225.79 mg, 1.63 mmol) at 20° C. The mixture was stirred at 60° C. for 12 hr. The reaction mixture was quenched with water (10 mL), extracted with ethyl acetate (2×5 mL). The combined organic layers were washed with brine (10 mL), dried over Na2SO4, filtered and concentrated under reduced pressure. The residue was purified by prep-TLC (petroleum ether/ethyl acetate=1/1) to give the intermediate compound 9 (220 mg, yield 90%) as colorless oil.

LCMS (ESI position ion) m/z: 747.4 (M+H)+ (calculated: 746.4)

Intermediate Compound 10:

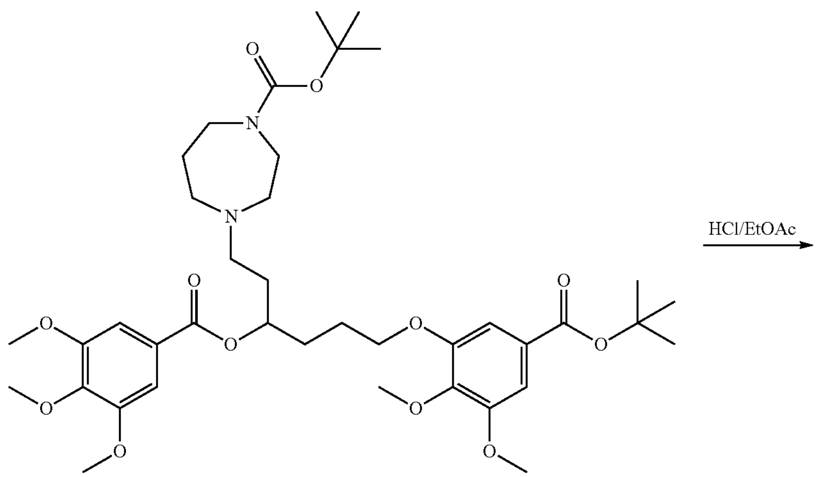

-continued

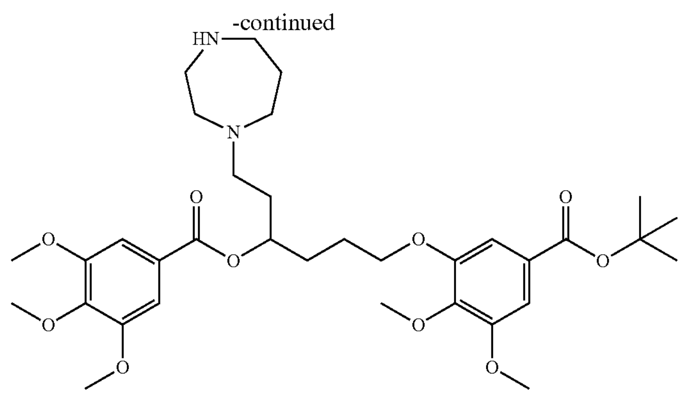

To a mixture of intermediate compound 9 (220 mg, 294.56 umol) in ethyl acetate (3 mL) was added HCl/EtOAc (5 mL, 4 M) at 20° C. The mixture was stirred at 20° C. for 2 hr. The solvent was removed under reduced pressure to give a crude intermediate compound 10 (220 mg, crude, HCl salt) as white solid, which was used directly for the next step, without any further purification.

LCMS (ESI position ion) m/z: 647.4 (M+H)+ (calculated: 646.3)

Intermediate Compound 11:

To a mixture of intermediate compound 10 (220 mg, 340.15 umol) in acetonitrile (2 mL) was added K2CO3 (141.03 mg, 1.02 mmol) and (3-bromopropoxy)(tert-butyl) dimethylsilane (103.37 mg, 408.18 umol) at 25° C. The reaction mixture was stirred at 25° C. for 12 hr. The reaction was quenched with water (10 mL), extracted with ethyl acetate (2×5 mL). The combined organic layers were washed with brine (10 mL), dried over Na2SO4, filtered and concentrated under reduced pressure to give a crude inter-

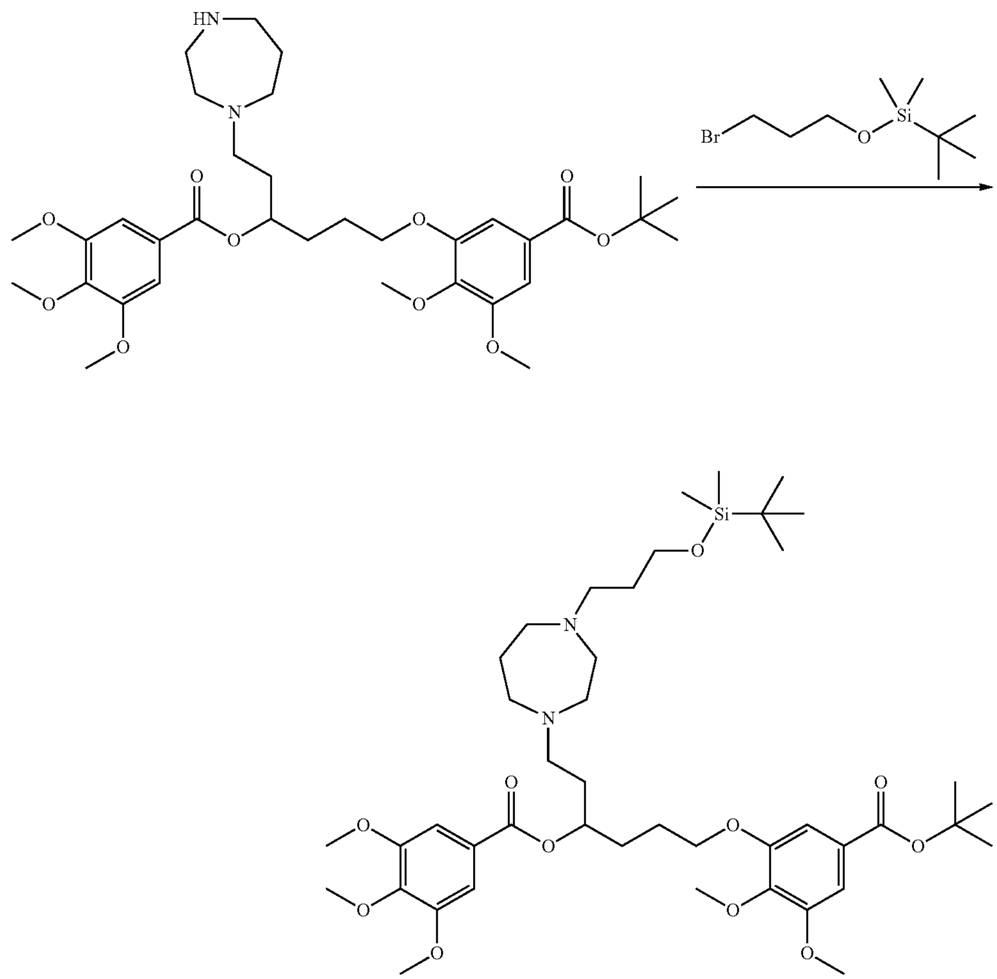

mediate compound 11 (200 mg, yield 72%) as yellow oil, which was used directly for the next step, without further purification.

LCMS (ESI position ion) m/z: 819.5 (M+H)+ (calculated: 818.4)

Intermediate Compound 12:

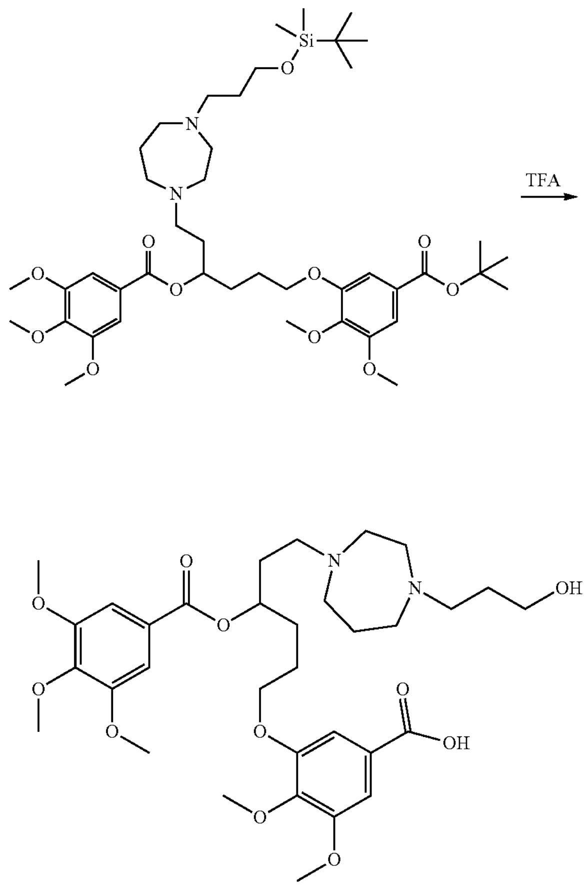

To a solution of intermediate compound 11 (50 mg, 61.04 umol) in dichloromethane (1.5 mL) was added trifluoroacetic acid (0.5 mL) at 20° C. The reaction mixture was stirred at 20° C. for 3 hr. The reaction mixture was concentrated under reduced pressure to dryness and give the crude intermediate compound 12 (50 mg, crude) as yellow oil, which was used directly for the next step, without further purification. LCMS (ESI position ion) m/z: 649.4 (M+H)+ (calculated: 648.3)

Intermediate Compound 13:

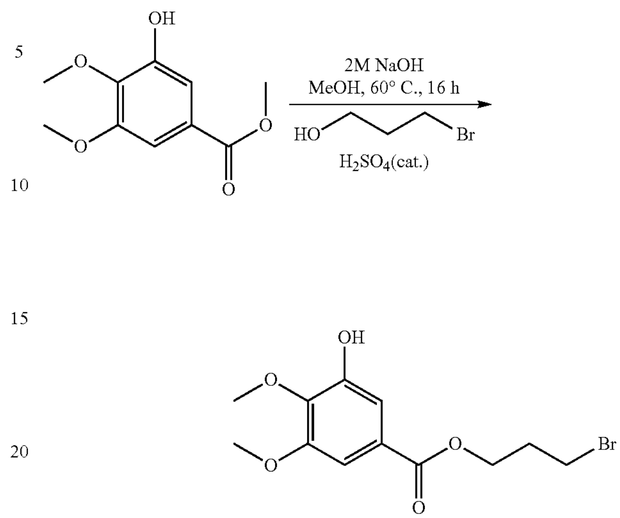

NaOH (2M, 200 mL) was added to a solution of methyl 3-hydroxy-4,5-dimethoxybenzoate (25.0 g, 118 mmol, 1.0 equiv) in MeOH (200 mL), and the resulting mixture was stirred under N2 for 16 h at 60° C. The mixture was allowed to cool down to room temperature and then was concentrated under reduced pressure. The mixture was acidified to pH=2-3 with 6 M HCl. The precipitate was collected by filtration and washed with water (3×50 mL), yielding to 3-hydroxy-4,5-dimethoxybenzoic acid (20 g, 86%) as an off-white solid.

LC-MS (ES+) m/z: 199 (M+H)+ (calculated: 198.0).

To a stirred mixture of 3-hydroxy-4,5-dimethoxybenzoic acid (20.0 g, 101 mmol, 1.0 equiv) and 3-bromopropanol (56.1 g, 404 mmol, 4.0 equiv) was added H2SO4 (0.99 g, 10.1 mmol, 0.1 equiv). The resulting mixture was stirred for 10-20 min at 120° C., and then at 100° C. for 4 h. The mixture was allowed to cool down to room temperature, and then was diluted with EtOAc (300 mL), and washed sequentially with H2O (100 mL), sat. NH4CO3 (2×100 mL) and brine (100 mL). The organic layer was dried over Na2SO4, concentrated under reduced pressure, and the residue was purified by reverse phase chromatography (column, C18 silica gel; mobile phase, MeCN in water (0.05% TFA), 30% to 70% gradient in 10 min; detector, UV 254 nm) to give the intermediate compound 13 (21 g, 65% yield) as a light-yellow solid.

LC-MS (ES+) m/z: 319 (M+H)+ (calculated: 318.0).

1H NMR (300 MHz, DMSO-d6) δ ppm 9.62 (br, 1H), 7.16 (s, 1H), 7.06 (s, 1H), 4.36-4.31 (m, 2H), 3.80 (s, 3H), 3.72 (s, 3H), 3.68-3.63 (m, 2H), 2.28-2.22 (m, 2H).

Intermediate Compound 14:

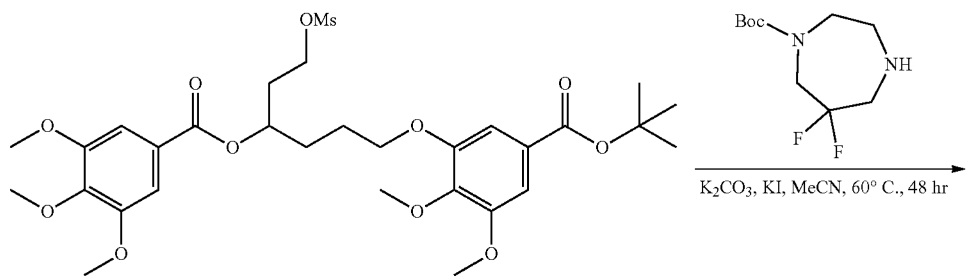

-continued

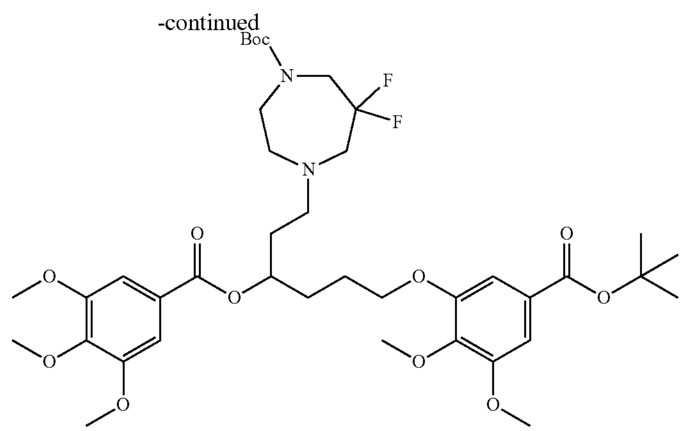

To a solution of intermediate compound 8 (3.4 g, 5.29 mmol) in ACN (50 mL) were added tert-butyl 6,6-difluoro-1,4-diazepane-1-carboxylate (1.50 g, 6.35 mmol, 1.2 eq), K2CO3 (3.66 g, 26.45 mmol, 5 eq) and KI (878.17 mg, 5.29 mmol, 1 eq). The mixture was stirred at 60° C. for 60 hr. The reaction mixture was diluted by EtOAc (100 mL) and stirred at 20° C. for 30 min. Then the mixture was filtered. The filter cake was washed with EtOAc (30 mL×3). The filtrate was concentrated and the residue was purified by column chromatography (SiO2, Petroleum ether/Ethyl acetate=6/1 to 3/1) to give the intermediate compound 14 (1.93 g, 47% yield) as colorless oil.

LCMS (ESI position ion) m/z: 783.4 (M+H)+ (calculated: 782.4)

1H NMR: (400 MHz, CDCl3) δ=7.29 (s, 2H), 7.24-7.21 (m, 2H), 5.35 (br s, 1H), 4.10-4.03 (m, 2H), 3.91 (s, 9H), 3.89 (s, 3H), 3.87 (s, 3H), 3.52-3.48 (m, 4H), 2.99-2.95 (m, 4H), 2.78-2.65 (m, 4H), 1.92 (br s, 4H), 1.59 (s, 9H), 1.45 (s, 9H)

Intermediate Compound 15:

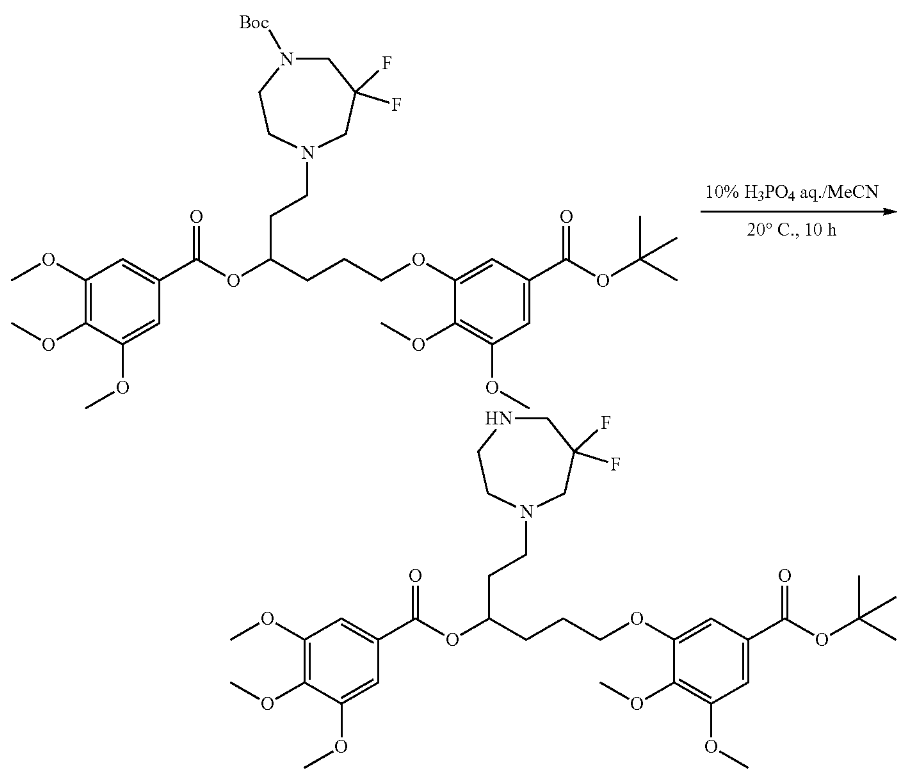

To a solution of intermediate compound 14 (1100 mg, 1.41 mmol, 1 eq) in ACN (22 mL) were added water (66 mL) and 40% H3PO4 in water (64.67 g, 659.98 mmol, 38.50 mL). The mixture was stirred at 20° C. for 16 hr. The reaction mixture was diluted with water and extracted with DCM (100 mL×3). The organic layer was washed with saturated aqueous NaHCO3 and brine, dried by Na2SO4. The solution was concentrated and the residue was purified by chromatography on a silica gel eluted with petroleum ether:ethyl acetate (from 5/1 to 0/1) to give the intermediate compound 15 (290 mg, 30% yield) as colorless oil.

LCMS (ESI position ion) m/z: 683.3 (M+H)+ (calculated: 682.3)

Intermediate Compound 16:

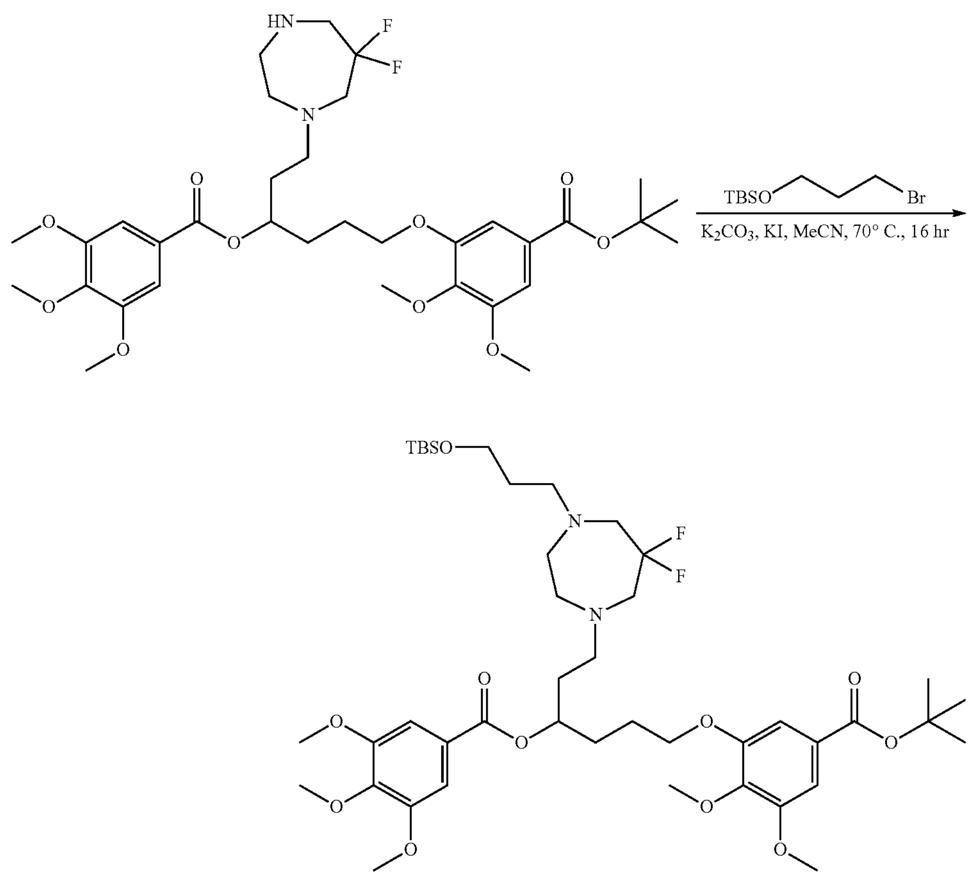

To a solution of intermediate compound 15 (330 mg, 483.34 umol, 1 eq) in ACN (6 mL) were added KI (80.23 mg, 483.34 umol, 1 eq), K2CO3 (200.41 mg, 1.45 mmol, 3 eq) and (3-bromopropoxy)(tert-butyl)dimethylsilane (979.25 mg, 3.87 mmol, 8 eq). The mixture was stirred at 70° C. for 12 hr. The reaction mixture was diluted by DCM (30 mL) and stirred at 20° C. for 30 min. Then the mixture was filtered. The filter cake was washed with DCM (10 mL×3). The filtrate was concentrated and purified by preparative TLC (SiO2, petroleum ether/EtOAc=3/1, Rf=0.29) to give the intermediate compound 16 (405 mg, 98% yield) as colorless oil.

LCMS (ESI position ion) m/z: 855.4 (M+H)+ (calculated: 854.5)

1H NMR: (400 MHz, CDCl3) δ=7.30 (s, 2H), 7.23 (q, J=1.8 Hz, 2H), 5.31 (br s, 1H), 4.08 (br s, 2H), 3.93-3.87 (m, 15H), 3.65 (t, J=6.2 Hz, 2H), 3.08-2.89 (m, 4H), 2.75-2.57 (m, 8H), 2.01-1.79 (m, 6H), 1.68-1.61 (m, 2H), 1.59 (s, 9H), 0.91-0.86 (m, 9H), 0.05 (s, 6H)

Intermediate Compound 17:

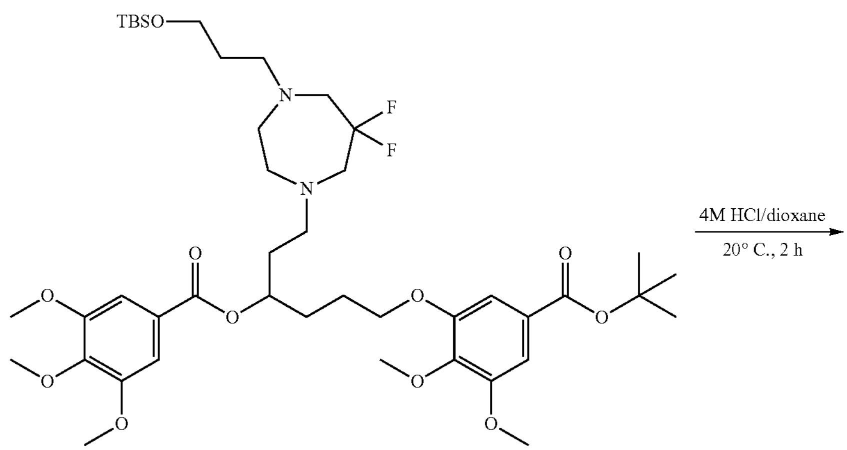

-continued

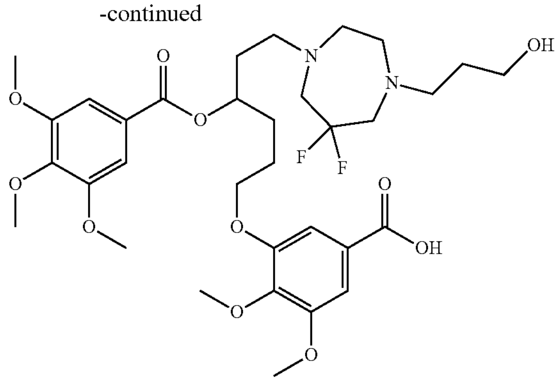

A solution of intermediate compound 16 (400 mg, 467.79 umol, 1 eq) in HCl/dioxane (4 M, 40.00 mL, 342.03 eq) was stirred at 20° C. for 2 hr. The reaction mixture was concentrated and purified by reversed-phase HPLC (column: Phenomenex Synergi C18 150*25*10 um; mobile phase: [water (0.225% FA)-ACN]; B %: 38%-68%, 9 min) to give the intermediate compound 17 (285 mg, 89% yield) as an off white solid.

LCMS (ESI position ion) m/z: 685.3 (M+H)+ (calculated: 684.3)

1H NMR: (400 MHz, CDCl3) δ=7.21 (d, J=6.9 Hz, 4H), 5.25 (br s, 1H), 4.05 (br s, 2H), 3.84 (s, 15H), 3.77 (t, J=5.4 Hz, 2H), 3.02-2.89 (m, 4H), 2.73-2.58 (m, 8H), 1.89-1.72 (m, 6H), 1.65 (quin, J=5.6 Hz, 2H)

Intermediate Compound 18:

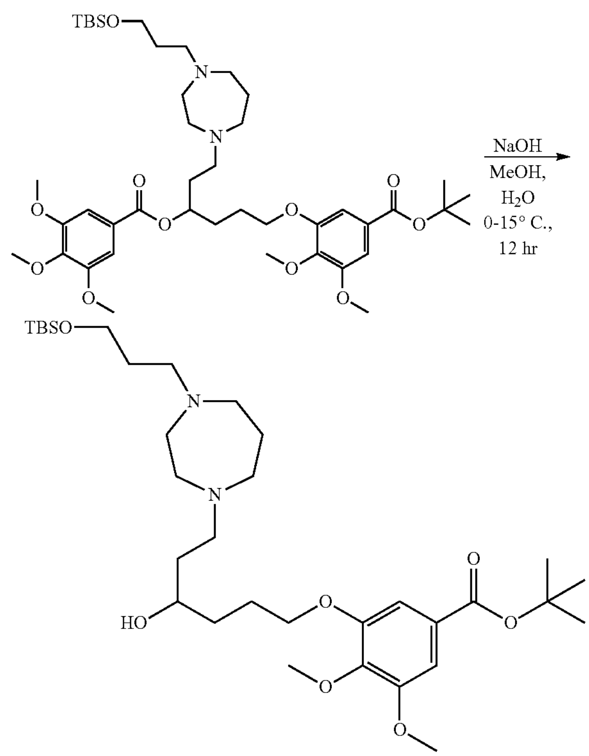

To a solution of intermediate compound 6 (500 mg, 610.42 umol, 1 eq) in THF (8 mL), MeOH (8 mL) and H2O (8 mL) was added NaOH (244.15 mg, 6.10 mmol) at 0° C. under N2. The reaction mixture was stirred at 15° C. for 1 hr. The reaction was concentrated under vacuum and the solution was extracted with ethyl acetate (3×20 mL). The organic layer was combined and washed with water (20 mL), dried over Na2SO4 and concentrated under vacuum. The residue was purified by preparative acid HPLC to give the intermediate 18 (65 mg, yield 11.5%) as yellow oil.

Intermediate Compound 19:

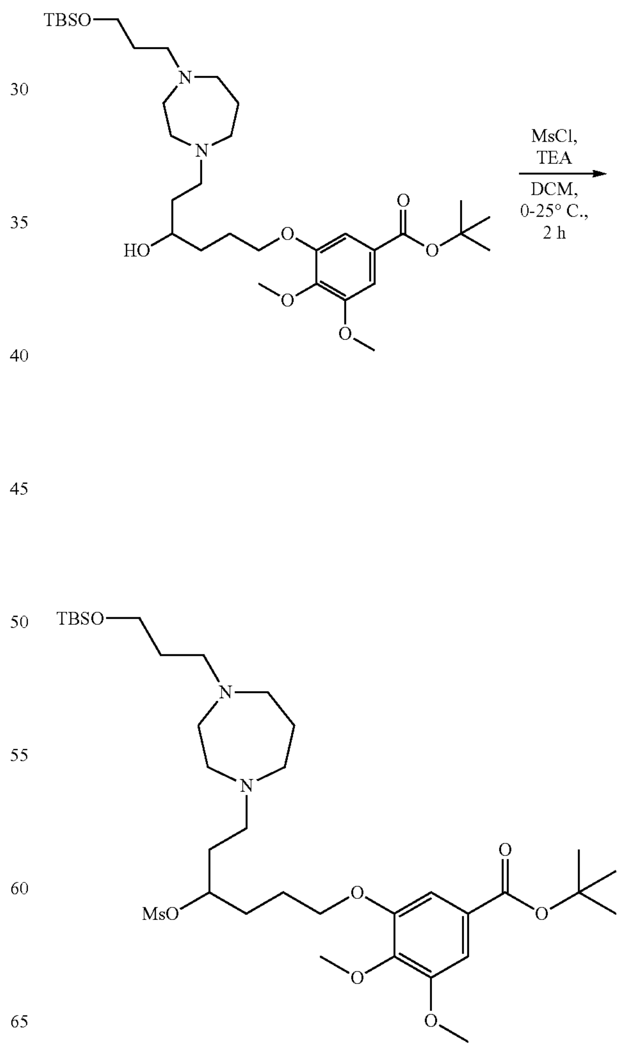

To a solution of intermediate compound 18 (96 mg, 153.63 umol) in DCM (5 mL) were added TEA (46.62 mg, 406.86 umol) and mesyl chloride (26.4 mg, 230.43 umol) at 0° C. The reaction mixture was stirred at 25° C. for 2 hr. The reaction mixture was diluted with ice water (10 mL) and extracted with dichloromethane (3×5 mL). The combined organic layers were washed with brine (10 mL), dried over Na2SO4, filtered and concentrated under vacuum to give the crude intermediate compound 19 (80 mg) as yellow oil and used without further purification.

Intermediate Compound 20:

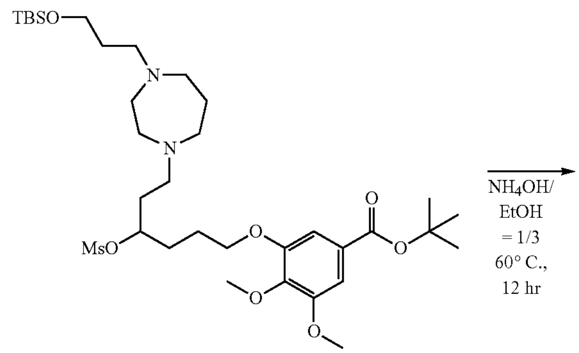

-continued

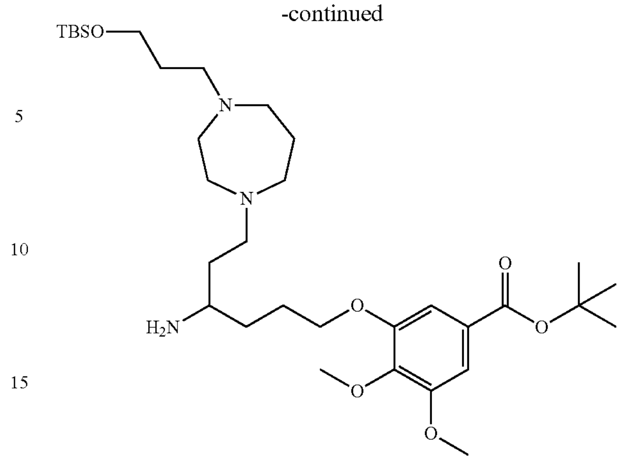

To a solution of intermediate compound 19 (80 mg, 113.76 umol, 1 eq) in ethanol (1 mL) was added NH40H (0.3 mL, 30% purity) at 20° C., and the mixture was stirred at 60° C. for 12 hr. The reaction was concentrated under reduced pressure to give the crude intermediate compound 20 (70 mg) as yellow oil used without further purification.

Intermediate Compound 21:

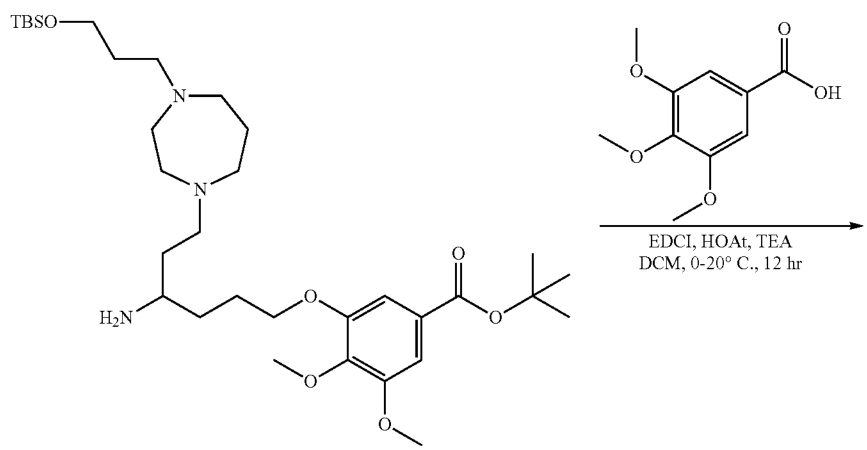

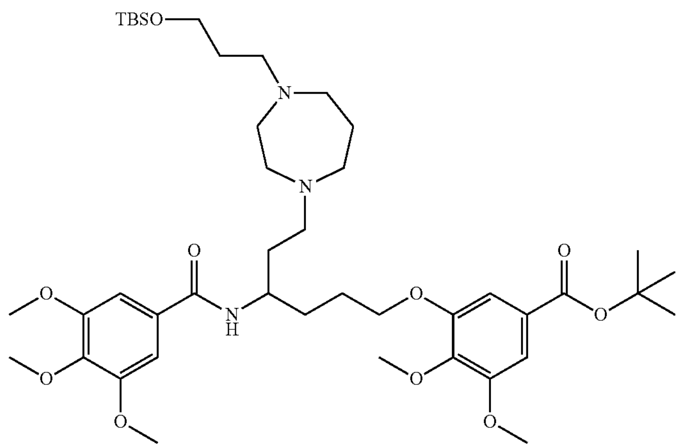

To a solution of intermediate compound 1 (28.56 mg, 113.76 umol, 1.1 eq) in DCM (1 mL) was added TEA (68.11 mg, 673.12 umol), EDCI (53.76 mg, 280.49 umol) and HOAt (30.52 mg, 224.35 umol) at 0° C. The mixture was stirred at 0° C. for 5 min. Then intermediate compound 20 (70 mg, 112.21 umol, 1 eq) was added. The mixture was stirred at 20° C. for 12 hr. The reaction mixture was concentrated under vacuum to give the crude intermediate 21 (160 mg, crude) as yellow oil used without further purification.

Intermediate Compound 22:

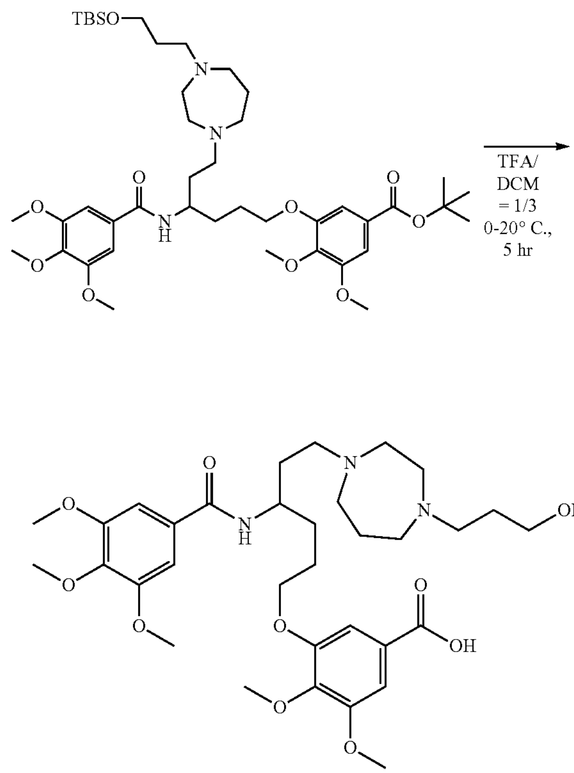

To a solution of intermediate compound 21 (100 mg, 122.2 umol) in DCM (5 mL) were added TFA (1.5 mL, 20.3 mmol) at 0° C. The mixture was stirred at 20° C. for 5 hr. The reaction mixture was concentrated under vacuum. The residue was purified by pre-HPLC to give the intermediate compound 22 (41.0 mg, yield 48%) as yellow oil.

LCMS (ESI position ion) m/z: 648.3 (M+H)+ (calculated: 647.3)

Intermediate Compound 23:

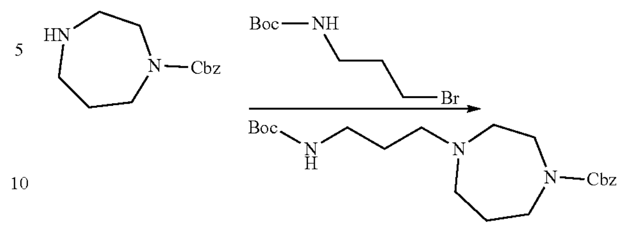

To a solution of benzyl 1,4-diazepane-1-carboxylate (2000 mg, 8.54 mmol, 1.77 mL) in ACN (30 mL) was added tert-butyl (3-bromopropyl)carbamate (2.03 g, 8.54 mmol), KI (283.41 mg, 1.71 mmol) and DIPEA (2.21 g, 17.07 mmol, 2.97 mL), stirred at 100° C. for 12 h, which was still white suspension. The mixture was directly concentrated and poured into H2O (30 mL). Then it was extracted with DCM 40 mL×2) and dried over anhydrous Na2SO4, filtered and concentrated. The residue was purified by silica column chromatography (EtOAc to EtOAc/MeOH=10/1) to give the intermediate compound 23 (2.7 g, 81% yield) as yellow oil.

LCMS (ESI position ion) m/z: 392.3 (M+H)+ (calculated: 391.2)

Intermediate Compound 24:

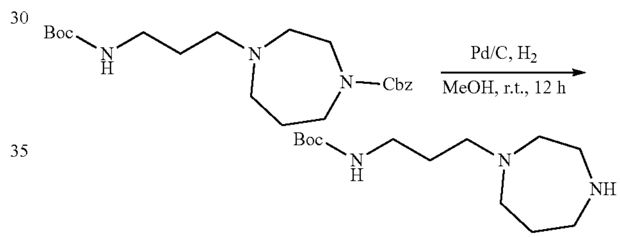

To a mixture of intermediate compound 23 (1.5 g, 3.83 mmol, 1 eq) in MeOH (10 mL) was added Pd/C (2 g, 3.83 mmol, 10% purity, 1 eq) under H2 at 20 psi atmosphere, stirred at 25° C. for 12 hrs. The mixture was directly filtered with celite and filtrate was concentrated under vacuum to give the crude intermediate compound 24 (750 mg, 76% yield) as a yellow oil.

1H NMR (400 MHz, CD3OD-d4) δ 3.08 (t, J=6.8 Hz, 2H), 2.97-2.90 (m, 4H), 2.75-2.69 (m, 4H), 2.58-2.52 (m, 2H), 1.86-1.79 (m, 2H), 1.70-1.61 (m, 2H), 1.43 (s, 9H)

Intermediate Compound 25:

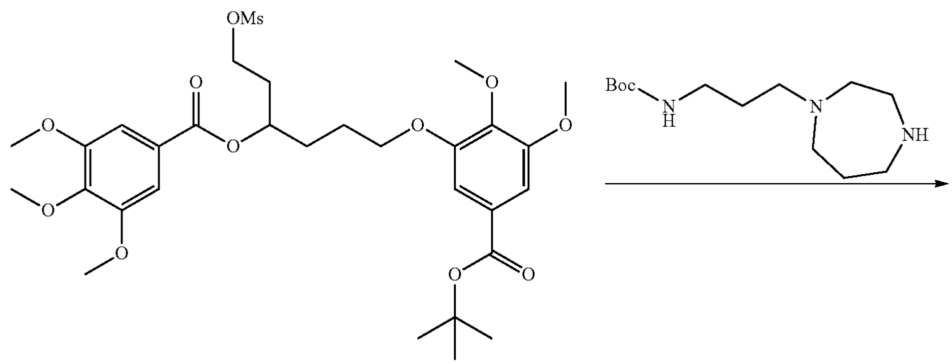

-continued

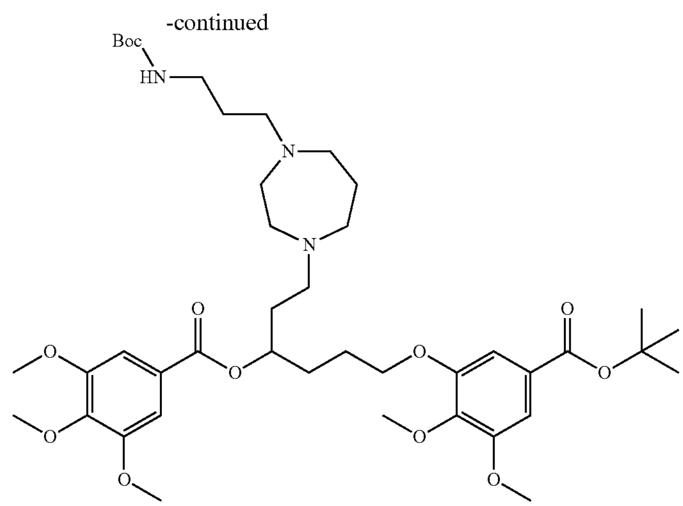

To a solution of intermediate compound 8 (1.7 g, 2.65 mmol, 1 eq) and intermediate compound 24 (748.84 mg, 2.91 mmol, 1.1 eq) in MeCN (20 mL) was added KI (439.08 mg, 2.65 mmol, 1 eq) and K2CO3 (1.83 g, 13.23 mmol, 5 eq). The mixture was stirred at 60° C. for 12 hrs. The reaction mixture was diluted with H2O (100 mL) and then extracted with ethyl acetate (3×50 mL). The combined organic layers were washed with brine (50 mL), dried over anhydrous Na2SO4, filtered and concentrated under vacuum. The residue was purified by column chromatography on silica gel eluting with (petroleum ether/EtOAc=1/1 to DCM/MeOH=10/1) to give the intermediate compound 25 (2 g, 94% yield) as a yellow oil.

LCMS (ESI position ion) m/z: 804.3 (M+H)+ (calculated: 803.5)

1H NMR (400 MHz, CDCl3-d) δ 7.31 (s, 2H), 7.22 (s, 2H), 5.38-5.27 (m, 1H), 4.12-4.09 (m, 2H), 3.89-3.85 (m, 9H), 3.84 (d, J=4.4 Hz, 6H), 3.09 (t, J=6.7 Hz, 2H), 2.91-2.76 (m, 8H), 2.73-2.61 (m, 4H), 2.02-1.82 (m, 8H), 1.70 (quin, J=7.1 Hz, 2H), 1.59 (s, 9H), 1.44 (s, 9H).

Intermediate Compound 26:

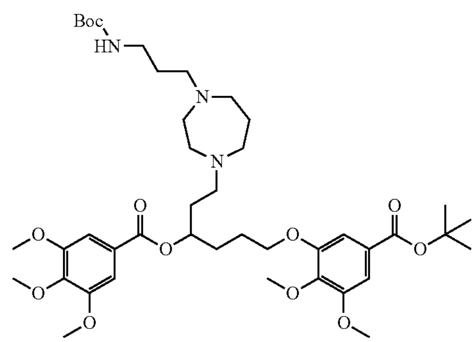

HCl/
dioxane

-continued

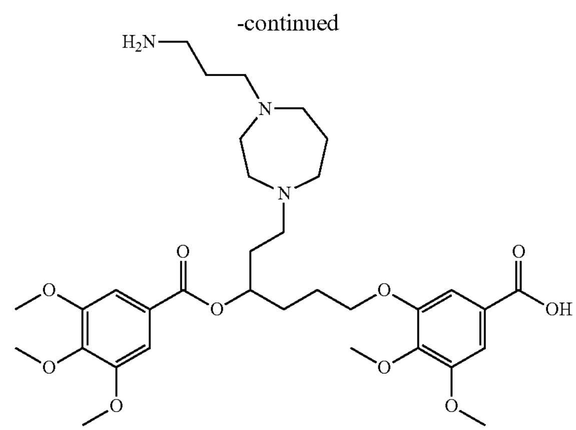

To a solution of intermediate compound 25 (500 mg, 621.91 umol, 1 eq) was added HCl/dioxane (4 M, 155.48 uL, 1 eq) The reaction was stirred at 25° C. for 12 hr. The reaction mixture was concentrated under vacuum to give the crude intermediate compound 26 (380 mg, 94% yield) as a yellow solid.

LCMS (ESI position ion) m/z: 648.2 (M+H)+ (calculated: 647.3)

1H NMR (400 MHz, CD3OD-d4) δ 7.19 (s, 2H), 7.18-7.16 (m, 2H), 5.25-5.15 (m, 1H), 4.05-3.99 (m, 2H), 3.77-3.75 (m, 9H), 3.72 (d, J=2.9 Hz, 10H), 3.52-3.40 (m, 4H), 3.31-3.24 (m, 2H), 3.23 (br s, 1H), 3.19 (br s, 1H), 2.93 (t, J=7.6 Hz, 2H), 2.25 (br s, 2H), 2.20-2.12 (m, 2H), 2.08-1.98 (m, 2H), 1.96-1.91 (m, 2H), 1.89-1.81 (m, 2H).

Intermediate Compound 27:

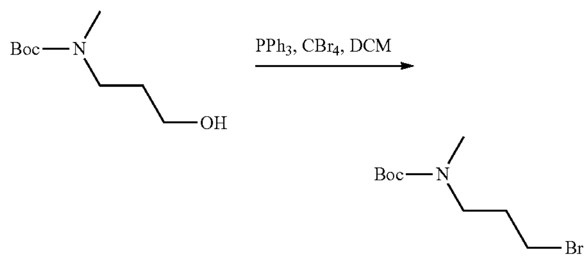

To a solution of tert-butyl N-(3-hydroxypropyl)-N-methyl-carbamate (2 g, 10.57 mmol, 1 eq) in DCM (20 mL) was added triphenylphosphine (4.16 g, 15.85 mmol, 1.5 eq) at 0° C., then tetrabromomethane (5.26 g, 15.85 mmol, 1.5 eq) was added and stirred for 30 min. The mixture was concentrated undfer vacuum. The residue was purified by silica column chromatography (petroleum ether/EtOAc=10/1 to 5/1) to give the intermediate compound 27 (2 g, 75% yield) as a yellow liquid.

LCMS (ESI position ion) m/z: 195.7 (M+H-56)+ (calculated: 251.05)

1H NMR (400 MHz, CHLOROFORM-d) δ 3.41-3.37 (m, 2H), 3.36-3.31 (m, 2H), 2.86 (s, 3H), 2.11-2.03 (m, 2H), 1.45 (s, 9H)

Intermediate Compound 28:

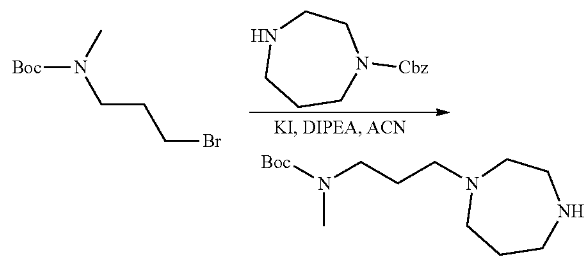

To a solution of intermediate compound 27 (753.34 mg, 2.99 mmol, 1.4 eq) and benzyl 1,4-diazepane-1-carboxylate (500 mg, 2.13 mmol, 1 eq) in MeCN (30 mL), was added KI (70.85 mg, 426.82 umol, 0.2 eq) and DIPEA (551.63 mg, 4.27 mmol, 2 eq), the reaction mixture was stirred at 100° C. for 12 hrs. The mixture was concentrated under vacuum and poured into H2O (30 mL) then extracted with EtOAc (30 mL×3) and concentrated under vacuum. The residue was purified by silica column chromatography (EtOAc to DCM/MeOH=20/1) to give the intermediate compound 28 (800 mg, 92% yield) as a brown liquid.

LCMS (ESI position ion) m/z: 406.1 (M+H)+ (calculated: 405.3)

1H NMR (400 MHz, METHANOL-d4) δ 7.41-7.27 (m, 5H), 5.16-5.09 (m, 2H), 3.60-3.51 (m, 4H), 3.27-3.21 (m, 2H), 2.84 (br s, 3H), 2.81-2.65 (m, 4H), 2.61-2.45 (m, 2H), 1.91-1.82 (m, 2H), 1.79-1.67 (m, 2H), 1.45 (d, J=1.8 Hz, 9H)

Intermediate Compound 29:

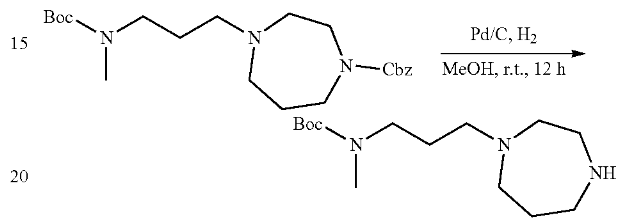

To a mixture of intermediate compound 28 (800 mg, 1.97 mmol, 1 eq) in MeOH (15 mL) was added Pd/C (800 mg, 1.97 mmol, 10% purity, 1.00 eq) under H2 (25 psi), and stirred at 30° C. for 12 hrs. The mixture was filtered and concentrated under vacuum to give the intermediate compound 29 (500 mg, 93% yield) as brown liquid.

1H NMR (400 MHz, MeOD-d4) δ 3.31-3.26 (m, 2H), 2.97-2.92 (m, 4H), 2.98-2.91 (m, 3H), 2.96-2.91 (m, 4H), 2.56-2.49 (m, 2H), 1.89-1.72 (m, 4H), 1.49-1.45 (m, 9H)

Intermediate Compound 30:

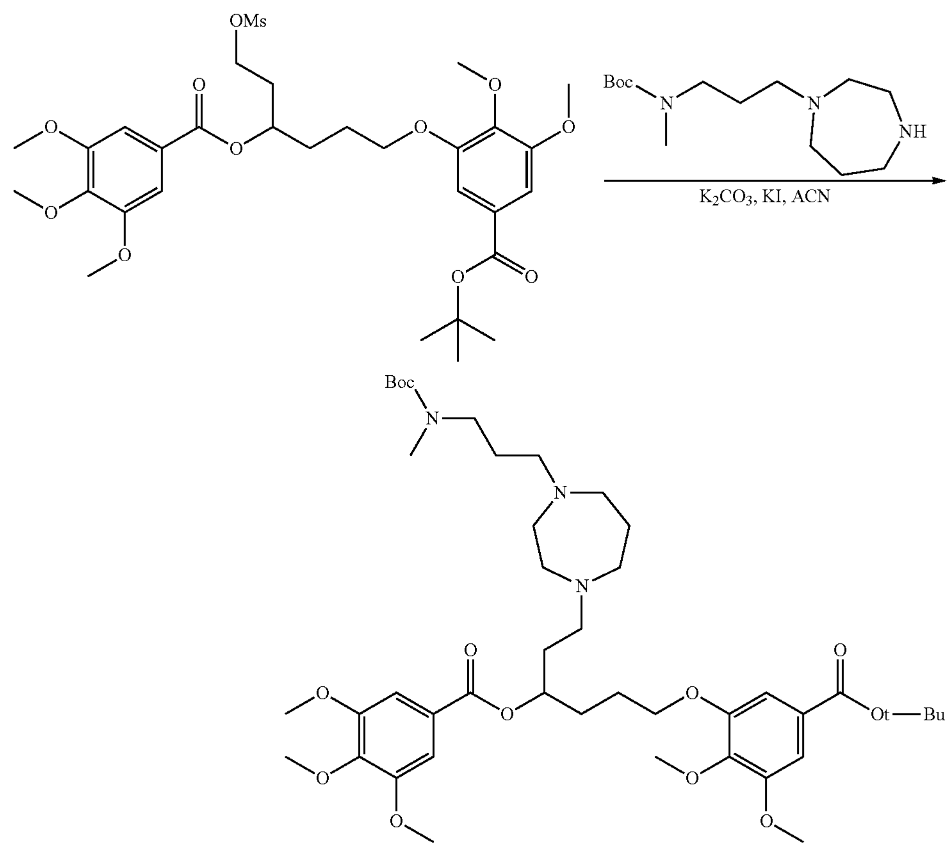

To a mixture of intermediate compound 8 (900 mg, 1.40 mmol, 1 eq) and intermediate compound 29 (500 mg, 1.84 mmol, 1.32 eq) in MeCN (30 mL) was added KI (232.46 mg, 1.40 mmol, 1 eq) and K2CO3 (967.66 mg, 7.00 mmol, 5 eq), the reaction mixture was stirred at 60° C. for 12 hrs. The mixture was poured into H2O (30 mL) and extracted with EtOAc (30 mL×3). The organic layer was dried over Na2SO4, filtered and concentrated. The residue was purified by silica column chromatography (DCM/MeOH=10/1) to give the intermediate compound 30 (1 g, 87% yield) as yellow liquid.

LCMS (ESI position ion) m/z: 818.5 (M+H)+ (calculated: 817.5)

1H NMR (400 MHz, METHANOL-d4) 6=7.29 (s, 2H), 7.20 (s, 2H), 5.31-5.25 (m, 1H), 4.12-4.06 (m, 2H), 3.87-3.84 (m, 9H), 3.82 (d, J=4.0 Hz, 6H), 3.23 (t, J=7.1 Hz, 2H), 2.87-2.81 (m, 3H), 2.74 (br s, 8H), 2.62 (br t, J=7.2 Hz, 2H), 2.54-2.43 (m, 2H), 2.05-1.86 (m, 6H), 1.85-1.77 (m, 2H), 1.75-1.66 (m, 2H), 1.57 (s, 9H), 1.45 (s, 9H)

Intermediate Compound 31:

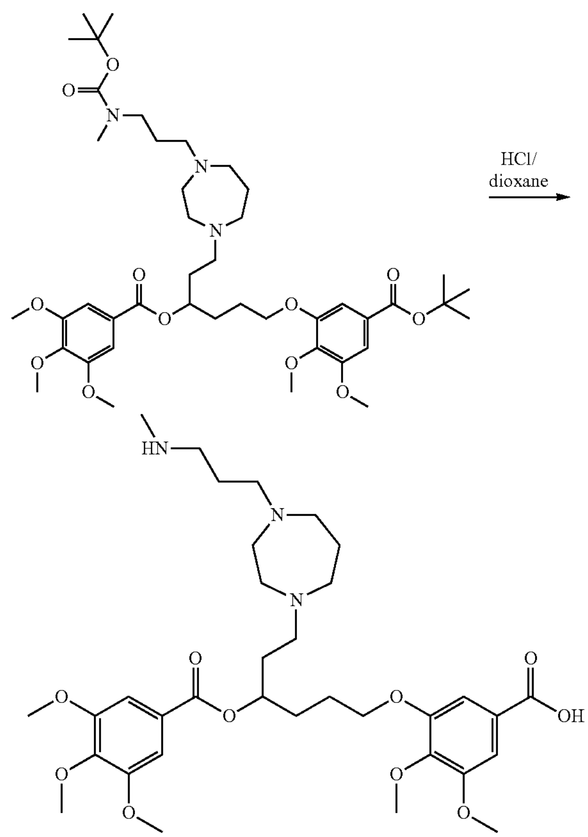

A solution of intermediate compound 30 (950 mg, 1.16 mmol, 1 eq) in HCl/dioxane (4 M, 10 mL, 34.44 eq) was stirred at 25° C. for 2 hrs. The reaction was concentrated under vacuum to give the intermediate compound 31 (700 mg, 91% yield) as yellow solid.

LCMS (ESI position ion) m/z: 662.3 (M+H)+ (calculated: 661.4)

1H NMR (400 MHz, MeOD-d4) δ 7.29 (s, 2H), 7.20 (s, 2H), 5.31-5.25 (m, 1H), 4.12-4.06 (m, 2H), 3.87-3.84 (m, 9H), 3.82 (d, J=4.0 Hz, 6H), 3.23 (t, J=7.1 Hz, 2H), 2.87-2.81 (m, 3H), 2.74 (br s, 8H), 2.62 (br t, J=7.2 Hz, 2H), 2.54-2.43 (m, 2H), 2.05-1.86 (m, 6H), 1.85-1.77 (m, 2H), 1.75-1.66 (m, 2H)

Intermediate Compound 32:

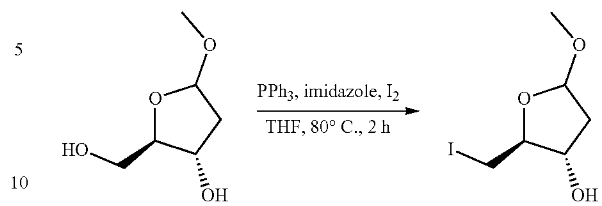

To a stirred solution of (2R,3S)-2-(hydroxymethyl)-5-methoxytetrahydrofuran-3-ol (19 g, 128.24 mmol, 1 eq) in dry THF (650 mL) was added triphenylphosphine (50.45 g, 192.36 mmol, 1.5 eq) followed by imidazole (17.46 g, 256.49 mmol, 2 eq) at 25° C. and the resulting mixture was stirred at 80° C. for 0.5 h. After cooling to 25° C., a solution of 12 (48.82 g, 192.36 mmol, 1.5 eq) in dry THF (190 mL) was added slowly and the resulting mixture was stirred at 80° C. for 2 h. The reaction mixture was filtered. The filter cake was washed with EtOAc (500 mL) and the combined filtrates were concentrated under vacuum to remove the solvent. The residue was purified by column chromatography on silica gel eluting with (petroleum ether/ethyl acetate=10/1 to 3/1) to give the intermediate compound 32 (23.2 g, 56% yield) as a light yellow oil.

1H NMR (400 MHz, DMSO-d6) δ 5.26-5.15 (m, 1H), 5.06-4.92 (m, 1H), 4.17-4.10 (m, 0.5H), 3.85-3.77 (m, 1H), 3.56 (dt, J=3.8, 5.8 Hz, 0.5H), 3.51-3.45 (m, 0.5H), 3.34-3.28 (m, 1H), 3.26 (d, J=3.0 Hz, 3H), 3.21 (dd, J=7.3, 10.3 Hz, 0.5H), 2.40 (ddd, J=5.8, 8.3, 13.8 Hz, 0.5H), 2.16-2.07 (m, 0.5H), 1.95 (td, J=5.6, 13.4 Hz, 0.5H), 1.69 (ddd, J=2.6, 5.3, 13.6 Hz, 0.5H).

Intermediate Compound 33:

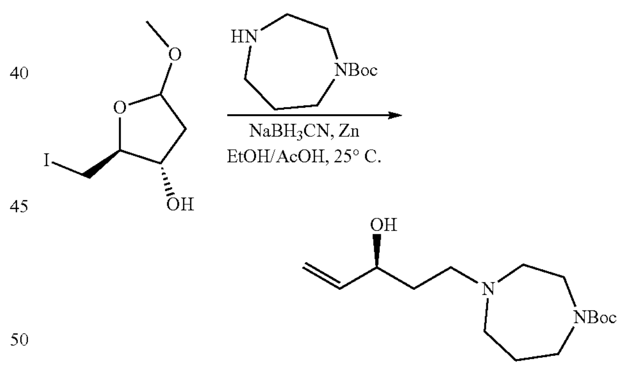

To a stirred solution of intermediate compound 32 (23.19 g, 89.88 mmol) in EtOH (350 mL) were added successively Zn (49.07 g, 750.42 mmol), tert-butyl 1,4-diazepane-1-carboxylate (15 g, 74.90 mmol, 14.71 mL, 1 eq) in EtOH (90 mL), NaBH3CN (11.77 g, 187.24 mmol) and AcOH (5.40 g, 89.88 mmol, 5.14 mL) at 25° C. and the resulting mixture was stirred at 25° C. for 2 h. The reaction mixture was quenched with saturated NaHCO3 aqueous solution (1000 mL) and stirred for 30 min. After dilution with EtOAc (500 mL), the mixture was filtered over celite and the cake was washed with EtOAc (200 mL). The water layer was extracted with EtOAc (2×300 mL). The combined organic layers were washed with brine (2×300 mL), dried over Na2SO4, filtered and concentrated under vacuum to give the crude intermediate compound 33 (27 g,) as a light yellow oil.

1H NMR (400 MHz, CDCl3-d) δ 5.89 (ddd, J=5.0, 10.5, 17.1 Hz, 1H), 5.36-5.27 (m, 1H), 5.13 (td, J=1.6, 10.5 Hz, 1H), 4.38 (dtd, J=1.7, 3.3, 8.0 Hz, 1H), 3.57-3.43 (m, 4H), 2.86-2.61 (m, 6H), 1.97-1.83 (m, 2H), 1.80-1.59 (m, 2H), 1.48 (s, 9H)

Intermediate Compound 34:

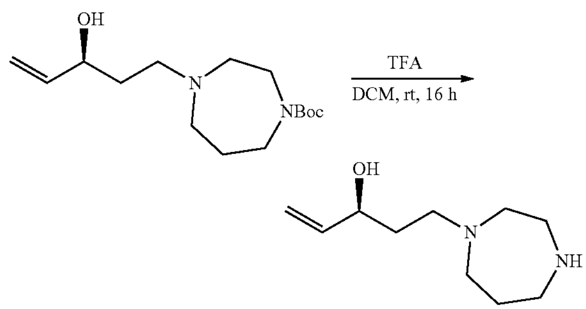

A mixture of intermediate compound 33 (5 g, 17.58 mmol, 1 eq) in HCl/MeOH (4 M, 4.40 mL, 1 eq) with stirring at 25° C. for 1 h. The reaction mixture was concentrated under vacuum to give the crude intermediate compound 34 (4.50 g) as a yellow oil.

LCMS (ESI position ion) m/z: 185.1 (M+H)+ (calculated: 184.2)

1H NMR (400 MHz, MeOD-d4) δ 5.93 (ddd, J=5.6, 10.6, 17.2 Hz, 1H), 5.37-5.31 (m, 1H), 5.18 (td, J=1.3, 10.5 Hz, 1H), 4.27 (qd, J=4.2, 5.5 Hz, 1H), 4.13-3.55 (m, 6H), 3.51-3.38 (m, 4H), 2.42-2.30 (m, 2H), 2.13-1.92 (m, 2H)

Intermediate Compound 35:

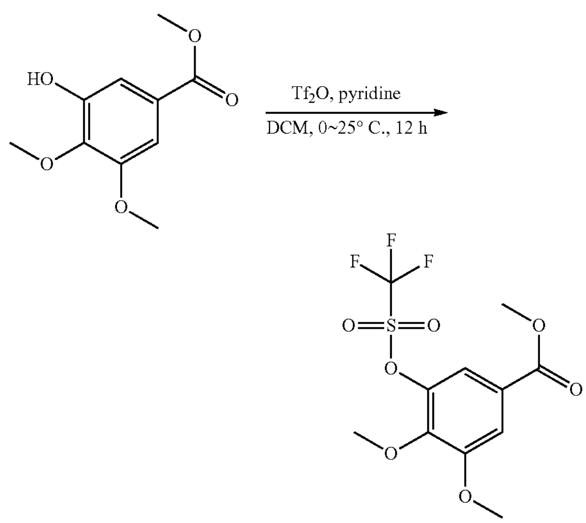

To a solution of methyl 3-hydroxy-4,5-dimethoxybenzoate (4 g, 18.85 mmol, 1 eq) and pyridine (2.98 g, 37.70 mmol, 2 eq) in DCM (50 mL) was added trifluoromethanesulfonic anhydride (7.98 g, 28.28 mmol, 1.5 eq) dropwise at 0° C. under N2 atmosphere. Then the reaction was warmed to 25° C. and stirred for 12 h. The reaction mixture was diluted with water (100 mL) and then extracted with DCM (2×40 mL). The combined organic layers were washed with brine (20 mL), dried over anhydrous Na2SO4, filtered and concentrated under vacuum. The residue was purified by flash chromatography on silica gel (petroleum ether/EtOAc=93/7) to give the intermediate compound 35 (6.36 g, 98% yield) as a yellow oil.

LCMS (ESI position ion) m/z: 345.2 (M+H)+ (calculated: 344.0)

Intermediate Compound 36:

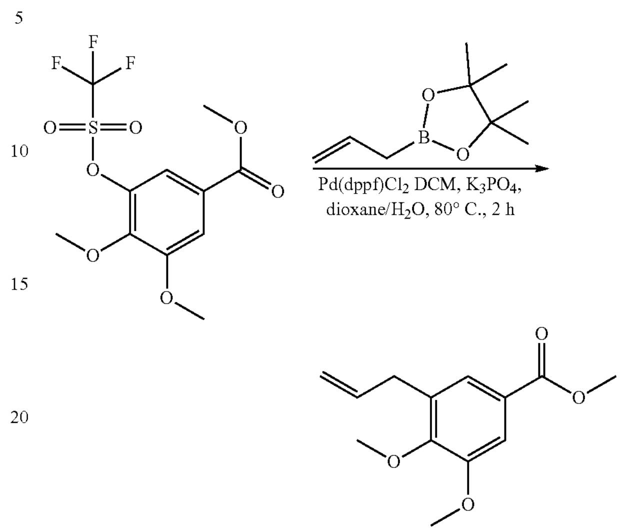

To a solution of intermediate compound 35 (100 mg, 290.48 umol, 1 eq) and 2-allyl-4,4,5,5-tetramethyl-1,3,2-dioxaborolane (244.06 mg, 1.45 mmol, 5 eq) in dioxane (4 mL) and H2O (1.3 mL) was added Pd(dppf)Cl2·CH2Cl2 (23.72 mg, 29.05 umol, 0.1 eq) and K3PO4 (308.29 mg, 1.45 mmol, 5 eq). The mixture was degassed with N2 3 times and then stirred at 80° C. for 2 hrs under N2 atmosphere. The reaction mixture was filtered and the filter cake was washed with EtOAc (50 mL). The filtrate was diluted with water (100 mL) and then extracted with ethyl acetate (40 mL×2). The combined organic layers were washed with brine (30 mL), dried over Na2SO4, filtered and concentrated under vacuum. The residue was purified on silica gel eluting with (petroleum ether/EtOAc=95/5) to give the intermediate compound 36 (2.3 g) as a light yellow oil.

LCMS (ESI position ion) m/z: 237.2 (M+H)+ (calculated: 236.1)

1H NMR (400 MHz, CDCl3-d) δ 7.44 (d, J=2.0 Hz, 1H), 7.40 (d, J=1.9 Hz, 1H), 5.95-5.83 (m, 1H), 5.01 (m, 1H), 4.98 (qd, J=1.5, 7.4 Hz, 1H), 3.83 (s, 3H), 3.82 (s, 3H), 3.79 (s, 3H), 3.35 (d, J=6.6 Hz, 2H).

Intermediate Compound 37:

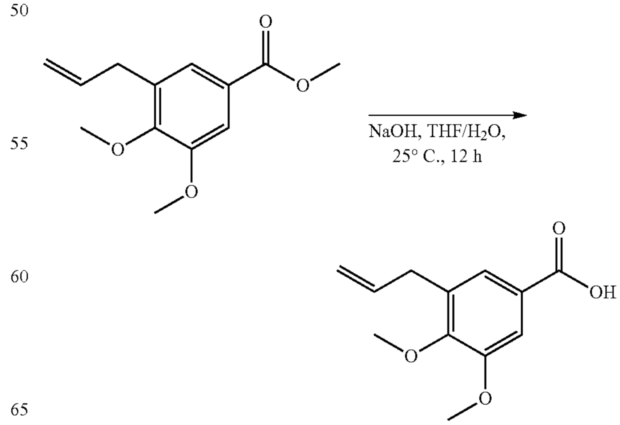

To a solution of intermediate compound 36 (1.1 g, 4.66 mmol) in THF (9 mL) and H2O (3 mL) was added NaOH (372.44 mg, 18.62 mmol, 4 eq). The reaction was stirred at 25° C. for 12 hr. The reaction solution was diluted with H2O (50 mL), extracted with EtOAc (20 mL). The organic layer was discarded. The water phase was acidified to pH=2 by 1 M HCl aqueous solution and then extracted with ethyl acetate (3×20 mL). The combined organic layers were washed with brine (20 mL), dried over Na2SO4, filtered and concentrated under vacuum to give the intermediate compound 37 (440 mg, 42% yield,) as a brown solid.

LCMS (ESI position ion) m/z: 223.0 (M+H)+ (calculated: 222.1)

1H NMR (400 MHz, CD3OD-d4) δ 7.54-7.50 (m, 2H), 6.03-5.92 (m, 1H), 5.08-5.02 (m, 2H), 3.91 (s, 3H), 3.86 (s, 3H), 3.42 (d, J=6.5 Hz, 2H).

Intermediate Compound 38:

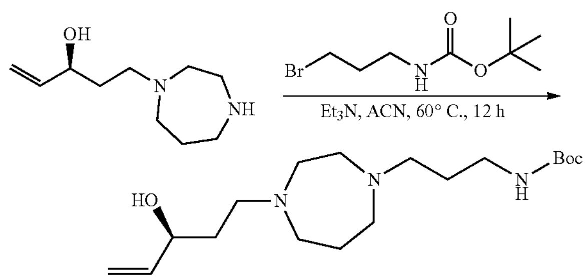

To a solution of tert-butyl N-(3-bromopropyl)carbamate (4.17 g, 17.50 mmol, 1 eq) and intermediate compound 34 (4.5 g, 17.50 mmol, 1 eq, 2HCl) in ACN (45 mL) was added TEA (17.70 g, 174.96 mmol, 24.35 mL, 10 eq) with stirring at 60° C. for 12 h. The reaction mixture was concentrated under reduced pressure. The residue was purified over silica gel (DCM/Methanol=10/1 to 5/1, Rf=0.5) to give the intermediate compound 38 (3.2 g, 54% yield) as a brown oil.

1H NMR (400 MHz, MeOD-d4) δ=5.89 (ddd, J=5.8, 10.5, 17.2 Hz, 1H), 5.26 (td, J=1.6, 17.3 Hz, 1H), 5.11 (td, J=1.5, 10.5 Hz, 1H), 4.22-4.16 (m, 1H), 3.09 (t, J=6.8 Hz, 2H), 2.87-2.72 (m, 10H), 2.60-2.55 (m, 2H), 1.88 (td, J=5.9, 11.7 Hz, 2H), 1.76-1.64 (m, 4H), 1.45 (s, 9H)

Intermediate Compound 39:

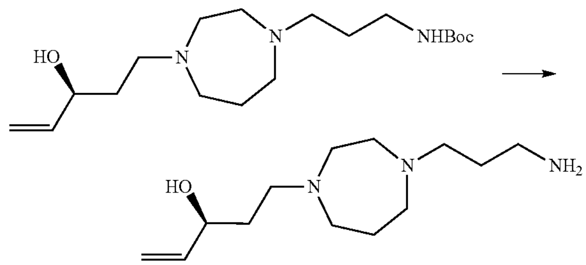

A mixture of intermediate compound 38 (3.2 g, 9.37 mmol, 1 eq) in HCl/MeOH (4 M, 106.66 mL, 45.53 eq) was stirred at 25° C. for 1 hr. The reaction was concentrated under vacuum to give the intermediate 39 (2.7 g, 82% yield) as an off white solid.

1H NMR (400 MHz, METHANOL-d4) 6=1.87-2.11 (m, 2H) 2.17-2.29 (m, 2H) 2.32-2.53 (m, 2H) 3.05-3.16 (m, 2H) 3.37-3.55 (m, 5H) 3.61-4.06 (m, 6H) 4.22-4.32 (m, 1H) 5.19-5.25 (m, 1H) 5.29-5.40 (m, 1H) 5.87-5.99 (m, 1H)

Intermediate Compound 40:

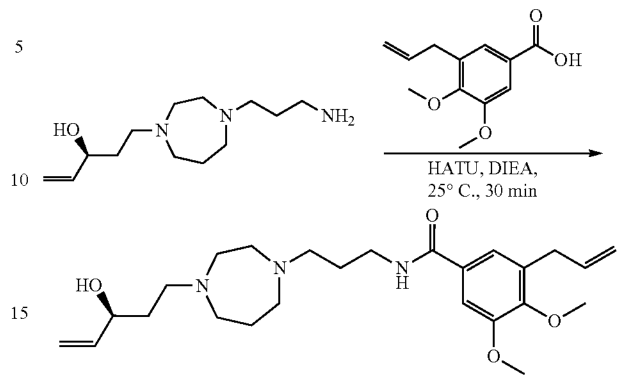

To a mixture of intermediate compound 39 (473.49 mg, 1.35 mmol, 1.2 eq, 3HCl), intermediate compound 37 (250 mg, 1.12 mmol, 1 eq) and DIPEA (581.56 mg, 4.50 mmol, 4 eq) in DMF (7.5 mL) was added HATU (641.60 mg, 1.69 mmol, 1.5 eq). The reaction was stirred at 25° C. for 10 min. The reaction mixture was concentrated under vacuum. The residue was purified by reverse phase chromatography to give the intermediate compound 40 (580 mg, 93% yield) as an off white solid.

LCMS (ESI position ion) m/z: 446.4 (M+H)+ (calculated: 445.3)

1H NMR (400 MHz, MeOD-d4) δ 7.44 (d, J=2.1 Hz, 1H), 7.37-7.35 (m, 1H), 6.08-5.84 (m, 2H), 5.40-5.29 (m, 1H), 5.24-5.15 (m, 1H), 5.12-5.01 (m, 2H), 4.31-4.24 (m, 1H), 4.08-3.71 (m, 15H), 3.59-3.37 (m, 9H), 2.89-2.80 (m, 5H), 2.48-2.34 (m, 2H), 2.19-1.90 (m, 5H)

Intermediate Compound 41:

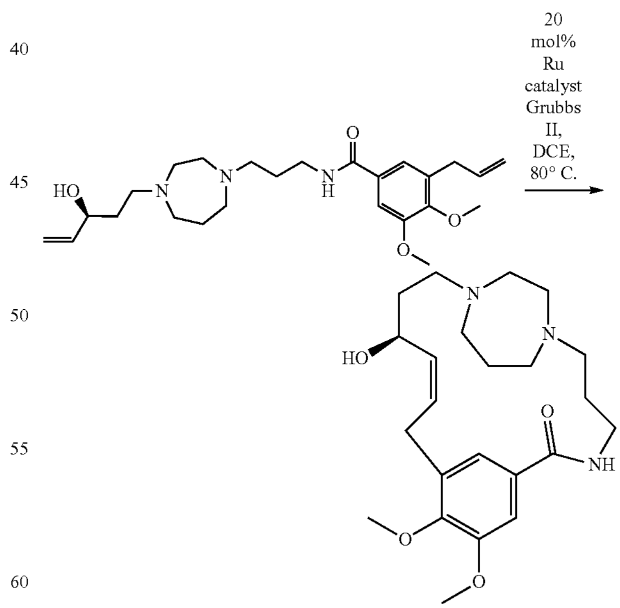

To a solution of intermediate compound 40 (480 mg, 1.08 mmol, 1 eq) in DCM (270 mL) was added [1,3-bis(2,4,6-trimethylphenyl)imidazolidin-2-ylidene]-dichloro-[(2-isopropoxyphenyl) methylene]ruthenium (135.00 mg, 215.44 umol, 0.2 eq). The reaction mixture was degassed with N2

3 times and then stirred at 25° C. for 48 hrs under N2 atmosphere. The reaction mixture was concentrated under vacuum. The residue was purified by preparative HPLC (column: Waters Xbridge 150*25 mm*5 um; mobile phase: [water (10 mM NH4HCO3)-ACN]; B %:12%-42%, 9 min) to give the intermediate compound 41 (12 mg, 3% yield) as an off white solid.

LCMS (ESI position ion) m/z: 418.2 (M+H)+ (calculated: 417.3)

1H NMR (400 MHz, MeOD-d4) δ 7.39-7.35 (m, 1H), 7.27-7.23 (m, 1H), 5.90-5.79 (m, 1H), 5.52-5.40 (m, 1H), 4.16-4.06 (m, 1H), 3.93 (s, 3H), 3.88 (s, 3H), 3.60-3.38 (m, 5H), 2.88-2.30 (m, 10H), 1.86-1.66 (m, 7H)

Intermediate Compound 42:

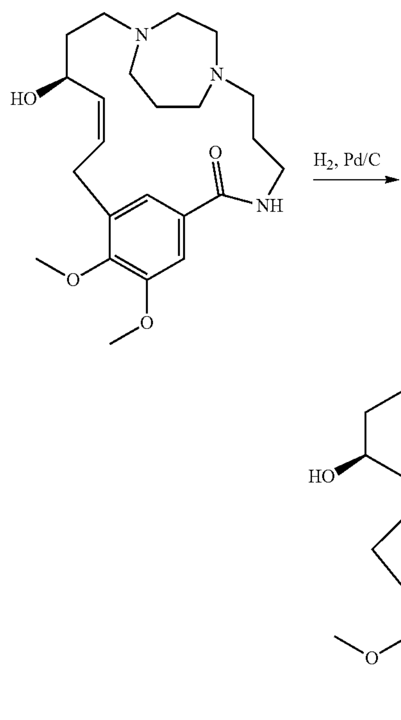

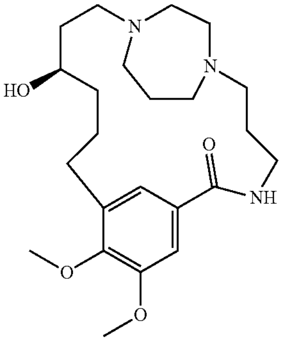

To a solution of intermediate compound 41 (10 mg, 23.95 umol, 1 eq) in MeOH (1 mL) was added wet Pd/C (23.95 umol, 10% purity) under H2 balloon (15 psi). The reaction was stirred at 25° C. for 0.5 hr under H2 balloon (15 psi). The mixture was filtered, the filtrate was concentrated under vacuum to give the crude intermediate compound 42 (10 mg) as an off-white solid.

LCMS (ESI position ion) m/z: 420.2 (M+H)+ (calculated: 419.3)

Intermediate Compound 43:

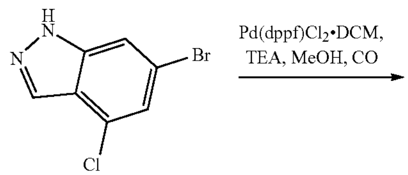

-continued

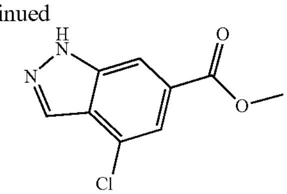

A mixture of 6-bromo-4-chloro-1H-indazole (4.5 g, 19.44 mmol, 1 eq), Pd(dppf)Cl2·CH2Cl2 (1.59 g, 1.94 mmol, 0.1 eq) and TEA (3.93 g, 38.88 mmol, 5.41 mL, 2 eq) in MeOH (100 mL) was stirred at 80° C. for 12 hr under CO (194.40 mmol, 10 eq) 50 psi. The reaction mixture was concentrated under vacuum to give a residue. The residue was purified by silica on column chromatography (petroleum ether/ethyl acetate=5/1) to give the intermediate compound 43 (3.3 g, 80% yield) as a yellow solid.

1H NMR (400 MHz, DMSO-d6) δ 13.74-13.95 (m, 1H) 8.28 (s, 1H) 8.15 (s, 1H) 7.67 (s, 1H) 3.91 (s, 3H)

Intermediate Compound 44:

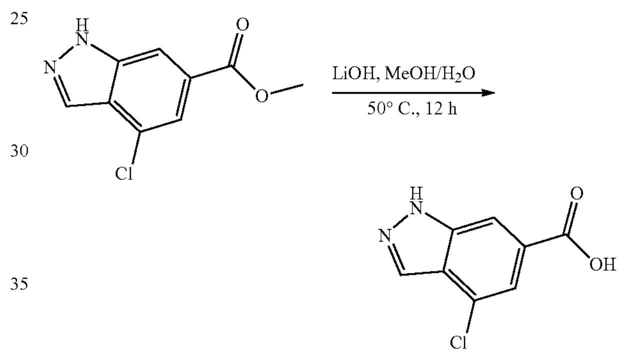

A mixture of intermediate compound 43 (3.3 g, 15.67 mmol, 1 eq) and LiOH (1.13 g, 47.00 mmol, 3 eq) in MeOH (30 mL) and H2O (6 mL) was stirred at 50° C. for 12 hrs. The reaction mixture was acidified by 1N HCl to pH 5, then the mixture was concentrated under vacuum to give a yellow solid. The yellow solid was triturated with water (100 mL) and filtered, the filter cake was dried under vacuum to give the intermediate compound 44 (3 g, 97% yield) as a white solid.

LCMS (ESI position ion) m/z: 195.0 (M+H)+ (calculated: 196.0)

Intermediate Compound 45:

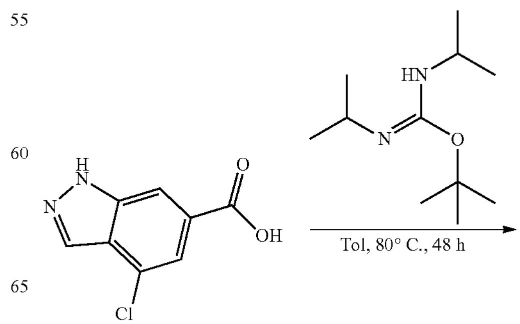

-continued

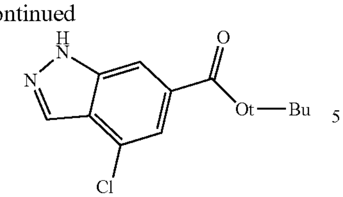

A mixture of intermediate compound 44 (3 g, 15.26 mmol, 1 eq) and tert-butyl (E)-N,N'-diisopropylcarbamimidate (12.23 g, 61.04 mmol, 4 eq) in toluene (50 mL) was stirred at 80° C. for 48 hrs under N2 atmosphere. The reaction mixture was poured into water (50 mL) and extracted with ethyl acetate (3×30 mL), the combined organic phase was dried and concentrated under vacuum. The residue was purified silica on column chromatography (petroleum ether/ethyl acetate=5/1) to give the intermediate Compound 45 (1.3 g, 34% yield) as a yellow solid.

1H NMR (400 MHz, CDCl3-d) δ 10.35-10.49 (m, 1H) 8.21 (s, 1H) 8.11 (s, 1H) 7.78 (s, 1H) 1.64 (s, 9H)

Intermediate Compound 46:

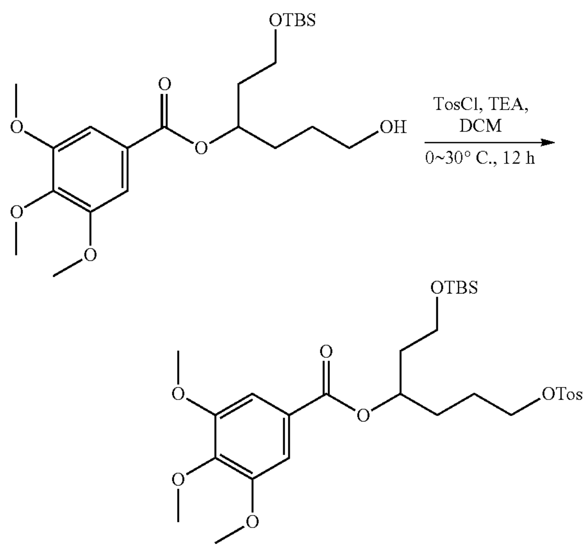

To a mixture of intermediate compound 5 (4 g, 9.04 mmol, 1 eq), TEA (1.83 g, 18.07 mmol, 2.52 mL, 2 eq) and DMAP (220.81 mg, 1.81 mmol, 0.2 eq) in DCM (50 mL) was added 4-toluenesulfonyl chloride (2.58 g, 13.56 mmol, 1.5 eq), then the reaction mixture was stirred at 30° C. for 12 hrs. The reaction mixture was poured into water (50 mL) and extracted with ethyl acetate (3×30 mL), the combined organic phase was dried and concentrated under vacuum. The residue was purified by silica on column chromatography (petroleum ether/ethyl acetate=3/1) to give the intermediate compound 46 (3.7 g, 67% yield) as a yellow oil.

LCMS (ESI position ion) m/z: 597.3 (M+H)+ (calculated: 596.2)

1H NMR (400 MHz, CDCl3-d) δ 7.77 (d, J=8.31 Hz, 2H) 7.33 (d, J=7.95 Hz, 2H) 7.26 (s, 2H) 5.15-5.26 (m, 1H) 4.03-4.07 (m, 2H) 3.92 (s, 3H) 3.64-3.72 (m, 2H) 2.42-2.46 (m, 3H) 1.81-1.99 (m, 2H) 1.70-1.80 (m, 4H) 0.87 (s, 9H) 0.01 (s, 6H)

Intermediate Compound 47 and Intermediate Compound 48:

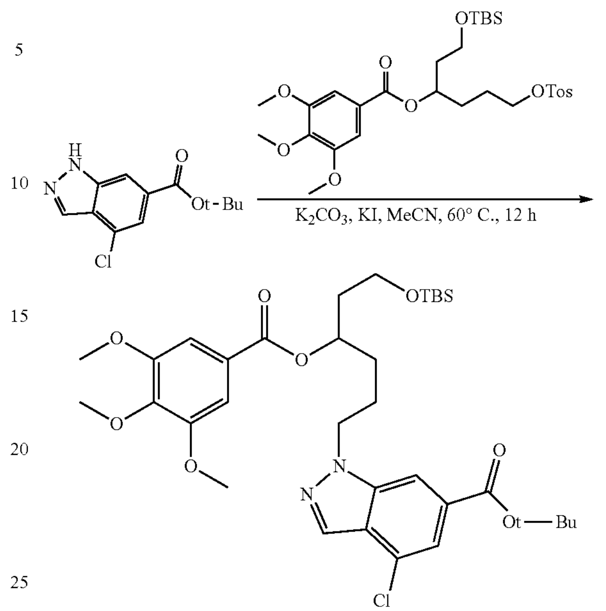

Intermediate compound 47

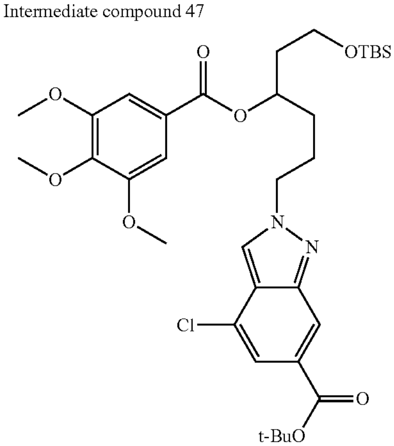

Intermediate compound 48

A mixture of intermediate compound 45 (1.3 g, 5.14 mmol, 1 eq), intermediate compound 46 (3.7 g, 6.20 mmol, 1.21 eq), KI (1.71 g, 10.29 mmol, 2 eq) and K2CO3 (2.13 g, 15.43 mmol, 3 eq) in MeCN (20 mL) was stirred at 60° C. for 12 hrs. The reaction mixture was filtered and concentrated under vacuum. The residue was purified by silica on column chromatography (petroleum ether/ethyl acetate=5/1) to give the intermediate compound 47 (2 g, 2.95 mmol, 57% yield) as a yellow oil and the intermediate compound 48 (1.3 g, 37% yield) as a yellow oil.

Intermediate Compound 47:

1H NMR (400 MHz, CDCl3-d) δ 8.08 (s, 1H) 8.03 (s, 1H) 7.71 (s, 1H) 5.24-5.34 (m, 1H) 4.47 (t, J=6.94 Hz, 2H) 3.87-3.93 (m, 9H) 3.67 (t, J=6.19 Hz, 2H) 2.02-2.10 (m, 2H) 1.82-1.97 (m, 2H) 1.71-1.79 (m, 2H) 1.64 (s, 9H) 0.85 (s, 9H) −0.01 (s, 6H)

Intermediate Compound 48:

LCMS (ESI position ion) m/z: 677.6 (M+H)+ (calculated: 596.2)

1H NMR (400 MHz, CDCl3-d) δ 8.32 (s, 1H) 8.00 (s, 1H) 7.65 (d, J=0.75 Hz, 1H) 5.28-5.36 (m, 1H) 4.50 (t, J=6.94 Hz, 2H) 3.86-3.94 (m, 9H) 3.63-3.71 (m, 2H) 2.06-2.24 (m, 2H) 1.82-1.97 (m, 2H) 1.76 (br d, J=6.88 Hz, 2H) 1.61 (s, 9H) 0.85 (s, 9H) −0.01 (s, 6H)

Intermediate Compound 49:

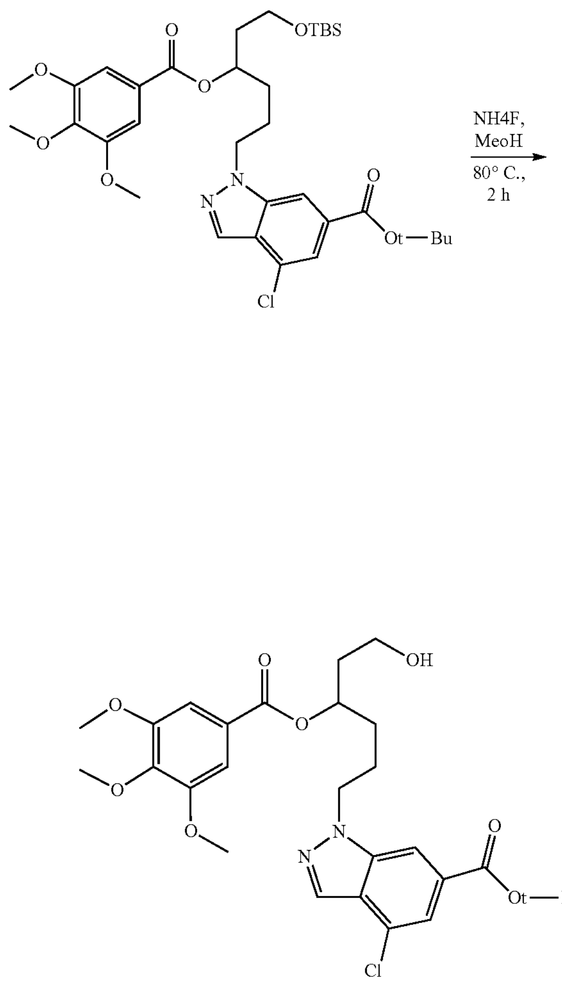

Intermediate compound 47 (1.9 g, 2.81 mmol, 1 eq) and NH4F (1.04 g, 28.05 mmol, 10 eq) in MeOH (30 mL) was stirred at 80° C. for 12 hrs. The reaction mixture was filtered and concentrated under vacuum. The residue was dissolved in ethyl acetate (50 mL) and filtered, the filtrated was concentrated under vacuum to give the crude intermediate compound 49 (1.57 g, 99% yield) as a yellow oil.

LCMS (ESI position ion) m/z: 563.2 (M+H)+ (calculated: 562.2)

Intermediate Compound 50:

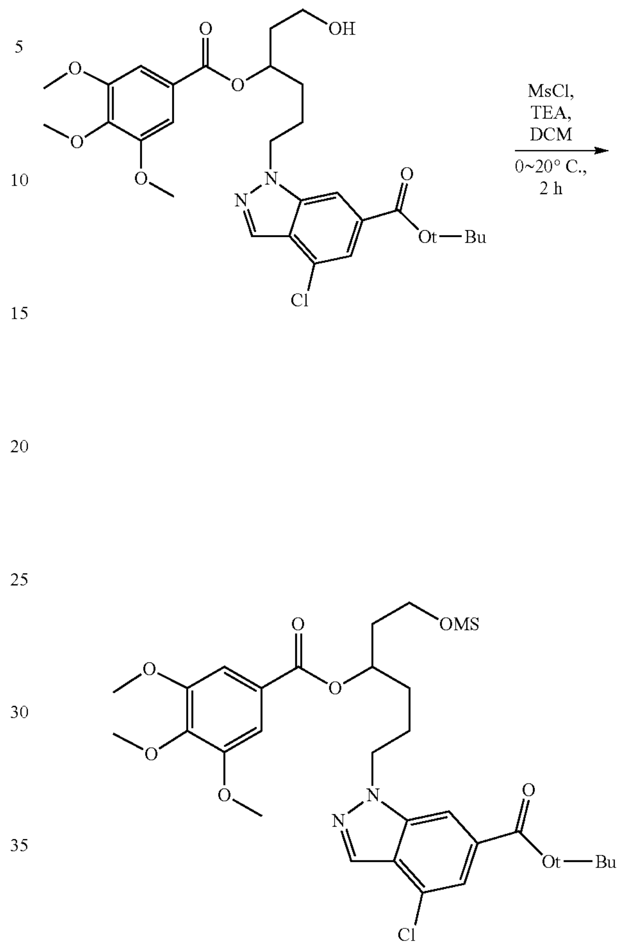

To a solution of intermediate compound 49 (1.65 g, 2.93 mmol, 1 eq) and TEA (889.61 mg, 8.79 mmol, 1.22 mL, 3 eq) in DCM (30 mL) was added methanesulfonyl chloride (671.39 mg, 5.86 mmol, 453.64 uL, 2 eq) slowly under 0° C., then the reaction mixture was stirred at 20° C. for 2 hrs. The reaction mixture was poured into saturated aqueous solution of NaHCO3 (20 mL) at 0° C. and extracted with dichloromethane (3×20 mL). The combined organic phase was dried and concentrated under vacuum to give the crude intermediate compound 50 (1.4 g, 74% yield) as a brown oil and used without further purification.

Intermediate Compound 51:

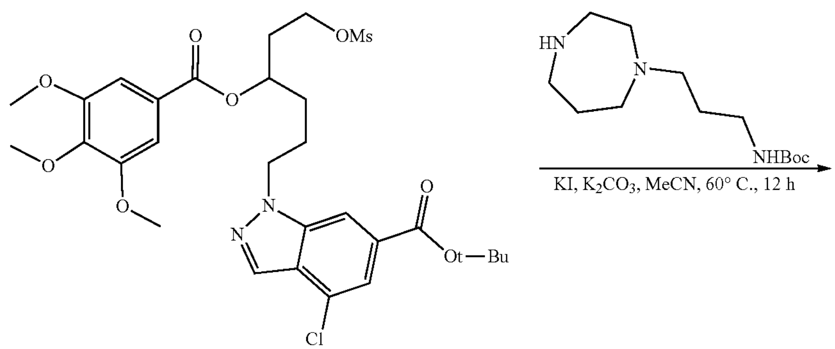

-continued

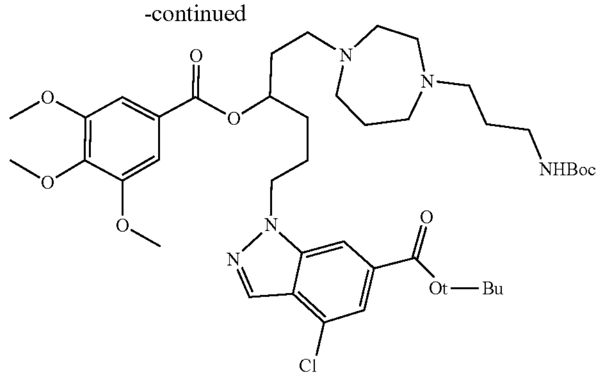

A mixture of intermediate compound 50 (500 mg, 779.88 umol, 1 eq), intermediate compound 24 (301.08 mg, 1.17 mmol, 1.5 eq), K2CO3 (323.35 mg, 2.34 mmol, 3 eq) and KI (258.92 mg, 1.56 mmol, 2 eq) in MeCN (10 mL) was stirred at 60° C. for 12 hrs. The reaction mixture was filtered and concentrated under vacuum. The residue was purified by preparative HPLC (column: Phenomenex Synergi C18 150*25*10 um; mobile phase: [water (0.225% FA)-ACN]; B %: 38%-68%, 9 min), to give the intermediate compound 51 (200 mg, 32% yield) as a brown oil.

LCMS (ESI position ion) m/z: 802.3 (M+H)+ (calculated: 801.4)

Intermediate Compound 52:

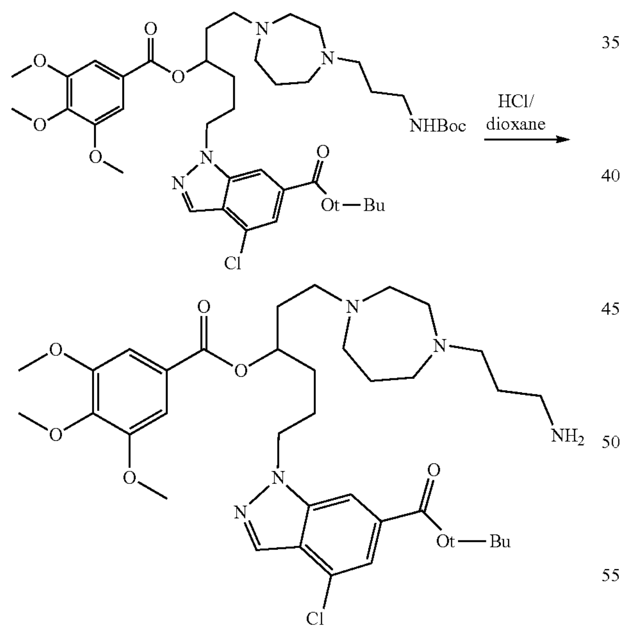

A mixture of intermediate compound 51 (200 mg, 249.25 umol, 1 eq) in HCl/dioxane (4 M, 5 mL, 80.24 eq) was stirred at 30° C. for 1 hr. The reaction mixture was concentrated under vacuum to give the crude intermediate compound 51 (130 mg, 76% yield, HCl) as a brown solid used without further purification.

LCMS (ESI position ion) m/z: 646.5 (M+H)+ (calculated: 645.3)

Intermediate Compound 53:

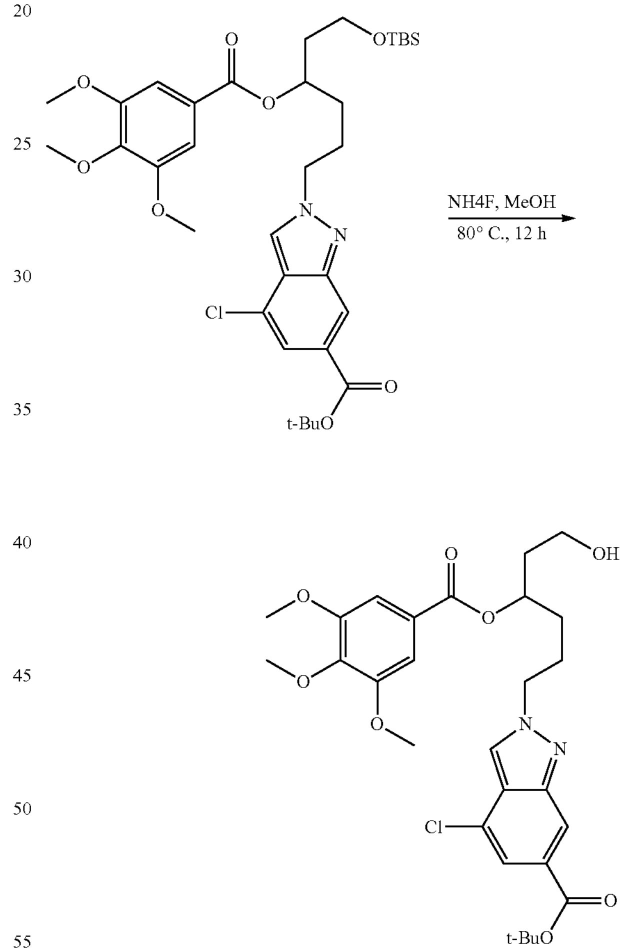

Intermediate compound 48 (1.2 g, 1.77 mmol, 1 eq) and NH4F (656.20 mg, 17.72 mmol, 10 eq) in MeOH (20 mL) was stirred at 80° C. for 12 hr. The reaction mixture was filtered and concentrated under vacuum to give a residue. The residue was dissolved in ethyl acetate (30 mL) and filtered, the filtrate was concentrated under vacuum to give the crude intermediate compound 53 (970 mg, 99% yield) as a yellow oil.

LCMS (ESI position ion) m/z: 563.2 (M+H)+ (calculated: 662.2)

Intermediate Compound 54:

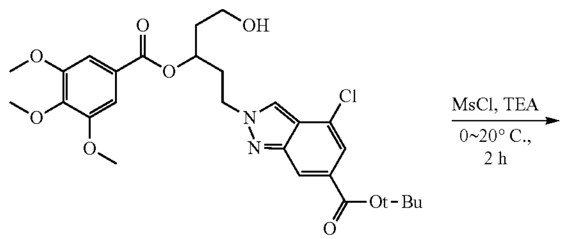

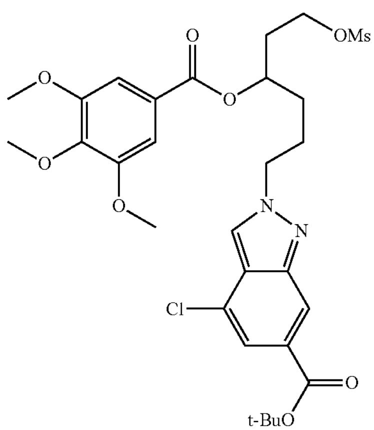

To a solution of intermediate compound 53 (1.05 g, 1.91 mmol, 1 eq) and TEA (580.59 mg, 5.74 mmol, 798.61 uL, 3 eq) in DCM (30 mL) was added methanesulfonyl chloride (438.16 mg, 3.83 mmol, 296.05 uL, 2 eq) slowly under 0° C., then the reaction mixture was stirred at 20° C. for 2 hr. The reaction mixture was poured into saturated aqueous solution of NaHCO3 (20 mL) at 0° C. and extracted by DCM (20 mL×3). The combined organic phase was dried over Na2SO4 and concentrated under vacuum to give the intermediate compound 54 (1.2 g, 98% yield) as a brown oil and used without further purification.

LCMS (ESI position ion) m/z: 541.5 (M+H-100)+ (calculated: 640.2)

Intermediate Compound 55:

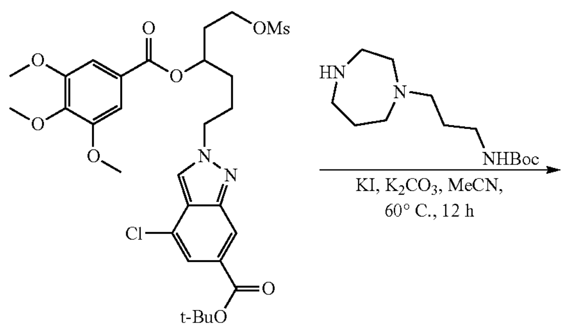

-continued

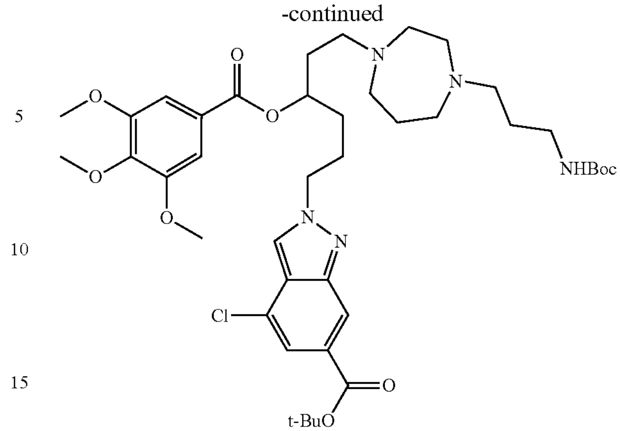

A mixture of intermediate compound 54 (500.00 mg, 779.88 umol, 1 eq), intermediate compound 24 (301.08 mg, 1.17 mmol, 1.5 eq), K2CO3 (323.35 mg, 2.34 mmol, 3 eq) and KI (258.92 mg, 1.56 mmol, 2 eq) in MeCN (10 mL) was stirred at 60° C. for 12 hrs. The reaction mixture was filtered and the filtrate was concentrated under vacuum. The residue was purified by prep-HPLC (water (0.225% FA)-MeCN, 50%) to give the intermediate compound 55 (300 mg, 48% yield) as a brown oil.

LCMS (ESI position ion) m/z: 802.3 (M+H)+ (calculated: 801.4)

Intermediate Compound 56:

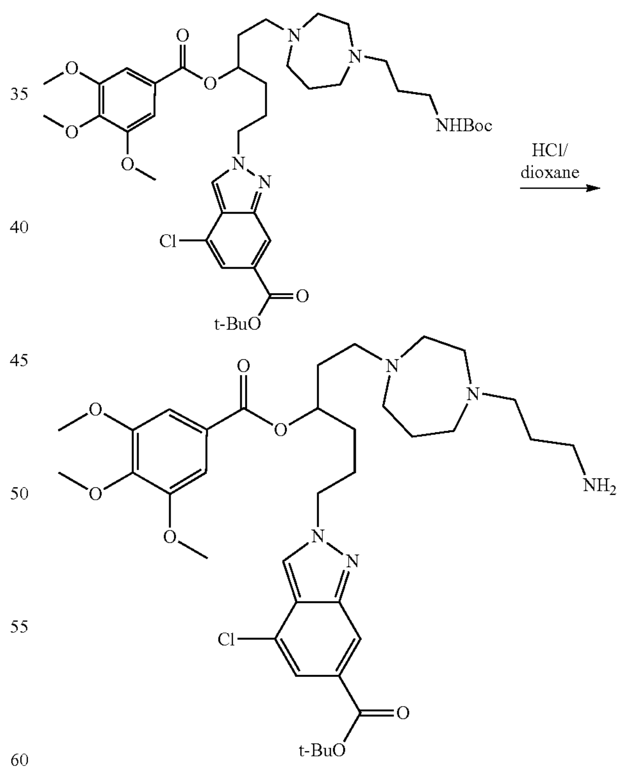

A mixture of intermediate compound 55 (300.00 mg, 373.88 umol, 1 eq) in HCl/dioxane (4 M, 5.00 mL, 53.49 eq) was stirred at 30° C. for 6 hrs. The reaction mixture was concentrated under vacuum to give the intermediate compound 56 (250 mg, 98% yield, HCl) as a brown solid and used without further purification.

LCMS (ESI position ion) m/z: 646.2 (M+H)+ (calculated: 645.3)

Intermediate Compound 57:

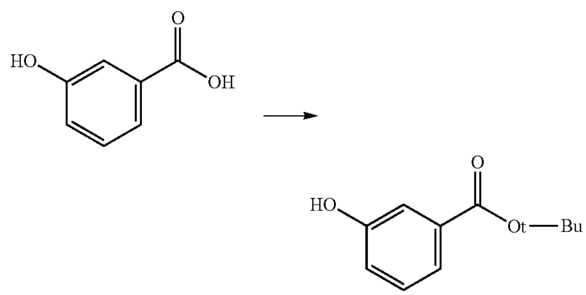

To a solution of compound 3-hydroxybenzoic acid (0.2 g, 1.45 mmol, 1 eq) in toluene (2 mL) was added 1,1-ditert-butoxy-N,N-dimethyl-methanamine (294.41 mg, 1.45 mmol, 347.18 uL, 1 eq), and then the mixture was stirred at 105° C. for 12 hr. The reaction mixture was filtered and concentrated under reduced pressure. The residue was purified by column chromatography (SiO2, petroleum ether/EtOAc=100/1 to 3/1) to give the intermediate compound 57 (0.1 g, 35% yield) as a colorless oil.

1H NMR (400 MHz, CDCl3-d) δ=7.66-7.52 (m, 2H), 7.33 (s, 1H), 7.10-7.01 (m, 1H), 6.27-5.79 (m, 1H), 1.66-1.58 (m, 9H)

Intermediate Compound 58:

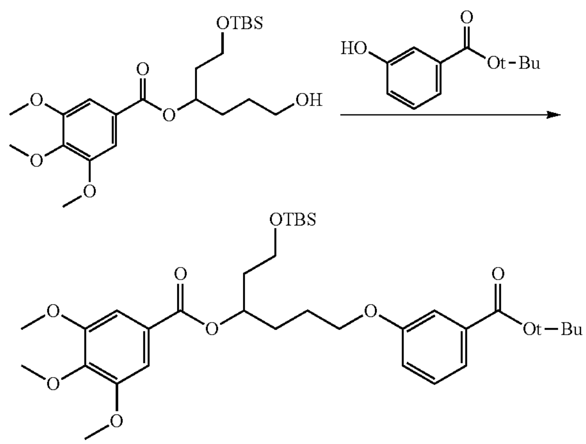

To a solution of intermediate compound 5 (0.7 g, 1.58 mmol, 1 eq), intermediate compound 57 (307.17 mg, 1.58 mmol, 1 eq) and triphenylphosphine (746.65 mg, 2.85 mmol, 1.8 eq) in toluene (30 mL) was added DEAD (413.14 mg, 2.37 mmol, 431.25 uL, 1.5 eq) at 0° C. The mixture was stirred at 115° C. for 12 hr. The reaction mixture was concentrated under reduced pressure. The residue was purified by column chromatography (SiO2, petroleum ether/EtOAc=100/1 to 10/1) to give the intermediate compound 58 (0.4 g, 41% yield) as a colorless oil.

LCMS (ESI position ion) m/z: 641.2 (M+Na+)+ (calculated: 618.3)

Intermediate Compound 59:

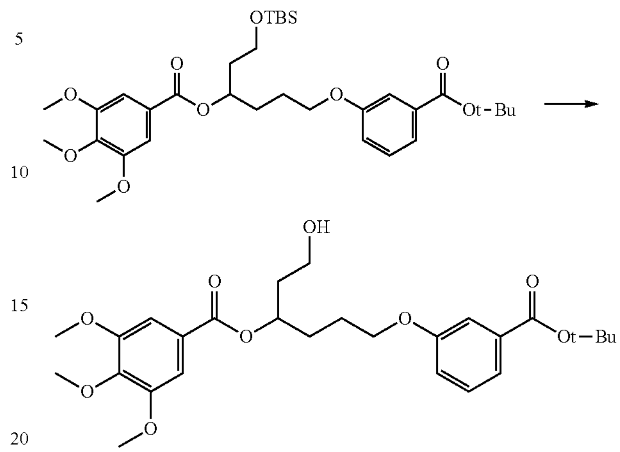

To a solution of intermediate compound 58 (430 mg, 694.86 umol, 1 eq) in MeOH (1 mL) was added NH4F (514.71 mg, 13.90 mmol, 20 eq), then the mixture was stirred at 75° C. for 2 hr. The residue was filtered and concentrated under reduced pressure. The residue was purified by column chromatography (SiO2, petroleum ether/EtOAc=10/1 to 3/1) to give the intermediate compound 59 (450 mg) as a colorless oil.

LCMS (ESI position ion) m/z: 627.1 (M+Na+)+ (calculated: 504.2)

Intermediate Compound 60:

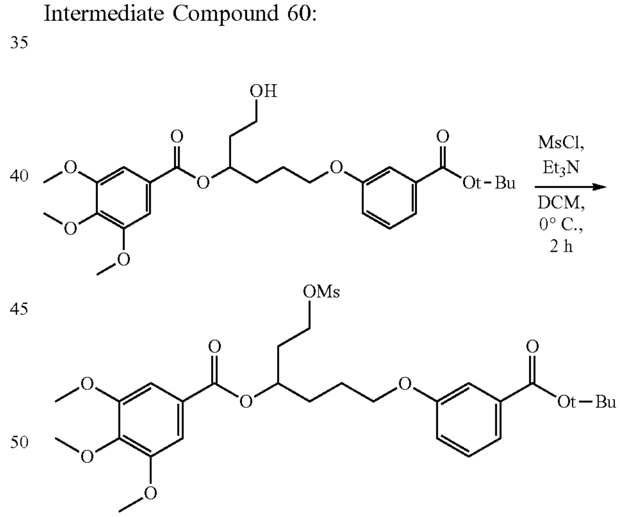

To a solution of intermediate compound 59 (450 mg, 891.85 umol, 1 eq) and TEA (360.98 mg, 3.57 mmol, 496.54 uL, 4 eq) in DCM (5 mL) was added methanesulfonyl chloride (306.49 mg, 2.68 mmol, 207.09 uL, 3 eq) dropwise at 0° C. The mixture was stirred at 0° C. for 2 hr. The mixture was quenched by ice-water (30 mL) slowly and then extracted with DCM (40 mL×3). The combined organic phase was washed with brine (60 mL×2), dried over Na2SO4, filtered and concentrated in vacuum to give the crude intermediate compound 60 (500 mg) as a yellow oil.

LCMS (ESI position ion) m/z: 605.1 (M+Na+)+ (calculated: 582.2)

Intermediate Compound 61:

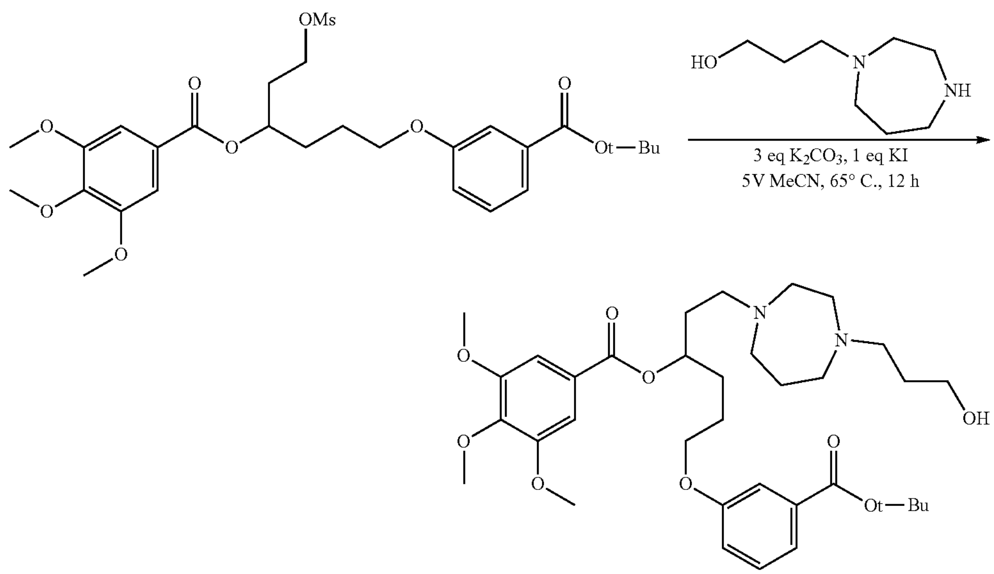

To a solution of compound 60 (500 mg, 858.14 umol, 1 eq) and 3-(1,4-diazepan-1-yl)propan-1-ol (167.08 mg, 858.14 umol, 1 eq, HCl) in CH3CN (15 mL) was added K2CO3 (355.80 mg, 2.57 mmol, 3 eq) and KI (142.45 mg, 858.14 umol, 1 eq), then the mixture was stirred at 65° C. for 12 hr. The reaction mixture was filtered and concentrated under reduced pressure to give the crude intermediate compound 61 (500 mg, crude) as a yellow oil.

LCMS (ESI position ion) m/z: 645.3 (M+Na+)+ (calculated: 644.3)

Intermediate Compound 62:

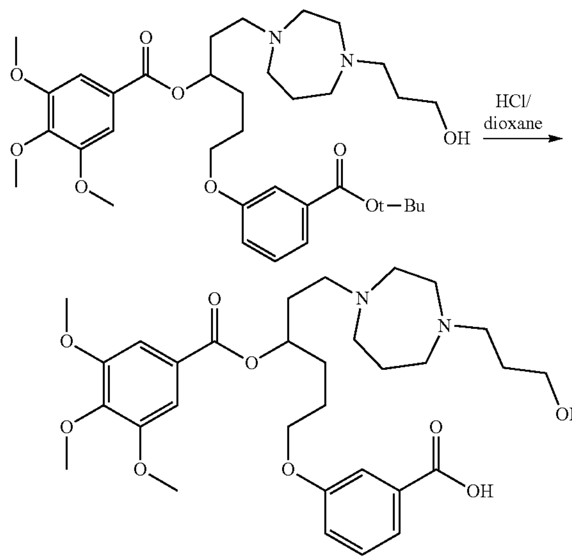

A solution of compound 61 (400 mg, 620.35 umol, 1 eq) in HCl/dioxane (4 M, 40.00 mL, 257.92 eq) was stirred at 20° C. for 2 hr. The reaction mixture was concentrated under reduced pressure. The residue was purified by reversed phase (column: Phenomenex Synergi C18 150*25*10 um; mobile phase: [water (0.225% FA)-ACN]; B %: 38%-68%, 9 min) to give the intermediate compound 62 (350 mg) as a red solid.

LCMS (ESI position ion) m/z: 589.2 (M+H+)+ (calculated: 588.3)

Intermediate Compound 63:

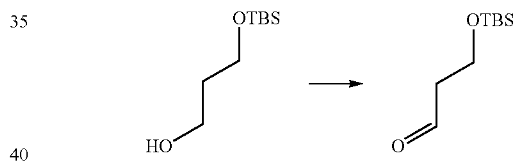

To a solution of 3-((tert-butyldimethylsilyl)oxy)propan-1-ol (10 g, 52.53 mmol, 1 eq) in CH3CN (200 mL) was added 2-Iodoxybenzoic acid (IBX) (14.71 g, 52.53 mmol, 1 eq), the mixture was stirred at 80° C. for 2 hr. The reaction mixture was filtered and concentrated under reduced pressure. The residue was purified by flash silica gel chromatography (petroleum ether/EtOAc=100/1-20/1) to give the intermediate compound 63 (7 g, 71% yield) as a colorless oil.

1H NMR (400 MHz, CDCl3-d) δ 7.90 (s, 1H), 3.98 (t, J=6.0 Hz, 2H), 2.60-2.56 (m, 2H), 0.87 (s, 9H), 0.05 (s, 6H)

Intermediate Compound 64:

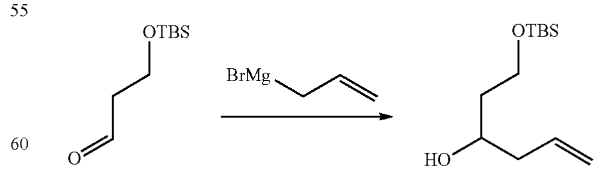

Allylmagnesium bromide (1 M, 63.72 mL, 1.2 eq) was added to a solution of intermediate compound 63 (10 g, 53.10 mmol, 1 eq) in THF (60 mL) drop-wise at 0° C. The mixture was allowed to warm to 20° C. and stirred for 16 hr. The reaction mixture was diluted with a saturated aqueous solution of $NH4Cl$ (100 mL) and extracted with EtOAc (100 mL×3). The combined organic layers were washed with brine (300 mL×3), dried over Na2SO4, filtered and concentrated under reduced pressure. The residue was purified by flash silica gel chromatography (petroleum ether/EtOAC=100/1 to 20/1) to give the intermediate compound 64 (10 g, 82% yield) as a colorless oil.

1H NMR (400 MHz, CDCl3-d) δ 5.88-5.67 (m, 1H), 5.09-4.96 (m, 2H), 3.86-3.68 (m, 3H), 3.27 (d, J=2.0 Hz, 1H), 2.23-2.11 (m, 2H), 1.64-1.55 (m, 2H), 0.84-0.81 (m, 9H), 0.04-0.02 (m, 6H)

Intermediate Compound 65:

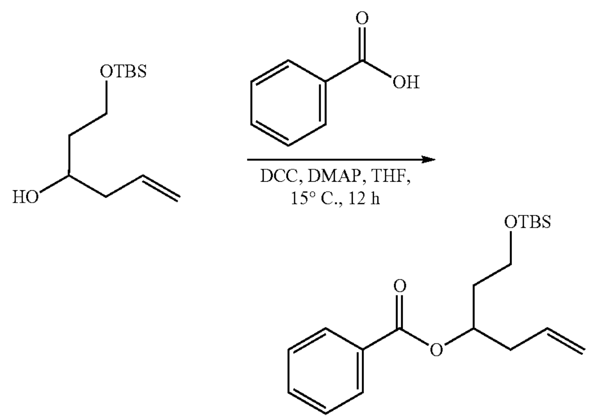

To a solution of intermediate compound 64 (1.20 g, 5.21 mmol, 1 eq) and benzoic acid (763.20 mg, 6.25 mmol, 1.2 eq) in THF (12 mL) was added DCC (1.61 g, 7.81 mmol, 1.5 eq) and DMAP (954.36 mg, 7.81 mmol, 1.5 eq), then the mixture was stirred at 25° C. for 12 hrs. The reaction mixture was poured into water (100 ml) and extracted with EtOAc (2×50 mL). The combined organic layers were dried over Na2SO4 and filtered, the filtrate was concentrated under reduced pressure. The residue was purified by column chromatography (SiO2, petroleum ether/EtOAc=5/1), to give the intermediate compound 65 (1.46 g) as a colorless oil.

LCMS (ESI position ion) m/z: 335.3 (M+H)+ (calculated: 334.2)

1H NMR (400 MHz, CDCl3-d) δ 8.04 (dd, J=1.0, 8.1 Hz, 2H), 7.59-7.54 (m, 1H), 7.47-7.41 (m, 2H), 5.89-5.78 (m, 1H), 5.34-5.27 (m, 1H), 5.15-5.05 (m, 2H), 3.76-3.70 (m, 2H), 2.55-2.46 (m, 2H), 1.99-1.89 (m, 2H), 0.89-0.87 (m, 12H), 0.03-0.01 (m, 6H).

Intermediate Compound 66:

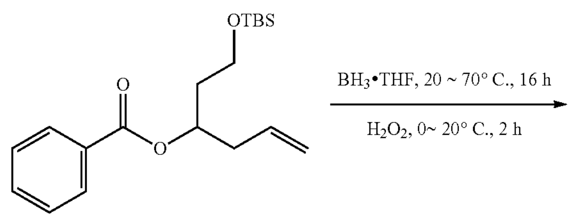

-continued

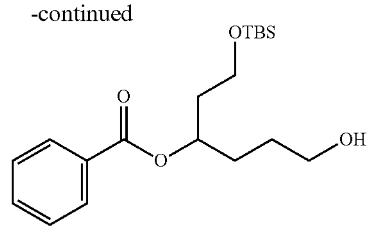

To a solution of intermediate compound 65 (3 g, 8.97 mmol, 1 eq) in THF (50 mL) was added BH3·THF (1 M, 35.87 mL, 4 eq) slowly at 25° C. under N2 atmosphere, then the reaction mixture was stirred at 70° C. for 12 hrs. The reaction mixture was quenched by 2 N NaOH (20 mL, aqueous) at 10° C., then H2O2 (5.08 g, 44.84 mmol, 4.31 mL, 30% purity, 5 eq) was added into the reaction mixture slowly at 0° C., the resulting mixture was stirred at 20° C. for 2 hrs. The reaction mixture was quenched by saturated aqueous solution of Na2SO3 (100 mL) and extracted by EtOAc (3×50 mL), the combined organic phase was dried and concentrated under vacuum. The residue was purified by silica on column chromatography (SiO2, petroleum ether/EtOAc=2/1) to gioive the intermediate compound 66 (1.5 g, 47% yield) as a yellow oil.

1H NMR (400 MHz, MeOD-d4) δ ppm 8.02 (d, J=7.34 Hz, 2H) 7.55-7.65 (m, 1H) 7.42-7.52 (m, 2H) 5.22-5.40 (m, 1H) 3.68-3.80 (m, 2H) 3.54-3.60 (m, 2H) 1.89-1.97 (m, 2H) 1.76-1.84 (m, 2H) 1.58-1.67 (m, 2H) 0.87 (s, 9H) 0.00 (d, J=4.77 Hz, 6H)

Intermediate Compound 67:

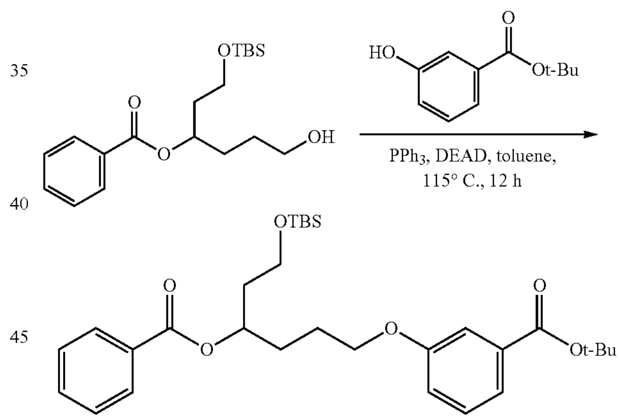

To a solution of intermediate compound 66 (500 mg, 1.42 mmol, 1 eq), intermediate compound 57 (287.14 mg, 1.48 mmol, 1.04 eq) and triphenylphosphine (503.81 mg, 1.92 mmol, 1.35 eq) in toluene (5 mL) was added DEAD (295.24 mg, 1.70 mmol, 308.18 uL, 1.20 eq) at 0° C. The resulting mixture was stirred at 115° C. for 12 hrs under N2 atmosphere. The reaction mixture was poured into water (100 mL) and extracted with EtOAc (2×50 mL), the combined organic layers were dried over Na2SO4 and filtered, the filtrate was concentrated under reduced pressure. The residue was purified by silica on column chromatography (SiO2, petroleum ether/EtOAc=20/1) to give the intermediate compound 67 (259 mg) as a colorless oil.

1H NMR (400 MHz, DMSO-d6) δ 7.99 (d, J=7.9 Hz, 2H), 7.71-7.66 (m, 1H), 7.55 (t, J=7.5 Hz, 2H), 7.51-7.47 (m, 1H), 7.44-7.38 (m, 2H), 7.20-7.16 (m, 1H), 5.33-5.22 (m, 1H), 4.07 (brt, J=5.4 Hz, 2H), 3.74-3.69 (m, 2H), 1.96-1.85 (m, 6H), 1.57 (s, 9H), 0.85 (s, 9H), 0.01 (d, J=5.1 Hz, 6H)

Intermediate Compound 68:

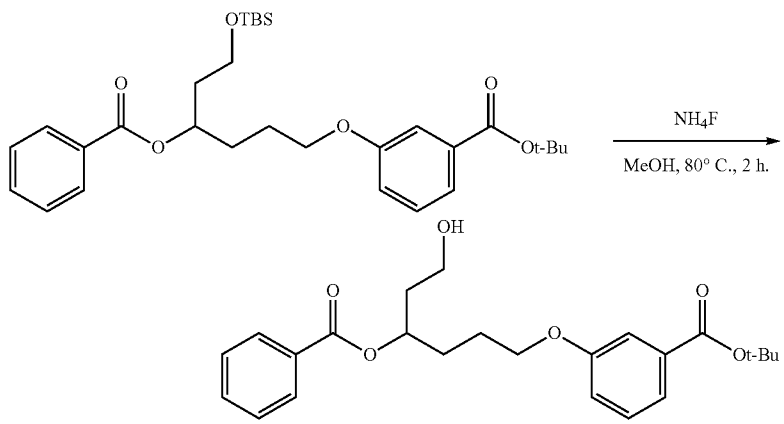

A solution of intermediate compound 67 (212 mg, 400.95 umol, 1 eq) and NH4F (148.50 mg, 4.01 mmol, 10 eq) in MeOH (4.2 mL) was stirred at 80° C. for 2 hrs. The mixture was filtered. The filtrate was concentrated under reduced pressure. The residue was suspended in ethyl acetate (10 mL) and filtered. The filtrate was concentrated under reduced pressure to give the crude intermediate compound 68 (227 mg) as a colorless oil.

LCMS (ESI position ion) m/z: 437.1 (M+Na+)+ (calculated: 414.2)

Intermediate Compound 69:

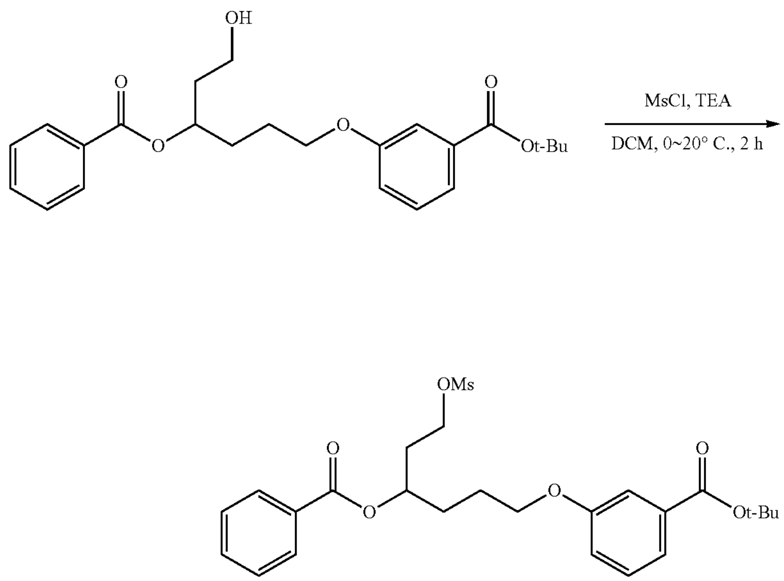

To a mixture of intermediate compound 68 (1.9 g, 4.58 mmol, 1 eq) and TEA (1.39 g, 13.75 mmol, 1.91 mL, 3 eq) in DCM (20 mL) was added methanesulfonyl chloride (1.05 g, 9.17 mmol, 709.59 uL, 2 eq) slowly at 0° C. Then the reaction mixture was stirred at 20° C. for 2 hrs. The reaction mixture was poured into saturated aqueous solution of NaHCO3 (30 mL) and extracted by DCM (3×30 mL). The combined organic layers were dried and concentrated under vacuum to give the crude intermediate compound 69 (2.2 g) as a yellow oil and used without further purification.

Intermediate Compound 70:

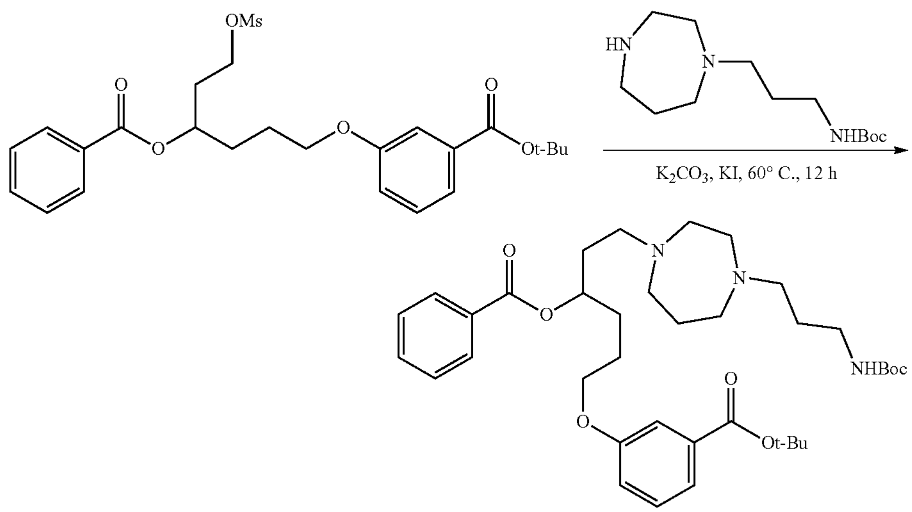

To a solution of intermediate compound 69 (250 mg, 507.53 umol, 1 eq) and intermediate compound 24 (391.87 mg, 1.52 mmol, 3 eq) in CH3CN (5 mL) was added K2CO3 (280.58 mg, 2.03 mmol, 4 eq) and KI (168.50 mg, 1.02 mmol, 2 eq), then the mixture was stirred at 60° C. for 12 hrs. The reaction mixture was poured into water (50 mL) and extracted with EtOAc (2×25 mL). The combined organic layers were dried over Na2SO4 and filtered. The filtrate was concentrated under reduced pressure. The residue was purified by prep-HPLC (water (0.225% FA)/MeCN, 40% to 50%) to give the intermediate compound 70 (134 mg, 40% yield) as a yellow oil.

LCMS (ESI position ion) m/z: 654.6 (M+H)+ (calculated: 653.4)

Intermediate Compound 71:

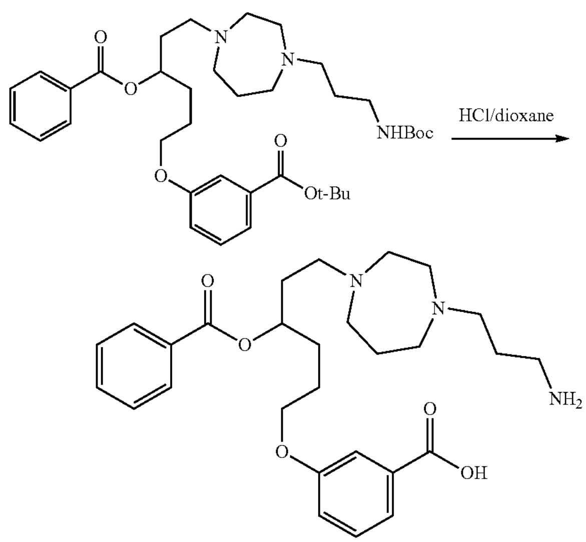

A mixture of intermediate compound 70 (134 mg, 204.94 umol, 1 eq) in HCl/dioxane (4 M, 1.54 mL, 30 eq) with stirred at 20° C. for 2 hrs. The mixture was concentrated under vacuum to give the crude intermediate compound 71 (82 mg, 75% yield, HCl) as a yellow oil.

LCMS (ESI position ion) m/z: 498.4 (M+H)+ (calculated: 497.3)

Intermediate Compound 72:

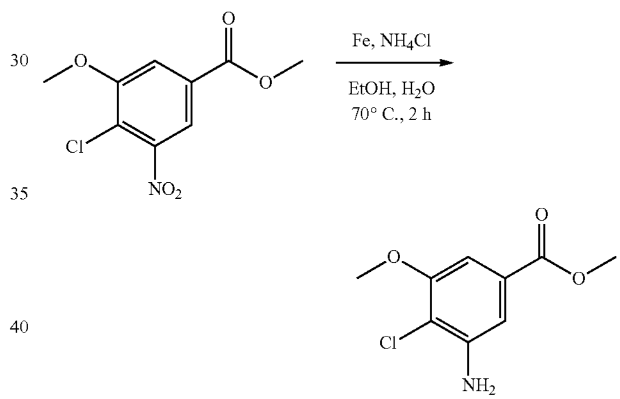

A solution of methyl 4-chloro-3-methoxy-5-nitrobenzoate (15 g, 61.07 mmol, 1 eq), iron (13.64 g, 244.28 mmol, 4 eq) and NH4Cl (26.13 g, 488.57 mmol, 8 eq) in EtOH (225 mL) and H2O (75 mL) was stirred at 70° C. for 2 hrs. After cooled to the ambient temperature, the reaction mixture was filtered. The filtrate was concentrated under reduced pressure. The residue was diluted with H2O (300 mL) and extracted with EtOAc (2×200 mL). The combined organic layers were dried over Na2SO4 and filtered. The filtrate was concentrated under reduced pressure to give the crude intermediate compound 72 (14.38 g) as a light yellow solid.

1H NMR (400 MHz, DMSO-d6) δ 7.11 (s, 1H), 6.86-6.71 (m, 1H), 5.74-5.60 (m, 2H), 3.82 (s, 6H).

Intermediate Compound 73:

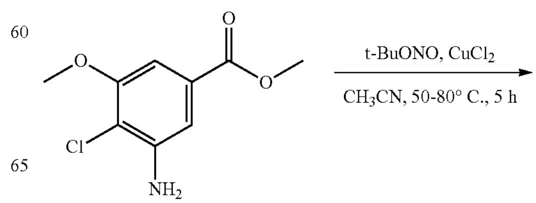

-continued

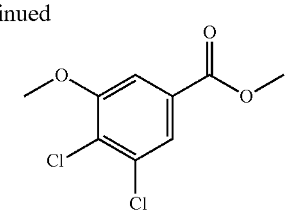

A suspension of CuCl2 (4.49 g, 33.39 mmol, 1.2 eq) and tert-Butyl nitrite (4.30 g, 41.74 mmol, 4.96 mL, 1.5 eq) in CH3CN (60 mL) was heated to 50° C. A solution of intermediate compound 72 (6 g, 27.83 mmol, 1 eq) in CH3CN (60 mL) was added dropwised at 50° C. The above reaction mixture was stirred at 80° C. for 5 hr. The reaction mixture was concentrated under reduced pressure. The residue was suspended in water (300 mL) and extracted with EtOAc (2×200 mL). The combined organic layers were washed with brine (200 mL), dried over Na2SO4 and filtered. The filtrate was concentrated under reduced pressure to give the crude intermediate compound 73 (5.38 g) as a light yellow solid.

1H NMR (400 MHz, DMSO-d6) δ 7.70 (d, J=1.75 Hz, 1H), 7.55 (d, J=1.63 Hz, 1H), 3.97 (s, 3H), 3.88 (s, 3H).

Intermediate Compound 74:

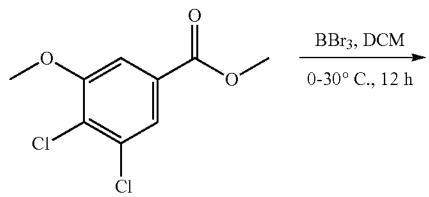
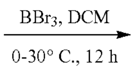

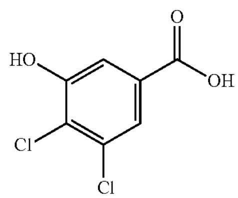

To a solution of intermediate compound 73 (5.38 g, 22.89 mmol, 1 eq) in DCM (200 mL) was added boron tribromide (11.47 g, 45.77 mmol, 4.41 mL, 2 eq) at 0° C. The above mixture was stirred at 30° C. for 12 hrs. The reaction mixture was dropped into saturated aqueous solution of Na2CO3 (200 mL). A large quantity of white precipitate was formed, dissolved by addition of ethyl acetate (100 mL). The organic layer was washed by saturated aqueous Na2CO3 (100 mL). The combined aqueous layer was washed with ethyl acetate (200 mL). The organic layers were discarded. The aqueous layer was acidified with HCl (12 M) to pH=4 and extracted with ethyl acetate (2×150 mL). The combined organic layers were dried over Na2SO4, filtered and concentrated under reduced pressure. The residue was dissolved with MeOH (40 mL) and H2O (10 mL). The above reaction mixture was added NaOH (2 g, 50 mmol, 2.2 eq). The reaction mixture was stirred at 50° C. for 12 h. After being cooled to room temperature, the reaction mixture was diluted with H2O (100 mL) and acidified with HCl (12 M) to pH 2. The above mixture was extracted with EtOAc (100 mL×2). The combined organic layers were dried over Na2SO4 and filtered. The filtrate was concentrated under reduced pressure to give the crude intermediate compound 74 (4.57 g, 96% yield) as a light yellow solid.

1H NMR (400 MHz, DMSO-d6) δ 14.12-12.37 (m, 1H), 11.76-10.96 (m, 1H), 7.51 (s, 2H).

Intermediate Compound 75:

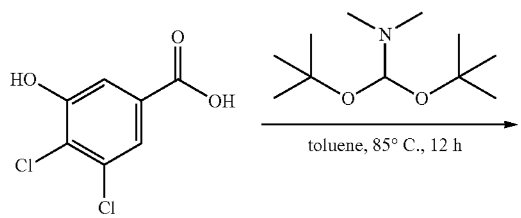

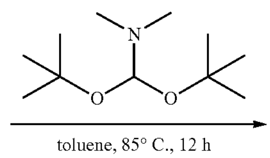

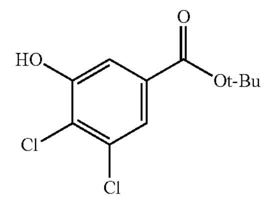

To a solution of intermediate compound 74 (1 g, 4.83 mmol, 1 eq) in toluene (20 mL) was added 1,1-di-tert-butoxy-N,N-dimethylmethanamine (3.92 g, 19.32 mmol, 4.64 mL, 4 eq). The above mixture was stirred at 85° C. for 12 hrs. The reaction was concentrated under reduced. The residue was purified by column chromatography on silica gel (petroleum ether/EtOAc 100/1 to 25/1) and to give the intermediate compound 75 (540 mg, 42% yield) as a white solid.

1H NMR (400 MHz, DMSO-d6) δ 11.15 (s, 1H), 7.47 (s, 2H), 1.53 (s, 9H).

Intermediate Compound 76:

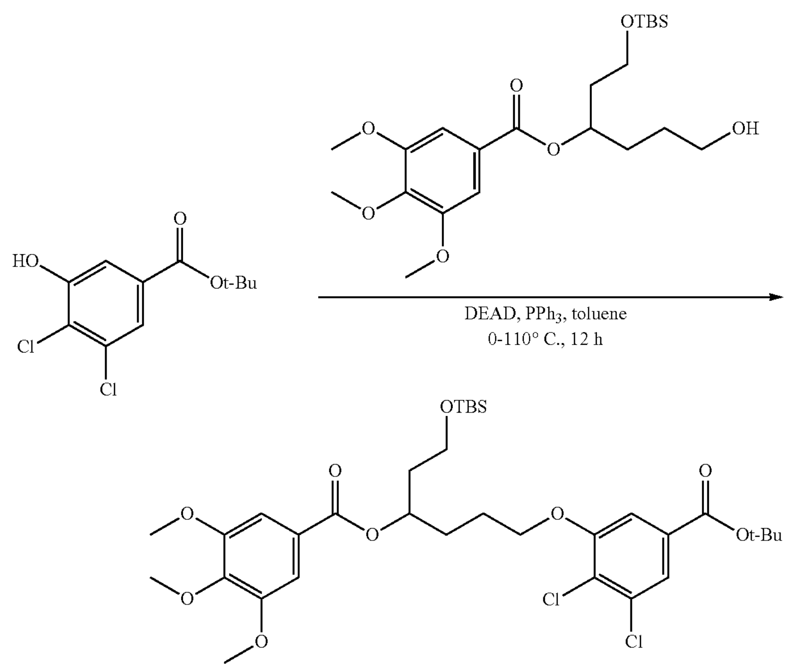

To a solution of intermediate compound 75 (540 mg, 2.05 mmol, 1 eq), intermediate compound 5 (908.39 mg, 2.05 mmol, 1 eq) and PPh3 (968.94 mg, 3.69 mmol, 1.8 eq) in toluene (12 mL) was added DEAD (536.15 mg, 3.08 mmol, 559.65 uL, 1.5 eq) at 0° C. The reaction mixture was concentrated under reduced pressure. The residue was purified by column chromatography on silica gel (petroleum ether/EtOAc 100/1 to 20/1) to give the intermediate compound 76 (1.2 g, 84% yield) as a pink oil.

1H NMR (400 MHz, DMSO-d6) δ 7.54 (d, J=1.59 Hz, 1H), 7.41-7.43 (m, 1H), 7.15-7.18 (m, 2H), 5.21-5.28 (m, 1H), 4.19 (br s, 2H), 3.79 (s, 6H), 3.72 (s, 3H), 3.65-3.70 (m, 2H), 1.96 (br dd, J=13.57, 5.62 Hz, 2H), 1.78-1.88 (m, 4H), 1.54 (s, 9H), −0.03 (d, J=4.52 Hz, 6H).

Intermediate Compound 77:

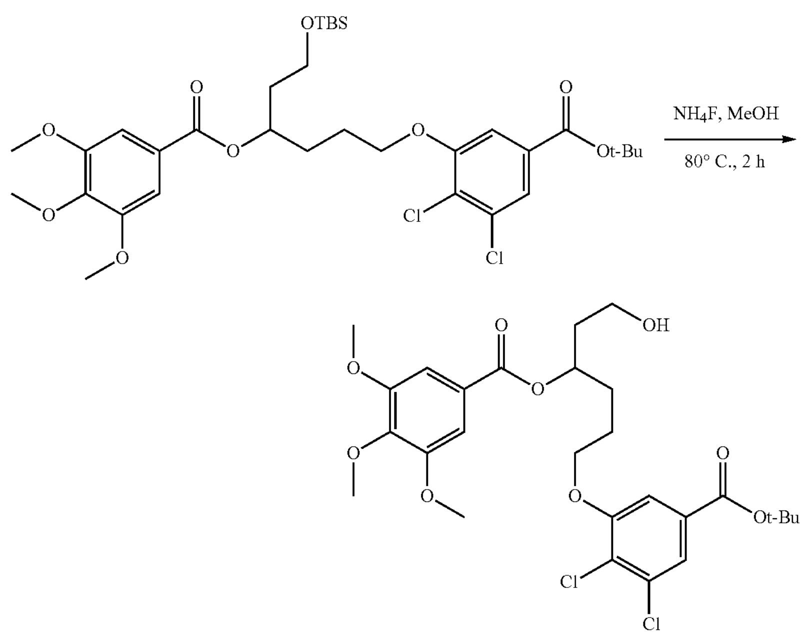

To a solution of intermediate compound 76 (500 mg, 727.04 umol, 1 eq) in MeOH (10 mL) was added NH4F (269.27 mg, 7.27 mmol, 10 eq). The reaction mixture was stirred at 80° C. for 2 hrs. The reaction mixture was concentrated under reduced pressure to give the crude intermediate compound 77 (440 mg) as a light pink oil.

LCMS (ESI position ion) m/z: 573.1 (M+H)+ (calculated: 572.1)

1H NMR (400 MHz, DMSO-d6) δ 7.54 (d, J=1.63 Hz, 1H), 7.42 (d, J=1.63 Hz, 1H), 7.17-7.16 (m, 2H), 5.27-5.20 (m, 1H), 4.22-4.16 (m, 2H), 3.79 (s, 6H), 3.72 (s, 3H), 3.49 (s, 2H), 1.99 (s, 1H), 1.91-1.79 (m, 6H), 1.54 (s, 9H).

Intermediate Compound 78:

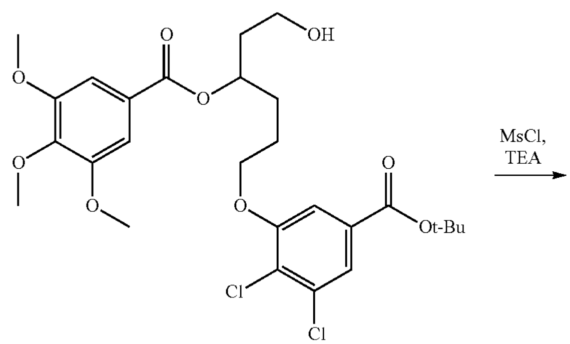

-continued

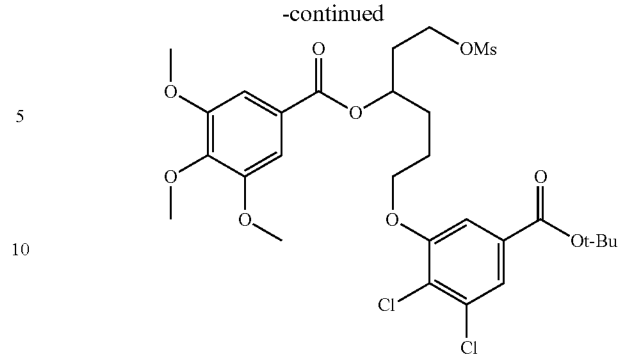

To a solution of intermediate compound 77 (1 g, 1.74 mmol, 1 eq) and TEA (529.36 mg, 5.23 mmol, 728.15 uL, 3 eq) in DCM (10 mL) was added methanesulfonyl chloride (399.51 mg, 3.49 mmol, 269.94 uL, 2 eq) slowly at 0° C., then the reaction mixture was stirred at 20° C. for 2 hrs. The reaction mixture was poured into saturated aqueous solution of NaHCO3 (10 mL) at 0° C. and extracted by DCM (3×20 mL). The combined organic layers were dried and concentrated under vacuum to give the crude intermediate compound 78 (1.1 g, 96% yield) as a brown oil and used without further purification.

1H NMR (400 MHz, CDCl3-d) δ=7.65 (d, J=1.63 Hz, 1H) 7.41 (d, J=1.63 Hz, 1H) 7.28 (s, 2H) 5.35-5.45 (m, 1H) 4.27-4.41 (m, 2H) 4.09-4.13 (m, 2H) 3.92 (s, 9H) 3.15 (s, 1H) 2.99 (s, 3H) 2.22 (q, J=6.30 Hz, 2H) 1.92-2.03 (m, 4H) 1.59 (s, 9H)

Intermediate Compound 79:

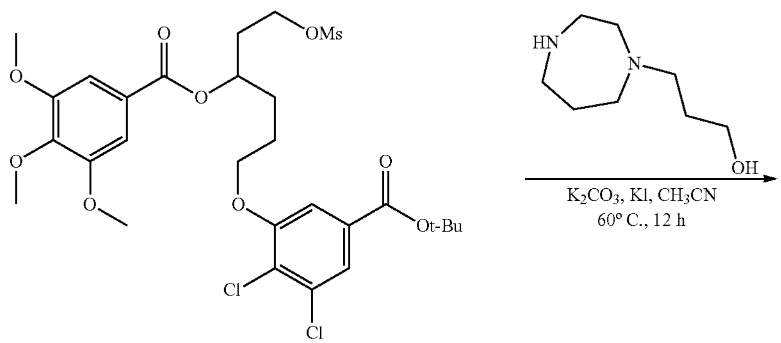

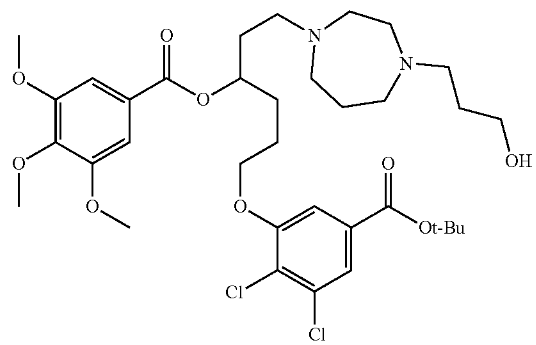

To a suspension of intermediate compound 78 (500 mg, 767.40 umol, 1 eq.) in CH3CN (10 mL) was added 3-(1,4-diazepan-1-yl)propan-1-ol (182.15 mg, 1.15 mmol, 1.5 eq.), K2CO3 (318.18 mg, 2.30 mmol, 3 eq.) and KI (254.78 mg, 1.53 mmol, 2 eq.). The reaction mixture was stirred at 60° C. for 12 hr. The reaction was filtered. The filtrate was concentrated under reduced pressure. The residue was purified by prep-HPLC (column: Phenomenex Synergi C18 150*25*10 um; mobile phase: [water (0.225% FA)-ACN]; B %: 38%-68%, 9 min) to give the intermediate compound 79 (470 mg, 84% yield) as a brown oil.

1H NMR (400 MHz, DMSO-d6) δ 7.56-7.54 (m, 1H), 7.45-7.41 (m, 1H), 7.27-7.21 (m, 2H), 5.19 (br d, J=5.00 Hz, 1H), 4.12-4.18 (m, 2H), 3.80 (s, 6H), 3.72 (s, 3H), 2.84-2.78 (m, 4H), 2.72-2.65 (m, 6H), 2.57 (brt, J=7.07 Hz, 3H), 2.30 (s, 2H), 1.99-1.79 (m, 7H), 1.78-1.71 (m, 2H), 1.64-1.58 (m, 2H), 1.54 (s, 9H).

Intermediate Compound 80:

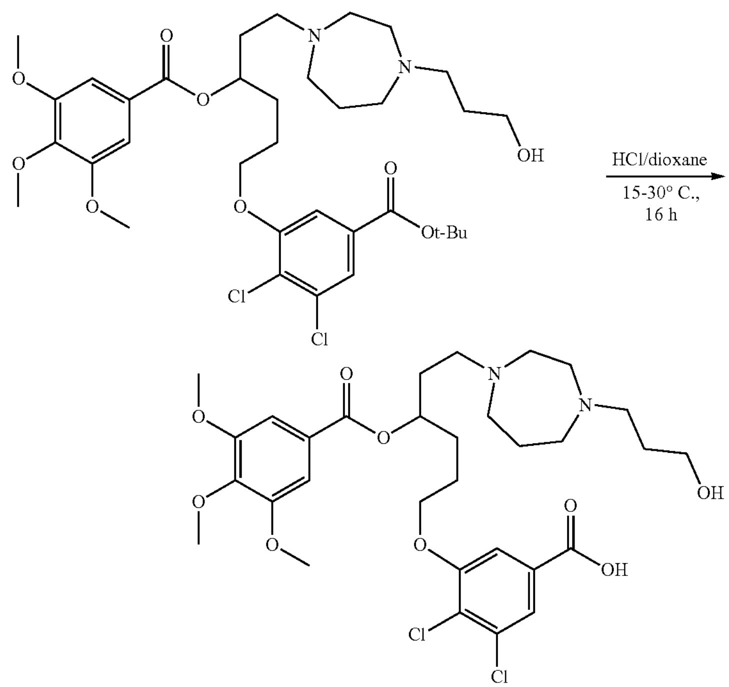

A solution of intermediate compound 79 (470 mg, 658.55 umol, 1 eq.) in HCl/dioxane (10 mL) was stirred at 30° C. for 12 hrs. The mixture was concentrated under reduced pressure to give the crude intermediate compound 80 (350 mg, 81% yield) as a yellow solid.

LCMS (ESI position ion) m/z: 657.1 (M+H)+ (calculated: 656.2)

Intermediate Compound 81:

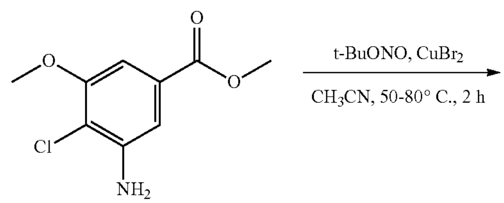

-continued

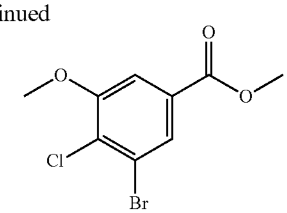

A suspension of CuBr2 (4.41 g, 19.76 mmol, 925.04 uL, 1.2 eq) and tert-Butyl nitrite (2.55 g, 24.69 mmol, 2.94 mL, 1.5 eq) in CH3CN (35 mL) was warmed to 50° C. A solution of intermediate compound 72 (3.55 g, 16.46 mmol, 1 eq) in CH3CN (35 mL) was added dropwised at 50° C. The reaction mixture was stirred at 80° C. for 2 hrs. The reaction mixture was concentrated under reduced pressure. The residue was dissolved with H2O (300 mL) and extracted with EtOAc (3×100 mL). The combined organic layers were washed with H2O (2×100 mL). The organic layer was dried over Na2SO4, filtered and. concentrated under reduced pressure. The residue was purified by column chromatography on silica gel (petroleum ether/EtOAc 100/1 to 50/1) to give the intermediate compound 81 (2.64 g, 57% yield) as a light yellow solid.

1H NMR (400 MHz, DMSO-d6) δ 7.84 (d, J=1.75 Hz, 1H), 7.58 (d, J=1.88 Hz, 1H), 3.97 (s, 3H), 3.89 (s, 3H).

Intermediate Compound 82:

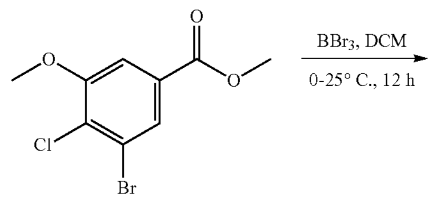

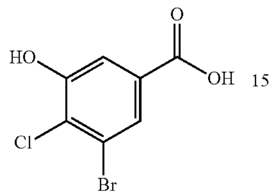

To a solution of intermediate compound 81 (2.64 g, 9.44 mmol, 1 eq) in DCM (100 mL) was added boron tribromide (4.73 g, 18.89 mmol, 1.82 mL, 2 eq) at 0° C. The mixture was stirred at 25° C. for 12 hrs. The reaction mixture was poured into saturated aqueous solution of Na2CO3 (200 mL). A large quantity of white precipitate was formed dissolved by addition of EtOAc (100 mL). The organic layer was washed by saturated aqueous solution of Na2CO3 (100 mL). The combined aqueous layers were extracted with EtOAc (200 mL). The aqueous layer was acidified with hydrochloride (12 M) to pH=3 and extracted with EtOAC (2×150 mL). The combined organic layers were dried over Na2SO4, filtered and concentrated under reduced pressure to give the crude intermediate compound 82 (5.38 g) as a light yellow solid.

1H NMR (400 MHz, DMSO-d6) δ 7.70 (d, J=1.75 Hz, 1H), 7.55 (d, J=1.63 Hz, 1H), 3.97 (s, 3H), 3.88 (s, 3H).

Intermediate Compound 83:

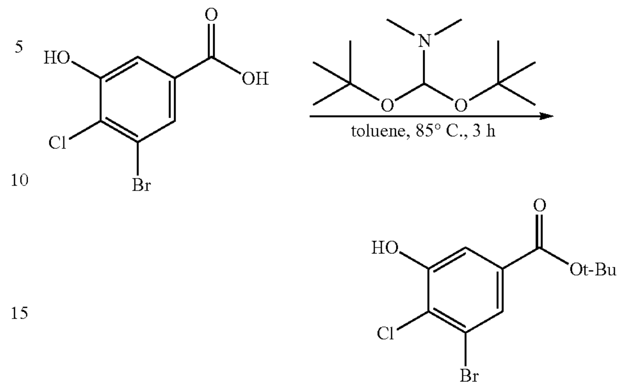

To a solution of intermediate compound 82 (500 mg, 1.99 mmol, 1 eq) in toluene (10 mL) was added 1,1-di-tert-butoxy-N,N-dimethylmethanamine (808.56 mg, 3.98 mmol, 953.49 uL, 2 eq). The mixture was stirred at 85° C. for 3 hr. The reaction mixture was concentrated under reduced pressure. The residue was purified by column chromatography on silica gel (petroleum ether/EtOAc 100/1 to 20/1) to give the intermediate compound 83 (170 mg, 28% yield) as a white solid.

1H NMR (400 MHz, DMSO-d6) δ 11.13 (s, 1H), 7.60 (d, J=1.88 Hz, 1H), 7.50 (d, J=1.88 Hz, 1H), 1.53 (s, 9H).

Intermediate Compound 84:

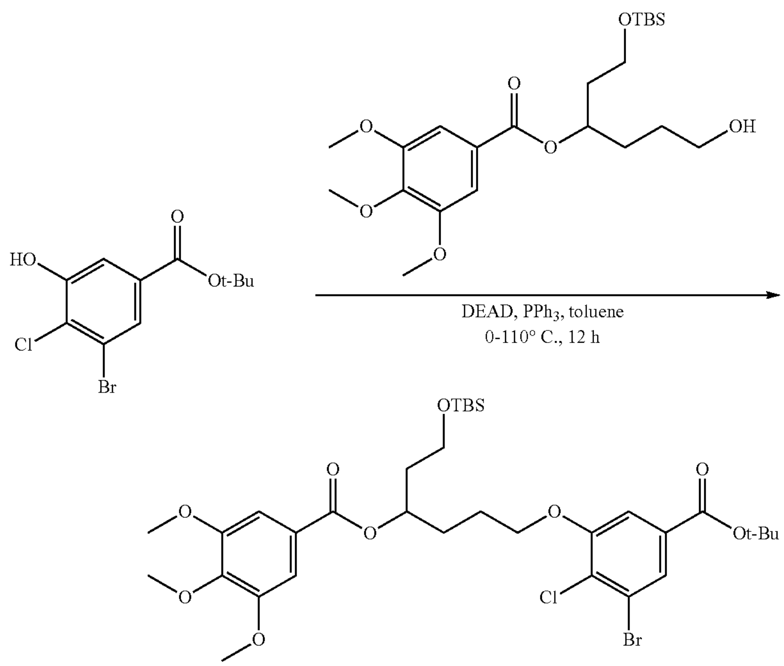

To a solution of intermediate compound 83 (210 mg, 682.78 umol, 1 eq), intermediate compound 5 (302.21 mg, 682.78 umol, 1 eq) and triphenylphosphine (322.35 mg, 1.23 mmol, 1.8 eq) in toluene (4 mL) was added DEAD (178.36 mg, 1.02 mmol, 186.18 uL, 1.5 eq) at 0° C. The reaction mixture was stirred at 110° C. for 12 hrs. The reaction mixture was concentrated under reduced pressure. The residue was purified by prep-TLC (petroleum ether/EtOAc=5/1) to give the intermediate compound 84 (390 mg, 73% yield,) as a colorless oil.

1H NMR (400 MHz, DMSO-d6) δ 7.66 (d, J=1.63 Hz, 1H), 7.44 (d, J=1.50 Hz, 1H), 7.14-7.18 (m, 2H), 5.24 (br d, J=3.38 Hz, 1H), 4.15-4.21 (m, 2H), 3.79 (s, 6H), 3.72 (s, 3H), 3.64-3.70 (m, 2H), 1.90-2.02 (m, 2H), 1.79-1.89 (m, 4H), 1.54 (s, 9H), 0.81 (s, 9H), −0.03 (d, J=4.63 Hz, 6H)

Intermediate Compound 85:

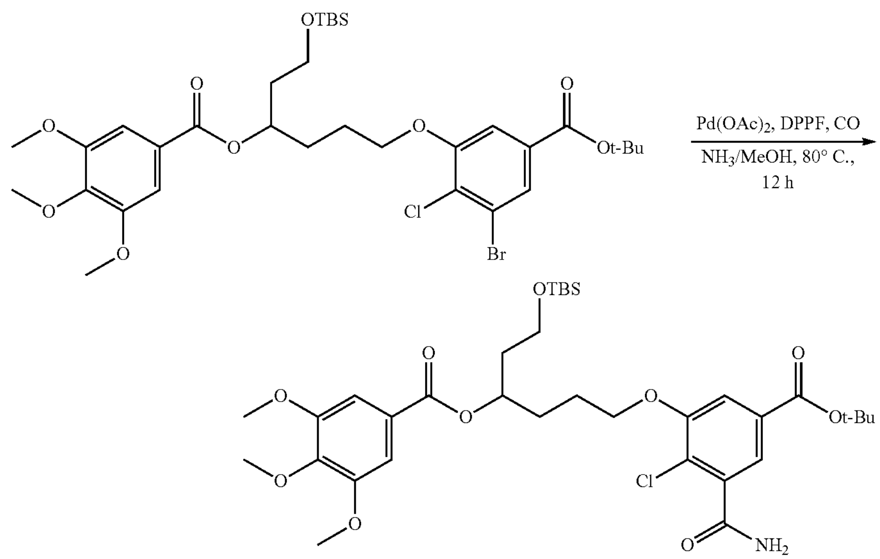

A suspension of intermediate compound 84 (70 mg, 95.61 umol, 1 eq), Pd(OAc)2 (2.15 mg, 9.56 umol, 0.1 eq), DPPF (10.60 mg, 19.12 umol, 0.2 eq) in NH3/MeOH (7M, 10 mL) was stirred at 80° C. for 12 hrs under CO (50 psi) atmosphere. The reaction mixture was filtered and the filtrate was concentrated under reduced pressure. The residue was purified by prep-TLC (petroleum ether/EtOAc=1/1) to give the intermediate compound 85 (20 mg, 30% yield) as a white solid.

LCMS (ESI position ion) m/z: 696.2 (M+H)+ (calculated: 695.3)

Intermediate Compound 86:

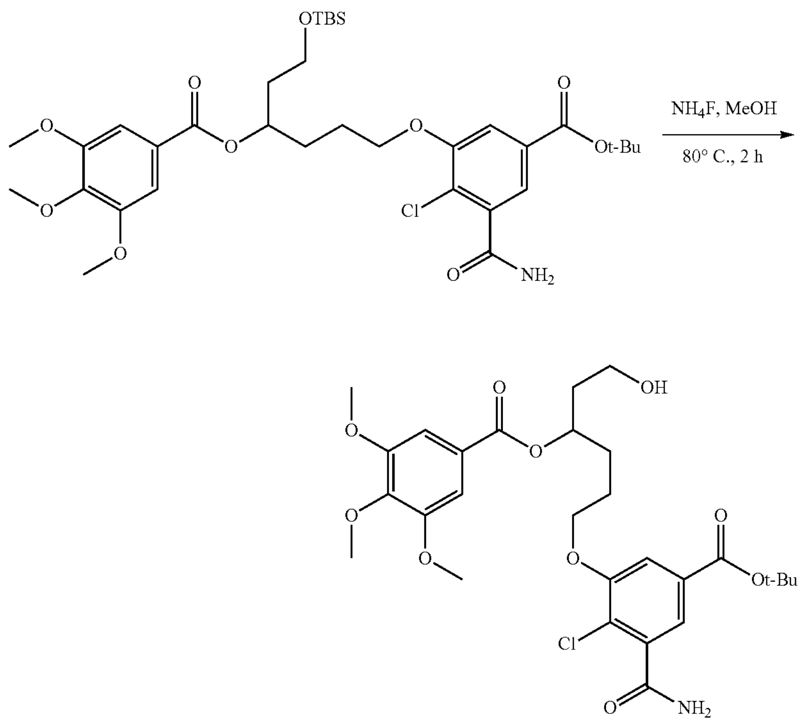

To a solution of intermediate compound 85 (40 mg, 57.45 umol, 1 eq) in MeOH (3 mL) was added NH4F (21.28 mg, 574.47 umol, 10 eq). The reaction mixture was stirred at 80° C. for 2 hrs. The reaction mixture was concentrated under reduced pressure. The residue was suspended in EtOAc (30 mL) and stirred at 15° C. for 0.5 h. The suspension was filtered and the filtrate was concentrated under reduced pressure to give the crude intermediate compound 86 (38 mg) as a colorless oil.

LCMS (ESI position ion) m/z: 582.1 (M+H)+ (calculated: 581.2)

Intermediate Compound 87:

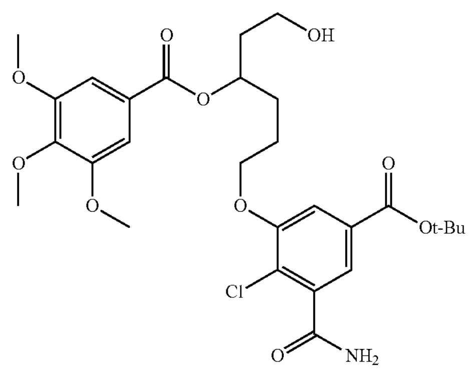

-continued

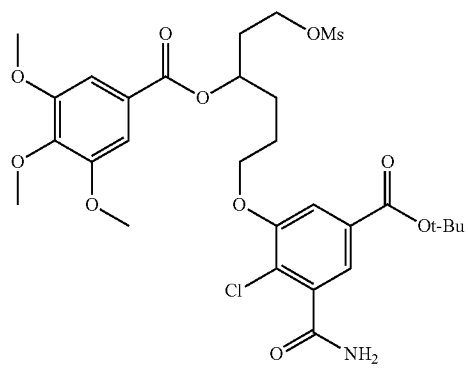

To a mixture of intermediate compound 86 (38 mg, 65.29 umol, 1 eq) and TEA (13.21 mg, 130.58 umol, 18.17 uL, 2 eq) in DCM (3 mL) was added methanesulfonyl chloride (15 mg, 130.95 umol, 10.14 uL, 2.01 eq) at 0° C. The mixture was stirred at 25° C. for 2 hrs. The mixture was poured into water (20 mL) and extracted with DCM (3×20 mL). The combined organic layers were washed with brine (2×30 mL), dried over Na2SO4, filtered and concentrated under vacuum to give the crude intermediate compound 87 (45 mg) as a colorless oil.

Intermediate Compound 88:

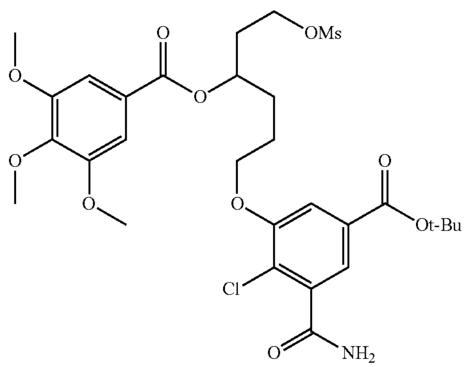

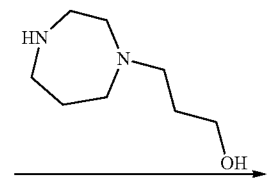

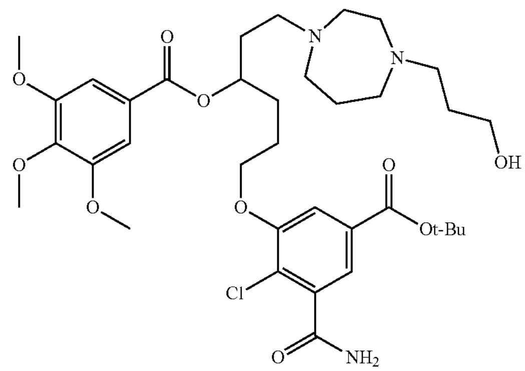

A mixture of intermediate compound 87 (45 mg, 68.17 umol, 1 eq), 3-(1,4-diazepan-1-yl)propan-1-ol (16.18 mg, 102.25 umol, 1.5 eq), K2CO3 (28.26 mg, 204.51 umol, 3 eq) and KI (22.63 mg, 136.34 umol, 2 eq) in MeCN (4 mL) was stirred at 60° C. for 16 hrs. The mixture was filtered and washed with MeCN (5×10 mL). The combined filtrate was concentrated under vacuum. The residue was purified by reversed phase (column: spherical C18 20-35 mm 100A 80 g; mobile phase: [water (0.5% FA)-ACN]; B %: 25%-34%, 15 min) to give the intermediate compound 88 (31 mg, 62% yield) as a colorless oil.

LCMS (ESI position ion) m/z: 722.2 (M+H)+ (calculated: 721.3)

Intermediate Compound 89:

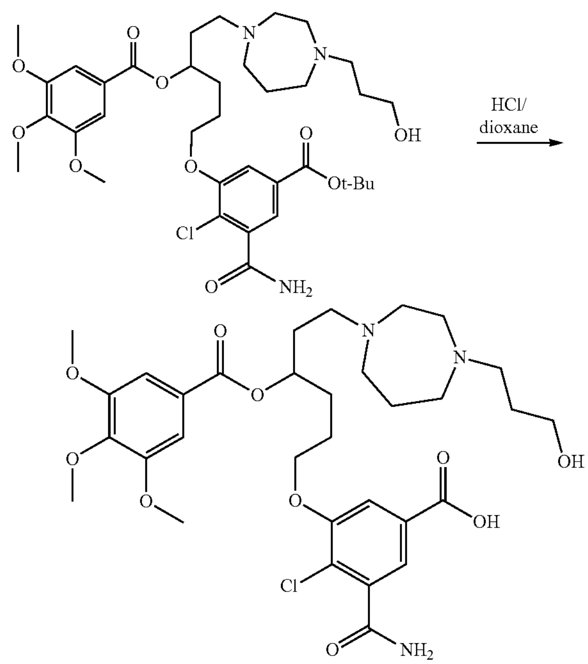

A mixture of intermediate compound 88 (31 mg, 42.49 umol, 99% purity, 1 eq) in HCl/dioxane (4 M, 531.14 uL, 50 eq) and DCM (0.5 mL) was stirred at 30° C. for 12 hrs. The mixture was concentrated under vacuum to give the crude intermediate compound 89 (33 mg) as a yellow oil.

LCMS (ESI position ion) m/z: 666.1 (M+H)+ (calculated: 665.3)

Intermediate Compound 90:

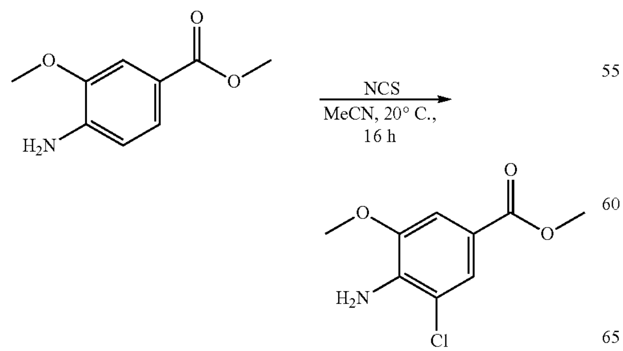

To a solution of methyl 4-amino-3-methoxybenzoate (20 g, 110.38 mmol, 1 eq) in CH3CN (200 mL) was added N-chlorosuccinimide (16.21 g, 121.42 mmol, 1.1 eq), then the mixture was stirred at 20° C. for 12 hr. The reaction mixture was diluted with water (800 mL) and extracted with EtOAc (3×500 mL). The combined organic layers were washed with brine (3×400 mL), dried over Na2SO4, filtered and concentrated under reduced pressure. The residue was purified by column chromatography (SiO2, petroleum ether/EtOAC=100/1 to 5/1) to give the intermediate compound 90 (18 g, 76% yield) as an off-white solid.

1H NMR (400 MHz, CDCl3-d) δ 7.67 (d, J=1.6 Hz, 1H), 7.37 (d, J=1.6 Hz, 1H), 4.73-4.32 (m, 2H), 3.92 (s, 3H), 3.88 (s, 3H)

Intermediate Compound 91:

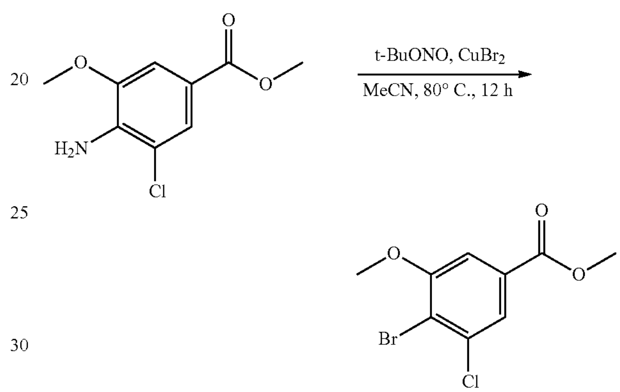

To a solution of tert-butyl nitrite (11.48 g, 111.30 mmol, 13.24 mL, 1.5 eq) and CuBr2 (19.89 g, 89.04 mmol, 4.17 mL, 1.2 eq) in CH3CN (160 mL) was added intermediate compound 90 (16 g, 74.20 mmol, 1 eq) in CH3CN (50 mL) at 50° C. slowly, then the mixture was stirred at 80° C. for 12 hr. The reaction mixture was concentrated under reduced pressure. The residue was diluted with EtOAc (1000 mL) and washed with water (3×600 mL). The combined organic layers were washed with brine (3×500 mL), dried over Na2SO4, filtered and concentrated under reduced pressure. The residue was purified by column chromatography (SiO2, petroleum ether/EtOAc=100/1 to 5/1) to give the intermediate compound 91 (16 g, 77% yield) as a white solid.

1H NMR (400 MHz, CDCl3-d) δ 7.76 (d, J=1.7 Hz, 1H), 7.44 (d, J=1.7 Hz, 1H), 3.96 (d, J=13.1 Hz, 6H)

Intermediate Compound 92:

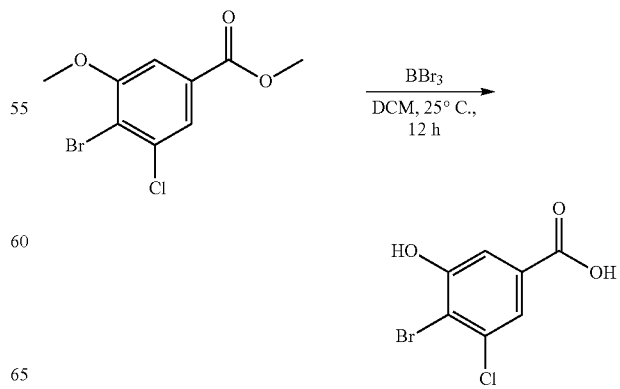

To a solution of intermediate compound 91 (6 g, 21.47 mmol, 1 eq) in DCM (110 mL) was added boron tribromide (21.51 g, 85.86 mmol, 8.27 mL, 4 eq) at 0° C., then the mixture was stirred at 25° C. for 12 hr. The reaction mixture was quenched by addition to water (600 ml), and then diluted with DCM (500 mL) and extracted with water (3×400 mL). The combined organic layers were washed with brine (3×400 mL), dried over Na2SO4, filtered and concentrated under reduced pressure. The residue was triturated with water (500 mL) at 25° C. for 30 min to give the intermediate compound 92 (5 g) as an off-white solid.

1H NMR (400 MHz, DMSO-d6) δ 11.70-10.71 (m, 1H), 7.54-7.42 (m, 2H)

Intermediate Compound 93:

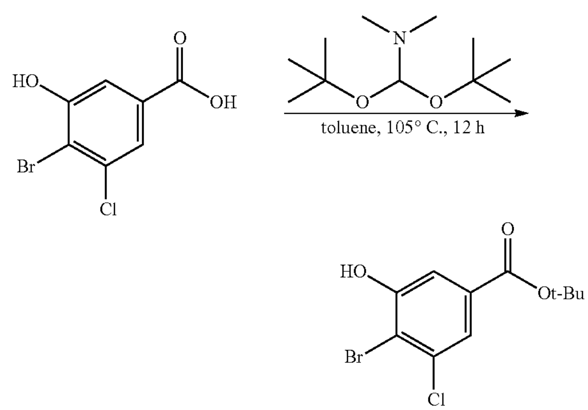

To a solution of intermediate compound 92 (0.75 g, 2.98 mmol, 1 eq) in toluene (20 mL) was added 1,1-di-tert-butoxy-N,N-dimethylmethanamine (2.43 g, 11.93 mmol, 2.86 mL, 4 eq), then the mixture was stirred at 105° C. for 12 hr. The reaction mixture was concentrated under reduced pressure. The residue was purified by column chromatography (SiO2, petroleum ether/EtOAc=100/1 to 5/1) to give the intermediate compound 93 (0.3 g, 33% yield) as a white solid.

1H NMR (400 MHz, CDCl3-d) δ 7.65 (d, J=2.0 Hz, 1H), 7.53 (d, J=1.8 Hz, 1H), 5.79 (s, 1H), 1.59 (s, 9H)

Intermediate Compound 94:

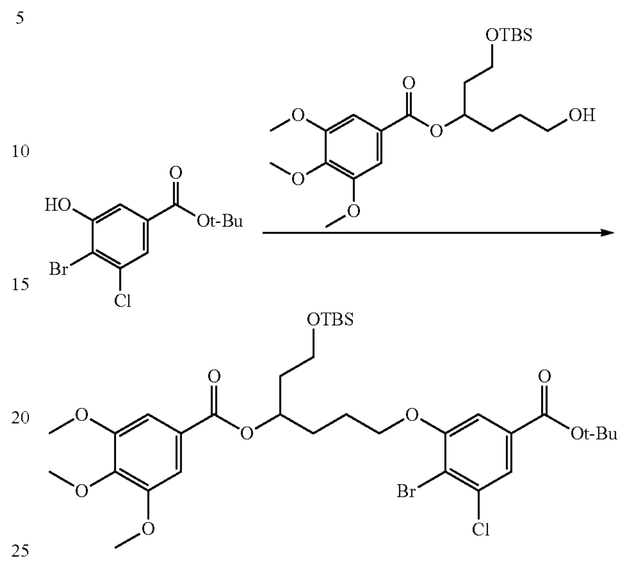

To a solution of intermediate compound 5 (1.3 g, 2.94 mmol, 1 eq) and intermediate compound 93 (903.35 mg, 2.94 mmol, 1 eq) in toluene (13 mL) was added triphenylphosphine (1.39 g, 5.29 mmol, 1.8 eq), then the DEAD (767.26 mg, 4.41 mmol, 800.90 uL, 1.5 eq) was added at 0° C. The mixture was stirred at 0-110° C. for 12 hr. The reaction mixture was diluted with EtOAc (800 mL) and extracted with water (3×500 mL). The combined organic layers were washed with brine (3×400 mL), dried over Na2SO4, filtered and concentrated under reduced pressure. The residue was purified by column chromatography (SiO2, petroleum ether/EtOAc=100/1 to 10/1) to give the intermediate compound 94 (1.5 g, 70% yield) as a colorless oil.

Intermediate Compound 95:

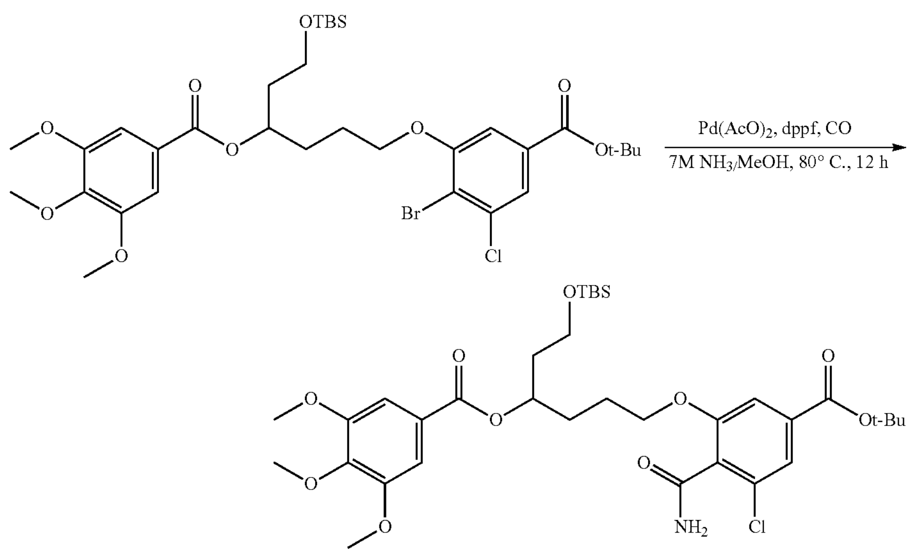

A suspension of intermediate compound 94 (1.5 g, 2.05 mmol, 1 eq) Pd(OAc)2 (46.00 mg, 204.87 umol, 0.1 eq), DPPF (227.15 mg, 409.74 umol, 0.2 eq) in NH3 (7 M, 80 mL, 273.34 eq) (MeOH) was stirred at 80° C. for 72 h under CO (50 psi) atmosphere. The reaction mixture was filtered and concentrated under reduced pressure. The residue was purified by column chromatography ($SiO_2$, petroleum ether/EtOAc=10/1 to 3/1) to give the intermediate compound 95 (350 mg, 24% yield) as a colorless oil.

LCMS (ESI position ion) m/z: 696.2 (M+H)+ (calculated: 695.3)

Intermediate Compound 96:

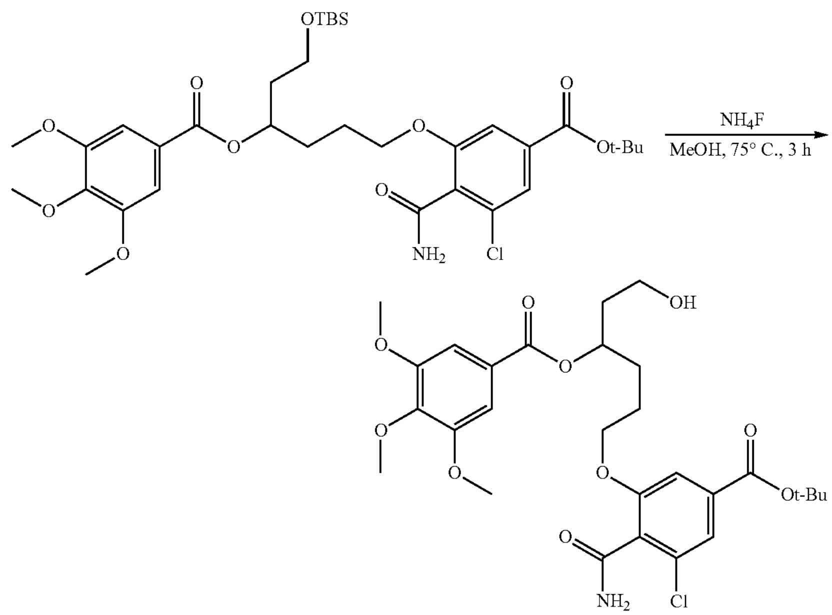

To a solution of intermediate compound 95 (300 mg, 430.85 umol, 1 eq) in MeOH (5 mL) was added $NH_4F$ (319.15 mg, 8.62 mmol, 20 eq). The mixture was stirred at 75° C. for 3 hr. The reaction mixture was filtered and concentrated under reduced pressure. The residue was purified by preparative HPLC (column: 3_Phenomenex Luna C18 75*30 mm*3 um; mobile phase: [water (0.1% TFA)-ACN]; B %: 52%-72%, 7 min) to give the intermediate compound 96 (250 mg) as a colorless oil.

LCMS (ESI position ion) m/z: 582.2 (M+H)+ (calculated: 581.2)

1H NMR (400 MHz, $CDCl_3$-d) δ 7.52 (d, J=1.0 Hz, 1H), 7.37 (d, J=0.8 Hz, 1H), 7.24 (s, 2H), 6.50 (br s, 1H), 6.24 (br s, 1H), 5.36 (br d, J=3.4 Hz, 1H), 4.20-4.02 (m, 3H), 3.89 (s, 8H), 3.75-3.50 (m, 2H), 1.99-1.72 (m, 6H), 1.57 (s, 9H)

Intermediate Compound 97:

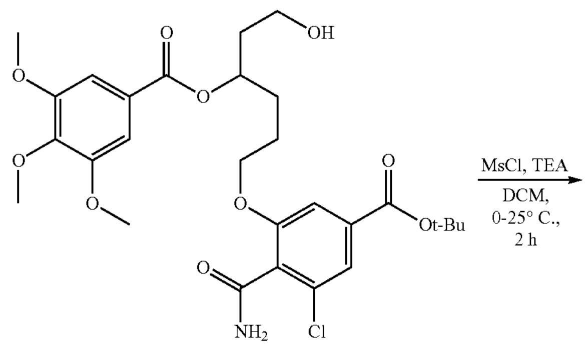

-continued

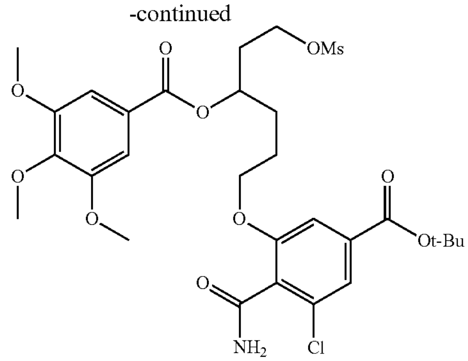

To a solution of intermediate compound 96 (120 mg, 206.17 umol, 1 eq) and $Et_3N$ (52.16 mg, 515.43 umol, 71.74 uL, 2.5 eq) in DCM (3 mL) was added methanesulfonyl chloride (0.25 g, 2.18 mmol, 168.92 uL, 10.59 eq) drop-wise at 0° C. The mixture was stirred at 0° C. for 2 hr. The mixture was quenched by ice-water (30 mL) slowly and then extracted with DCM (3×20 mL). The combined organic layers were washed with brine (3×20 mL), dried over anhydrous $Na_2SO_4$, filtered and concentrated in vacuum to give the crude intermediate compound 97 (120 mg) as a yellow oil. LCMS (ESI position ion) m/z: 660.1 (M+H)+ (calculated: 659.2)

Intermediate Compound 98:

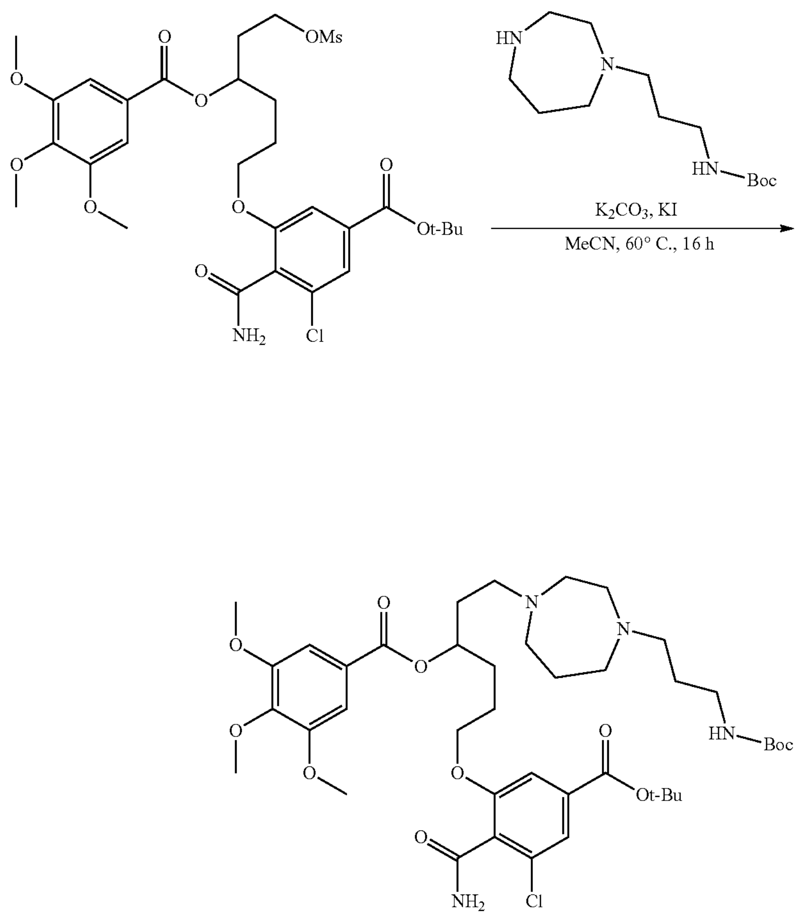

To a solution of intermediate compound 97 (120 mg, 181.78 umol, 1 eq) in CH3CN (3 mL) were added intermediate compound 24 (56.14 mg, 218.14 umol, 1.2 eq), K2CO3 (125.62 mg, 908.91 umol, 5 eq) and KI (30.18 mg, 181.78 umol, 1 eq). The mixture was stirred at 60° C. for 12 hr. The reaction mixture was filtered and concentrated under reduced pressure. The residue was purified by preparative HPLC (column: Phenomenex Gemini-NX C18 75*30 mm*3 um; mobile phase: [water (0.225% FA)-ACN]; B %: 18%-48%, 7 min) to give the intermediate compound 98 (50 mg) as a off-white solid.

LCMS (ESI position ion) m/z: 821.3 (M+H)+ (calculated: 820.4)

Intermediate Compound 99:

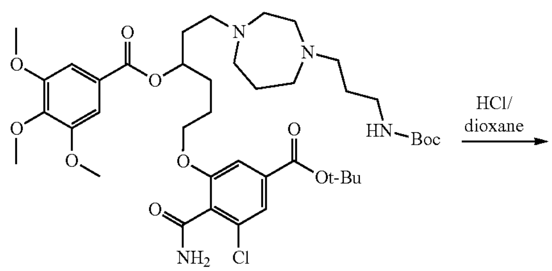

-continued

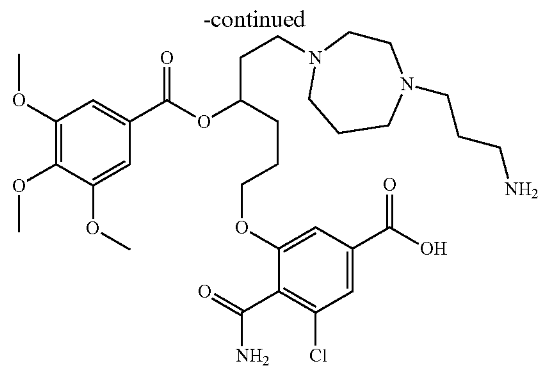

To a solution of intermediate compound 98 (30 mg, 36.52 umol, 1 eq) in HCl/dioxane (4 M, 1 mL, 109.52 eq) The mixture was stirred at 20° C. for 2 hr. The reaction mixture was concentrated under reduced. The residue was purified by preparative HPLC (column: Phenomenex Gemini-NX C18 75*30 mm*3 um; mobile phase: [water (0.225% FA)-ACN]; B %: 1%-30%, 8 min) to give the intermediate compound 99 (30 mg) as a colorless oil.

LCMS (ESI position ion) m/z: 665.2 (M+H)+ (calculated: 664.3)

Intermediate Compound 100:

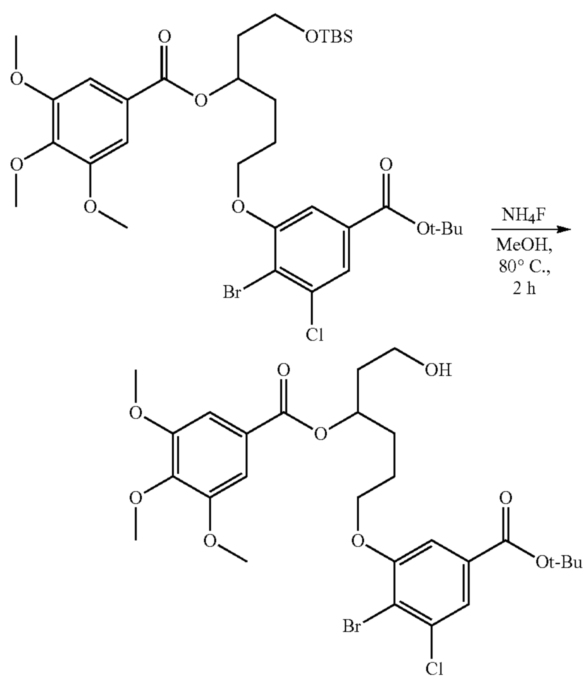

To a solution of intermediate compound 94 (1.2 g, 1.64 mmol, 1 eq) in MeOH (15 mL) was added NH4F (1.21 g, 32.78 mmol, 20 eq). The mixture was stirred at 75° C. for 12 hr. The reaction mixture was filtered and concentrated under reduced pressure. The residue was purified by column chromatography (SiO2, petroleum ether/EtOAc=10/1 to 1/1) to give the intermediate compound 100 (0.5 g) as a colorless oil/

1H NMR: (400 MHz, CDCl3) δ 7.64 (d, J=1.3 Hz, 1H), 7.34 (d, J=1.1 Hz, 1H), 7.30-7.27 (m, 2H), 5.39 (br d, J=5.3 Hz, 1H), 4.15-4.08 (m, 2H), 3.90 (s, 9H), 3.71 (br d, J=5.6 Hz, 2H), 2.51 (br s, 1H), 2.03-1.82 (m, 6H), 1.58 (s, 9H)

Intermediate Compound 101:

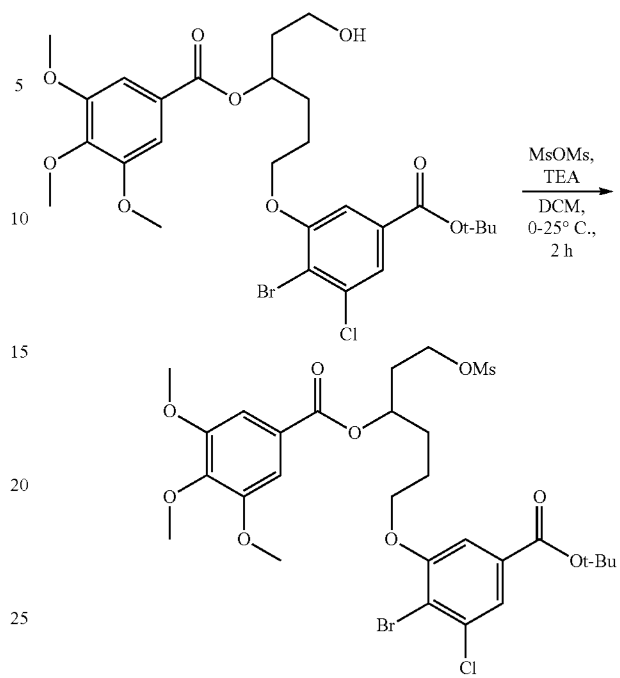

To a solution of intermediate compound 100 (360 mg, 582.61 umol, 1 eq) and TEA (235.82 mg, 2.33 mmol, 324.37 uL, 4 eq) in DCM (10 mL) was added methanesulfonic anhydride (304.46 mg, 1.75 mmol, 3 eq) drop-wise at 0° C. The mixture was stirred at 0° C. for 2 hr. The mixture was quenched by ice-water (200 mL) slowly and then extracted with DCM (3×100 mL). The combined organic layers were washed with brine (3×150 mL), dried over Na2SO4, filtered and concentrated in vacuum to give the crude intermediate compound 101 (400 mg) as a yellow oil and used without further purification.

Intermediate Compound 102:

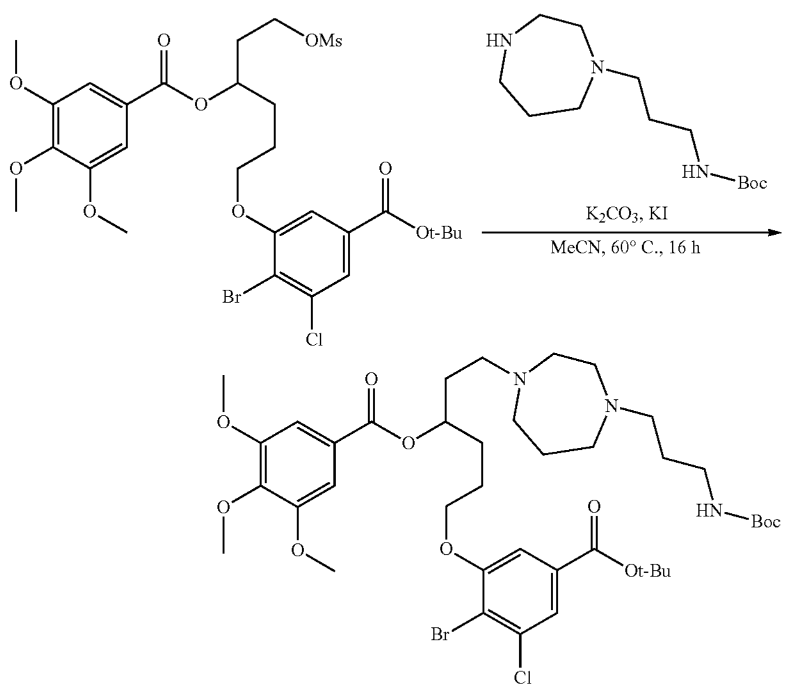

To a solution of intermediate compound 101 (360 mg, 517.24 umol, 1 eq) in CH3CN (6 mL) were added intermediate compound 24 (159.75 mg, 620.69 umol, 1.2 eq), K2CO3 (357.44 mg, 2.59 mmol, 5 eq) and KI (85.86 mg, 517.24 umol, 1 eq). The mixture was stirred at 60° C. for 12 hr. The reaction mixture was filtered and concentrated under reduced pressure. The residue was purified by preparative HPLC (column: Phenomenex luna C18 150*40 mm*15 um; mobile phase: [water (0.225% FA)-ACN]; B %: 25%-55%, 10 min) to give the intermediate compound 102 (400 mg, 80% yield) as a colorless oil. 1H NMR: (400 MHz, CDCl3) δ 7.65 (br d, J=1.8 Hz, 1H), 7.35 (s, 1H), 7.29-7.27 (m, 2H), 5.31 (br s, 1H), 4.12 (br s, 2H), 3.92 (s, 9H), 3.19 (br s 2H), 3.01 (br s, 4H), 2.94-2.89 (m, 2H), 2.83 (br d, J=7.1 Hz, 4H), 2.79-2.64 (m, 4H), 2.07-1.77 (m, 10H), 1.59 (s, 9H), 1.43 (s, 9H)

Intermediate Compound 103:

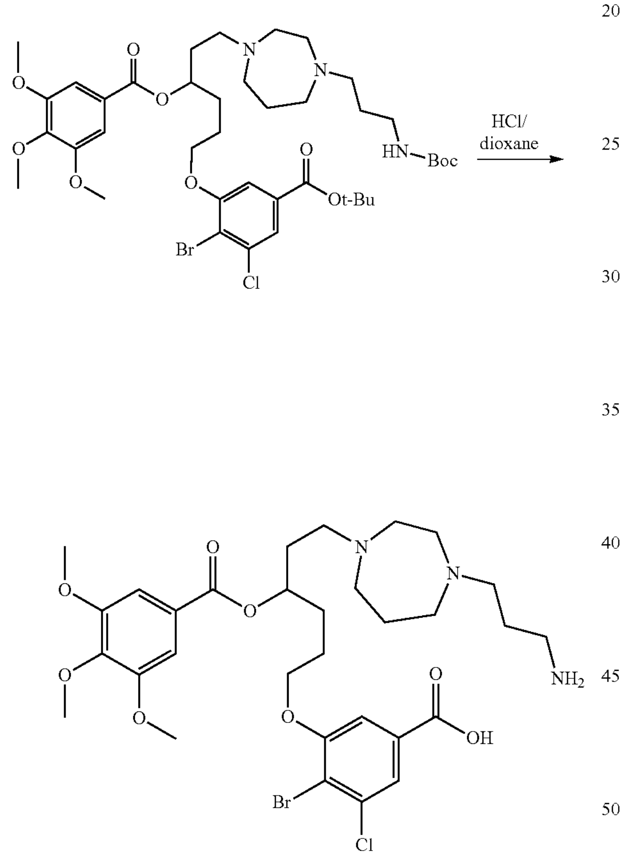

To a solution of intermediate compound 102 (300 mg, 349.95 umol, 1 eq) in HCl/dioxane (4 M, 12.27 mL, 140.21 eq) The mixture was stirred at 20° C. for 2 hr. The reaction mixture was concentrated under reduced pressure. The residue was purified by preparative HPLC (column: Waters Xbridge 150*25 mm*5 um; mobile phase: [water (0.05% ammonia hydroxide v/v)-ACN]; B %: 21%-51%, 8 min) to give the intermediate compound 103 (52 mg, 52% yield) as a white solid.

1H NMR: (400 MHz, MeOD) δ 7.66 (d, J=1.6 Hz, 1H), 7.51 (s, 1H), 7.30 (s, 2H), 5.30 (br d, J=3.7 Hz, 1H), 4.21 (br s, 2H), 3.92-3.79 (m, 9H), 3.13 (br d, J=1.3 Hz, 4H), 3.07-2.70 (m, 10H), 2.17-1.81 (m, 10H)

Intermediate Compound 104:

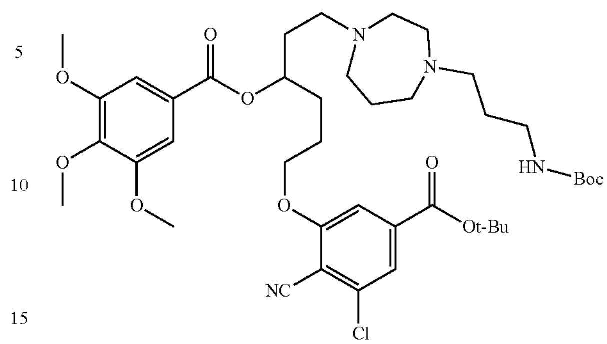

The intermediate 104 has been isolated as a side compound in the preparation of the intermediate compound 98.

LCMS (ESI position ion) m/z: 803.5 (M+H)+ (calculated: 802.4)

Intermediate Compound 105:

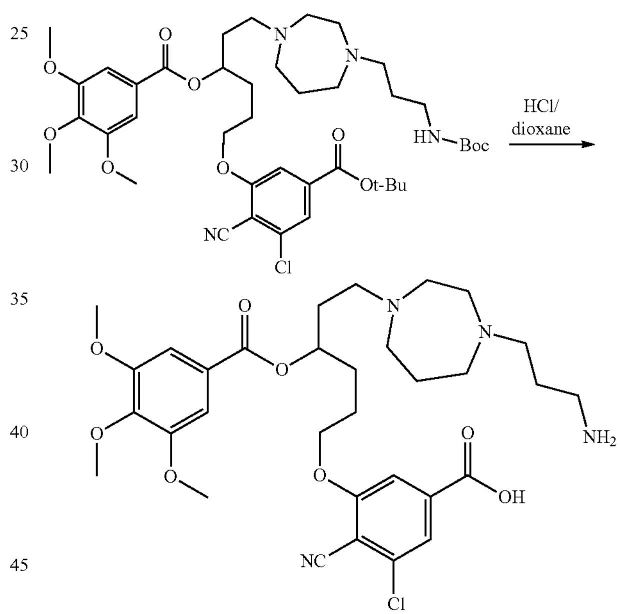

A mixture of intermediate compound 104 (50 mg, 62.24 umol, 1 eq) in HCl/dioxane (4 M, 1.70 mL, 109.52 eq) was stirred at 20° C. for 0.5 hr. The reaction mixture was concentrated under reduced pressure. The residue was purified by preparative HPLC (column: Waters Xbridge 150*25 mm*5 um; mobile phase: [water (0.05% ammonia hydroxide v/v)-ACN]; B %: 16%-46%, 8 min) to give the intermediate compound 105 (18 mg, 45% yield) as a white solid.

LCMS (ESI position ion) m/z: 647.3 (M+H)+ (calculated: 646.3)

Intermediate Compound 106:

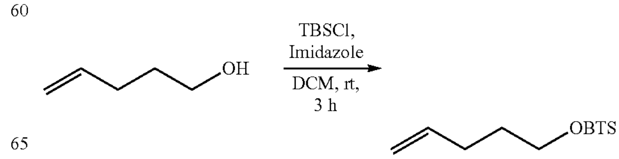

To a stirred solution of 4-penten-1-ol (100 g, 1161 mmol, 1.0 equiv) and imidazole (118.6 g, 1741 mmol, 1.5 equiv) in DCM (800 mL) were added tert-butyldimethylsilyl chloride (192.5 g, 1277 mmol, 1.1 equiv) in portions at 0° C. The resulting mixture was stirred for 3 h at room temperature under a nitrogen atmosphere. The resulting mixture was washed with a solution of 0.5 M aq. HCl (3×500 mL). The organic layer was concentrated under reduced pressure, to give the intermediate compound 106 (190 g, 82% yield) as a colorless oil.

LC-MS (ES+) m/z: 201 (M+H)+ (calculated: 200.1)

Intermediate Compound 107:

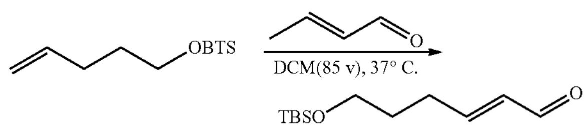

A solution of intermediate compound 106 (95 g, 474 mmol, 1.0 equiv), Grubbs 2nd generation catalyst (20.1 g, 23.7 mmol, 0.05 equiv), crotonaldehyde (56.5 g, 806 mmol, 1.7 equiv) in DCM (8075 mL) was stirred at 37° C. overnight. The mixture was then allowed to cool down to room temperature and concentrated under reduced pressure. The resulting residue was purified by silica gel column chromatography (SiO2, EtOAc/petroleum ether=1/100 to 1/10) to give the intermediate compound 107 (70 g, 65% yield) as a yellow oil.

LC-MS (ES+) m/z: 229 (M+H)+ (calculated: 228.1)

Intermediate Compound 108:

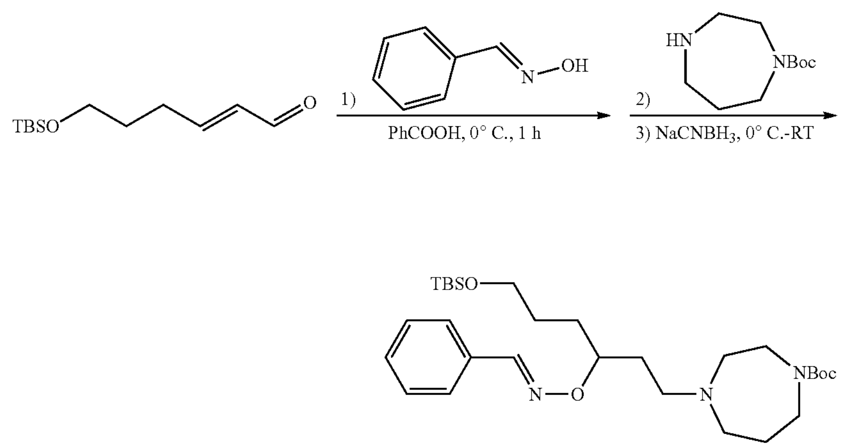

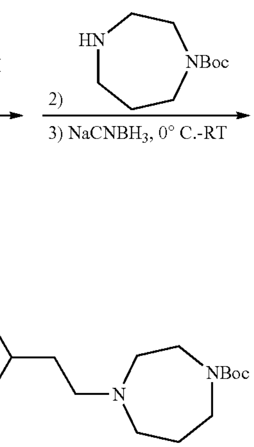

To a stirred solution of (2S)-2-[bis[3,5-bis(trifluoromethyl)phenyl][(trimethylsilyl)oxy]methyl]pyrrolidine (261 mg, 0.43 mmol, 0.1 equiv) and benzoic acid (54 mg, 0.43 mmol, 0.1 equiv) in toluene (2.2 mL) at 0° C. was added intermediate compound 107 (1.0 g, 4.4 mmol, 1.0 equiv), followed by E-benzaldoxime (1.6 g, 13.1 mmol, 3.0 equiv) and the solution was stirred for 4 h at 0° C. The reaction mixture was diluted with DCM (15 mL), followed by the addition of tert-butyl 1,4-diazepane-1-carboxylate (1.4 g, 7.0 mmol, 1.6 equiv) and the reaction mixture was stirred at room temperature for a further 1 h. Sodium borohydride (324 mg, 8.8 mmol, 2.0 equiv) was added and the reaction mixture was stirred at room temperature for a further 1 h. The reaction mixture was diluted with saturated aqeuous solution of NH4Cl and extracted with DCM (3×20 mL). The combined organic layers were washed with brine, dried over MgSO4 and evaporated under reduced pressure. The crude oil was purified by preparative HPLC (Column (C18-I, 20-40 m); mobile phase (MeOH/H2O=40% to 100%: 6 min; 100%: 5 min); Detector (254 and 220 nm)), to give the intermediate compound 108 (650 mg, 28% yield) as a colourless oil. Note: the compound has been determined as racemic.

LC-MS (ES+) m/z: 534 (M+H)+ (calculated: 533.4)

Intermediate Compound 109:

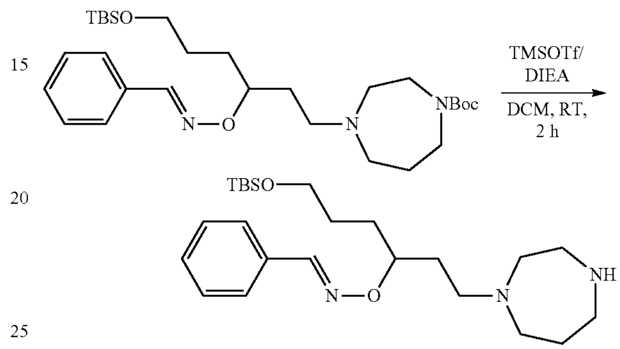

To a solution of intermediate compound 108 (5.6 g, 10.5 mmol, 1.0 equiv) and DIEA (5.4 g, 42 mmol, 4.0 equiv) in DCM (100 mL), was added trimethylsilyl trifluoromethanesulfonate (7.0 g, 31.5 mmol, 3.0 equiv) at 0° C. The resulting solution was stirred for 2 h at room temperature, and then quenched by the addition of 20 mL of water. The organic phase was washed with 20 mL of water and brine (2×30 mL). The organic layer was dried over Na2SO4 and concentrated. The residue was purified by preparative HPLC (Column (C18-I, 20-40 m); mobile phase (MeOH/H2O=20% to 100%: 7 min; 100%: 3 min); Detector (254 and 220 nm)) to give the intermediate compound 9 (4 g, 75% yield) as a light brown oil.

LC-MS (ES+) m/z: 434 (M+H)+ (calculated: 433.3)

1H NMR (300 MHz, DMSO-d6) δ 7.21 (s, 1H), 7.10 (s, 1H), 4.30-4.26 (m, 2H), 3.84-3.74 (m, 6H), 2.80-2.71 (m, 4H), 2.65-2.57 (m, 6H), 1.84-1.60 (m, 4H), 0.99 (s, 9H), 0.16 (s, 6H).

Intermediate Compound 110:

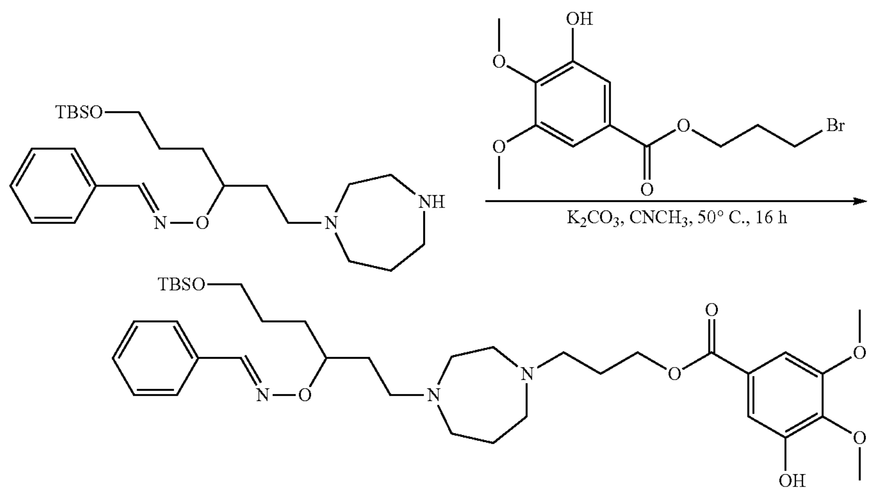

A solution of intermediate compound 109 (3.4 g, 7.8 mmol, 1.0 equiv), intermediate compound 13 (2.6 g, 8.2 mmol, 1.05 equiv), K2CO3 (1.2 g, 8.6 mmol, 1.1 equiv) in CH3CN (53 mL) was stirred for 16 h at 50° C. The reaction mixture was then poured into 150 mL of water/ice. The resulting solution was extracted with EtOAc (3×100 mL), the combined organic layers were dried over Na2SO4 and concentrated. The residue was purified by preparative HPLC (Column (C18-I, 20-40 μm); mobile phase (MeOH/H2O=40% to 100%: 7 min; 100%: 5 min); Detector (254 and 220 nm)) to give the intermediate compound 110 (4.1 g, 78% yield) as a light brown oil.

LC-MS (ES+) m/z: 672 (M+H)+ (calculated: 671.4)

Intermediate Compound 111:

To a solution of intermediate compound 110 (4.1 g, 6.1 mmol, 1.0 equiv) in DCM (50 mL) was added 3 M HCl (120 mL) at room temperature. The resulting mixture was stirred for 1 h at room temperature, after which the DCM layer was discarded. The pH value of the aqueous layer was adjusted pH to 7-8 with saturated solution of NaHCO3. The resulting solution was extracted with DCM (3×100 mL), the combined organic layers were dried over Na2SO4 and concentrated. The residue was purified by preparative HPLC (Column (C18-I, 20-40 m); mobile phase (MeOH/H2O=20% to 95%: 8 min); Detector (254 and 220 nm)) to give the intermediate compound 111 (2.7 g, 79% yield) as colorless oil.

LC-MS (ES+) m/z: 558 (M+H)+ (calculated: 557.3)

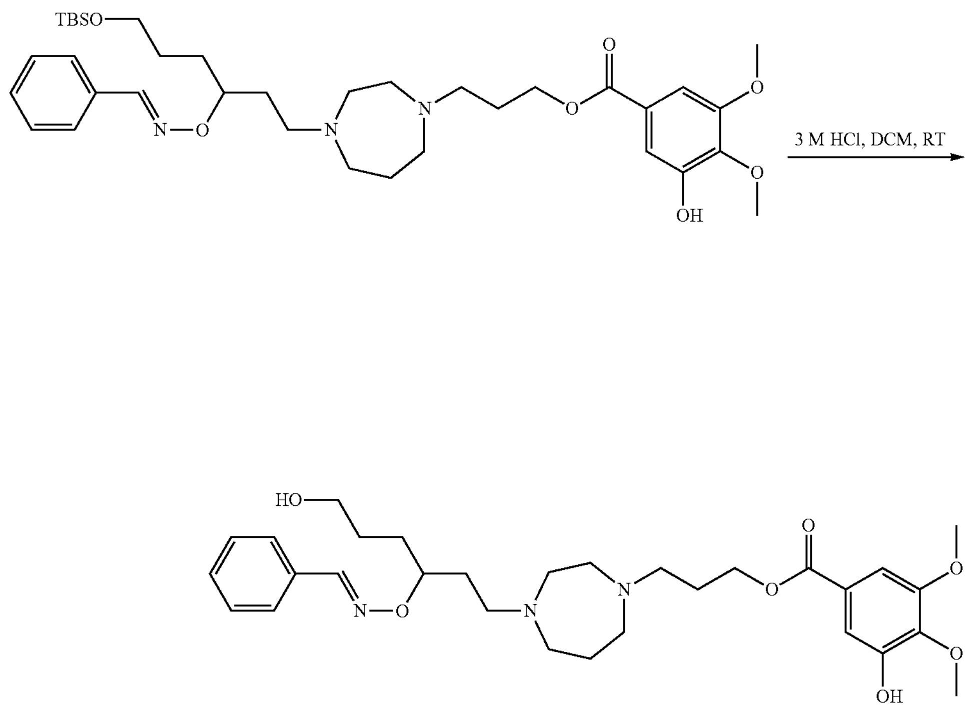

1H NMR (300 MHz, CDCl3) δ 8.07 (s, 1H), 7.58-7.56 (m, 2H), 7.38-7.28 (m, 5H), 7.19 (s, 1H), 4.49-4.31 (m, 3H), 3.96 (s, 3H), 3.91 (s, 3H), 3.78-3.69 (m, 2H), 2.80-2.66 (m, 12H), 1.93-1.88 (m, 6H), 1.74-1.71 (m, 4H).

Intermediate Compound 112:

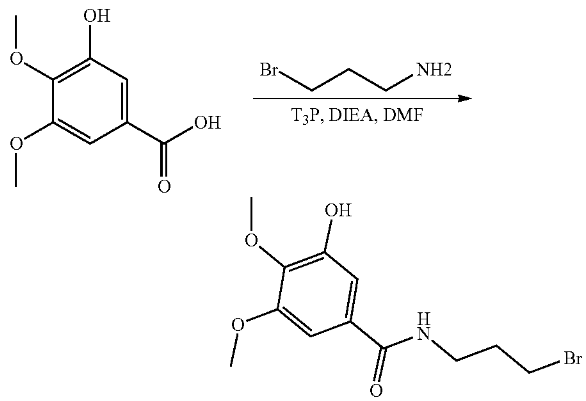

To a mixture of 3-hydroxy-4,5-dimethoxybenzoic acid (20.0 g, 101 mmol, 1.0 equiv) and 3-bromopropan-1-amine (16.7 g, 121 mmol, 1.2 equiv) in DMF (400 mL) were added DIEA (39.1 g, 303 mmol, 3.0 equiv) and propylphosphonic anhydride solution (77.0 g, 121 mmol, 1.2 equiv) dropwise at 0° C. under a nitrogen atmosphere. The resulting mixture was stirred overnight at room temperature. The reaction was quenched by the addition of water (1.2 L) at room temperature. The resulting mixture was extracted with EtOAc (3×500 mL). The combined organic layers were washed with brine (1×500 mL), dried over Na2SO4 and concentrated under reduced pressure. The residue was purified by silica gel column chromatography (petroleum ether/EtOAc=5/1 to 1/1) to give the intermediate compound 112 (15 g, 47% yield) as an off-white solid.

LC-MS (ES+) m/z: 318 (M+H)+ (calculated: 317.0)

Intermediate Compound 113:

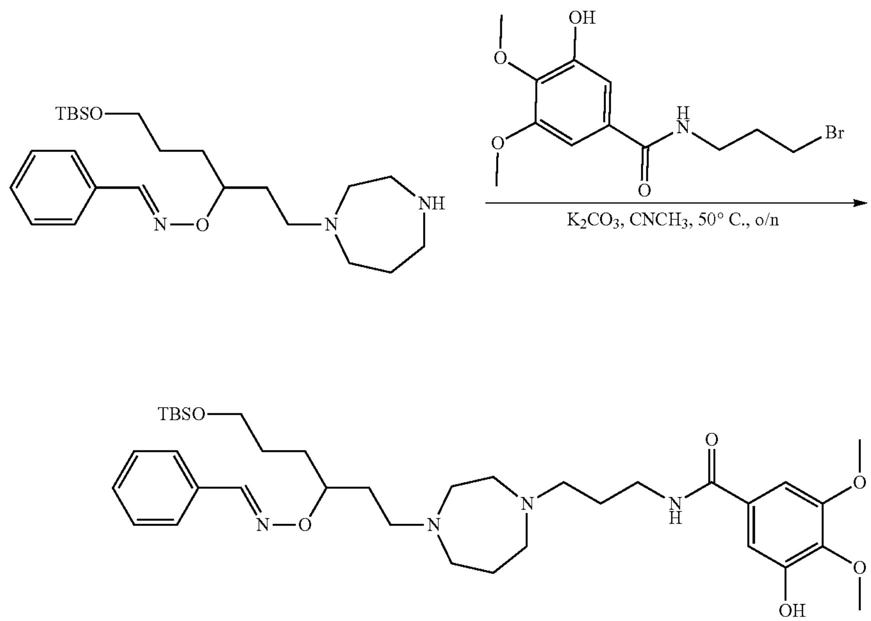

To a stirred solution of intermediate compound 109 (10.0 g, 23.1 mmol, 1.0 equiv) and K2CO3 (7.97 g, 57.7 mmol, 2.5 equiv) in CH3CN (250 mL) was added intermediate compound 112 (11.0 g, 34.6 mmol, 1.5 equiv) in portions at room temperature under a nitrogen atmosphere. The reaction mixture was stirred overnight at 50° C., and was allowed to cool down to room temperature. The resulting suspension was filtered, the precipitate was washed with acetonitrile (1×100 mL), and the filtrate was concentrated under reduced pressure. The residue was purified by reverse flash chromatography (column, C18 silica gel; mobile phase, MeOH in water, 80% to 95% gradient in 8 min and 95% to 100% gradient in 9 min; detector, UV 254 nm and 220 nm) to give the intermediate compound 113 (5 g, 32% yield) as a light yellow oil.

LC-MS (ES+) m/z: 671 (M+H)+ (calculated: 670.4)

Intermediate Compound 114:

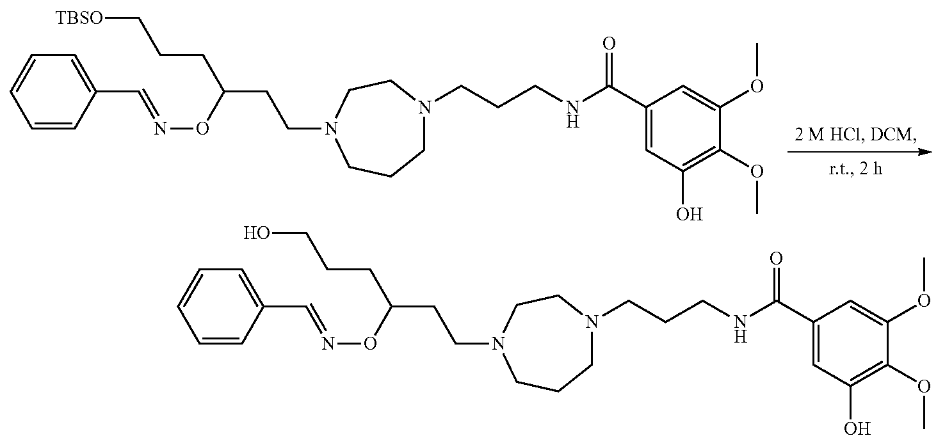

To a stirred solution of intermediate compound 113 (5.0 g, 7.6 mmol, 1.0 equiv) in DCM (50 mL) was added HCl (2 M in water, 50 mL) at 0° C. under nitrogen atmosphere. The resulting mixture was stirred for additional 2 h at room temperature. The aqueous layer was extracted with DCM (1×50 mL). The pH of the aqueous layer was adjusted to pH=7 with saturated aqueous solution of NaHCO3, and extracted with THF (3×50 mL). The combined organic layers were dried over Na2SO4 and concentrated under reduced pressure to give the crude intermediate compound 114 (3.6 g, 87% yield) as a light yellow oil. The crude product was used in the next step without further purification.

LC-MS (ES+) m/z: 557 (M+H)+ (calculated: 556.3)

Intermediate Compound 115:

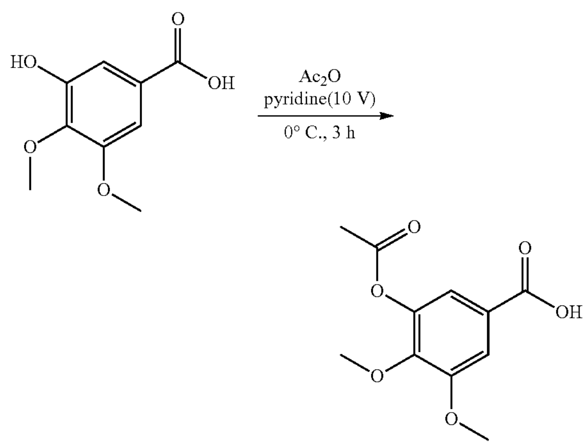

$Ac_2O$ (7.65 g, 75 mmol, 1.5 equiv) was added dropwise at 0° C. to a solution of 3-hydroxy-4,5-dimethoxybenzoic acid (9.90 g, 50 mmol, 1.00 equiv) in pyridine (100 mL). The resulting solution was stirred for 3 h at 0° C., and then was concentrated. The crude intermediate compound 115 (10 g) was used in the next step directly without further purification.

LC-MS (ES+) m/z: 241 (M+H)+ (calculated: 240.1).

Intermediate Compound 116:

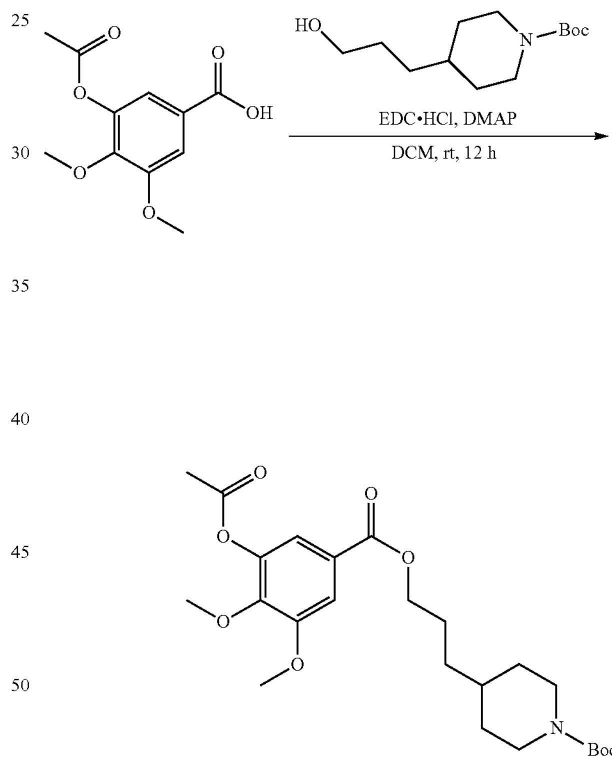

A solution of intermediate compound 115 (10 g, 41.7 mmol, 1.0 equiv), tert-butyl 4-(3-hydroxypropyl)piperidine-1-carboxylate (12.15 g, 50 mmol, 1.2 equiv), EDCI (11.98 g, 62.5 mmol, 1.5 equiv) and DMAP (7.62 g, 62.5 mmol, 1.5 equiv) in DCM (100 mL) was stirred at room temperature for 12 h. The reaction mixture was then quenched with 100 mL H2O and extracted with DCM (3×100 mL). The combined organic layers were concentrated and the residue was purified by silica gel column chromatography (petroleum ether/EtOAc=3/1) to give the intermediate compound 116 (7 g, 30% yield, over 2 steps) as a colourless oil.

LC-MS (ES+) m/z: 466 (M+H)+ (calculated: 465.2).

Intermediate Compound 117:

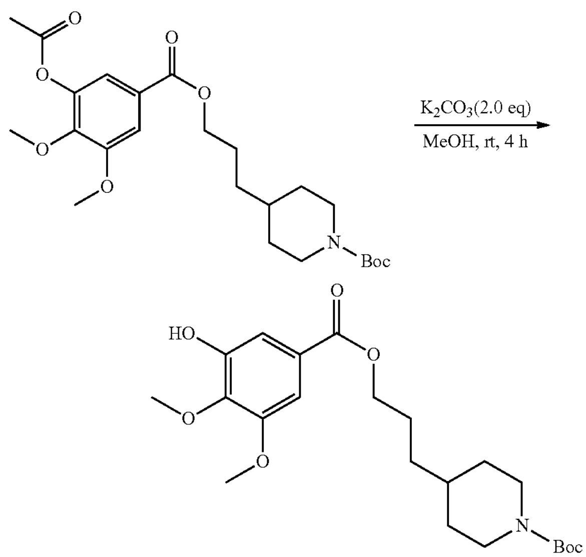

A solution of intermediate compound 116 (6.50 g, 14.0 mmol, 1.0 equiv), potassium carbonate (3.85 g, 28.0 mmol, 2.0 equiv) in MeOH (65 mL) was stirred for 2 h at room temperature. The mixture was then filtered and the filtrate concentrated under reduced pressure. The crude intermediate compound 117 (5.8 g) was used in the next step directly without further purification.

LC-MS (ES+) m/z: 424 (M+H)+ (calculated: 423.2).

Intermediate Compound 118:

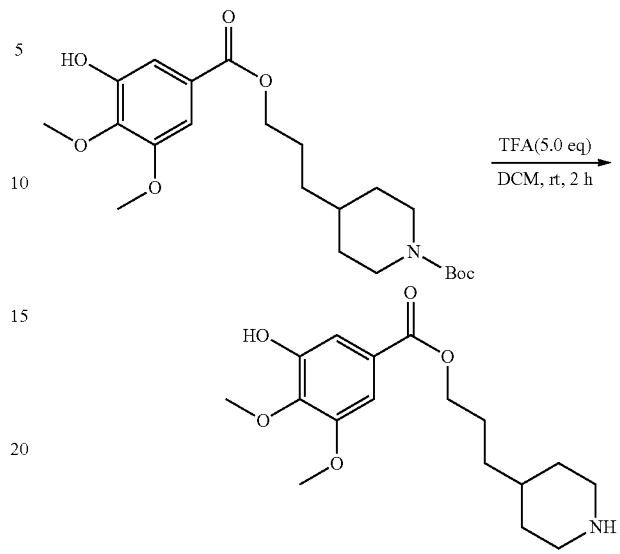

A solution of intermediate compound 117 (5.8 g), TFA (7.8 g) in DCM (110 mL) was stirred at room temperature for 2 h. The mixture was then basified to pH=7 with saturated solution of NaHCO3 and filtered. The precipitate was washed with DCM (2×20 mL), and the filtrate was concentrated under reduced pressure. The crude intermediate compound 118 (4.02 g) was used in the next step directly without further purification as a yellow oil.

LC-MS (ES+) m/z: 324 (M+H)+ (calculated: 323.2).

Intermediate Compound 119:

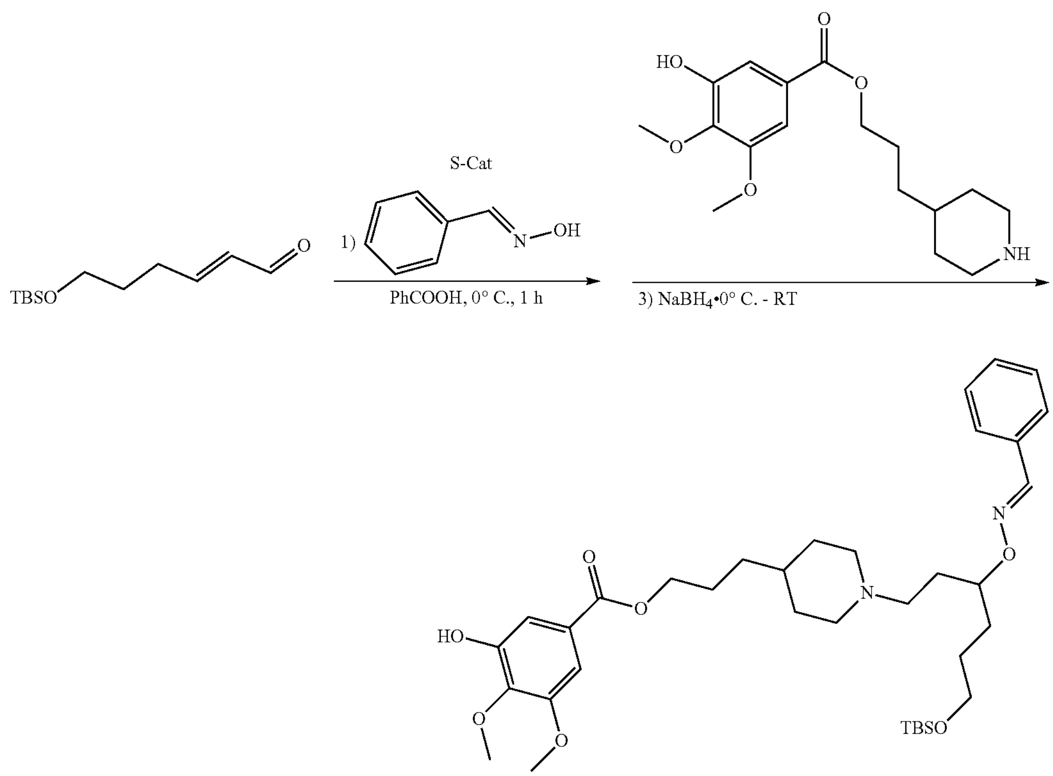

To a stirred solution of (2S)-2-[bis[3,5-bis(trifluoromethyl)phenyl][(trimethylsilyl)oxy]methyl]pyrrolidine (261 mg, 0.43 mmol, 0.1 equiv) and benzoic acid (54 mg, 0.43 mmol, 0.1 equiv) in toluene (2.2 mL) was added at 0° C. the intermediate compound 107 (1.0 g, 4.4 mmol, 1.0 equiv), followed by E-benzaldoxime (1.6 g, 13.1 mmol, 3.0 eq.) and the solution was stirred for 4 h at 0° C. The reaction mixture was diluted with DCM (15 mL), followed by the addition of the intermediate compound 118 (2.25 g, 7.0 mmol, 1.6 equiv) and the reaction mixture was stirred at room temperature for a further 1 h. Sodium borohydride (324 mg, 8.8 mmol, 2.0 equiv) then was added and the reaction mixture was stirred at room temperature for a further 1 h. The reaction mixture was quenched with sat.NH4Cl and extracted with DCM (3×20 mL). The combined organic components were dried over MgSO4 and evaporated to dryness. The resulting oil was purified by preparative HPLC (Column (C18-I, 20-40 μm); mobile phase (MeOH/H2O=50% to 100%: 6 min; 100%: 5 min)); Detector (220 nm) to give the intermediate compound 119 (750 mg, 16% yield) as a colourless oil.

LC-MS (ES+) m/z: 657 (M+H)+ (calculated: 656.4).

Intermediate Compound 120:

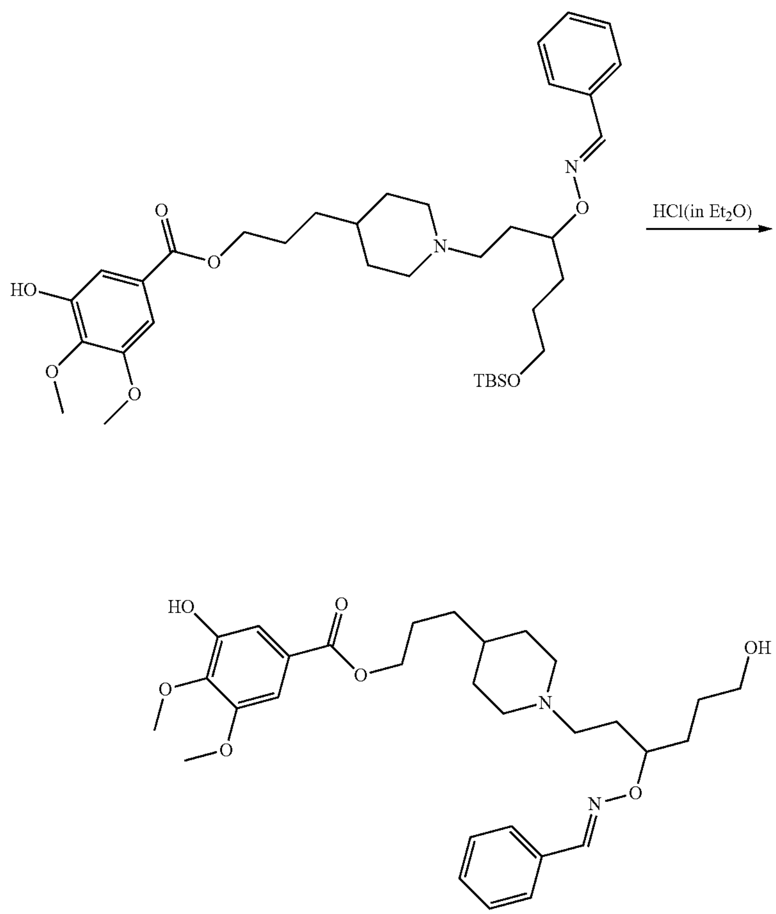

A solution of intermediate compound 119 (670 mg, 1.0 mmol, 1.0 equiv) in 2 M HCl in Et20 (10 mL) was stirred for 2 h at room temperature. The Et20 was removed and the pH value of the residue was adjusted to pH=7-8 with a saturated solution of NaHCO3. The resulting solution was extracted with DCM (3×10 mL), the combined organic layers were dried over Na2SO4 and concentrated. The crude product was purified by preparative HPLC (Column (C18-I, 20-40 m); mobile phase (MeOH/H2O=30% to 80%: 8 min); Detector (254 and 220 nm) to give the intermediate compound 120 (300 mg, 54% yield) as a yellow oil.

LC-MS (ES+) m/z: 543 (M+H)+ (calculated: 542.3).

Intermediate Compound 121:

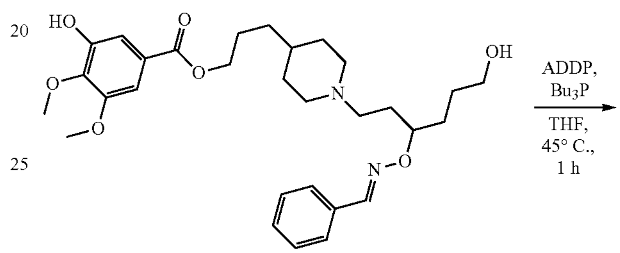

-continued

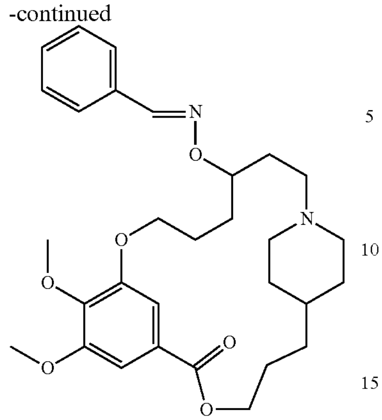

A solution of ADDP (0.19 g, 0.75 mmol, 1.5 equiv) and n-Bu3P (0.15 g, 0.75 mmol, 1.5 equiv) in dry THF (2.0 mL) was stirred under N2 for 15 min, and then a solution of intermediate compound 120 (271 mg, 0.5 mmol, 1.0 equiv) in THF (3 mL) was added. The mixture solution was stirred for 1 h at 45° C. The reaction was then quenched by the addition of H2O (5 mL), and the resulting solution was extracted with EtOAC (2×5 mL). The combined organic layers were dried by Na2SO4 and concentrated. The crude product was purified by preparative HPLC (Column (C18-I, 20-40 m); mobile phase (MeOH/H2O=30% to 100%: 7 min; 100%: 3 min); Detector (254 and 220 nm) to give the intermediate compound 121 (55 mg, 21% yield) of as an off-white solid.

LC-MS (ES+) m/z: 525 (M+H)+ (calculated: 524.3).

Intermediate Compound 122:

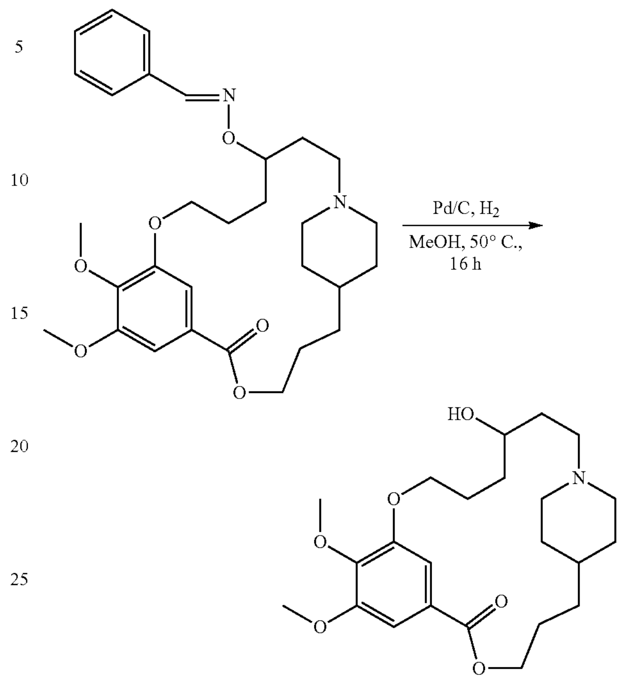

A mixture of intermediate compound 121 (55 mg, 0.1 mmol, 1.0 equiv) and Pd/C (5 mg) in MeOH (5 mL) was stirred under H2 (3 atm) for 2 h at room temperature. The resulting mixture was then filtered; the solid was washed with MeOH (5 mL) and the filtrate was concentrated under reduced pressure. The crude intermediate compound 122 (43 mg) was used in the next step directly without further purification.

LC-MS (ES+) m/z: 422 (M+H)+ (calculated: 421.4).

Intermediate Compound 123:

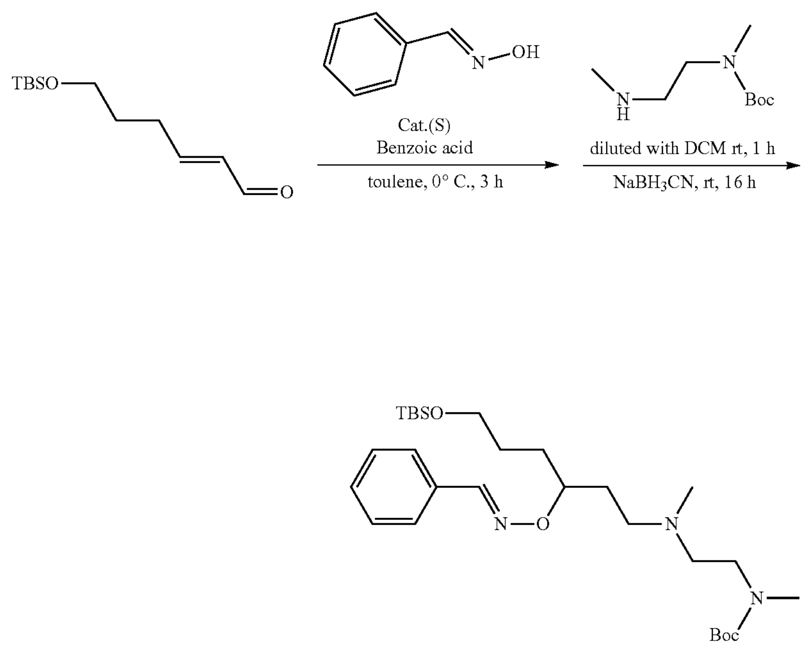

To a stirred solution of (2S)-2-{bis[3,5-bis(trifluoromethyl)phenyl][(trimethylsilyl)oxy]methyl}pyrrolidine (0.26 g, 0.44 mmol, 0.1 equiv), benzoic acid (0.05 g, 0.44 mmol, 0.1 equiv) in toluene (2.3 mL) at 0° C. was added the intermediate compound 107 (1.0 g, 4.4 mmol, 1.0 equiv), followed by benzaldoxime (1.6 g, 13.1 mmol, 3.0 equiv). The resulting mixture was stirred for 4 h at 0° C., and then was diluted with DCM (15.3 mL). tert-Butyl 1,4-diazepane-1-carboxylate (1.23 g, 6.1 mmol, 1.4 equiv) was then added and the resulting mixture was stirred for 1 h at room temperature, before NaBH3CN (0.55 g, 8.8 mmol, 2.0 equiv) was added. The resulting mixture was stirred for 1 h at room temperature, and then quenched with sat. NH4Cl (10 mL), and extracted with DCM (3×20 mL). The combined organic layers were washed with brine (20 mL), dried over anhydrous Na2SO4 and concentrated under reduced pressure. The residue was purified by silica gel column chromatography (petroleum ether/THF:8/2 to 0/10) to give the intermediate compound 123 (600 mg, 26% yield) as a yellow oil.

LC-MS (ES+) m/z: 522 (M+H)+ (calculated: 521.4).

Intermediate Compound 124:

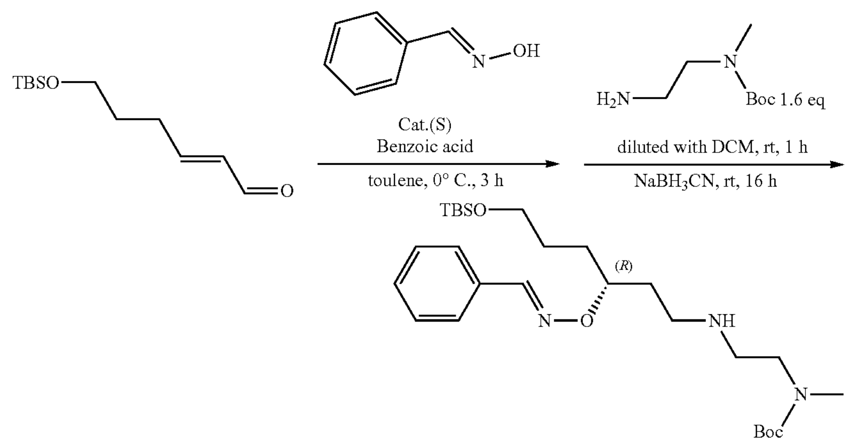

The light-yellow oil intermediate compound 124 (2.1 g, 47% yield) has been synthetized from the tert-butyl N-(2-aminoethyl)-N-methylcarbamate (2.14 g, 12.3 mmol, 1.4 equiv) using the protocol described for the intermediate compound 123.

LC-MS (ES+) m/z: 508 (M+H)+ (calculated: 507.3).

Intermediate Compound 125:

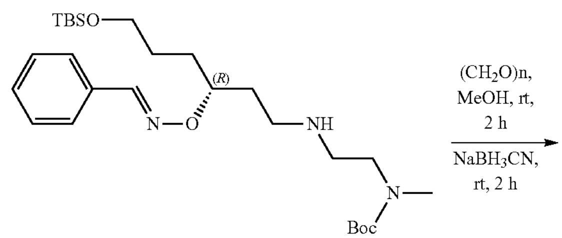

-continued

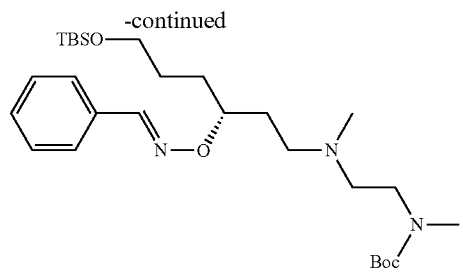

To a stirred mixture of intermediate compound 124 (2.1 g, 4.1 mmol, 1.0 equiv) and in MeOH (40 mL) was added (CH2O)n (0.91 g) in portions at room temperature. The resulting mixture was stirred for 2 h at room temperature under N2. NaBH3CN (0.78 g, 12.4 mmol, 3.0 equiv) was then added in portions and the resulting mixture was stirred for an additional 2 h at room temperature. The reaction was quenched with 50 mL sat. NH4Cl, and extracted with EtOAc (3×100 mL). The combined organic layers were washed with water (100 mL) and brine (100 mL), dried over anhydrousNa2SO4, and was concentrated under reduced pressure. The residue was purified by silica gel column chromatography (petroleum ether/THF:5/1 to 1/1) to give the intermediate compound 125 (2.1 g, 97% yield) as a light-yellow oil.

LC-MS (ES+) m/z: 522 (M+H)+ (calculated: 521.4).

Intermediate Compound 126 and 127:

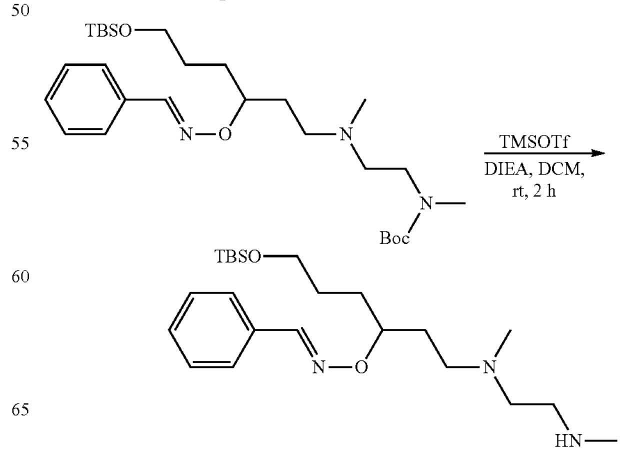

TMSOTf (639 mg, 2.9 mmol, 3.0 equiv) was added dropwise to a stirred solution of intermediate compound 123 (500 mg, 0.96 mmol, 1.0 equiv) and DIEA (619 mg, 4.8 mmol, 5.0 equiv) in DCM (10 mL) at room temperature. The resulting mixture was stirred for 2 h at room temperature, and then quenched with 10 mL NH4Cl, and extracted with DCM (3×10 mL). The combined organic layers were washed with brine (20 mL), dried over Na2SO4 and concentrated under reduced pressure to give the intermediate compound 126 (450 mg, 89% yield) as a yellow oil.

LC-MS (ES+) m/z: 422 (M+H)+ (calculated: 421.3).

The yellow oil intermediate compound 127 (850 mg, 50% yield) has been synthetized from the intermediate compound 125 (2.1 g, 4.0 mmol, 1.0 equiv) using the same protocol.

LC-MS (ES+) m/z: 422 (M+H)+ (calculated: 421.3).

Intermediate Compound 128 and 129:

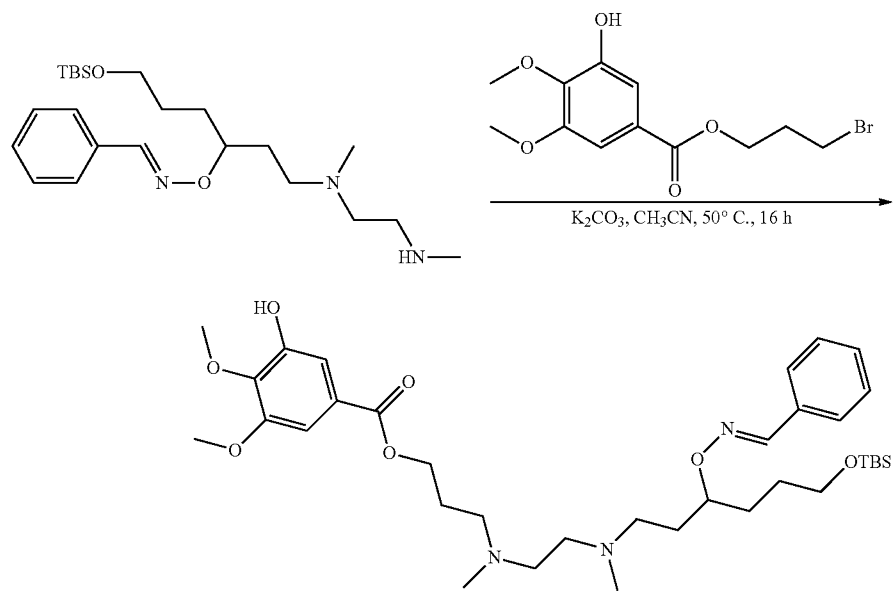

K2CO3 (221 mg, 1.6 mmol, 1.5 equiv) was added to a stirred solution of intermediate compound 126 (450 mg, 1.1 mmol, 1.0 equiv) and intermediate compound 13 (375 mg, 1.2 mmol, 1.1 equiv) in MeCN (10 mL) at room temperature. The resulting mixture was stirred for 16 h at 50° C., and then was allowed to cool down to room temperature and filtered. The solid was washed with MeCN (3×10 mL), and the filtrate was concentrated under reduced pressure. The residue was purified by silica gel column chromatography (petroleum ether/THF 10/1/to 3/1) to give the intermediate compound 128 (500 mg, 71% yield) as a brown oil.

LC-MS (ES+) m/z: 660 (M+H)+ (calculated: 659.4).

The brown oil intermediate compound 129 (1.4 g, 84% yield) has been synthetized from the intermediate compound 127 (850 mg, 2.0 mmol, 1.0 equiv) using the same protocol.

LC-MS (ES+) m/z: 660 (M+H)+ (calculated: 659.4).

Intermediate Compound 130 and 131:

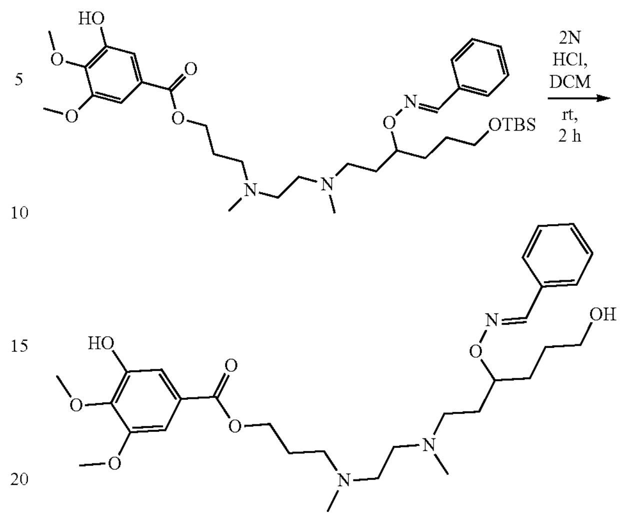

HCl (2M, 10 mL) was added to a stirred solution of intermediate compound 128 (600 mg, 0.9 mmol, 1.0 equiv) in DCM (10 mL) at room temperature. The resulting mixture was stirred for 2 h at room temperature, and then the organic layer was separated. The aqueous layer was basified to pH=8 with sat. NaHCO3, and extracted with DCM (3×50 mL). The combined organic layers were washed with water (10 mL) and brine (10 mL), dried over Na2SO4, and concentrated under reduced pressure. The residue was purified by reverse phase chromatography (column, C18 silica gel; mobile phase, CH3CN and 0.05% TFA, 20% to 60% gradient in 10 min; detector, UV 254 nm) to give the intermediate compound 130 (200 mg, 40% yield) as a colorless oil.

LC-MS (ES+) m/z: 546 (M+H)+ (calculated: 545.3).

The yellow oil intermediate compound 131 (500 mg, 43% yield) has been synthetized from the intermediate compound 129 (1.4 g, 2.1 mmol, 1.0 equiv) using the same protocol.

LC-MS (ES+) m/z: 546 (M+H)+ (calculated: 545.3).

Intermediate Compound 132 and 133:

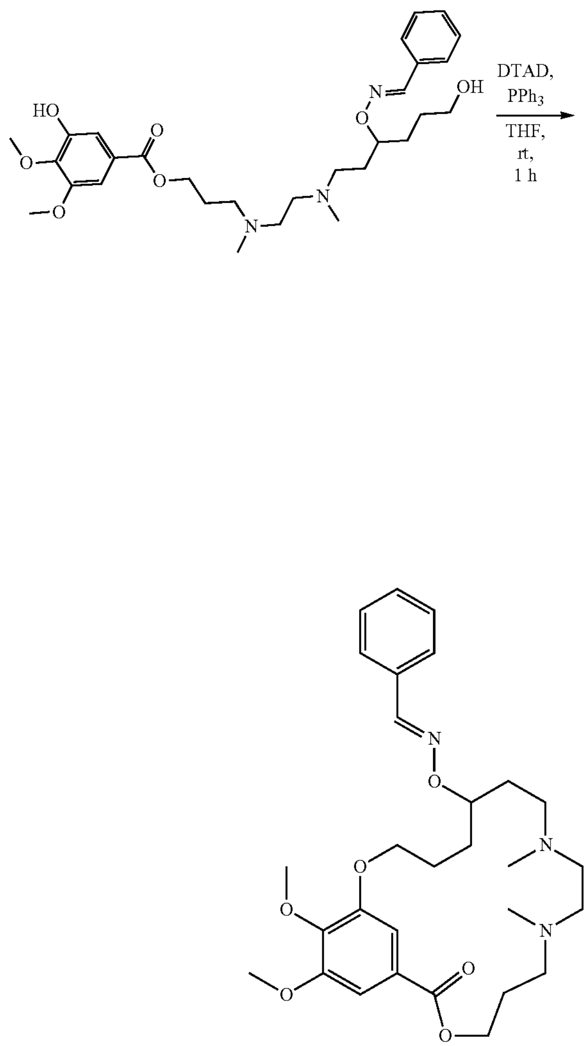

ADDP (222 mg, 0.9 mmol, 3.0 equiv) was added to a stirred solution of intermediate compound 130 (160 mg, 0.3 mmol, 1.0 equiv) and triphenylphosphine (231 mg, 0.9 mmol, 3.0 equiv) in THF (5 mL) at room temperature. The resulting mixture was stirred for 1 h at room temperature under N2, and then quenched with sat. NH4Cl (10 mL). The resulting mixture was extracted with EtOAc (3×20 mL), the combined organic layers were washed with water (10 mL) and brine (10 mL), dried over anhydrous Na2SO4 and concentrated under reduced pressure. The residue was purified by reverse phase chromatography (column, C18 silica gel; mobile phase, CH3CN and 0.05% TFA, 30% to 70% gradient in 10 min; detector, UV 254 nm) o give the intermediate compound 132 (56 mg, 36% yield) as a light-yellow oil.

LC-MS (ES+) m/z: 528 (M+H)+ (calculated: 527.3).

The light yellow oil intermediate compound 133 (300 mg, 62% yield) has been synthetized from the intermediate compound 131 (500 mg, 0.9 mmol, 1.0 equiv) using the same protocol.

LC-MS (ES+) m/z: 528 (M+H)+ (calculated: 527.3).

Intermediate Compound 134 and 135:

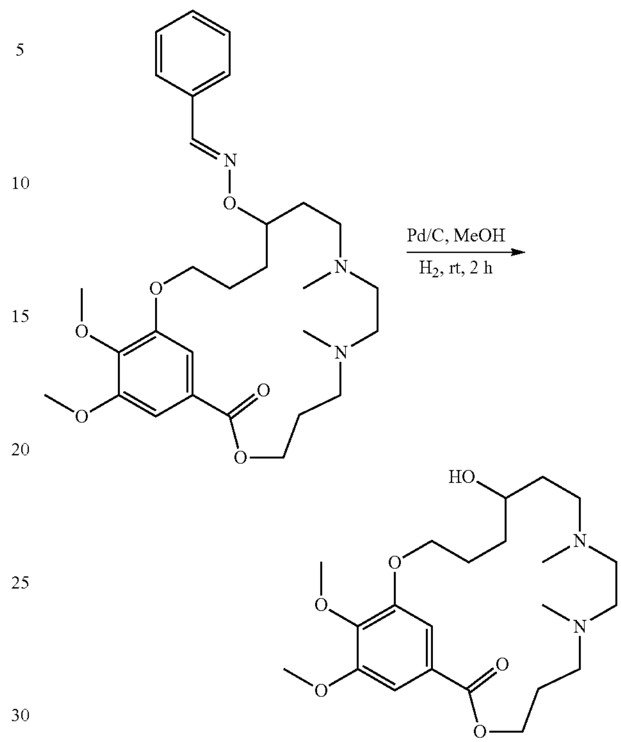

A mixture of intermediate compound 132 (46 mg, 0.09 mmol, 1.0 equiv) and Pd/C (20 mg) in MeOH (5 mL) was stirred under H2 (3 atm) for 2 h at room temperature. The resulting mixture was then filtered; the solid was washed with MeOH (5 mL) and the filtrate was concentrated under reduced pressure to give the intermediate compound 134 (27 mg, 73% yield) as a light-yellow oil LC-MS (ES+) m/z: 425 (M+H)+ (calculated: 424.3).

1H NMR (300 MHz, DMSO-d6) δ ppm 8.22 (s, 1H), 7.32 (s, 1H), 7.22 (s, 1H), 4.27-3.99 (m, 4H), 3.83 (s, 3H), 3.80-3.76 (m, 4H), 2.92-2.87 (m, 1H), 2.75-2.46 (m, 11H), 1.97-1.88 (m, 10H).

The light yellow oil intermediate compound 135 (200 mg, 74% yield) has been synthetized from the intermediate compound 133 (300 mg, 0.57 mmol, 1.0 equiv) using the same protocol.

LC-MS (ES+) m/z: 425 (M+H)+ (calculated: 424.3).

Intermediate Compound 136:

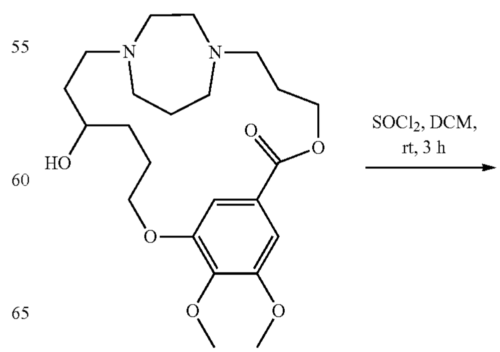

-continued

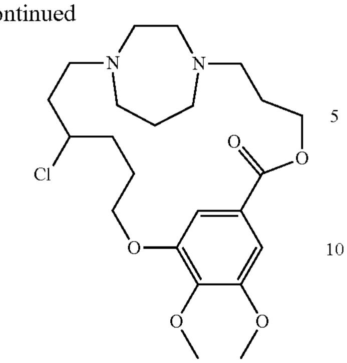

A solution of compound 38 (300 mg, 0.69 mmol, 1.0 equiv) and SOCl2 (409 mg, 3.4 mmol, 5.0 equiv) in DCM (10 mL) was stirred for 3 h at room temperature. The resulting mixture was then concentrated under reduced pressure, and the residue was purified by preparative HPLC ((Column: C18-I, 20-40 m; Mobile Phase A: Water: 0.05% TFA, Mobile Phase B: ACN; Flow rate: 80 mL/min; Gradient: 10% B to 60% B in 7 min, 55% B; Detector 254 and 220 nm) to give the intermediate compound 136 (230 mg, 74% yield) as a colorless oil.

LC-MS (ES+) m/z: 455 (M+H)+ (calculated: 454.2).

1HNMR (300 MHz, CDCl3) δ ppm 7.33 (s, 1H), 7.21 (s, 1H), 4.44-4.42 (m, 2H), 4.20-40.9 (m, 3H), 3.94-3.84 (m, 7H), 3.74-3.13 (m, 11H), 2.32-1.98 (m, 10H).

Intermediate Compound 137:

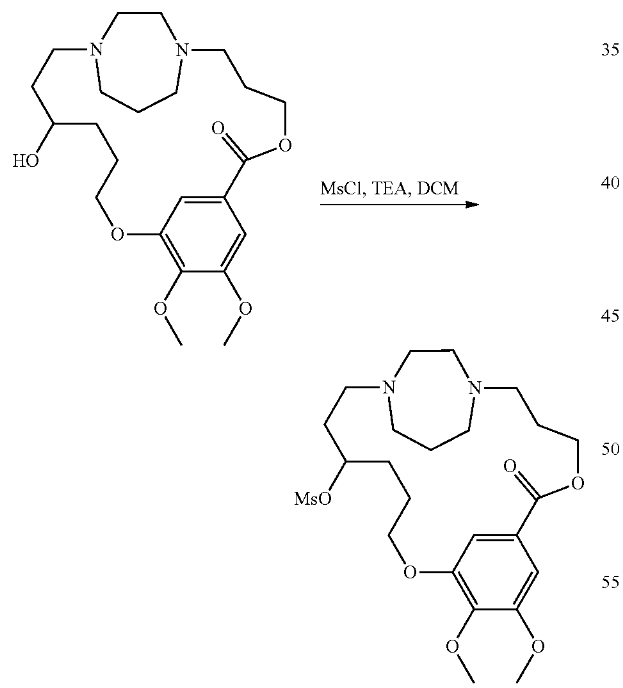

MsCl (32 mg, 0.28 mmol, 1.2 equiv) was added dropwise to a stirred solution of compound 38 (100 mg, 0.23 mmol, 1.0 equiv) and TEA (35 mg, 0.34 mmol, 1.5 equiv) in DCM (3 mL) at 0° C. under nitrogen. The resulting mixture was stirred for 1 h at room temperature, and then diluted with DCM (5 mL), and washed with water (3×2 mL). The organic layer was dried over Na2SO4 and evaporated under reduced pressure. The crude intermediate 137 (110 mg, 93% yield) was used without purification.

LC-MS (ES+) m/z: 515 (M+H)+ (calculated: 514.2).

Example I.2. Synthesis of Final Compounds

Compound 1:

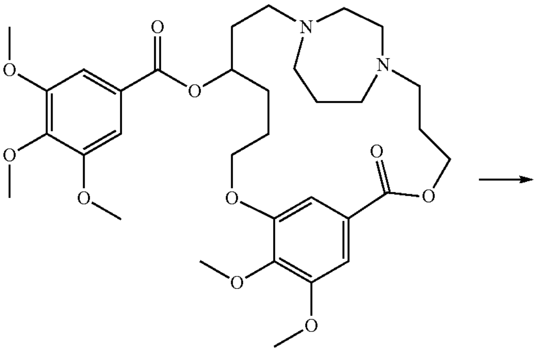

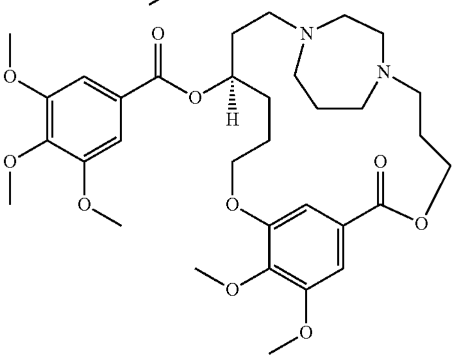

Compound 2

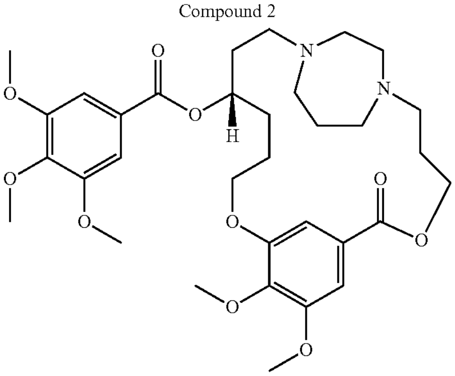

Compound 1

Compound 1 was separated from compound 5 by preparative SFC following the conditions Chiral SFC method A.

LCMS (ESI position ion) m/z: 631.5 (M+H)+ (calculated: 630.3)

SFC: retention time=1.392 min, ee=97.46%

1H NMR (400 MHz, MeOD) δ 7.42 (d, J=1.7 Hz, 1H), 7.36-7.30 (m, 3H), 5.58 (br d, J=5.0 Hz, 1H), 4.45-4.33 (m, 2H), 4.31-4.23 (m, 1H), 4.10-3.98 (m, 1H), 3.90-3.84 (m, 9H), 3.82 (d, J=2.7 Hz, 6H), 3.14-3.03 (m, 1H), 2.96-2.77 (m, 4H), 2.74-2.66 (m, 3H), 2.66-2.51 (m, 4H), 2.10-1.76 (m, 10H)

Compound 2:

Compound 2 was separated from compound 5 by preparative SFC following the conditions Chiral SFC method A.

LCMS (ESI position ion) m/z: 631.4 (M+H)+ (calculated: 630.3)

SFC: retention time=0.576 min, ee=100%

1H NMR (400 MHz, MeOD) δ 7.41 (d, J=1.7 Hz, 1H), 7.32 (s, 3H), 5.64-5.51 (m, 1H), 4.42-4.32 (m, 2H), 4.31-4.22 (m, 1H), 4.08-3.98 (m, 1H), 3.90-3.84 (m, 9H), 3.82 (d, J=2.6 Hz, 6H), 3.14-3.03 (m, 1H), 2.96-2.76 (m, 4H), 2.75-2.66 (m, 3H), 2.65-2.49 (m, 4H), 2.09-1.76 (m, 10H)

Compound 3:

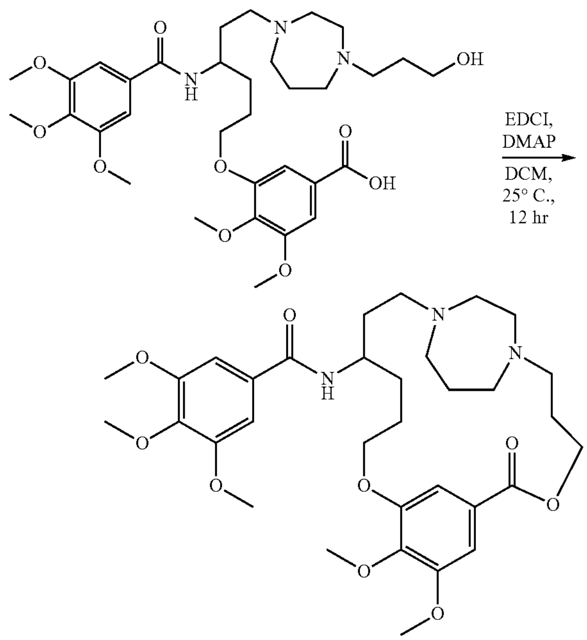

To a solution of intermediate compound 22 (40 mg, 61.76 umol, 1 eq) in DCM (2 mL) were added EDCI (35.52 mg, 185.24 umol) and DMAP (22.64 mg, 185.24 umol) at 20° C. The resulting mixture was stirred at 20° C. for 12 hr. After cooling to the room temperature, the reaction mixture was filtered and the filtrate was concentrated under reduced pressure. the residue was purified by pre-HPLC to give the compound 3 (11.8 mg, yield 30%) as a light yellow solid.

LCMS (ESI position ion) m/z: 630.3 (M+H)+ (calculated: 629.3)

1H NMR (400 MHz, CDOD3) δ ppm 7.29-7.43 (m, 2H), 7.22 (s, 2H), 4.59-4.76 (m, 1H), 4.04-4.56 (m, 5H), 3.36-4.03 (m, 23H), 1.60-2.64 (m, 10H).

Compound 4:

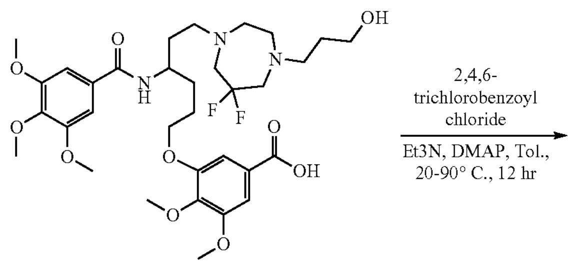

-continued

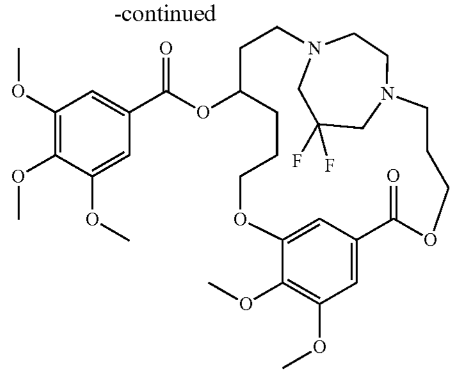

To a solution of intermediate compound 17 (50 mg, 73.02 umol, 1 eq) in toluene (12.5 mL) were added Et3N (44.33 mg, 438.14 umol, 60.98 uL, 6 eq) and 2,4,6-trichlorobenzoyl chloride (89.05 mg, 365.11 umol, 57.08 uL, 5 eq). The mixture was stirred at 20° C. for 1 hr. The mixture was diluted with toluene (25 mL) and added a solution of DMAP (103.48 mg, 847.06 umol, 11.6 eq) in toluene (12.5 mL). The mixture was stirred at 90° C. for 12 hr. The solvent was removed under reduced pressure and purified by preparative TLC (SiO2, petroleum ether/EtOAc=1/5, Rf=0.55) to give the compound 4 (25 mg, 51% yield) as white solid.

LCMS (ESI position ion) m/z: 667.3 (M+H)+ (calculated: 666.3)

1H NMR: (400 MHz, MeOD) δ 7.47 (d, J=1.8 Hz, 1H), 7.36 (s, 1H), 7.32 (s, 2H), 5.60 (br s, 1H), 4.52-4.31 (m, 3H), 4.13 (br s, 1H), 3.91-3.87 (m, 9H), 3.84 (d, J=1.0 Hz, 6H), 3.14-2.58 (m, 11H), 2.17-1.71 (m, 9H)

Compound 5:

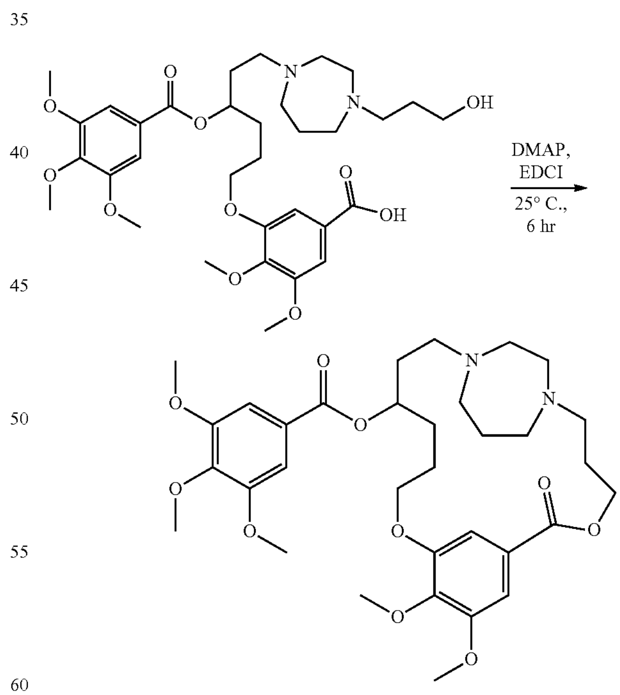

To a solution of intermediate compound 12 (50 mg, 77.07 umol) in dichloromethane (3 mL) was added 1-ethyl-3-(3-dimethylaminopropyl) carbodiimide (44.32 mg, 231.22 umol) and dimethylaminopyridine (28.25 mg, 231.22 umol) at 20° C. The reaction mixture was stirred at 25° C. for 6 hr. The reaction mixture was quenched with water (10 mL), extracted with dichloromethane (3×5 mL). The combined organic layers were washed with brine (10 mL), dried over Na2SO4, filtered and concentrated under reduced pressure. The residue was purified by prep-HPLC to give the compound 1 (6.2 mg, yield 12%) as white solid. LCMS (ESI position ion) m/z: 631.3 (M+H)+ (calculated: 631.3)

1H NMR (400 MHz, CD3OD-d4) 1.76-2.13 (m, 11H), 2.53-2.67 (m, 4H), 2.67-3.02 (m, 7H), 3.82 (d, J=2.69 Hz, 6H), 3.84-3.90 (m, 9H), 4.02-4.10 (m, 1H), 4.25-4.33 (m, 1H), 4.34-4.44 (m, 2H), 5.59 (br s, 1H), 7.33 (s, 3H), 7.44 (s, 1H)

Compound 6:

Compound 6 was separated from compound 4 by preparative SFC following the conditions Chiral SFC method A.

LCMS (ESI position ion) m/z: 667.3 (M+H)+ (calculated: 666.3)

SFC: retention time=1.727 min, ee=98.95%

1H NMR (400 MHz, MeOD) δ 7.45 (d, J=1.8 Hz, 1H), 7.34 (d, J=1.7 Hz, 1H), 7.30 (s, 2H), 5.56 (br d, J=5.5 Hz, 1H), 4.45-4.29 (m, 3H), 4.16-4.06 (m, 1H), 3.96-3.84 (m, 9H), 3.82 (d, J=1.2 Hz, 6H), 3.24 (br t, J=13.9 Hz, 2H), 3.10-2.87 (m, 6H), 2.87-2.79 (m, 1H), 2.79-2.59 (m, 3H), 2.09-1.75 (m, 8H)

Compound 8:

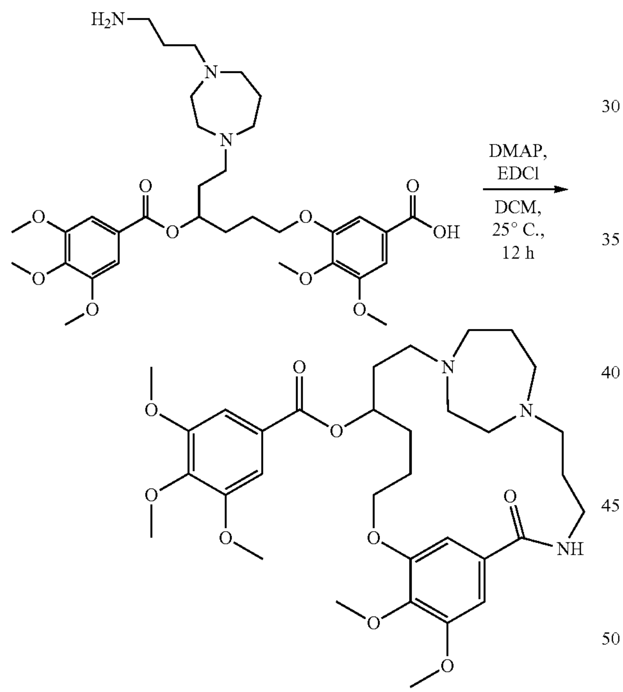

To a solution of intermediate compound 26 (380 mg, 586.64 umol, 1 eq) in DCM (120 mL) was added EDCI (337.38 mg, 1.76 mmol, 3 eq) and DMAP (286.68 mg, 2.35 mmol, 4 eq). The reaction was stirred at 25° C. for 12 hr. The reaction mixture was concentrated under vacuum. The residue was diluted with H2O (60 mL) and then extracted with ethyl acetate (3×20 mL). The combined organic layers were washed with brine (20 mL), dried over Na2SO4, filtered and concentrated under vacuum. The crude product was dissolved in DMF (5 mL) and then purified by Prep-HPLC (column: Phenomenex Synergi C18 150*25 mm*10 um; mobile phase: [water (0.225% FA)-ACN]; B %: 8%-38%, 10 min) to give the compound 8 (150 mg, 41% yield) as a white solid.

LCMS (ESI position ion) m/z: 630.3 (M+H)+ (calculated: 629.3)

1H NMR (400 MHz, CD3OD-d4) δ 7.34 (s, 2H), 7.22 (d, J=2.0 Hz, 1H), 7.13 (d, J=2.0 Hz, 1H), 5.52 (br d, J=6.2 Hz, 1H), 4.38-4.28 (m, 1H), 4.25-4.16 (m, 1H), 3.92-3.87 (m, 9H), 3.85 (s, 3H), 3.83 (s, 3H), 3.68-3.58 (m, 1H), 3.51-3.41 (m, 1H), 3.04-2.95 (m, 1H), 2.89-2.54 (m, 11H), 2.01-1.73 (m, 10H)

Compound 9:

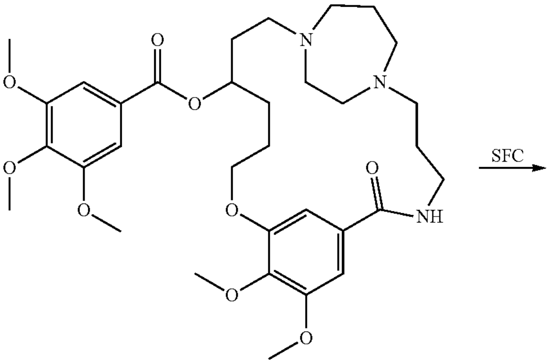

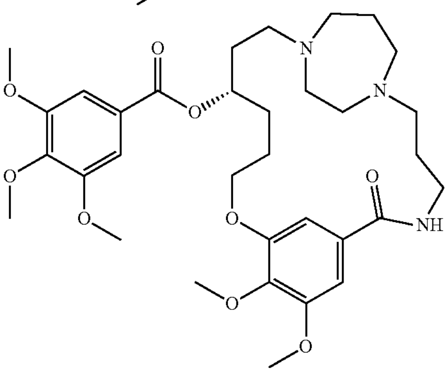

Compound 9

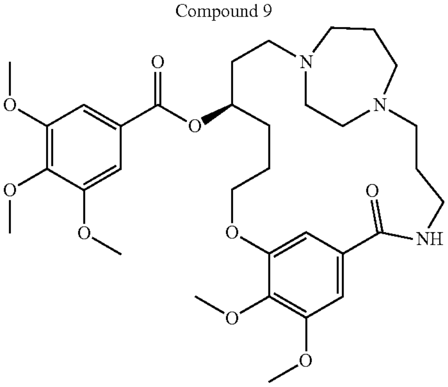

Compound 10

Compound 9 was separated from compound 8 by preparative SFC following the conditions Chiral SFC method B.

LCMS (ESI position ion) m/z: 630.6 (M+H)+ (calculated: 629.3)

SFC: retention time=4.099 min, ee=95.48%

1H NMR (400 MHz, MeOD) δ 7.36-7.30 (m, 3H), 7.21 (d, J=1.8 Hz, 1H), 5.43 (br d, J=3.9 Hz, 1H), 4.42-4.31 (m, 1H), 4.27-4.16 (m, 1H), 3.89 (s, 3H), 3.85 (s, 6H), 3.81 (d, J=6.1 Hz, 6H), 3.72-3.61 (m, 1H), 3.53-3.44 (m, 1H), 3.14-2.97 (m, 4H), 2.94 (br t, J=6.4 Hz, 2H), 2.90-2.78 (m, 4H), 2.74 (br t, J=6.7 Hz, 2H), 2.16-2.04 (m, 1H), 2.00-1.89 (m, 9H)

Compound 10:

Compound 10 was separated from compound 8 by preparative SFC following the conditions Chiral SFC method B.

LCMS (ESI position ion) m/z: 630.6 (M+H)+ (calculated: 629.3)

SFC: retention time=6.989 min, ee=95.48%

1H NMR (400 MHz, MeOD) δ 7.32 (s, 2H), 7.20 (d, J=1.7 Hz, 1H), 7.16 (d, J=1.6 Hz, 1H), 5.48 (br d, J=5.7 Hz, 1H), 4.36-4.27 (m, 1H), 4.23-4.14 (m, 1H), 3.90-3.85 (m, 9H), 3.82 (d, J=7.2 Hz, 6H), 3.67-3.58 (m, 1H), 3.49-3.40 (m, 1H), 3.03-2.95 (m, 1H), 2.89 (brt, J=5.2 Hz, 2H), 2.86-2.77 (m, 3H), 2.76-2.63 (m, 4H), 2.59 (br t, J=6.5 Hz, 2H), 2.01-1.87 (m, 5H), 1.87-1.72 (m, 5H)

Compound 11:

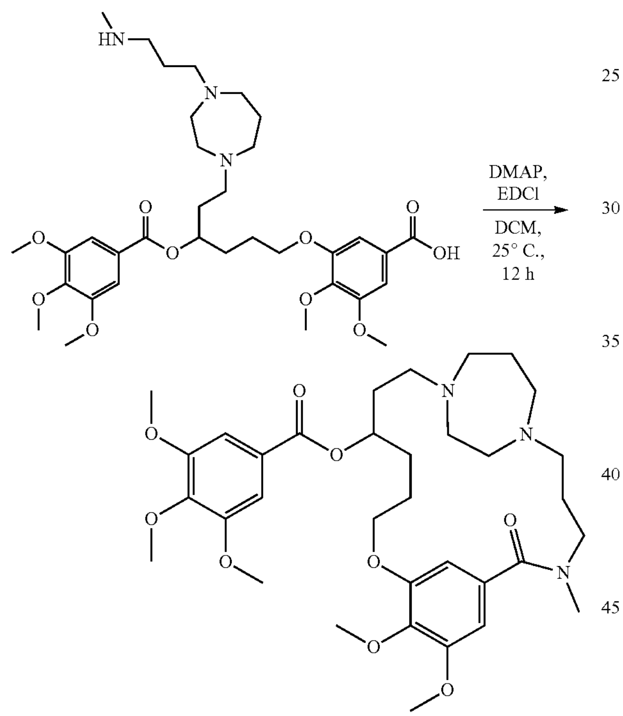

To a solution of intermediate compound 31 (700 mg, 1.06 mmol, 1 eq) in DCM (200 mL) was added EDCI (608.31 mg, 3.17 mmol, 3 eq) and DMAP (516.90 mg, 4.23 mmol, 4 eq). The reaction was stirred at 25° C. for 12 hrs. The mixture was directly concentrated in vacuo to give an oil. The residue was purified by prep-HPLC (column: Waters Xbridge C18 150*50 mm*10 um; mobile phase: [water (10 mM NH4HCO3)-ACN]; B %: 37%-67%, min) to give the compound 11 (220 mg, 32% yield) as a white solid.

LCMS (ESI position ion) m/z: 644.6 (M+H)+ (calculated: 643.3)

1H NMR (400 MHz, METHANOL-d4) δ 7.32 (s, 2H), 6.79-6.69 (m, 2H), 5.54-5.46 (m, 1H), 4.33-4.24 (m, 1H), 4.19-4.10 (m, 1H), 3.87 (d, J=9.4 Hz, 9H), 3.84-3.79 (m, 6H), 3.55-3.44 (m, 1H), 3.40-3.32 (m, 1H), 3.12-3.02 (m, 3H), 2.74-2.39 (m, 12H), 2.06-1.49 (m, 10H)

Compound 12:

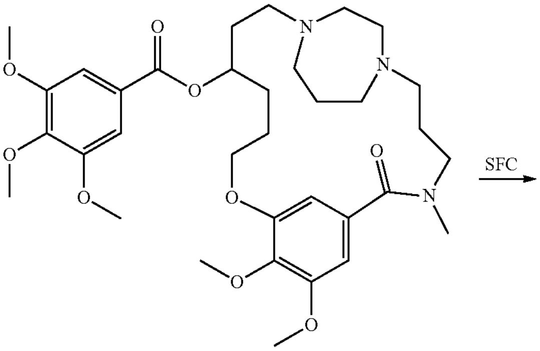

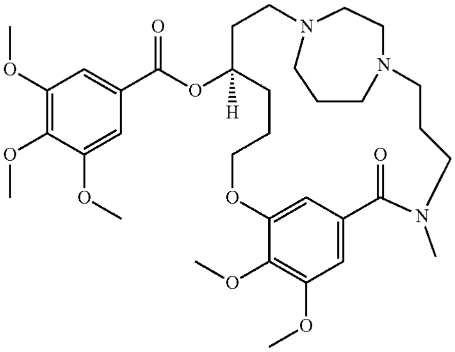

Compound 12

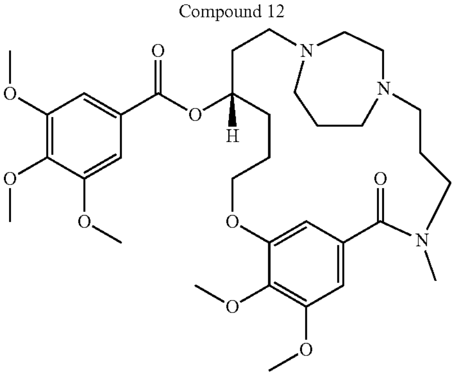

Compound 13

Compound 12 was separated from compound 11 by preparative SFC following the conditions Chiral SFC method A.

LCMS (ESI position ion) m/z: 644.6 (M+H)+ (calculated: 643.3)

SFC: retention time=2.653 min, ee=100%

1H NMR (400 MHz, MeOD-d4) δ 7.32 (s, 2H), 6.79-6.69 (m, 2H), 5.59-5.43 (m, 1H), 4.33-4.11 (m, 2H), 3.87 (d, J=9.3 Hz, 9H), 3.85-3.78 (m, 6H), 3.55-3.45 (m, 1H), 3.40-3.34 (m, 1H), 3.15-3.03 (m, 3H), 2.78-2.41 (m, 12H), 2.07-1.49 (m, 10H)

Compound 13:

Compound 13 was separated from compound 11 by preparative SFC following the conditions Chiral SFC method A.

LCMS (ESI position ion) m/z: 644.6 (M+H)+ (calculated: 643.3)

SFC: retention time=3.358 min, ee=99.12%

1H NMR (400 MHz, MeOD-d4) δ 7.32 (s, 2H), 6.79-6.69 (m, 2H), 5.59-5.43 (m, 1H), 4.33-4.11 (m, 2H), 3.87 (d, J=9.3 Hz, 9H), 3.85-3.78 (m, 6H), 3.55-3.45 (m, 1H), 3.40-3.34 (m, 1H), 3.15-3.03 (m, 3H), 2.78-2.41 (m, 12H), 2.07-1.49 (m, 10H)

Compound 14:

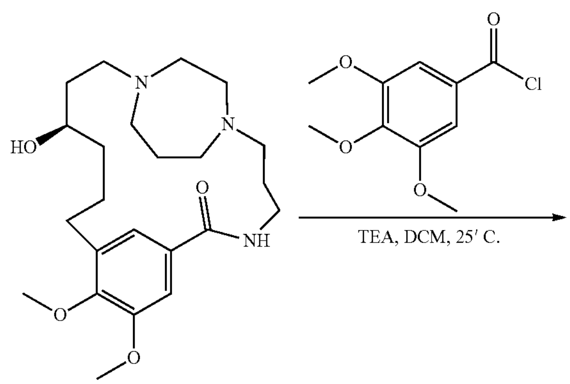

To a solution of intermediate compound 42 (6 mg, 14.30 umol, 1 eq) in DCM (1 mL) were added 3,4,5-trimethoxy-benzoyl chloride (16.49 mg, 71.50 umol, 5 eq) and Et3N (10.13 mg, 100.11 umol, 13.93 uL, 7 eq). The mixture was stirred at 25° C. for 12 hrs under N2. The reaction mixture was concentrated under vacuum. The residue was purified by pre-HPLC (column: Waters Atlantis T3 150*30 mm*5 um; mobile phase: [water (0.225% FA)-ACN]; B %: 10%-40%, 10 min) to give the compound 14 (2.2 mg, 25% yield) as an off white solid.

LCMS (ESI position ion) m/z: 614.4 (M+H)+ (calculated: 613.3)

1H NMR (400 MHz, MeOD-d4) δ 7.50-7.44 (m, 1H), 7.41-7.37 (m, 1H), 7.33-7.28 (m, 2H), 5.34-5.20 (m, 2H), 3.91-3.86 (m, 3H), 3.86-3.82 (m, 6H), 3.74-3.63 (m, 1H), 3.54-3.38 (m, 2H), 3.29-3.17 (m, 5H), 3.12-2.99 (m, 1H), 2.86-2.76 (m, 6H), 2.59-2.41 (m, 2H), 2.08-1.82 (m, 7H), 1.78-1.54 (m, 4H)

Compound 15 and Compound 16:

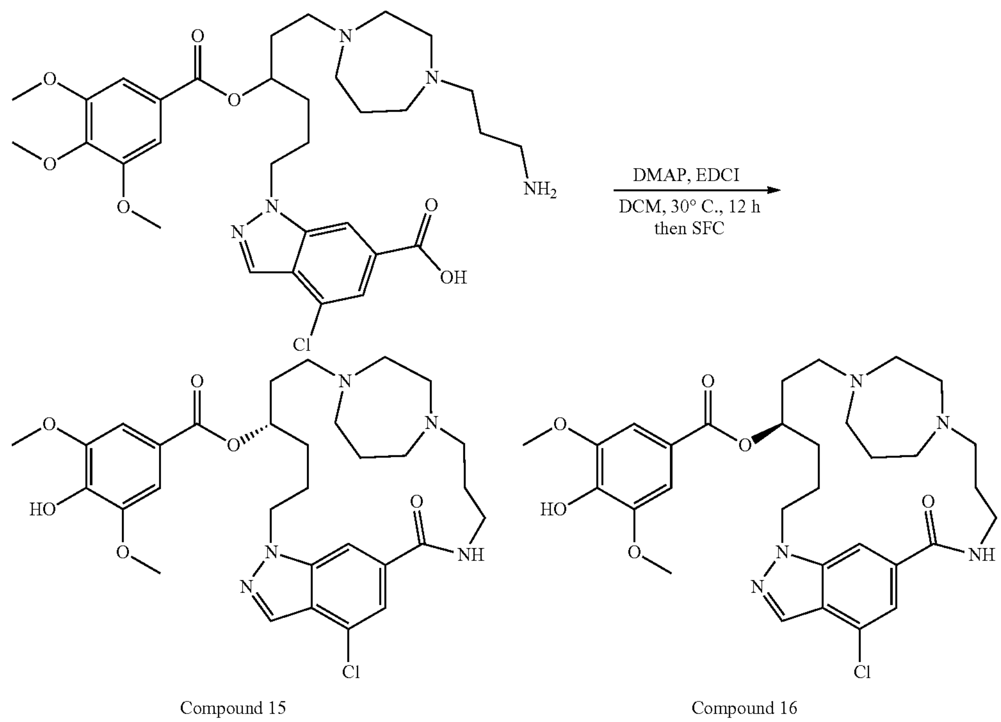

Compound 15

Compound 16

-continued

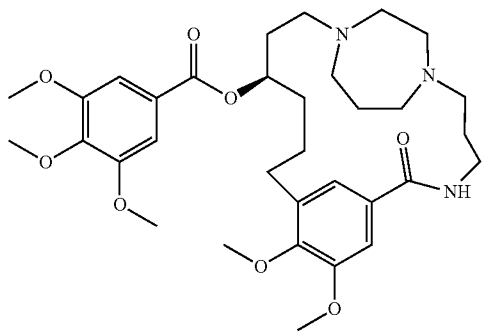

A mixture of intermediate compound 52 (120 mg, 175.79 umol, 1 eq, HCl), EDCI (101.10 mg, 527.37 umol, 3 eq) and DMAP (85.90 mg, 703.16 umol, 4 eq) in DCM (10 mL) was stirred at 30° C. for 1 hr. The reaction mixture was poured into water (10 mL) and extracted with dichloromethane (2×10 mL), the combined organic phase was dried and concentrated under vacuum. The residue was purified by prep-HPLC (column: Waters Xbridge 150*25 mm*5 um; mobile phase: [water (10 mM NH4HCO3)-ACN]; B %: 50%-80%, 9 min), followed by a chiral separation by SFC (column: DAICEL CHIRALPAK IC (250 mm*30 mm, 10 um); mobile phase: [0.1% NH3H2O MEOH]; B %: 45%-45%, 6.1 min; 45 minmin), to give the compound 15 (21.7 mg, 19% yield) as a colorless oil and the compound 16 (16 mg, 15% yield).

Compound 15:

LCMS (ESI position ion) m/z: 628.2 (M+H)+ (calculated: 627.3)

SFC: retention time=1.106 min, ee=100%

1H NMR (400 MHz, MeOD-d4) δ 8.17 (s, 1H) 8.13 (s, 1H) 7.63 (s, 1H) 7.28 (s, 2H) 5.33-5.44 (m, 1H) 4.52-4.68 (m, 2H) 4.30 (br s, 1H) 4.10-4.26 (m, 1H) 3.86 (s, 6H) 3.82 (s, 3H) 3.67-3.73 (m, 1H) 3.49-3.58 (m, 1H) 2.94 (br s, 2H) 2.91 (br d, J=5.25 Hz, 5H) 2.69 (br d, J=4.50 Hz, 1H) 2.62 (br dd, J=10.76, 5.25 Hz, 1H) 2.47 (br d, J=6.63 Hz, 2H) 2.16 (dt, J=13.98, 6.96 Hz, 1H) 1.92 (br s, 3H) 1.78-1.86 (m, 3H) 1.67-1.74 (m, 1H) 1.53-1.63 (m, 1H)

Compound 16:

LCMS (ESI position ion) m/z: 628.2 (M+H)+ (calculated: 627.3)

SFC: retention time=1.796 min, ee=98.75%

1H NMR (400 MHz, MeOD-d4) δ 8.12 (d, J=5.38 Hz, 2H) 7.63 (s, 1H) 7.27 (s, 2H) 5.26-5.37 (m, 1H) 4.52-4.68 (m, 2H) 3.86 (s, 6H) 3.82 (s, 3H) 3.64-3.73 (m, 1H) 3.40-3.49 (m, 1H) 2.68-2.81 (m, 6H) 2.59 (brt, J=5.19 Hz, 2H) 2.48-2.55 (m, 2H) 2.29-2.39 (m, 2H) 2.09-2.23 (m, 1H) 1.92-2.04 (m, 1H) 1.75-1.89 (m, 4H) 1.64-1.75 (m, 3H) 1.53-1.62 (m, 1H)

Compound 17 and Compound 18:

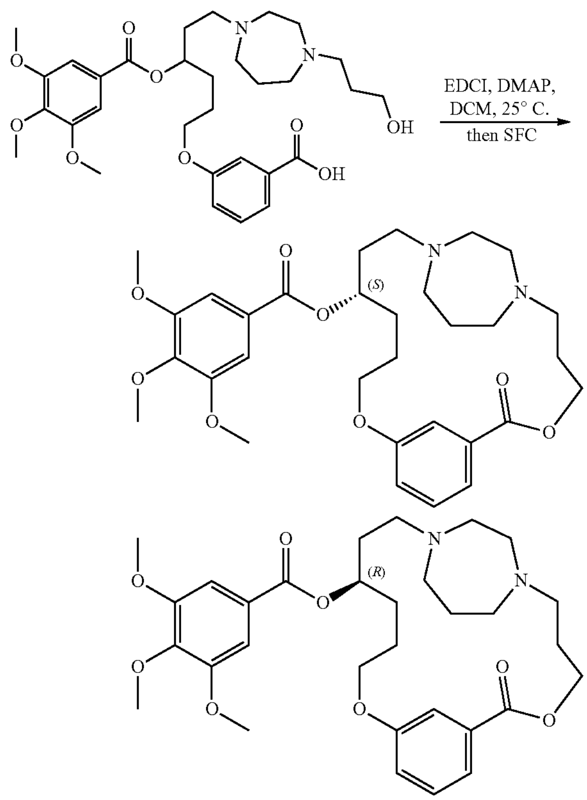

To a solution of intermediate compound 62 (200 mg, 339.74 umol, 1 eq) in DCM (20 mL) were added DMAP (207.53 mg, 1.70 mmol, 5 eq) and EDCI (195.39 mg, 1.02 mmol, 3 eq). The mixture was stirred at 20° C. for 12 hr. The reaction mixture was diluted with water (150 mL) and extracted with DCM (60 mL×3). The combined organic layers were washed with brine (60 mL×3), dried over Na2SO4, filtered and concentrated under reduced pressure. The residue was purified by prep-HPLC (column: Phenomenex luna C18 150*40 mm*15 um; mobile phase: [water (0.225% FA)-ACN]; B %: 13%-43%, 10 min) to give the racemic compound (100 mg, 52% yield) as an off-white solid.

Compound 17:

Compound 17 was separated from the racemic compound by preparative SFC following the conditions: DAICEL CHIRALCEL OD (250 mm*30 mm, 10 um); mobile phase: [0.10% NH3H2O MEOH]; B %: 40%-40%, 5.5 min; 40 min LCMS (ESI position ion) m/z: 571.2 (M+H)+ (calculated: 570.3)

SFC: retention time=1.914 min, ee=100%

1H NMR (400 MHz, MeOD-d4) δ 7.67 (d, J=2.3 Hz, 1H), 7.62 (d, J=7.6 Hz, 1H), 7.39 (t, J=7.9 Hz, 1H), 7.32 (s, 2H), 7.18-7.13 (m, 1H), 5.58-5.48 (m, 1H), 4.46-4.28 (m, 3H), 4.07 (br s, 1H), 3.90-3.80 (m, 9H), 3.17-3.05 (m, 1H), 3.00-2.84 (m, 4H), 2.77 (br d, J=3.9 Hz, 3H), 2.69-2.52 (m, 4H), 2.06 (br d, J=2.8 Hz, 2H), 1.99-1.80 (m, 8H)

Compound 18:

Compound 18 was separated from the racemic compound by preparative SFC following the conditions: DAICEL CHIRALCEL OD (250 mm*30 mm, 10 um); mobile phase: [0.10% NH3H2O MEOH]; B %: 40%-40%, 5.5 min; 40 min LCMS (ESI position ion) m/z: 571.2 (M+H)+ (calculated: 570.3)

SFC: retention time=2.281 min, ee=95.5%

1H NMR (400 MHz, MeOD-d4) δ 7.66 (d, J=1.5 Hz, 1H), 7.61 (d, J=7.6 Hz, 1H), 7.39 (t, J=7.9 Hz, 1H), 7.32 (s, 2H), 7.18-7.11 (m, 1H), 5.59-5.40 (m, 1H), 4.45-4.27 (m, 3H), 4.10-4.03 (m, 1H), 3.95- 3.74 (m, 9H), 3.05 (br d, J=3.3 Hz, 1H), 2.95-2.79 (m, 4H), 2.74 (s, 3H), 2.66-2.53 (m, 4H), 2.10-2.00 (m, 2H), 1.98-1.75 (m, 8H)

Compound 19 and Compound 20:

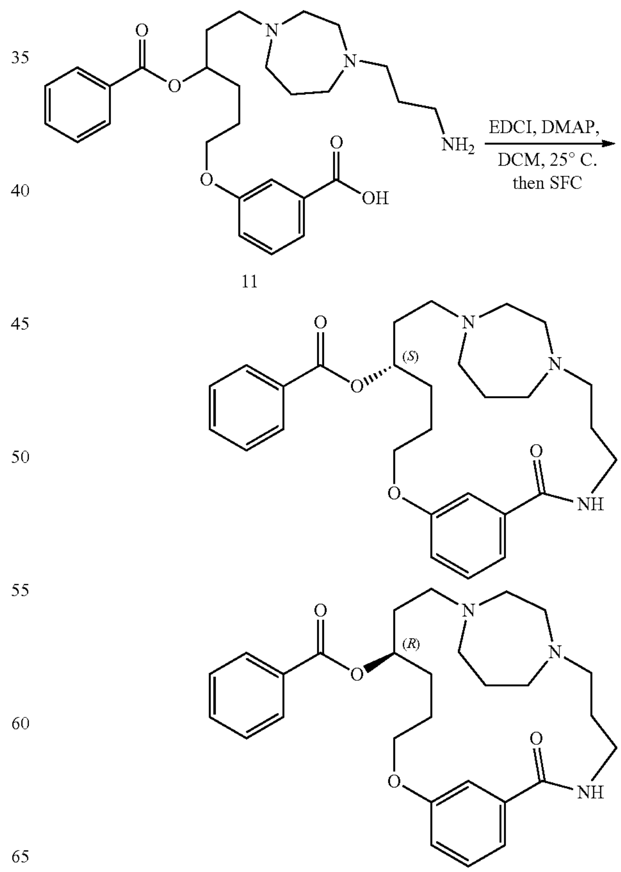

11

A mixture of intermediate compound 71 (70 mg, 131.07 umol, 1 eq, HCl), DMAP (64.05 mg, 524.26 umol, 4 eq) and EDCI (75.38 mg, 393.20 umol, 3 eq) in DCM (50 mL) was stirred at 30° C. for 12 hrs. The reaction mixture was washed with water (20 mL), the organic phase was dried and concentrated under vacuum. The residue was purified by prep-HPLC (column: Phenomenex Gemini-NX C18 75*30 mm*3 um; mobile phase: [water (10 mM NH4HCO3)-ACN]; B %: 38%-68%, 8 min), to give the racemic compound as a yellow solid. The racemic compound was separated by SFC (column: DAICEL CHIRALPAK IC (250 mm*30 mm, 10 um); mobile phase: [0.1% NH3H2O MeOH]; B %: 50%-50%, 5.3; 15 min), to give the compound 19 (4.3 mg, 7% yield) as a colorless oil and the compound 20 (5.8 mg, 9% yield) as a colorless oil.

Compound 19:

LCMS (ESI position ion) m/z: 480.3 (M+H)+ (calculated: 479.3)

SFC: retention time=1.221 min, ee=100%

1H NMR (400 MHz, MeOD-d4) δ 7.98-8.03 (m, 2H) 7.58-7.64 (m, 1H) 7.45-7.51 (m, 2H) 7.37-7.44 (m, 2H) 7.35 (d, J=1.63 Hz, 1H) 7.11 (dt, J=7.75, 1.94 Hz, 1H) 5.41 (quin, J=5.94 Hz, 1H) 4.13-4.26 (m, 2H) 3.54-3.62 (m, 1H) 3.45-3.53 (m, 1H) 2.88-2.97 (m, 1H) 2.71-2.83 (m, 7H) 2.57-2.68 (m, 4H) 1.86-2.04 (m, 6H) 1.80 (dt, J=11.69, 5.78 Hz, 2H) 1.69-1.76 (m, 2H)

Compound 20:

LCMS (ESI position ion) m/z: 480.3 (M+H)+ (calculated: 479.3)

SFC: retention time=1.684 min, ee=99%

1H NMR (400 MHz, MeOD-d4) δ 8.01 (d, J=7.13 Hz, 2H) 7.58-7.64 (m, 1H) 7.45-7.51 (m, 2H) 7.36-7.44 (m, 2H) 7.35 (s, 1H) 7.11 (dt, J=7.75, 1.88 Hz, 1H) 5.41 (brt, J=5.88 Hz, 1H) 4.12-4.26 (m, 2H) 3.54-3.62 (m, 1H) 3.45-3.53 (m, 1H) 2.88-2.98 (m, 1H) 2.72-2.83 (m, 7H) 2.58-2.68 (m, 4H) 1.87-2.04 (m, 6H) 1.78-1.85 (m, 2H) 1.69-1.76 (m, 2H)

Compound 21:

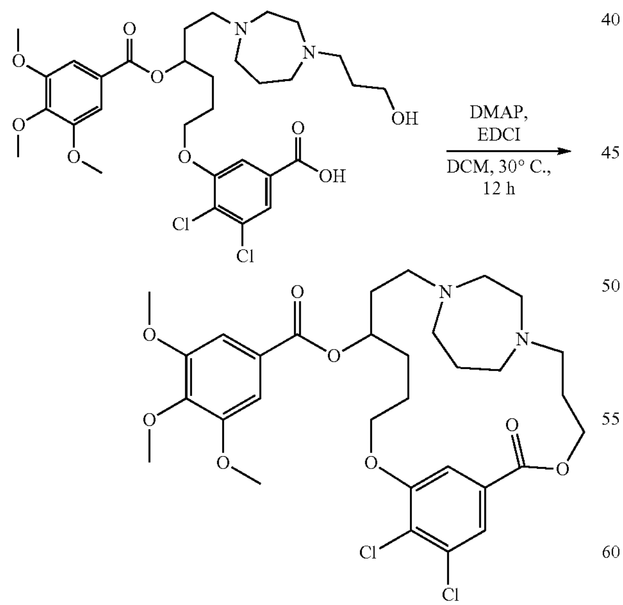

A suspension of intermediate compound 80 (50 mg, 76.04 umol, 1 eq.), DMAP (37.16 mg, 304.15 umol, 4 eq.) and EDCI (43.73 mg, 228.11 umol, 3 eq.) in DCM (50 mL) was stirred at 30° C. for 12 hrs. The reaction mixture was concentrated under reduced pressure. The residue was dissolved with DCM/MeOH (10/1, 20 mL) and was washed with H2O (30 mL). The aqueous layer was extracted with DCM/MeOH (10/1, 2×20 mL). The combined organic layers were dried over Na2SO4, filtered and concentrated under reduced pressure. The residue was purified by preparative HPLC (column: Phenomenex luna C18 150*25 mm*10 um; mobile phase: [water (0.225% FA)-ACN]; B %: 26%-56%, 10 min) to give the compound 21 (1.5 mg, 2% yield) as a white solid.

LCMS (ESI position ion) m/z: 639.2 (M+H)+ (calculated: 638.2)

1H NMR (400 MHz, MeOD-d4) δ 8.60-8.49 (m, 1H), 7.74 (d, J=1.5 Hz, 1H), 7.71-7.67 (m, 1H), 7.33-7.31 (m, 2H), 5.61-5.52 (m, 1H), 4.59-4.51 (m, 1H), 4.48-4.32 (m, 2H), 4.22-4.13 (m, 1H), 3.87 (s, 6H), 3.83-3.82 (m, 3H), 3.23 (br s, 4H), 3.02-2.92 (m, 1H), 2.88-2.82 (m, 1H), 2.79-2.71 (m, 1H), 2.65-2.59 (m, 4H), 2.27-2.13 (m, 2H), 2.06-1.97 (m, 3H), 1.93-1.86 (m, 6H).

Compound 22 and Compound 23:

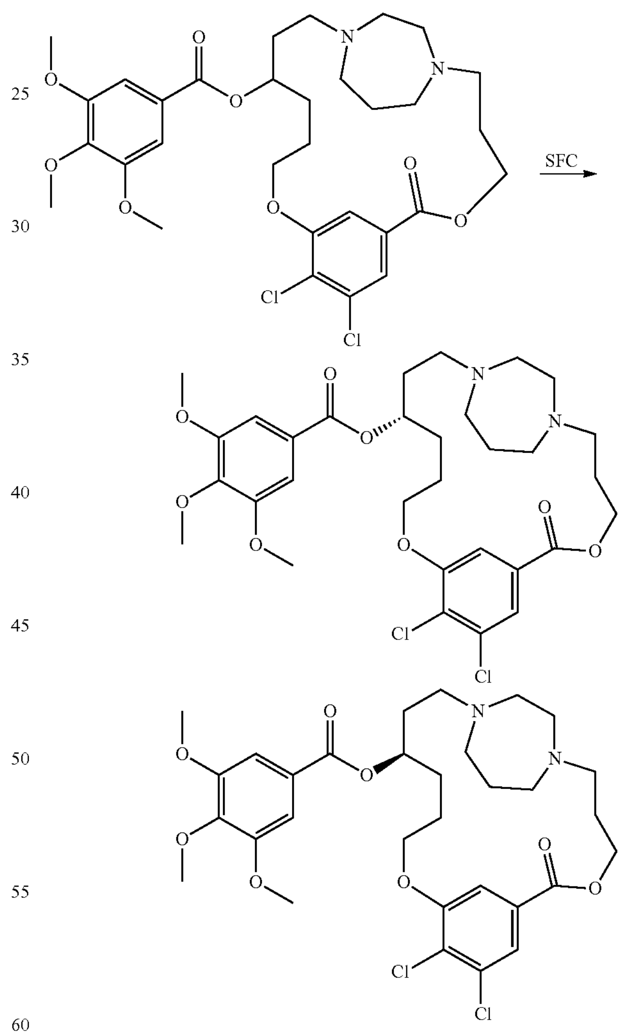

Enantiomers of compound 21 were separated by Chiral SFC (column: DAICEL CHIRALPAK AD-H (250 mm*30 mm, 5 um); mobile phase: [0.1% NH3H2O ETOH]; B %: 35%-35%, 3.6; 40 min) to give the compound 22 (11.4 mg, 4% yield) as a light yellow solid and compound 23 (11.1 mg, 4% yield) as a light yellow solid.

Compound 22:

LCMS (ESI position ion) m/z: 639.2 (M+H)+ (calculated: 638.2)

SFC: retention time=1.507 min, ee=86.7%

1H NMR (400 MHz, MeOD-d4) δ 7.71-7.68 (m, 1H), 7.65-7.62 (m, 1H), 7.32 (s, 2H), 5.61-5.52 (m, 1H), 4.56-4.48 (m, 1H), 4.45-4.38 (m, 1H), 4.38-4.31 (m, 1H), 4.13 (dt, J=4.4, 9.0 Hz, 1H), 3.86 (s, 6H), 3.82 (s, 3H), 3.25-3.08 (m, 4H), 2.95 (br t, J=9.3 Hz, 1H), 2.89-2.81 (m, 1H), 2.80-2.71 (m, 1H), 2.65-2.57 (m, 4H), 2.25-2.12 (m, 2H), 2.02-1.81 (m, 9H).

Compound 23:

LCMS (ESI position ion) m/z: 639.2 (M+H)+ (calculated: 638.2)

SFC: retention time=2.089 min, ee=96.2%

1H NMR (400 MHz, MeOD-d4) δ 7.71-7.67 (m, 1H), 7.62-7.59 (m, 1H), 7.31 (s, 2H), 5.61-5.52 (m, 1H), 4.53-4.43 (m, 1H), 4.43-4.34 (m, 1H), 4.33-4.24 (m, 1H), 4.12-4.03 (m, 1H), 3.86 (s, 6H), 3.82 (s, 3H), 3.11-3.01 (m, 1H), 2.95-2.76 (m, 4H), 2.71-2.66 (m, 1H), 2.72-2.66 (m, 2H), 2.58-2.48 (m, 3H), 2.06-1.85 (m, 8H), 1.84-1.76 (m, 3H).

Compound 24, 27, 29, 30, 110, 111 and Compound 41 to Compound 106:

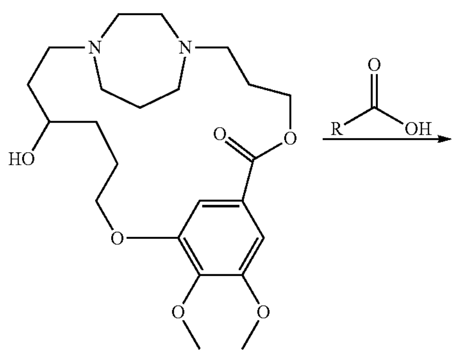

-continued

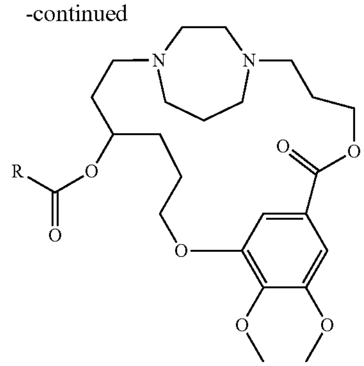

The compounds 24, 27, 29, 30, 110, 111, compound 41 to compound 54 to compound 106, summarized in the table below has been synthetized following the general procedure: To a solution of compound 38 (30 mg, 0.068 mmol, 1.0 equiv) in DCM (2 mL) was added DMAP (12.4 mg, 0.10 mmol, 1.5 equiv), EDC·HCl (19.5 mg, 0.10 mmol, 1.5 equiv) and the required carboxylic acid (24.1 mg, 0.10 mmol, 1.5 equiv). The reaction mixture was stirred for 16 h at room temperature, and then quenched with water and exacted with DCM. The organic layer was concentrated under vacuum. The residue was purified by preparative HPLC to give the desired compound.

In the case of compound 41 and compound 55, the benzyl protected compound obtained from the above general procedure has been isolated after benzyl deprotection following the general procedure below: To a solution of the benzylether (20 mg, 0.03 mmol, 1.0 equiv) in ethanol (10 mL) was added Pd/C (2 mg). The reaction mixture was stirred for 30 min at room temperature under 1 atm H2. After the reaction was completed, the mixture was filtered to remove the catalyst, and the resulting solution was concentrated under vacuum. The crude product was then purified by preparative HPLC to give the desired compound.

Summary Table:

| Compound | Carboxylic acid | LCMS (ES+) m/z | 1H NMR (300 MHz, DMSO-d6, ppm): δ ppm |
|---|---|---|---|
| Compound 41 | 4-hydroxybenzoic acid | 557.3 (M + H)+, (calculated 556.3) | |
| Compound 29 | 4-fluorobenzoic acid | 559.3 (M + H)+, (calculated 558.3) | 8.31 (s, 1H), 8.05-8.00 (m, 2H), 7.37-7.31 (m, 3H), 7.23 (s, 1H), 5.42 (br, 1H), 4.32-4.27 (m, 3H), 4.21 (br, 1H), 3.89 (s, 3H), 3.72 (s, 3H), 3.17-3.07(m, 1H), 2.71-2.45 (m, 11H), 1.96-1.85 (m, 10H). |
| Compound 43 | 4-isopropoxybenzoic acid | 599.4 (M + H)+, (calculated 598.3) | 8.19 (s, 0.4H), 7.89-7.80 (m, 2H), 7.33 (s, 1H), 7.23 (s, 1H), 7.01-6.92 (m, 2H), 5.38 (br, 1H), 4.76-4.68 (m, 1H), 4.34-4.20-4.06 (m, 4H), 3.83 (s, 3H), 3.72 (s, 3H), 3.14-3.02(m, 1H), 2.88-2.50 (m, 11H), 1.91-1.70 (m, 10H), 1.28 (d, J = 6.0 Hz, 6H). |
| Compound 44 | 3-(trifluoromethyl) benzoic acid | 609.3 (M + H)+, (calculated 608.3) | |
| Compound 45 | 3-(methylsulfonyl) benzoic acid | 619.3 (M + H)+, (calculated 618.3) | |
| Compound 46 | 3-phenoxybenzoic acid | 633.4 (M + H)+, (calculated 632.3) | 8.15 (s, 0.3H), 7.72 (d, J = 8.1 Hz, 1H), 8.20 (s, 1H), 7.56-7.40 (m, 3H), 7.33-7.17 (m, 4H), 7.08-7.05 (m, 2H), 5.37 (br, 1H), 4.34-4.23 (m, 3H), 4.08 (br, 1H), 3.83 (s, 3H), 3.73 (s, 3H), 3.54-2.50 (m, 12H), 2.09-1.69 (m, 10H). |

-continued

| Compound | Carboxylic acid | LCMS (ES+) m/z | 1H NMR (300 MHz, DMSO-d6, ppm): δ ppm |
|---|---|---|---|
| Compound 47 | 2-fluorobenzoic acid | 559.3 (M + H)+, (calculated 558.3) | |
| Compound 48 | 4-bromo-3-cyanobenzoic acid | 644.3 (M + H)+, (calculated 643.2) | 8.42 (s, 1H), 8.20 (s, 1H), 8.14-8.11(m, 1H), 8.03 (d, J = 9.0 Hz, 1H), 7.32 (s, 1H), 7.23 (s, 1H), 5.45 (br, 1H), 4.32-4.21 (m, 3H), 4.08 (br, 1H), 3.89 (s, 3H), 3.72 (s, 3H), 3.05-2.92 (m, 1H), 2.75-2.57 (m, 11H), 1.86-1.68 (m, 10H). |
| Compound 49 | 3-methyl-5-(trifluoromethyl) benzoic acid | 623.3 (M + H)+, (calculated 622.3) | |
| Compound 50 | 2-fluoro-4-methoxybenzoic acid | 589.3 (M + H)+, (calculated 588.3) | 8.32 (s, 0.2H), 7.86-7.80 (m, 1H), 7.32 (s, 1H), 7.23 (s, 1H), 6.95-6.85 (m, 2H), 5.40 (br, 1H), 4.32-4.21 (m, 3H), 4.06 (br, 1H), 3.83 (s, 6H), 3.73 (s, 3H), 2.98-2.94 (m, 1H), 2.71-2.50 (m, 11H), 1.83-1.66 (m, 10H). |
| Compound 51 | 4-methoxy-2-(trifluoromethoxy) benzoic acid | 655.3 (M + H)+, (calculated 654.3) | |
| Compound 52 | picolinic acid | 542.3 (M + H)+, (calculated 541.3) | 8.71 (s, 1H), 8.23 (s, 1H), 8.06-7.95 (m, 2H), 7.66-7.61 (m, 1H), 7.34 (s, 1H), 7.23 (s, 1H), 5.46 (br, 1H), 4.30-4.21 (m, 3H), 4.06 (br, 1H), 3.87 (s, 3H), 3.73 (s, 3H), 3.06-3.00 (m, 1H), 2.77-2.55 (m, 11H), 1.87-1.68 (m, 10H). |
| Compound 53 | nicotinic acid | 542.3 (M + H)+, (calculated 541.3) | |
| Compound 54 | pyrazine-2-carboxylic acid | 543.3 (M + H)+, (calculated 542.3) | |
| Compound 55 | 6-hydroxynicotinic acid | 558.3 (M + H)+, (calculated 557.3) | |
| Compound 56 | quinoline-5-carboxylic acid | 592.4 (M + H)+, (calculated 591.3) | |
| Compound 57 | oxazole-4-carboxylic acid | 532.3 (M + H)+, (calculated 531.3) | |
| Compound 58 | 1H-1,2,3-triazole-4-carboxylic acid | 532.3 (M + H)+, (calculated 531.3) | 8.47 (s, 1H), 8.20 (s, 1H), 7.33 (s, 1H), 7.23 (s, 1H), 5.44 (br, 1H), 4.64-4.13 (m, 3H), 4.05 (br, 1H), 3.83 (s, 3H), 3.73 (s, 3H), 3.08-3.04 (m, 1H), 2.84-2.50 (m, 11H), 1.84-1.72 (m, 10H). |
| Compound 59 | acetic acid | 479.3 (M + H)+, (calculated 478.3) | 10.35 (br, 1H), 7.35 (s, 1H), 7.26 (s, 1H), 4.93 (br, 1H), 4.57-4.09 (m, 5H), 3.84 (s, 3H), 3.77 (s, 3H), 3.64-2.67 (m, 11H), 2.13-1.77 (m, 13H). |
| Compound 60 | cyclopropanecarboxylic acid | 505.3 (M + H)+, (calculated 504.3) | 7.28 (s, 1H), 7.23 (s, 1H), 5.17 (br, 1H), 4.29-4.13 (m, 3H), 3.98 (br, 1H), 3.83 (s, 3H), 3.75 (s, 3H), 2.92-2.89 (m, 1H), 2.68-2.41 (m, 11H), 1.84-1.66 (m, 10H), 0.88-0.71 (m, 4H) |
| Compound 61 | 3-methylbutanoic acid | 521.3 (M + H)+, (calculated 520.3) | 8.19 (s, 1H), 7.29 (s, 1H), 7.23 (s, 1H), 5.19 (br, 1H), 4.25-3.91 (m, 4H), 3.84 (s, 3H), 3.74 (s, 3H), 2.95 (br, 1H), 2.74-2.43 (m, 11H), 2.17-2.15 (m, 2H), 1.98-1.63 (m, 11H), 0.88 (d, J = 6.6 Hz, 6H). |
| Compound 62 | 4,4,4-trifluorobutanoic acid | 561.3 (M + H)+, (calculated 560.3) | 8.21 (s, 1H), 7.29 (s, 1H), 7.23 (s, 1H), 5.20 (br, 1H), 4.30-3.89 (m, 4H), 3.84 (s, 3H), 3.75 (s, 3H), 2.98-2.76 (m, 1H), 2.70-2.50 (m, 15H), 1.90-1.58 (m, 10H). |
| Compound 63 | cyclohexanecarboxylic acid | 547.4 (M + H)+, (calculated 546.3) | 8.17 (s, 0.4H), 7.29 (s, 1H), 7.23 (s, 1H), 5.16 (br, 1H), 4.30-3.95 (m, 4H), 3.83 (s, 3H), 3.74 (s, 3H), 3.01 (br, 1H), 2.72-2.22 (m, 12H), 1.92-1.52 (m, 15H), 1.34-1.13 (m, 5H). |
| Compound 64 | 1-methylpiperidine-4-carboxylic acid | 562.4 (M + H)+, (calculated 561.3) | |

-continued

| Compound | Carboxylic acid | LCMS (ES+) m/z | 1H NMR (300 MHz, DMSO-d6, ppm): δ ppm |
|---|---|---|---|
| Compound 65 | 3,3-dimethylcyclobutane-1-carboxylic acid | 547.4 (M + H)+, (calculated 546.3) | 8.22 (s, 1H), 7.30 (s, 1H), 7.23 (s, 1H), 5.17 (br, 1H), 4.30-3.98 (m, 4H), 3.84 (s, 3H), 3.74 (s, 3H), 3.11-3.03 (m, 2H), 2.79-2.38 (m, 11H), 1.97-1.61 (m, 14H), 1.11 (s, 3H), 1.03 (s, 3H). |
| Compound 66 | 2-(oxetan-3-y1)acetic acid | 535.3 (M + H)+, (calculated 534.3) | |
| Compound 67 | (1R,5S,6r)-3-oxabicyclo[3.1.0]hexane-6-carboxylic acid | 547.3 (M + H)+, (calculated 546.3) | 8.28 (s, 0.4H), 7.27 (s, 1H), 7.22 (s, 1H), 5.16 (br, 1H), 4.29-3.94 (m, 4H), 3.84-3.74 (m, 8H), 3.61-3.50 (m, 3H), 2.94 (br, 1H), 2.72-2.43 (m, 10H), 2.09 (s, 2H), 1.83-1.64 (m, 10H), 1.41-1.39 (m, 1H). |
| Compound 68 | 5-oxopyrrolidine-3-carboxylic acid | 548.3 (M + H)+, (calculated 547.3) | 10.59 (br, 1H), 7.70 (s, 1H), 7.36 (s, 1H), 7.26 (s, 1H), 4.96 (br, 1H), 4.36-4.11 (m, 4H), 3.83 (s, 3H), 3.76 (s, 3H), 3.69-3.18 (m, 15H), 2.49-2.38 (m, 2H), 2.36-1.78 (m, 10H). |
| Compound 69 | 1-benzyl-5-oxopyrrolidine-3-carboxylic acid | 638.3 (M + H)+, (calculated 637.3) | |
| Compound 70 | 4-methoxycyclohexane-1-carboxylic acid | 577.4 (M + H)+, (calculated 576.3) | |
| Compound 71 | 2,6-difluorobenzoic acid | 577.3 (M + H)+, (calculated 576.3) | |
| Compound 30 | 4-(trifluoromethoxy) benzoic acid | 625.3 (M + H)+, (calculated 624.3) | |
| Compound 73 | 3-cyanobenzoic acid | 566.3 (M + H)+, (calculated 565.3) | |
| Compound 74 | 2-oxo-1,2,3,4-tetrahydroquinoline-6-carboxylic acid | 610.4 (M + H)+, (calculated 609.3) | |
| Compound 75 | 3-(difluoromethoxy) benzoic acid | 607.3 (M + H)+, (calculated 606.3) | |
| Compound 76 | 3,5-dichlorobenzoic acid | 609.3 (M + H)+, (calculated 608.2) | |
| Compound 24 | 3,4-dichlorobenzoic acid | 609.3 (M + H)+, (calculated 608.2) | |
| Compound 78 | 2,3-dichlorobenzoic acid | 609.3 (M + H)+, (calculated 608.2) | |
| Compound 79 | 2-chloro-6-fluoro-3-methylbenzoic acid | 607.3 (M + H)+, (calculated 606.3) | |
| Compound 80 | 3-fluoro-5-(trifluoromethyl)benzoic acid | 627.3 (M + H)+, (calculated 626.3) | |
| Compound 81 | 4-fluoro-3-(trifluoromethyl)benzoic acid | 627.3 (M + H)+, (calculated 626.3) | |
| Compound 82 | 4-cyano-3-fluorobenzoic acid | 584.3 (M + H)+, (calculated 583.3) | |
| Compound 83 | 4-(trifluoromethyl)benzoic acid | 609.3 (M + H)+, (calculated 608.3) | |
| Compound 84 | 3,5-difluorobenzoic acid | 577.3 (M + H)+, (calculated 576.3) | |
| Compound 85 | 3,4-difluorobenzoic acid | 577.3 (M + H)+, (calculated 576.3) | |
| Compound 86 | 3-cyano-4-fluorobenzoic acid | 584.3 (M + H)+, (calculated 583.3) | |
| Compound 87 | 4-cyanobenzoic acid | 566.3 (M + H)+, (calculated 565.3) | |
| Compound 27 | 3-chloro-4-fluorobenzoic acid | 593.3 (M + H)+, (calculated 592.2) | 10.41 (br, 1H), 8.14-7.99 (m, 2H), 7.64-7.58 (m, 1H), 7.38 (s, 1H), 7.27 (s, 1H), 5.20 (br, 1H), 4.59-4.52 (m, 4H), 3.84 (s, 3H), 3.76 (s, 3H), 3.66-2.97 (m, 12H), 2.34-1.76 (m, 10H). |
| Compound 89 | 1-methyl-1H-benzo[d]imidazole-5-carboxylic acid | 595.3 (M + H)+, (calculated 594.3) | |
| Compound 90 | 4-(oxazol-5-yl)benzoic acid | 608.3 (M + H)+, (calculated 607.3) | |

-continued

| Compound | Carboxylic acid | LCMS (ES+) m/z | 1H NMR (300 MHz, DMSO-d6, ppm): δ ppm |
|---|---|---|---|
| Compound 91 | 4,5-dichloro-2-fluorobenzoic acid | 627.3 (M + H)+, (calculated 626.2) | |
| Compound 92 | 3,4,5-triethoxybenzoic acid | 673.4 (M + H)+, (calculated 672.4) | |
| Compound 93 | 3-methoxypropanoic acid | 523.3 (M + H)+, (calculated 522.3) | |
| Compound 94 | 3-(1H-pyrazol-1-yl)propanoic acid | 559.4 (M + H)+, (calculated 558.3) | |
| Compound 95 | 3-cyanopropanoic acid | 518.3 (M + H)+, (calculated 517.3) | |
| Compound 96 | 4-cyanobutanoic acid | 532.3 (M + H)+, (calculated 531.3) | |
| Compound 97 | 4-acetamidobutanoic acid | 564.4 (M + H)+, (calculated 563.3) | 10.54 (br, 1H), 7.86 (s, 1H), 7.36 (s, 1H), 7.27 (s, 1H), 4.94 (br, 1H), 4.39-4.11 (m, 4H), 3.84 (s, 3H), 3.77 (s, 3H), 3.69-3.00 (m, 14H), 2.35-1.24 (m, 17H). |
| Compound 98 | 3-(1H-tetrazol-1-yl)propanoic acid | 561.3 (M + H)+, (calculated 560.3) | |
| Compound 99 | 4-(dimethylamino)-4-oxobutanoic acid | 564.4 (M + H)+, (calculated 563.3) | 10.42 (br, 1H), 7.36 (s, 1H), 7.26 (s, 1H), 4.96 (br, 1H), 4.35-4.12 (m, 4H), 3.84 (s, 3H), 3.77 (s, 3H), 3.60-3.28 (m, 11H), 2.95 (s, 3H), 2.79 (s, 3H), 2.56-2.34 (m, 5H), 2.14-1.77 (m, 10H). |
| Compound 100 | 3-acetamidopropanoic acid | 550.4 (M + H)+, (calculated 549.3) | |
| Compound 101 | 4-(methylamino)-4-oxobutanoic acid | 550.4 (M + H)+, (calculated 549.3) | |
| Compound 102 | 3-(1H-1,2,4-triazol-1-yl)propanoic acid | 560.3 (M + H)+, (calculated 559.3) | 10.51 (br, 1H), 8.51 (s, 1H), 7.95 (s, 1H), 7.34 (s, 1H), 7.26 (s, 1H), 4.95 (br, 1H), 4.44-4.01 (m, 8H), 3.87 (s, 3H), 3.77 (s, 3H), 3.60-3.09 (m, 9H), 3.00-2.93 (m, 2H), 2.13-1.63 (m, 11H). |
| Compound 103 | 4-morpholino-4-oxobutanoic acid | 606.4 (M + H)+, (calculated 605.3) | |
| Compound 104 | 3-(4-fluorophenoxy)propanoic acid | 603.3 (M + H)+, (calculated 602.3) | |
| Compound 105 | 4,4-difluorocyclohexane-1-carboxylic acid | 583.3 (M + H)+, (calculated 582.3) | 10.42 (br, 1H), 7.36 (s, 1H), 7.26 (s, 1H), 5.03 (br, 1H), 4.67-3.97 (m, 11H), 3.84 (s, 3H), 3.76 (s, 3H), 3.61-3.51 (m, 3H), 2.55-2.51 (m, 2H), 2.15-2.60 (m, 19H). |
| Compound 106 | 4-(trifluoromethyl) cyclohexane-1-carboxylic acid | 615.3 (M + H)+, (calculated 614.3) | |
| Compound 110 | 3-(2,5-dioxopyrrolidin-1-yl)propanoic acid | 590.4 (M + H)+, (calculated 589.3) | |
| Compound 111 | 3-methoxycyclohexane-1-carboxylic acid | 577.3 (M + H)+, (calculated 576.3) | |

Compound 25 and Compound 26:

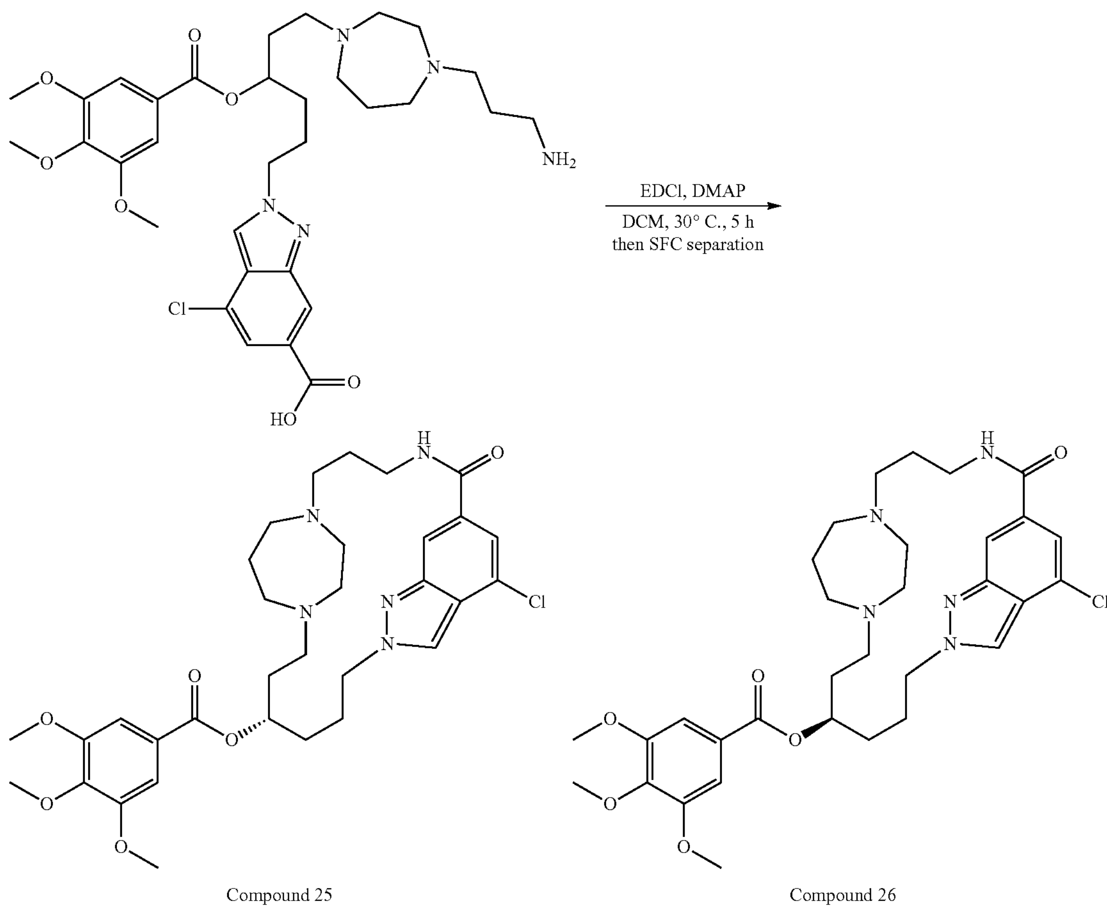

Compound 25

Compound 26

A mixture of intermediate compound 56 (220 mg, 322.28 umol, 1 eq, HCl), EDCI (185.34 mg, 966.84 umol, 3 eq) and DMAP (157.49 mg, 1.29 mmol, 4 eq) in DCM (100 mL) was stirred at 30° C. for 3 hr. The reaction mixture was poured into water (100 mL) and extracted with DCM (100 mL), the combined organic phase was dried and concentrated under vacuum. The residue was purified by prep-HPLC (column: Waters Xbridge 150*25 mm*5 um; mobile phase: [water (10 mM NH4HCO3)-ACN]; B %: 47%-77%, 9 min). The enantiomers were separated by SFC (column: REGIS (s,s) WHELK-O1 (250 mm*50 mm, 10 um); mobile phase: [0.1% NH3H2O MeOH]; B %: 50%-50%, 6 min; 75 min-min), to give the compound 25 (10.6 mg, 5% yield) as a white solid and the compound 26 (15.3 mg, 7% yield) as a white solid.

Compound 25:

LCMS (ESI position ion) m/z: 628.3 (M+H)+ (calculated: 627.3)

SFC: retention time=0.855 min, ee=98.6%

1H NMR (400 MHz, MeOD-d4) δ=8.46 (s, 1H) 8.00 (s, 1H) 7.47 (s, 1H) 7.28 (d, J=0.75 Hz, 2H) 4.96 (quin, J=5.47 Hz, 1H) 4.60 (br t, J=5.32 Hz, 2H) 3.86 (d, J=0.88 Hz, 6H) 3.82 (d, J=1.00 Hz, 3H) 3.59 (brt, J=5.13 Hz, 2H) 2.71-2.80 (m, 6H) 2.64 (brd, J=4.13 Hz, 2H) 2.46 (brd, J=5.50 Hz, 2H) 2.24-2.36 (m, 1H) 2.08-2.20 (m, 1H) 2.00-2.07 (m, 1H) 1.92-1.99 (m, 1H) 1.72-1.85 (m, 6H) 1.40 (br d, J=7.25 Hz, 2H)

Compound 26:

LCMS (ESI position ion) m/z: 628.3 (M+H)+ (calculated: 627.3)

SFC: retention time=1.158 min, ee=97.9%

1H NMR (400 MHz, MeOD-d4) δ=8.46 (s, 1H) 8.00 (s, 1H) 7.47 (d, J=0.88 Hz, 1H) 7.28 (s, 2H) 4.96 (t, J=5.88 Hz, 1H) 4.60 (t, J=5.57 Hz, 2H) 3.86 (s, 6H) 3.82 (s, 3H) 3.59 (t, J=5.38 Hz, 2H) 2.71-2.79 (m, 6H) 2.64 (brd, J=4.13 Hz, 2H) 2.46 (brd, J=5.38 Hz, 2H) 2.25-2.35 (m, 1H) 2.10-2.19 (m, 1H) 2.00-2.09 (m, 1H) 1.90-1.98 (m, 1H) 1.81-1.87 (m, 2H) 1.76-1.80 (m, 4H) 1.36-1.44 (m, 2H)

Compound 121 and Compound 28:

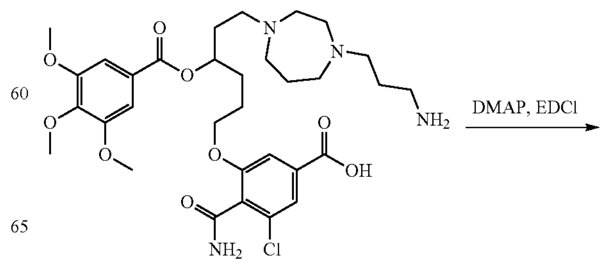

-continued

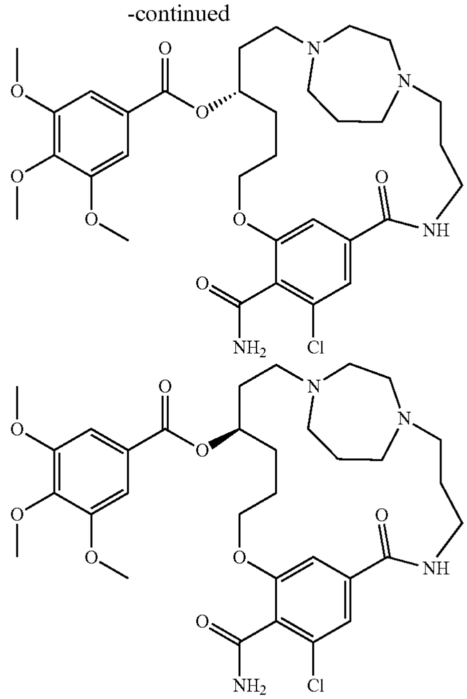

To a solution of intermediate compound 99 (10.28 mg, 15.45 umol, 1 eq) in DCM (8 mL) was added EDCI (8.89 mg, 46.36 umol, 3 eq) and DMAP (7.55 mg, 61.81 umol, 4 eq)) at 25° C. Then the reaction mixture was stirred at 25° C. for 4 hr. The reaction mixture was filtered and concentrated under reduced pressure. The residue was purified by preparative HPLC (column: Phenomenex Synergi C18 150*25 mm*10 um; mobile phase: [water (0.225% FA)-ACN]; B %: 2%-32%, 10 min) to give the racemic compound (10 mg) as a off-white solid. The enantiomers of the racemic compound was separated by SFC (column: DAICEL CHIRALPAK AD (250 mm*30 mm, 10 um); mobile phase: [0.1% NH3H2O IPA]; B %: 45%-45%, 7 min; 45 minmin) to give the compound 121 (1.98 mg, 20% yield) as a off-white solid and the compound 28 (2.02 mg, 20% yield) as a off-white solid.

Compound 121:

LCMS (ESI position ion) m/z: 647.3 (M+H)+ (calculated: 646.3)

SFC: retention time=0.629 min, ee=100%

1H NMR (400 MHz, MeOD-d4) δ 7.50 (d, J=1.0 Hz, 1H), 7.41 (s, 1H), 7.31 (s, 2H), 5.50 (br s, 1H), 4.45-4.15 (m, 2H), 4.00-3.71 (m, 9H), 3.58 (br s, 1H), 3.52-3.41 (m, 1H), 3.10-2.44 (m, 12H), 2.05-1.69 (m, 10H)

Compound 28:

LCMS (ESI position ion) m/z: 647.3 (M+H)+ (calculated: 646.3)

SFC: retention time=1.208 min, ee=95%

1H NMR (400 MHz, MeOD-d4) δ 7.50 (s, 1H), 7.41 (s, 1H), 7.31 (s, 2H), 5.49 (br d, J=5.1 Hz, 1H), 4.39 (br d, J=3.8 Hz, 1H), 4.24 (br d, J=6.8 Hz, 1H), 3.91-3.79 (m, 9H), 3.64-3.57 (m, 1H), 3.49 (br d, J=2.8 Hz, 1H), 2.78 (br s, 6H), 2.71-2.51 (m, 6H), 1.99-1.74 (m, 10H)

Compound 31:

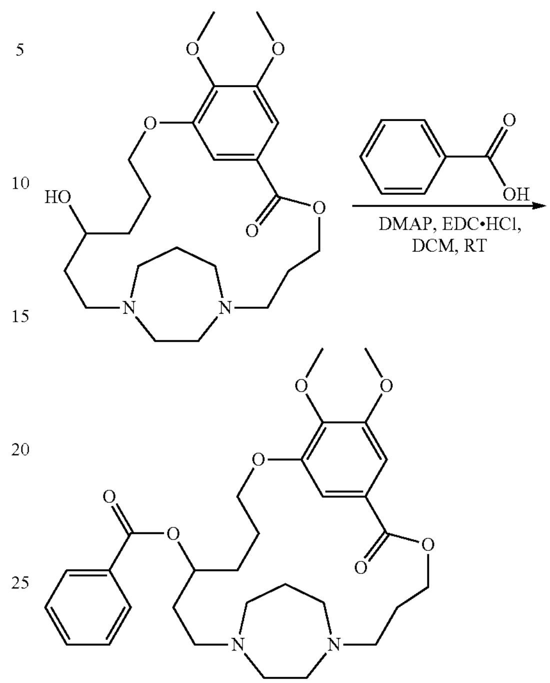

A mixture of compound 38 (120 mg, 0.28 mmol, 1.0 equiv), DMAP (50.4 mg, 0.41 mmol, 1.5 equiv), EDC·HCl (64.0 mg, 0.41 mmol, 1.5 equiv) and benzoic acid (50.4 mg, 0.41 mmol, 1.5 equiv) in DCM (3 mL) was stirred for 16 h at room temperature. The reaction was quenched with H2O (2 mL). The organic layer was dried over Na2SO4 and concentrated under reduced pressure. The residue was purified by preparative HPLC (Column: Atlantis Prep T3 OBD Column, 19*150 mm 5 um; Mobile Phase A: Water (0.1% FA), Mobile Phase B: ACN; Flow rate: 20 mL/min; Gradient: 15% B to 35% B in 7 min, 35% B; Wave Length: 220 nm)) to give the compound 31 (HCOOH salt, 63 mg, 42% yield) as a white solid.

LC-MS (ES+) m/z: 541 (M+H)+ (calculated: 540.3)

1H NMR (300 MHz, DMSO-d6) δ 8.25 (s, 1H), 7.98-7.95 (m, 2H), 7.68-7.63 (m, 1H), 7.54-7.49 (m, 2H), 7.33 (s, 1H), 7.23 (s, 1H), 5.43 (br, 1H), 4.32-4.25 (m, 3H), 4.19-4.30 (m, 1H), 3.83 (s, 3H), 3.72 (s, 3H), 2.96 (br, 1H), 2.73-2.51 (m, 11H), 1.86-1.74 (m, 10H).

Compound 32 and Compound 33:

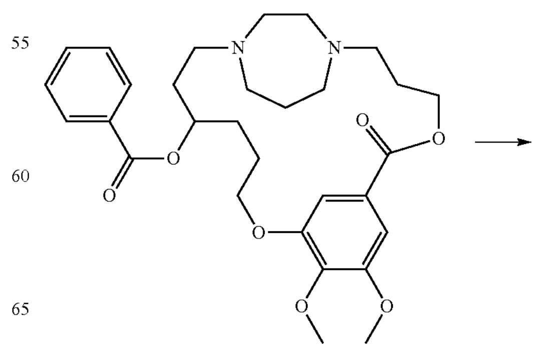

-continued

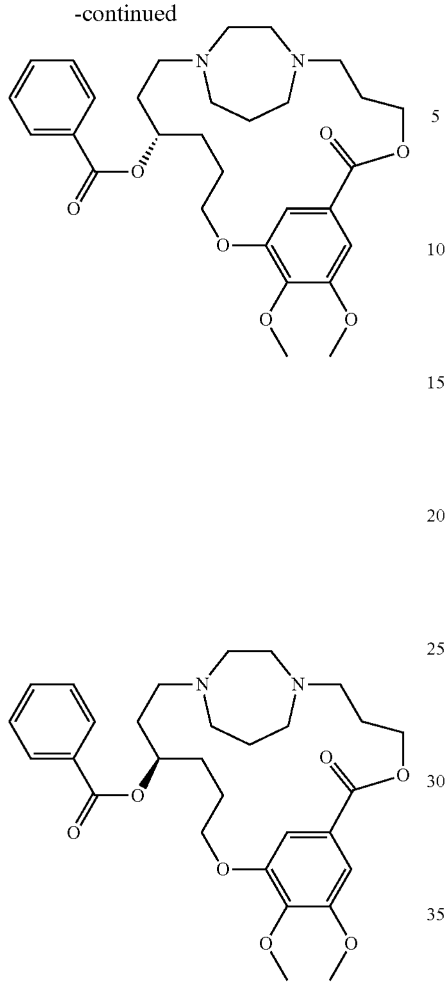

The enantiomers of compound 31 (50 mg) was separated by Chiral-HPLC with the following conditions (Column: CHIRAL ART Cellulose-SB, 3*25 cm, 5 μm; Mobile Phase, A: Hex (0.1% 2M NH3-MeOH)—HPLC; B: EtOH—HPLC; Flow Rate: 5 mL/min; Gradient: 50% B to 50% B in 18 min; Detection: 220/254 nm; RT1 (min): 10; RT2 (min): 13.). The chiral separation yielded to the compound 32 (20 mg, 40% yield) as white solid and compound 33 (17 mg, 34% yield) as white solid.

Compound 32:

LC-MS (ES+) m/z: 541 (M+H)+ (calculated: 540.3)

Chiral HPLC: retention time=2.67 min, ee=99.8%

1H NMR (300 MHz, DMSO-d6) δ ppm 7.98-7.95 (m, 2H), 7.68-7.63 (m, 1H), 7.54-7.49 (m, 2H), 7.33 (s, 1H), 7.23 (s, 1H), 5.43 (br, 1H), 4.32-4.25 (m, 3H), 4.19-4.30 (m, 1H), 3.83 (s, 3H), 3.72 (s, 3H), 2.96 (br, 1H), 2.73-2.51 (m, 11H), 1.86-1.74 (m, 10H).

Compound 33:

LC-MS (ES+) m/z: 541 (M+H)+ (calculated: 540.3)

Chiral HPLC: retention time=3.63 min, ee=99.8%

1H NMR (300 MHz, DMSO-d6) δ ppm 7.98-7.95 (m, 2H), 7.68-7.63 (m, 1H), 7.54-7.49 (m, 2H), 7.33 (s, 1H), 7.23 (s, 1H), 5.43 (br, 1H), 4.32-4.25 (m, 3H), 4.19-4.30 (m, 1H), 3.83 (s, 3H), 3.72 (s, 3H), 2.96 (br, 1H), 2.73-2.51 (m, 11H), 1.86-1.74 (m, 10H).

Compound 34:

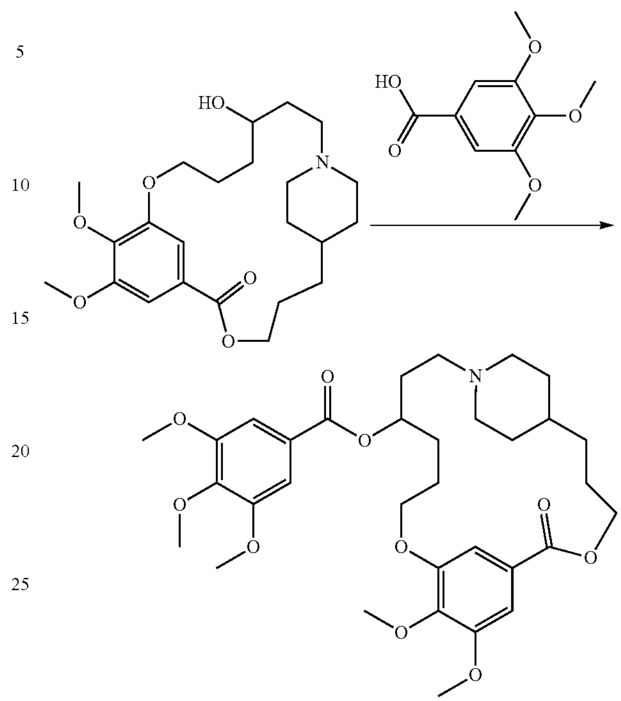

A mixture of intermediate compound 122 (40 mg, 0.10 mmol, 1.0 equiv), DMAP (17.4 mg, 0.14 mmol, 1.5 equiv), EDC·HCl (27 mg, 0.14 mmol, 1.5 equiv) and 3,4,5-trimethoxybenzoic acid (30 mg, 0.14 mmol, 1.5 equiv) in DCM (1 mL) was stirred for 12 h at room temperature. The reaction was then quenched with H2O (1 mL) and the resulting mixture was extracted with DCM (2×5 mL). The combined organic layers were dried over Na2SO4 and concentrated under reduced pressure. The crude residue was purified by preparative HPLC (Column: Atlantis Prep T3 OBD Column, 19*150 mm 5 um; Mobile Phase A: Water (0.1% FA), Mobile Phase B: ACN; Flow rate: 20 mL/min; Gradient: 15% B to 35% B in 7 min, 35% B; Wave Length: 220 nm) to give the compound 34 (HCOOH salt, 14 mg, 22% yield) as a white solid.

LC-MS (ES+) m/z: 616 (M+H)+ (calculated: 615.3)

1H NMR (300 MHz, DMSO-d6) δ ppm 8.33 (br, 1H), 7.34-7.24 (m, 4H), 5.32 (br, 1H), 4.32-3.98 (m, 4H), 3.83 (s, 9H), 3.73 (s, 6H), 2.83-2.77 (m, 2H), 2.55-2.45 (m, 2H), 2.03-1.79 (m, 8H), 1.75-1.23 (m, 9H).

Compound 35:

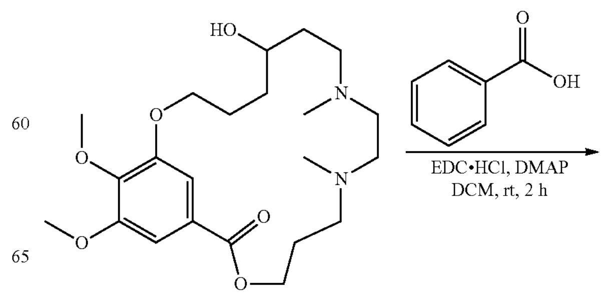

-continued

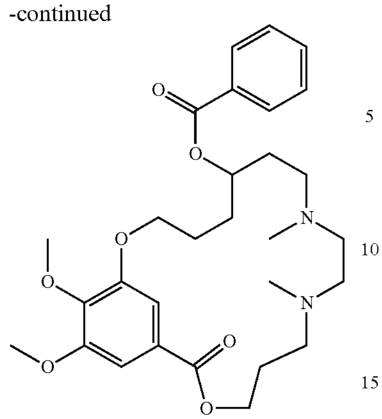

-continued

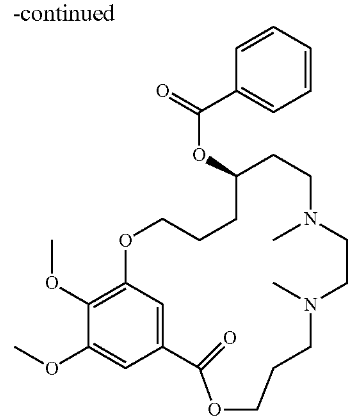

A mixture of intermediate compound 134 (27 mg, 0.06 mmol, 1.0 equiv), benzoic acid (11.7 mg, 0.1 mmol, 1.5 equiv), EDC·HCl (24.4 mg, 0.13 mmol, 2.0 equiv) and DMAP (19.42 mg, 0.16 mmol, 2.50 equiv) in DCM (2 mL) was stirred for 2 h at room temperature. The reaction was then quenched with a saturated solution of NH4Cl (2 mL), extracted with DCM (3×5 mL). The combined organic layers were dried over Na2SO4 and concentrated under reduced pressure. The crude product was purified by preparative HPLC (column: SunFire Prep C18 OBD 5 um, 19×150 mm, mobile phase: CH3CN in 0.05% HCOOH, 5% to 25% in 7 min; detector UV254 nm) to give the compound 35 (7 mg, 18% yield) as a off-white solid.

LC-MS (ES+) m/z: 529 (M+H)+ (calculated: 528.3)

1H NMR (300 MHz, DMSO-d6) δ ppm 8.21 (s, 2H), 7.97-7.94 (m, 2H), 7.68-7.63 (m, 1H), 7.54-7.49 (m, 2H), 7.30 (s, 1H), 7.25 (s, 1H), 5.18 (br, 1H), 4.32-4.30 (m, 2H), 4.18-4.16 (m, 2H), 3.64 (s, 3H), 3.61 (s, 3H), 2.68-2.36 (m, 8H), 2.21 (s, 3H), 2.17 (s, 3H), 1.86-1.64 (m, 8H).

Compound 36:

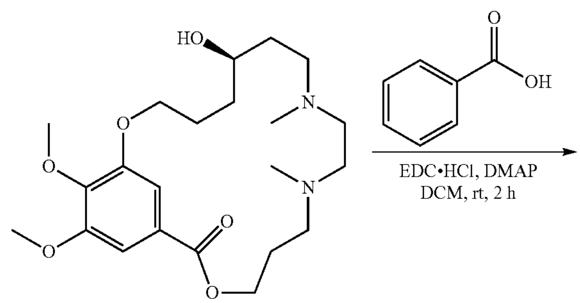

A mixture of intermediate compound 135 (100 mg, 0.24 mmol, 1.0 equiv), benzoic acid (585 mg, 0.47 mmol, 2.0 equiv), EDC·HCl (68 mg, 0.35 mmol, 1.5 equiv) and DMAP (58 mg, 0.47 mmol, 2.0 equiv) in DCM (5 mL) was stirred for 2 h at room temperature. The reaction was then quenched with a saturated solution of NH4Cl (5 mL) the resulting mixture was extracted with DCM (3×5 mL). The combined organic layers were washed with brine (5 mL), dried over Na2SO4 and concentrated under reduced pressure. The crude product was purified by preparative HPLC (column: SunFire Prep C18 OBD 5 um, 19×150 mm, mobile phase: MeCN in 0.1% NH3·H2O, 7% to 30% in 8 min; detector UV 254 nm), and then by preparative Chiral-HPLC (Column: XA-YMC Cellulose-SC, 4.6×100 mm, 3 um; Mobile Phase A: n-Hexane:DCM=(3:1)/IPA (0.1% DEA)=90/10; Flow rate: 1 mL/min; Gradient: 0% B to 0% B; Injection Volume: 5 ul) to give the compound 36 (40 mg, 32% yield) as an off-white solid.

LC-MS (ES+) m/z: 529 (M+H)+ (calculated: 528.3)

CHIRAL-HPLC (Column: YMC Cellulose-SC, 100×4.6 mm, 3 μm 119IA70110, Mobile Phase, A: n-Hexane/DCM=3/1; B: Isopropanol (0.1% DEA); Flow Rate: 1 mL/min; Conc. of Pump B: 10%; Detection: 254 nm; RT (min): 3.27; ee: 99.8%.

1H NMR (300 MHz, DMSO-d6) δ ppm 7.96-7.93 (m, 2H), 7.67-7.65 (m, 1H), 7.53-7.51 (m, 2H), 7.29 (s, 1H), 7.24 (s, 1H), 5.17 (br, 1H), 4.31-4.26 (m, 2H), 4.17-4.15 (m, 2H), 3.83 (s, 3H), 3.73 (s, 3H), 2.73-2.30 (m, 8H), 2.17 (s, 3H), 2.14 (s, 3H), 1.83-1.66 (m, 8H).

Compound 37:

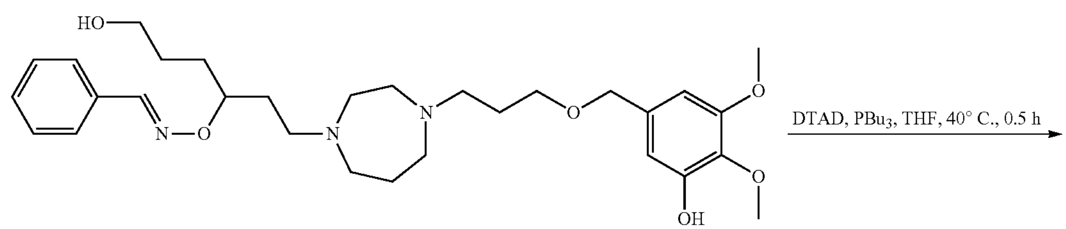

-continued

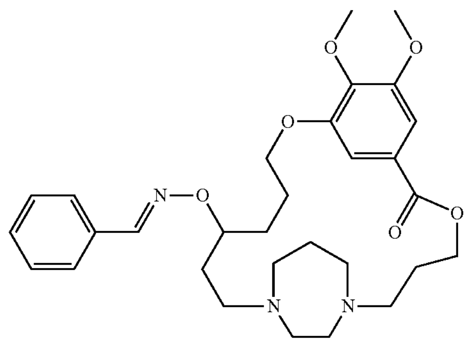

A solution of DTAD (0.74 g, 3.0 mmol, 1.5 equiv) and n-butylphosphine (0.60 g, 3.0 mmol, 1.5 equiv) in dry THF (20 mL) was stirred under nitrogen for 15 min, after which a solution of intermediate compound 111 (1.1 g, 2.0 mmol, 1.0 equiv) in THF (13 mL) was added. The mixture was stirred for 30 min at 40° C., and then quenched by the addition of H2O (50 mL). The resulting solution was extracted with EtOAc (2×15 mL). The combined organic layers were dried over Na2SO4 and concentrated. The residue was purified by preparative HPLC (Column (C18-I, 20-40 m); mobile phase (MeOH/H2O=30% to 100%: 7 min; 100%: 3 min); Detector (254 and 220 nm)) to give the compound 37 (0.48 g, 45% yield) as an off-white solid.

LC-MS (ES+) m/z: 540 (M+H)+ (calculated: 539.3).

1H NMR (300 MHz, DMSO-d6) δ 8.31 (s, 1H), 7.57-7.55 (m, 2H), 7.46-7.35 (m, 4H), 7.32 (s, 1H), 4.51-4.48 (m, 1H), 4.32-4.20 (m, 3H), 4.11-4.05 (m, 1H), 3.84 (s, 3H), 3.74 (s, 3H), 2.89-2.84 (m, 1H), 2.72-2.54 (m, 11H), 1.97-1.71 (m, 10H).

Compound 38:

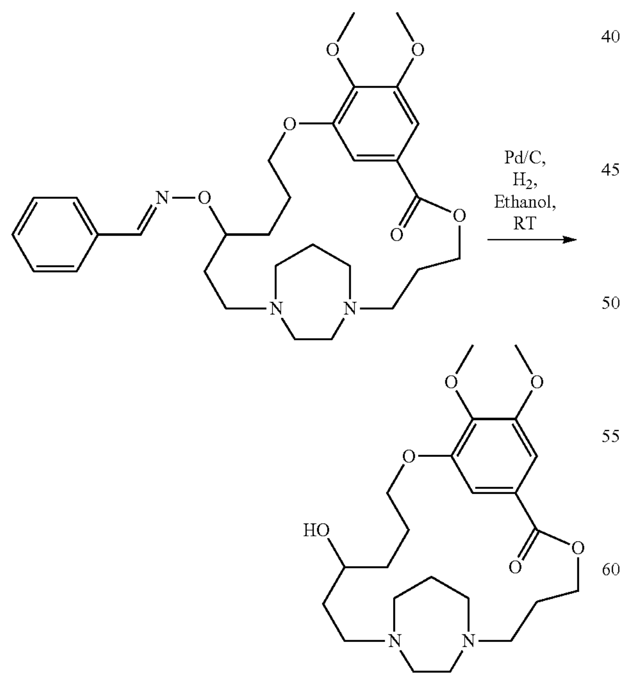

A suspension of compound 37 (300 mg, 0.56 mmol, 1.0 equiv) and Pd/C (30 mg) in MeOH (5 mL) was stirred for 2 h at room temperature under H2 (1 atm). The resulting mixture was then filtered; and the solid residue was washed with MeOH (15 mL). The filtrate was concentrated under reduced pressure, and the residue was purified by preparative HPLC (Column: Atlantis Prep T3 OBD Column, 19*150 mm 5 um; Mobile Phase A: Water (0.1% FA), Mobile Phase B: ACN; Flow rate: 20 mL/min; Gradient: 15% B to 35% B in 7 min, 35% B; Wave Length: 220 nm)) to give the compound 38 (HCOOH salt, 166 mg, 62% yield) as an off-white solid.

LC-MS (ES+) m/z: 437 (M+H)+ (calculated: 436.2)

1H NMR (300 MHz, DMSO-d6) δ 8.22 (s, 1H), 7.32 (s, 1H), 7.22 (s, 1H), 4.27-3.99 (m, 4H), 3.83 (s, 3H), 3.80-3.76 (m, 4H), 2.92-2.87 (m, 1H), 2.75-2.46 (m, 11H), 1.97-1.88 (m, 10H).

Compound 39:

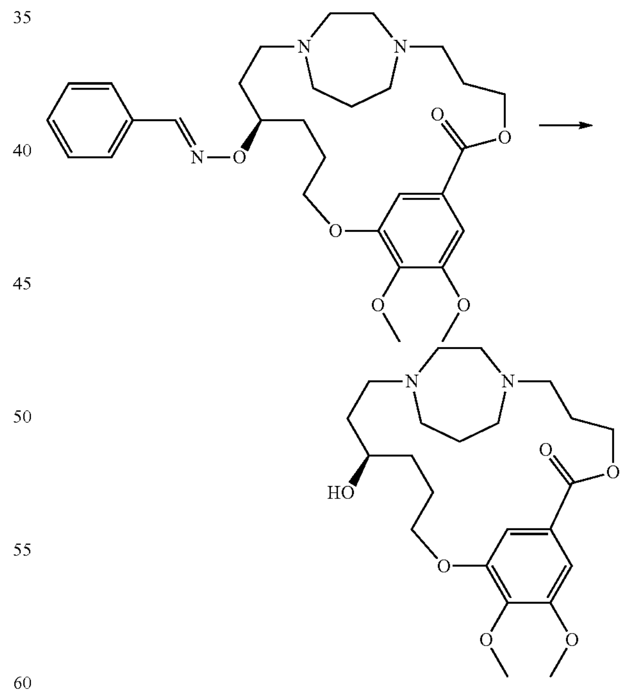

A solution of compound 119 (100 mg, 0.19 mmol, 1.0 equiv) and Pd/C (10 mg) in MeOH (4 mL) was stirred for 2 h at room temperature under H2 (1 atm). The resulting mixture was filtered; the solid was washed with MeOH (10 mL) and concentrated under reduced pressure. The crude product was purified by preparative HPLC (Column: Atlantis Prep T3 OBD Column, 19*150 mm 5 um; Mobile Phase A: Water (0.1% FA), Mobile Phase B: ACN; Flow rate: 20 mL/min; Gradient: 15% B to 35% B in 7 min, 35% B; Wave Length: 220 nm) to give the compound 39 (HCOOH salt, 55 mg, 62% yield) as off-white solid.

LC-MS (ES+) m/z: 437 (M+H)+ (calculated: 436.3).

Chiral HPLC: retention time=3.29 min, ee=100%

1H NMR (300 MHz, DMSO-d6) δ ppm 8.22 (s, 1H), 7.32 (s, 1H), 7.22 (s, 1H), 4.27-3.99 (m, 4H), 3.83 (s, 3H), 3.80-3.76 (m, 4H), 2.92-2.87 (m, 1H), 2.75-2.46 (m, 11H), 1.97-1.88 (m, 10H).

Compound 40:

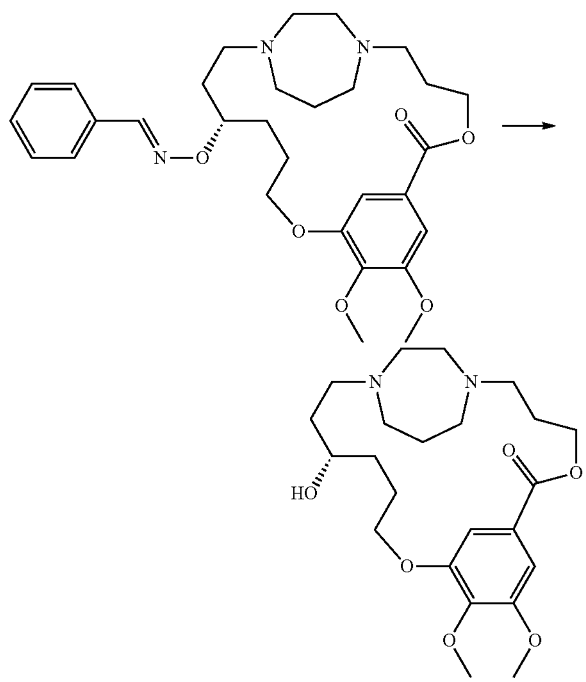

Compound 40 (HCOOH salt, 55 mg, 62% yield) as off-white solid has been obtained from compound 120 following the procedure described for compound 39.

LC-MS (ES+) m/z: 437 (M+H)+ (calculated: 436.3).

Chiral HPLC: retention time=3.89 min, ee=99%

1H NMR (300 MHz, DMSO-d6) δ ppm 8.22 (s, 1H), 7.32 (s, 1H), 7.22 (s, 1H), 4.27-3.99 (m, 4H), 3.83 (s, 3H), 3.80-3.76 (m, 4H), 2.92-2.87 (m, 1H), 2.75-2.46 (m, 11H), 1.97-1.88 (m, 10H).

Compound 107 and Compound 118:

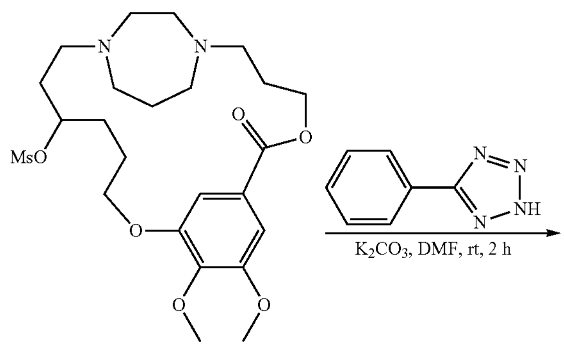

-continued

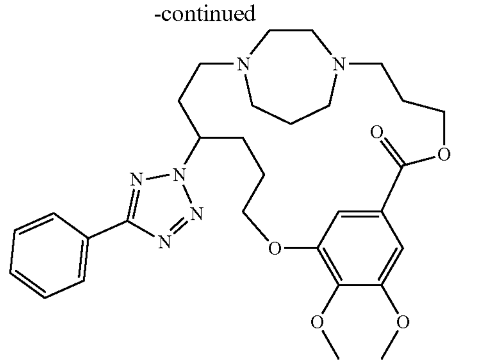

+ compound 108

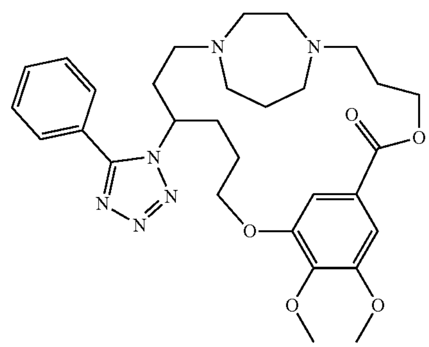

compound 118

K2CO3 (35 mg, 0.25 mmol, 2.0 equiv) was added to a solution of 1H-tetrazole, 5-phenyl-(28 mg, 0.19 mmol, 1.5 equiv) in DMF (1.3 mL) and the reaction mixture stirred at 50° C. for 1 h. The mixture was cooled to room temperature and the intermediate compound 137 (65 mg, 0.13 mmol, 1.0 equiv) was added. The resulting mixture was stirred for 16 h at room temperature, and then was filtered and the filtrate was purified by preparative HPLC (Column: SunFire Prep C18 OBD Column, 19×150 mm, 5 μm 10 nm; Mobile Phase A: Water (0.05% TFA), Mobile Phase B: ACN; Flow rate: 18 mL/min; Gradient: 15% B to 40% B in 7 min, 40% B; Wave Length: 220 nm) to give the compound 108 (TFA salt, 8.1 mg, 11% yield) as off-white solid and the compound 118 (TFA salt, 3.3 mg, 5% yield) as off-white solid.

Compound 108:

LC-MS (ES+) m/z: 565 (M+H)+ (calculated: 564.3).

1H-NMR (400 MHz, DMSO-d6) δ ppm 9.38 (br, 1H), 8.07-8.05 (m, 2H), 7.57-7.55 (m, 3H), 7.44 (s, 1H), 7.23 (s, 1H), 5.37 (br, 1H), 4.38-4.09 (m, 5H), 3.83 (s, 3H), 3.77 (s, 3H), 3.73-3.56 (m, 6H), 3.01 (br, 2H), 2.77 (br, 1H), 2.30-1.89 (m, 11H), 1.51 (br, 1H).

Compound 118:

LC-MS (ES+) m/z: 565 (M+H)+ (calculated: 564.3).

1H-NMR (400 MHz, DMSO-d6) δ ppm 9.70 (br, 1H), 8.07-8.05 (m, 2H), 7.57-7.55 (m, 3H), 7.30-7.27 (m, 1H), 7.20 (s, 1H), 4.84-4.75 (m, 2H), 4.27-4.11 (m, 5H), 3.83 (s, 3H), 3.73 (s, 3H), 3.55-3.07 (m, 6H), 2.91-2.67 (m, 3H), 2.40 (br, 1H), 2.32 (br, 1H), 2.12-2.03 (m, 3H), 1.84-1.56 (m, 6H).

Compound 108:

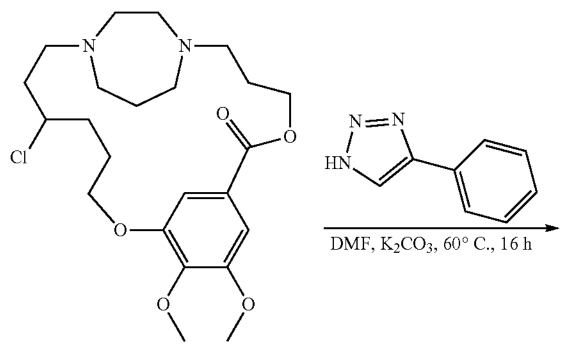

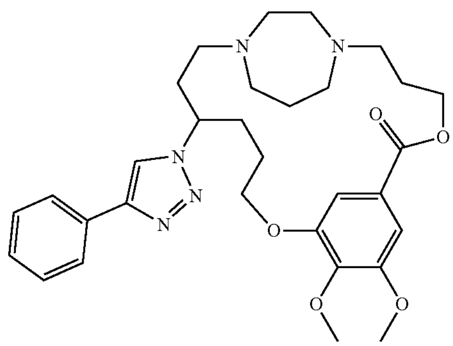

A mixture of intermediate compound 136 (70 mg, 0.15 mmol, 1.0 equiv), K2CO3 (42.5 mg, 0.31 mmol, 2.0 equiv) and 1H-1,2,3-triazole, 4-phenyl- (33.5 mg, 0.23 mmol, 1.5 equiv) in DMF (2 mL) was stirred for 16 h at 50° C. The reaction was then quenched with water (8 mL), and extracted with EtOAc (3×5 mL). The combined organic layers were washed with brine (8 mL), dried over anhydrous Na2SO4, and concentrated under reduced pressure. The crude product was purified by preparative HPLC (Column: Sunfire Prep C18 OBD Column, 50×250 mm, 5 μm; Mobile Phase A: Water (0.05% TFA), Mobile Phase B: ACN; Flow rate: 65 mL/min; Gradient: 10% B to 45% B in 12 min, 45% B; Wave Length: 220 nm) to give the compound 108 15 mg (TFA salt, 15 mg, 17% yield) as an off-white solid.

LC-MS (ES+) m/z: 564 (M+H)+ (calculated: 563.3).

1HNMR (300 MHz, DMSO-d6) δ ppm 9.81 (br, 1H), 8.27 (s, 1H), 7.85-7.82 (m, 2H), 7.48-7.21 (m, 5H), 4.69-4.54 (m, 2H), 4.27-4.18 (m, 4H), 3.83 (s, 3H), 3.73 (s, 3H), 3.63-2.87 (m, 10H), 2.21-1.45 (m, 11H).

Compound 110:

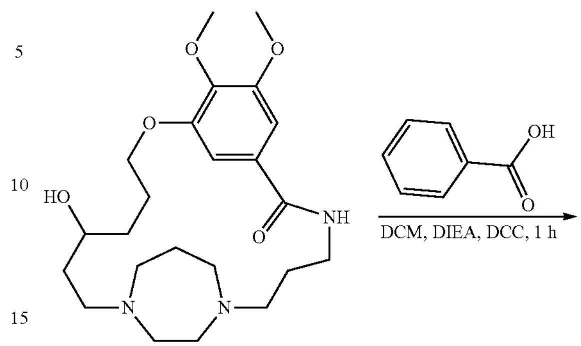

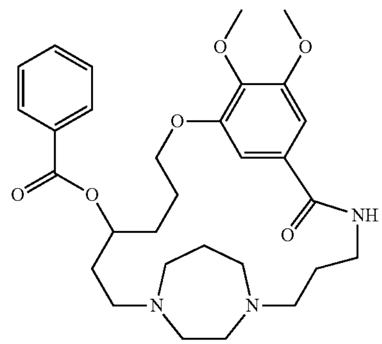

Compound 117 (21 mg, 0.048 mmol, 1.0 eq) was solubilized in DCM (0.4 mL), DIEA (12.45 mg, 0.096 mmol, 2.0 eq), DCC (19.91 mg, 0.096 mmol, 2.0 eq) and benzoic acid (7.06 mg, 0.058 mmol, 1.2 eq) were added at room temperature. The resulting solution was stirred for 1 h at room temperature. The reaction solution was diluted with H2O (1 mL) and extracted DCM (2×5 mL), the organic layer was dried over Na2SO4 and concentrated. The residue was purified by preparative HPLC (Column: SunFire Prep C18 OBD Column, 19*150 mm, 5 m 10 nm; Mobile Phase A: Water (0.05% TFA), Mobile Phase B: ACN; Flow rate: 20 mL/min; Gradient: 15% B to 40% B in 7 min, 40% B; Wave Length: 220 nm; RT: 6.9 min) to give the compound 110 (10 mg, 32% yield as an off-white solid.

LC-MS (ES+) m/z: 540.4 (M+H)+, (calculated 539.3).

1H-NMR (300 MHz, MeOH-d4) δ ppm 1.96-2.35 (m, 10H), 3.32-3.70 (m, 14H), 3.85 (s, 3H), 3.94 (s, 3H), 4.30-4.35 (m, 2H), 5.30-5.36 (m, 1H), 7.28 (s, 1H), 7.45 (s, 1H), 7.49-7.53 (m, 2H), 7.63-7.68 (s, 1H), 8.05-8.08 (s, 2H).

Compound 114:

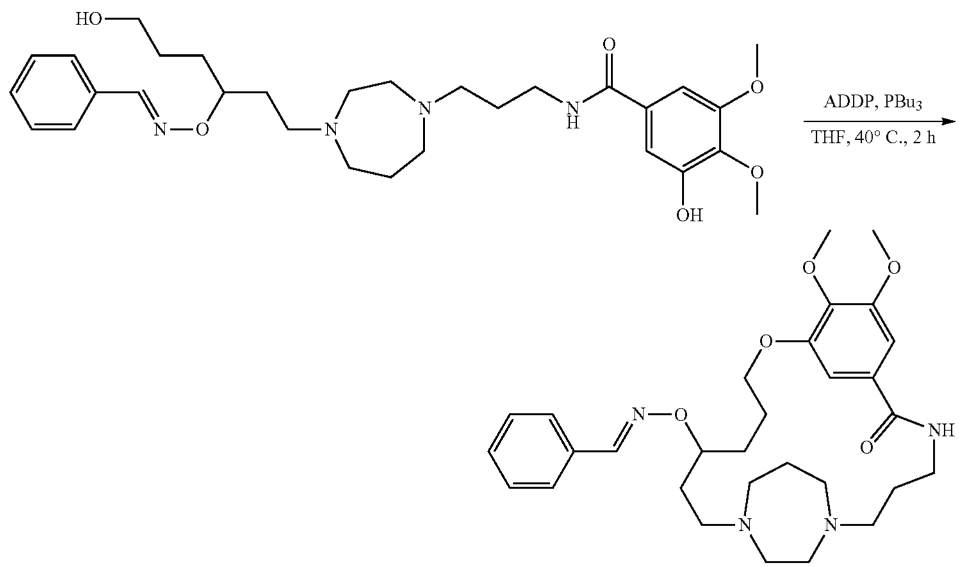

-continued

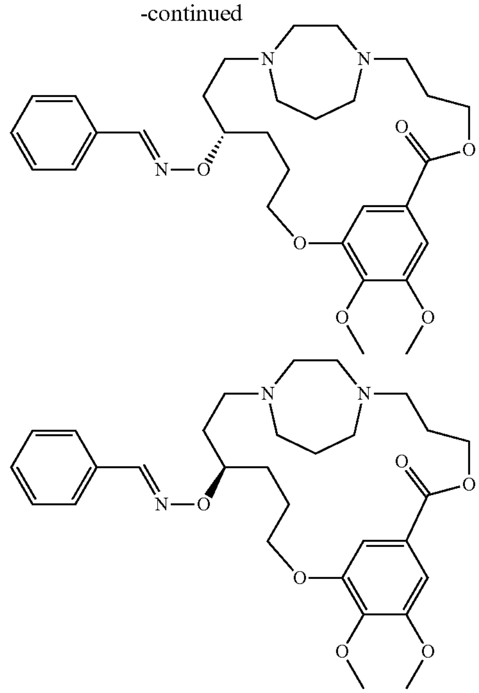

To a stirred mixture of intermediate compound 114 (3.6 g, 6.5 mmol, 1.0 equiv) and ADDP (3.24 g, 12.9 mmol, 2.0 equiv) in THF (100 mL) was added n-butylphosphine (2.62 g, 12.9 mmol, 2.0 equiv) in portions at room temperature under nitrogen atmosphere. The resulting mixture was stirred for additional 2 h at 40° C., and then allowed to cool down to room temperature. The reaction was quenched with saturated aqueous solution of NH4Cl (100 mL) at room temperature. The resulting mixture was extracted with EtOAc (3×100 mL). The combined organic layers were dried over Na2SO4 and concentrated under reduced pressure. The residue was purified by preparative HPLC (Column: C18-I, 20-40 m; mobile phase: MeOH/H2O=30% to 100%, 7 min; 100%, 3 min; detector 254 and 220 nm) to give the compound 114 (1.5 g, 43% yield) as a yellow oil.

LC-MS (ES+) m/z: 539 (M+H)+ (calculated: 538.3).

1H-NMR (300 MHz, MeOD-d4) δ ppm 8.09 (s, 1H), 7.57-7.54 (m, 2H), 7.37-7.33 (m, 3H), 7.18-7.14 (m, 2H), 4.50-4.49 (m, 1H), 4.28-4.24 (m, 2H), 3.89 (s, 3H), 3.84 (s, 3H), 3.54-3.48 (m, 2H), 2.84-2.54 (m, 12H), 1.96-1.73 (m, 10H).

Compound 115 and Compound 116:

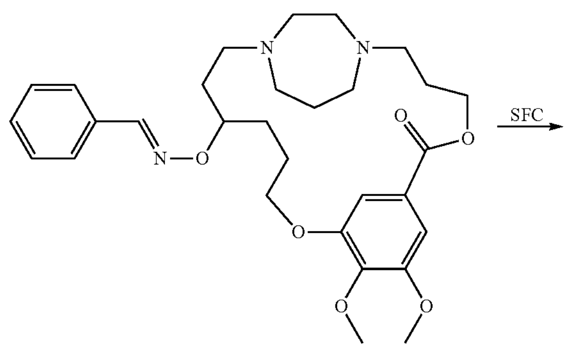

The enantiomers of the compound 114 (150 mg) was separated by SFC with the following conditions: Column: CHIRAL ART Cellulose-SC, 5*25 cm, 5 μm; Mobile Phase A: HEX:DCM=1:1 (0.1% DEA)-HPLC, Mobile Phase B: IPA (0.2% DEA); Flow rate: 100 mL/min; Gradient: 50% B to 50% B in 11 min; Wave Length: 220 nm; RT1 (min): 10.0; Sample Solvent: IPA:DCM=1:1; Injection Volume: 5 mL; Number Of Runs: 25) to give the compound 115 (50 mg, 34% yield) and compound 116 (43 mg, 28% yield).

Compound 115:

LC-MS (ES+) m/z: 539 (M+H)+ (calculated: 538.3)

1H-NMR (300 MHz, MeOD-d4) δ ppm 8.09 (s, 1H), 7.57-7.54 (m, 2H), 7.37-7.33 (m, 3H), 7.18-7.14 (m, 2H), 4.50-4.49 (m, 1H), 4.28-4.24 (m, 2H), 3.89 (s, 3H), 3.84 (s, 3H), 3.54-3.48 (m, 2H), 2.84-2.54 (m, 12H), 1.96-1.73 (m, 10H).

Compound 116:

LC-MS (ES+) m/z: 539 (M+H)+ (calculated: 538.3)

1H-NMR (300 MHz, MeO-d4) δ ppm 8.09 (s, 1H), 7.57-7.54 (m, 2H), 7.37-7.33 (m, 3H), 7.18-7.14 (m, 2H), 4.50-4.49 (m, 1H), 4.28-4.24 (m, 2H), 3.89 (s, 3H), 3.84 (s, 3H), 3.54-3.48 (m, 2H), 2.84-2.54 (m, 12H), 1.96-1.73 (m, 10H).

Compound 117:

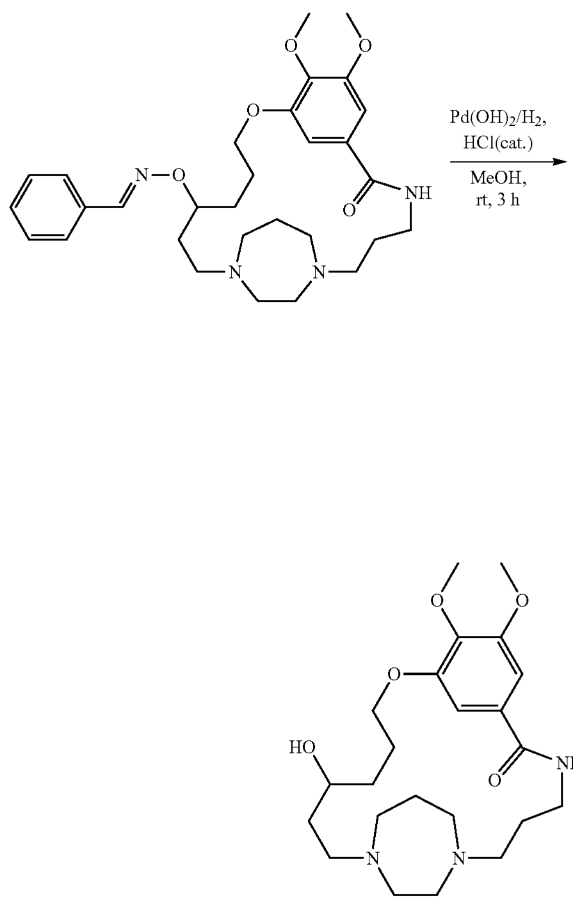

A mixture of compound 114 (100 mg, 0.19 mmol, 1.0 equiv) and palladium hydroxide on carbon (20 mg) in MeOH (5 mL) was stirred under an H2 atmosphere for 2 h at room temperature. The resulting suspension was filtered, the filtrate was concentrated under reduced pressure, and the crude product (100 mg) was purified by preparative HPLC (Column: SunFire Prep C18 OBD Column, 19*150 mm, 5 m 10 nm; Mobile Phase A: Water (0.1% TFA), Mobile Phase B: ACN; Flow rate: 20 mL/min; Gradient: 15% B to 38% B in 7.2 min, 40% B; Wave Length: 220 nm; RT: 5.3 min) to give the compound 117 (TFA salt, 49 mg, 50% yield) as a light yellow solid.

LC-MS (ES+) m/z: 436 (M+H)+, (calculated 435.3)

1H-NMR (300 MHz, MeOD-d4) δ ppm 7.39 (s, 1H), 7.24 (s, 1H), 4.32-4.26 (m, 2H), 3.91 (s, 4H), 3.82 (s, 3H), 3.67-3.30 (m, 14H), 2.42-2.40 (m, 2H), 2.12-1.69 (m, 8H).

Compound 119:

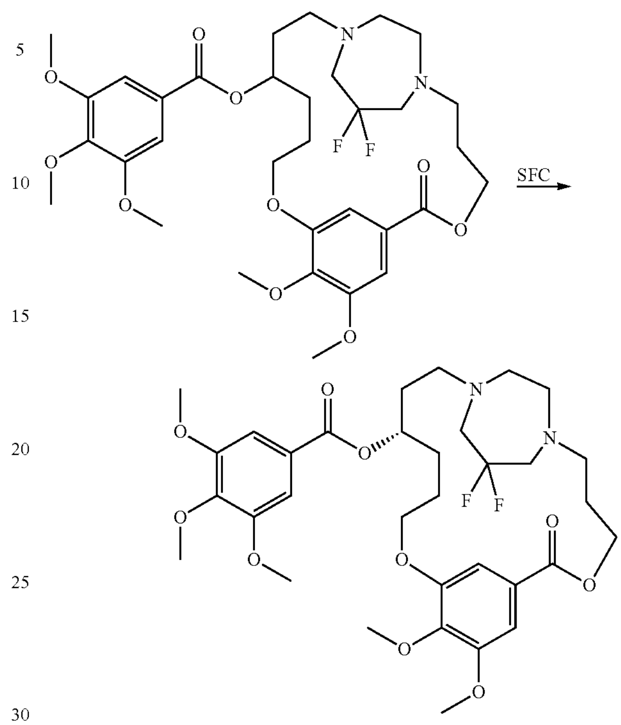

Compound 119

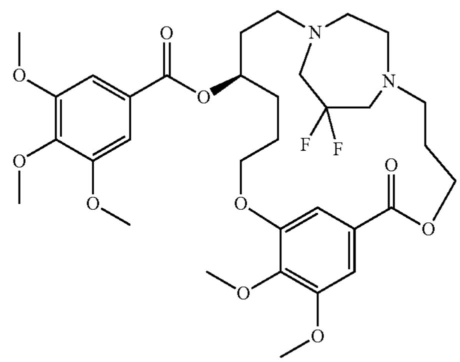

Compound 6

Compound 119 was separated from compound 4 by preparative SFC following the conditions Chiral SFC method A.

LCMS (ESI position ion) m/z: 667.3 (M+H)+ (calculated: 666.3)

SFC: retention time=1.649 min, ee=100%

1H NMR (400 MHz, MeOD) δ 7.46 (d, J=1.8 Hz, 1H), 7.34 (d, J=1.6 Hz, 1H), 7.30 (s, 2H), 5.56 (br d, J=4.4 Hz, 1H), 4.45-4.28 (m, 3H), 4.18-4.06 (m, 1H), 3.93-3.84 (m, 9H), 3.82 (d, J=1.2 Hz, 6H), 3.24 (br t, J=13.9 Hz, 2H), 3.09-2.87 (m, 6H), 2.87-2.79 (m, 1H), 2.78-2.60 (m, 3H), 2.09-1.74 (m, 8H)

Compound 120:

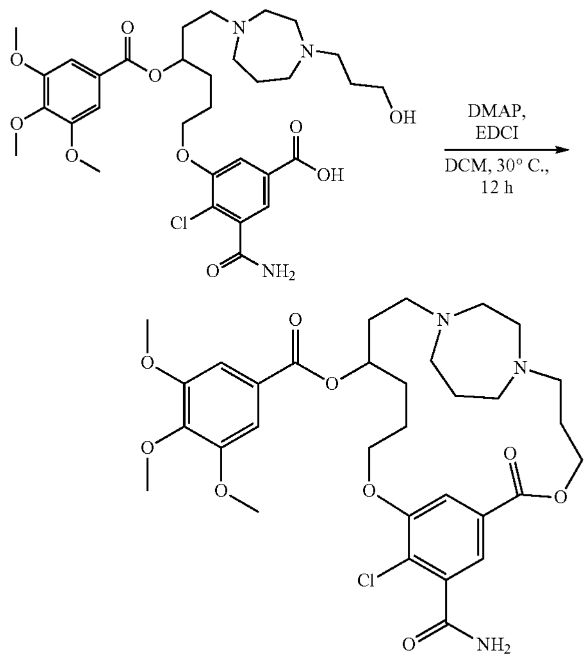

To a solution of intermediate compound 89 (30 mg, 45.03 umol, 1 eq) in DCM (30 mL) was added DMAP (22.00 mg, 180.12 umol, 4 eq) and EDCI (25.90 mg, 135.09 umol, 3 eq). The reaction mixture was stirred at 30° C. for 4 hrs. The reaction mixture was added MeOH (3 mL) and H2O (50 mL). The aqueous layer was extracted with DCM/MeOH (10/1, 2×30 mL). The combined organic layers were dried over Na2SO4, filtered and concentrated under reduced. The residue was purified by prep-HPLC (column: Phenomenex luna C18 150*25 mm*10 um; mobile phase: [water (0.225% FA)-ACN]; B %: 12%-42%, 10 min) to give the compound 120 (1.7 mg, 5% yield) as a white solid.

LCMS (ESI position ion) m/z: 648.3 (M+H)+ (calculated: 647.3)

1H NMR (400 MHz, MeOD-d4) δ 8.60-8.48 (m, 1H), 7.81 (s, 1H), 7.70 (d, J=1.5 Hz, 1H), 7.33 (s, 2H), 5.61-5.53 (m, 1H), 4.60-4.54 (m, 1H), 4.48-4.37 (m, 2H), 4.20-4.14 (m, 1H), 3.87 (s, 6H), 3.83 (s, 3H), 3.47-3.40 (m, 1H), 3.28-3.17 (m, 3H), 3.12-3.04 (m, 1H), 2.94-2.88 (m, 1H), 2.84-2.77 (m, 1H), 2.68-2.58 (m, 4H), 2.30-2.17 (m, 2H), 2.01-1.84 (m, 9H).

Compound 122:

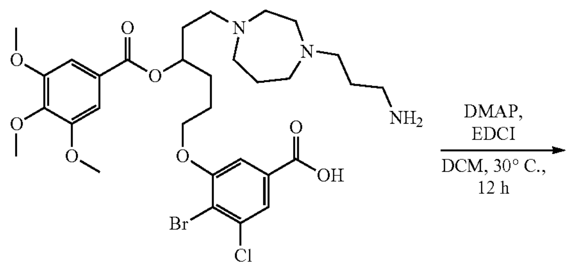

-continued

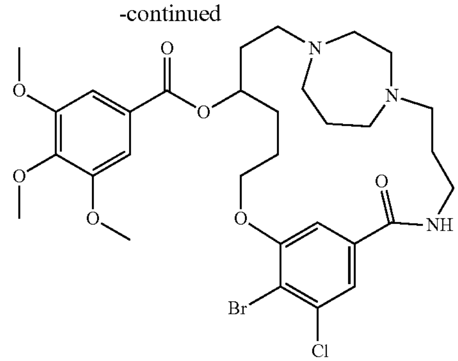

To a solution of intermediate compound 103 (25 mg, 35.66 umol, 1 eq) in DCM (10 mL) was added EDCI (20.51 mg, 106.98 umol, 3 eq) and DMAP (17.43 mg, 142.64 umol, 4 eq) at 25° C. Then the reaction mixture was stirred at 25° C. for 4 hr. The reaction mixture was filtered and concentrated under reduced pressure. The residue was purified by preparative HPLC (column: Phenomenex Synergi C18 150*25 mm*10 um; mobile phase: [water (0.225% FA)-ACN]; B %: 16%-46%, 10 min) to give the compound 122 (22 mg, 90% yield) as an off-white solid.

LCMS (ESI position ion) m/z: 682.3 (M+H)+ (calculated: 681.2)

1H NMR: (400 MHz, MeOD) δ 7.64-7.53 (m, 2H), 7.34 (s, 2H), 5.44 (br d, J=4.2 Hz, 1H), 4.51-4.28 (m, 2H), 3.88-3.79 (m, 9H), 3.71-3.45 (m, 2H), 3.10-2.74 (m, 12H), 2.18-1.88 (m, 10H)

Compound 123:

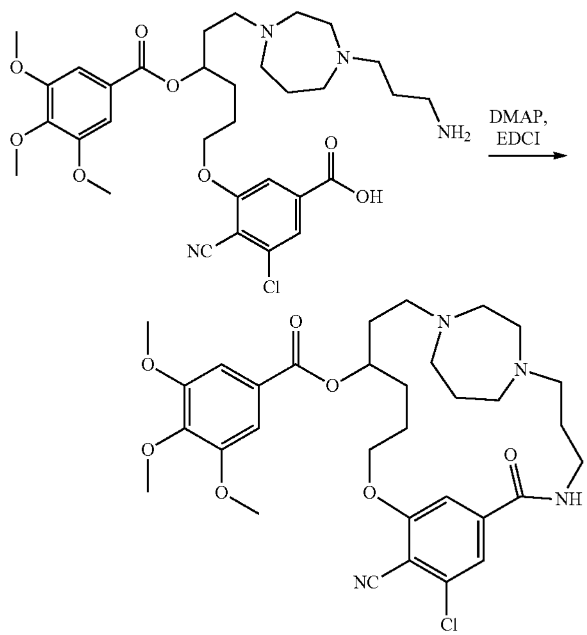

To a solution of intermediate compound 105 (10 mg, 15.45 umol, 1 eq) in DCM (8 mL) was added EDCI (8.89 mg, 46.36 umol, 3 eq) and DMAP (7.55 mg, 61.81 umol, 4 eq)) at 25° C. The reaction mixture was stirred at 25° C. for 4 hr. The reaction mixture was filtered and concentrated under reduced pressure. The residue was purified by preparative HPLC (column: Phenomenex Gemini-NX C18

75*30 mm*3 um; mobile phase: [water (0.225% FA)-ACN]; B %: 15%-4%, 5 min) to give the compound 123 (5.99 mg, 62% yield) as an off-white solid.

LCMS (ESI position ion) m/z: 629.2 (M+H)+ (calculated: 628.3)

1H NMR (400 MHz, MeOD-d4) δ 8.53 (s, 1H) 7.70 (s, 1H), 7.61 (s, 1H), 7.33 (s, 2H), 5.45 (br s, 1H), 4.66-4.35 (m, 2H), 3.90-3.76 (m, 9H), 3.70-3.52 (m, 2H), 3.19-2.72 (m, 12H), 2.17-1.83 (m, 10H)

Compound 124 and Compound 125:

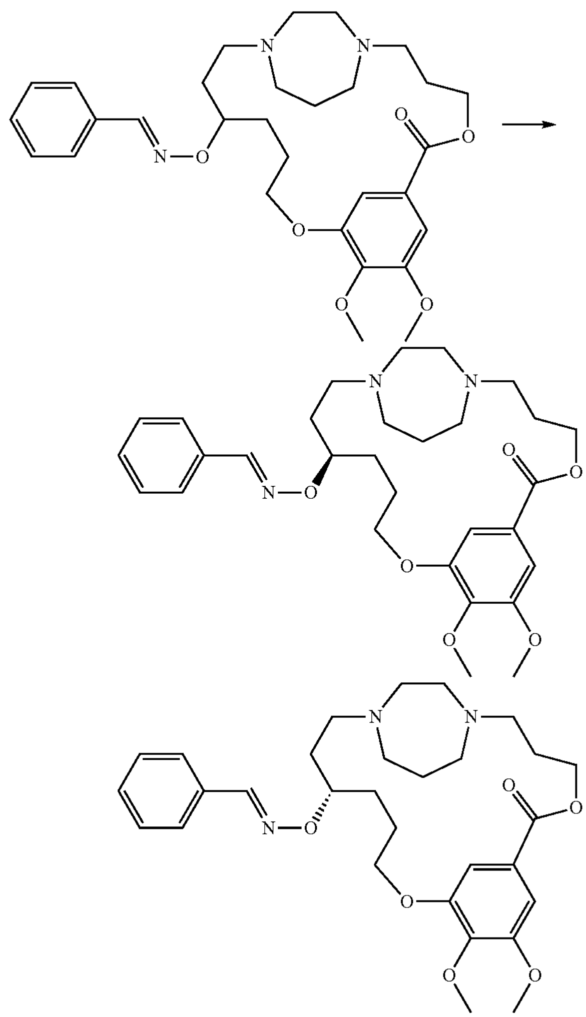

Enantiomers of compound 37 (480 mg) was separated by Chiral-HPLC with the following conditions (Column: CHIRAL ART Cellulose-SB, 3*25 cm, 5 μm; Mobile Phase A: CO2, Mobile Phase B: MeOH:DCM=1:1; Flow rate: 80 mL/min; Gradient: isocratic 40% B; Column Temperature (35° C.); Back Pressure (bar): 100; Wave Length: 220 nm; RT1 (min): 2.62; RT2 (min): 4.38) to give the compound 119 (130 mg) as a white solid and compound 120 (120 mg) as a white solid.

Compound 124:

LC-MS (ES+) m/z: 540 (M+H)+ (calculated: 539.3).

Chiral HPLC: retention time=1.78 min, ee=99.5%

1H NMR (300 MHz, DMSO-d6) δ ppm 8.31 (s, 1H), 7.57-7.55 (m, 2H), 7.46-7.35 (m, 4H), 7.32 (s, 1H), 4.51-4.48 (m, 1H), 4.32-4.20 (m, 3H), 4.11-4.05 (m, 1H), 3.84 (s, 3H), 3.74 (s, 3H), 2.89-2.84 (m, 1H), 2.72-2.54 (m, 11H), 1.97-1.71 (m, 10H).

Compound 125:

LC-MS (ES+) m/z: 540 (M+H)+ (calculated: 539.3).

Chiral HPLC: retention time=2.19 min, ee=99.5%

1H NMR (300 MHz, DMSO-d6) δ ppm 8.31 (s, 1H), 7.57-7.55 (m, 2H), 7.46-7.35 (m, 4H), 7.32 (s, 1H), 4.51-4.48 (m, 1H), 4.32-4.20 (m, 3H), 4.11-4.05 (m, 1H), 3.84 (s, 3H), 3.74 (s, 3H), 2.89-2.84 (m, 1H), 2.72-2.54 (m, 11H), 1.97-1.71 (m, 10H).

II. Biology Examples

Example II.1 Assay for ENT1 Activity

Example II.1.a Binding Assay

Purpose

The present assay aims at showing that the compounds of the present invention can bind to human ENT1. The principle of the assay is a competition between the compounds of this invention and Sahenta-DY647, an ENT1 inhibitor that emits fluorescence (Ex=630 nm, Em=670 nm). By measuring the fluorescence at the end of the assay we could assess the binding potency of the compounds of the present invention.

Method

JAR cells expressing ENT1 were bought from ATCC® (HTB-144™). Cells were cultured in RPMI 1640 medium (LONZA®, #BE12-702F/U1) supplemented with 10% FBS (GIBCO®, #10270-106), 10 mM Hepes (LONZA®, #BE17-737E), 1 mM Sodium Pyruvate (LONZA®, #BE13-115E) and 2% Penicillin/Streptomycin (LONZA®, #DE17-603E) at 37° C. and 5% CO2.

The assay was conducted on the following buffer: HBSS (LONZA®, #LO-527F) supplemented with 10 mM Hepes (LONZA®, #BE17-737E) and 0.1% BSA (Miltenyi®, #130-091-376) on the day of the assay. JAR cells were resuspended in the described buffer. Compounds of the present invention and Sahenta-DY647 were diluted 200× in the described buffer.

A total of 50 000 cells were pre-incubated for 30 min at 4° C. with the compounds of the present invention before adding the corresponded IC90 of Sahenta-DY647 (100 nM) and incubate once more for 30 min at 4° C. The total volume of the reaction was 100 μL (50 μL of cells, 25 μL of the compounds of the present invention and 25 μL of Sahenta-DY647) in a 96 well plate, U-bottom (Greiner®, #650-180). The plates were washed 2× by centrifugation (4 min, 400 rcf at 4° C.) in the same buffer. Cells were resuspended in 70 μL of the buffer and 50 μL was transferred to a Black 384 Optiplate (PerkinElmer®, #6007279). Fluorescence (Ex=630 nm, Em=670 nm) was acquired on a Spectramax i3x (Molecular Devices®).

Results

Results obtained from this protocol are summarized in Table 5.

Example II.1.b Functional Assay: Uridine Transport Inhibition Assay

Purpose

The aim of this study was to determine the potency of equilibrative nucleoside transporter 1 (ENT1) inhibitors by measuring ENT1-mediated transport is the cellular uptake assay. The human ENT1 transporter can be stably expressed in Madin-Darby Canine Kidney II (MDCKII) cells via transduction. Uridine is efficiently transported by ENT1 and is used as probe in the assay as 3H-uridine. The interaction is detected as the modulation of the initial rate of 3H-uridine transport by human ENT1 into MDCKII-ENT1-LV cells stably expressing ENT1 uptake transporter.

Results

Results obtained from this protocol are summarized in Table 6.

TABLE 3

| Assay parameters | | | | |
|---|---|---|---|---|
| Transporter | Incubation time (min) and temperature | Probe substrate (concentration) | Reference inhibitor (concentration) | Signal/Noise ratio |
| ENT1 | 1 min at 25 ° C. | Uridine (1 μM) | Dilazep (2 μM) | >3 |

Example II.1.c Functional Assay: T Cell Proliferation Assay

Purpose

The aim of this study was to determine the potency of equilibrative nucleoside transporter 1 (ENT1) inhibitors to rescue proliferation by stimulated primary human T cells incubated in the presence of 100 uM Adenosine triphosphate (ATP), in baseline conditions (condition A) or in the presence of various proteins known to bind small molecules (condition B).

Condition A: X-VIVO15

Condition B: X-VIVO15, 2% Human Serum Albumine (HSA) and 0.1% α-1-Acid Glycoprotein (AAG)

TABLE 4

| Materials for Functional Assay | | |
|---|---|---|
| Product | Source | Cat number |
| RPMI 1640 | LONZA | BE12-702F/U1 |
| FBS | GIBCO | 10270-106 |
| X-VIVO15 | Lonza | BE02-060Q |
| Human Serum Albumine (HSA) | Sigma-Aldrich | A1653 |
| α1-Acid Glycoprotein (AAG) | Sigma-Aldrich | G9885 |
| Dynabeads CD3/28 activation beads | Thermo Fisher Scientific | 11132D |
| CFDA, SE | Life Technologies | C1157 |
| EOS502085_1 (Dipyridamole) | Tocris | 0691 |
| ATP | Sigma Aldrich | A6419-1G |

Method

Cryopreserved purified human CD3+ T cells were thawed and washed twice with RPMI1640 medium, UltraGlutamine containing 10% hiFBS.

Cells were suspended in PBS containing 10% hiFBS. Cells were stained with CFSE by adding 2 μM solution in PBS, to get a final 1 μM CFSE solution. Cells were incubated while rotating for 5 minutes. Reaction was stopped by adding PBS with 10% FBS and cells were centrifuged for 5 minutes at 1500 rpm.

Cells were resuspended at 1.6×106 cells/mL, either in X-VIVO15 medium or in 4% Human Serum Albumin and 0.2% α-1-Acid Glycoprotein. 50 μL of cell suspension (8×104 T cells) was added to wells of sterile round-bottom 96-well plates. Cells were activated by adding 50 μL of anti-CD3 anti-CD28 coated microbeads, suspended either in XVIVO-15 medium or in 4% HSA and 0.2% α-1-Acid Glycoprotein, at a ratio of one microbead per two cells.

Serial dilutions of the ENT1 inhibitors were prepared in X-VIVO15 from 10 mM stock solutions in DMSO, and 50 μL was added to the wells.

ATP powder was diluted in X-VIVO15, and 50 μL of this compound was added to the wells to reach a final assay concentration of 100 μM. Final volume of 200 μL.

The experiments were also performed in 384 well plates—all volumes reduced by a factor of 4 (12.5 μL) with a final volume of 50 μL.

Experiments were performed in duplicate. The cells were placed in a 37° C. humidified tissue culture incubator with 5% CO2 for 72 hours for 96 well plates, 96 hours for 384 well plates. After 72 or 96 hours, proliferation was measured determined by CFSE dilution via flow cytometry.

Results.

Results are detailed below in Table 6. Compounds of the invention have good ENT1 inhibitory properties.

Example II.2. Results of ENT1 Inhibition

Results

The potency as been determined in the binding assay as is reported in Table 5. The compound of the invention presents a similar potency as compared to dilazep against ENT1.

The IC50 has been binned following the ranges: IC50 below 0.0001 μM: ++++; IC50 below 0.001 μM: +++; IC50 between 0.002 μM; ++; IC50 between 0.02 and 0.5 μM; +, above 0.5 μM: −

TABLE 5

| Compounds | Binding Assay IC50 |
|---|---|
| Dilazep | ++ |
| Compound 1 | ++ |
| Compound 2 | ++ |
| Compound 3 | − |
| Compound 4 | ++ |
| Compound 5 | ++ |
| Compound 6 | ++ |
| Compound 8 | ++ |
| Compound 9 | −− |
| Compound 10 | ++ |
| Compound 11 | ++ |
| Compound 12 | − |
| Compound 13 | ++ |
| Compound 14 | ++ |
| Compound 15 | − |
| Compound 16 | + |
| Compound 17 | − |
| Compound 18 | ++ |
| Compound 19 | − |
| Compound 20 | − |
| Compound 21 | ++ |
| Compound 22 | + |
| Compound 23 | + |
| Compound 24 | + |
| Compound 25 | − |
| Compound 26 | − |
| Compound 28 | ++ |
| Compound 29 | ++ |
| Compound 30 | + |
| Compound 31 | ++ |
| Compound 32 | ++ |
| Compound 33 | − |
| Compound 34 | ++ |
| Compound 35 | ++ |
| Compound 36 | ++ |
| Compound 37 | + |
| Compound 38 | − |
| Compound 39 | − |
| Compound 40 | − |

TABLE 5-continued

| Compounds | Binding Assay IC50 |
|---|---|
| Compound 41 | ++ |
| Compound 43 | + |
| Compound 44 | ++ |
| Compound 45 | ++ |
| Compound 46 | + |
| Compound 47 | ++ |
| Compound 48 | ++ |
| Compound 49 | + |
| Compound 50 | ++ |
| Compound 51 | + |
| Compound 52 | ++ |
| Compound 53 | ++ |
| Compound 54 | ++ |
| Compound 55 | ++ |
| Compound 56 | ++ |
| Compound 57 | ++ |
| Compound 58 | ++ |
| Compound 59 | ++ |
| Compound 60 | ++ |
| Compound 61 | + |
| Compound 62 | ++ |
| Compound 63 | ++ |
| Compound 64 | − |
| Compound 65 | + |
| Compound 66 | ++ |
| Compound 67 | + |
| Compound 68 | ++ |
| Compound 69 | ++ |
| Compound 70 | ++ |
| Compound 71 | ++ |
| Compound 73 | ++ |
| Compound 74 | ++ |
| Compound 75 | + |
| Compound 76 | + |
| Compound 78 | ++ |
| Compound 79 | ++ |
| Compound 81 | ++ |
| Compound 82 | ++ |
| Compound 83 | ++ |
| Compound 84 | ++ |
| Compound 85 | ++ |
| Compound 86 | ++ |
| Compound 87 | ++ |
| Compound 27 | ++ |
| Compound 89 | ++ |
| Compound 90 | ++ |
| Compound 91 | ++ |
| Compound 92 | ++ |
| Compound 93 | ++ |
| Compound 94 | ++ |
| Compound 95 | ++ |
| Compound 96 | ++ |
| Compound 97 | ++ |
| Compound 98 | ++ |
| Compound 99 | ++ |
| Compound 100 | ++ |
| Compound 101 | ++ |
| Compound 102 | ++ |
| Compound 103 | ++ |
| Compound 104 | ++ |
| Compound 105 | ++ |
| Compound 106 | ++ |
| Compound 107 | ++ |
| Compound 108 | − |
| Compound 110 | + |
| Compound 111 | ++ |
| Compound 114 | − |
| Compound 115 | − |
| Compound 116 | − |
| Compound 117 | − |
| Compound 119 | ++ |
| Compound 120 | ++ |
| Compound 121 | + |
| Compound 122 | ++ |
| Compound 123 | ++ |

Discussion of Results in Table 6:

The potency has been determined in two independent functional assays: (1) a transporter assay using cell lines, and (2) a proliferation assay including our primary target immune cells, T cells. Assay (2) also includes a Condition B representative for the challenging conditions in the tumor microenvironment (TME), containing elevated levels of proteins known to bind small molecules (which has a negative impact on potency). A summary of potencies identified in these assays is reported in Table 6. The compound of the invention presents a maintained, or strongly improved potency as compared to dilazep in all functional assays. In particular, the compounds of the invention present a significantly improved potency in the T Cell proliferation assay in baseline conditions (condition A) and in conditions mimicking the TME (condition B) as compared to dilazep. As the compound of the invention has greatly improved potency compared to dilazep in a biologically relevant functional assay, this implies a significantly better safety window regarding off-targets, in particular hERG inhibition.

TABLE 6

| COMPOUNDS | Uridine transport inhibition assay IC50 | T Cell proliferation (Condition A) IC50 | (2) T Cell proliferation (Condition B) IC50 |
|---|---|---|---|
| Dilazep | ++ | ++ | + |
| Compound 1 | | +++ | +++ |
| Compound 2 | | + | + |
| Compound 4 | ++ | +++ | ++ |
| Compound 5 | ++ | ++++ | +++ |
| Compound 6 | | +++ | + |
| Compound 10 | ++ | ++ | + |
| Compound 13 | ++ | ++ | − |
| Compound 14 | | ++ | − |
| Compound 18 | | ++ | − |
| Compound 32 | | +++ | + |
| Compound 33 | | − | − |
| Compound 37 | | ++ | − |
| Compound 39 | | + | − |
| Compound 43 | | +++ | ++ |
| Compound 46 | | ++ | + |
| Compound 54 | | + | − |
| Compound 58 | | ++ | − |
| Compound 59 | | ++ | − |
| Compound 60 | | ++ | − |
| Compound 93 | | ++ | − |
| Compound 94 | | ++ | − |
| Compound 96 | | ++ | − |
| Compound 97 | | +++ | − |
| Compound 99 | | +++ | + |
| Compound 100 | | ++ | − |

Example II.3. HERG Ion Channel Inhibition

These data have been generated by ApconiX Ltd., BIOHUB at Alderley Park, Mereside, Alderley Edge, Cheshire, SK10 4TG, UK.

Purpose

The compounds were tested for inhibition of hERG ion channel. 6-Point concentration-response curves were generated on the Patchliner automated patch-clamp using serial dilutions from a maximum test concentration of 100 μM.

Methods

Compounds were solubilised to 33 mM in DMSO before dilution in HBPS to 100 μM. 6-Point concentration-response curves were generated using serial dilutions from the top test concentration. Electrophysiological recordings were made from a Chinese Hamster Ovary cell lines stably expressing the full-length ion channel. Single cell ionic currents were measured in whole-cell configuration at room temperature (21-23° C.) using a Patchliner (Nanion Technologies). The internal solution for hERG contained (mM): 120 KF, 20 KCl, 10EGTA, 10 HEPES and was buffered to pH 7.3. The external solution (HEPES-buffered saline, HBPS) contained (mM): 138 NaCl, 4.5 KCl, 1.8 CaCl2), 1.0 MgCl2, 10 HEPES, 10 glucose, buffered to pH7.4. Cells were clamped at a holding potential of −80 mV before a depolarising step appropriate for the hERG channel. Currents were measured from the step and referenced to the holding current. Compounds were incubated for 90 seconds. Concentration-response curves were generated by cumulative addition of compound with concentrations low to high. In all cases, steady-state inhibition was achieved before the next concentration of compound was added.

The following QC conditions were applied:

(1) Individual cells with any of the following properties were excluded from subsequent analysis (1) seal resistances <500 MΩ (2) ionic currents <150 pA (3) seal resistances that changed by >50% during the experiment (2) Experiments in which the IC50 of the reference compound was outside of the expected range were failed.

Results

IC50 values were obtained from a 4-parameter logistic fit of the concentration-response data:

TABLE 7

| Compound | hERG IC50 |
|---|---|
| Dilazep | 0.9 μM |
| Compound 2 | 2.5 μM |
| Compound 5 | 0.8 μM |
| Compound 4 | 73.0 μM |
| Compound 10 | 3.4 μM |
| Compound 52 | 2.7 μM |

Reference compound values were consistent with those presented m the literature (Elkins et al., 2013 J.Pharm.Tox.Meth. 68:11-122)

Example III

T Cell Stimulation Assay

Peripheral blood mononuclear cells (PBMCs) were first isolated via centrifugation of fresh whole blood over Lymphoprep using SepMate-50 tubes (both from STEMCELL Technologies) according to the manufacturer's instructions. Human T cells were then isolated from the PBMCs using the EasySep Human T cell Isolation Kit (STEMCELL Technologies) according to the manufacturer's instructions and the cells were cryopreserved in FBS with 10% DMSO until required.

Cryopreserved human T cells were thawed on the day of the experiment and resuspended in PBS with 10% FBS at approximately $1\times10^7$ cells/ml. This cell suspension was diluted 1:1 with 2 μM CFSE solution (ThermoFisher Scientific) in PBS and incubated for 5 minutes at room temperature. The labelling reaction was quenched by further addition of PBS with 10% FBS, and then the cells were washed into X-VIVO15 medium (Lonza) for use in the T cell assay.

CFSE-labelled T cells were plated at $2\times10^4$ cells per well in 384 well plates in the presence of ATP (100 μM, Sigma-Aldrich) as a source of adenosine. Activation was driven by the addition of Dynabeads Human T-Activator CD3/CD28 (ThermoFisher Scientific) at a ratio of 0.5 beads per T cell. ENT1 inhibitor molecules including the reference molecule dilazep (Tocris Bioscience) were added, the volume of the wells was adjusted to 50 μl with X-VIVO15 medium and the plates were cultured in a humidified incubator for 96 h at 37° C. with 5% CO2. In some experiments the culture was supplemented with human serum albumin (HSA) and alpha-1-acid glycoprotein (AAG, both Sigma-Aldrich) at final concentrations of 2 and 0.1%, respectively.

Analysis of proliferation via CSFE dilution was performed by flow cytometry using a BD LSR Fortessa with data analysis on FlowJo (BD Biosciences).

Mixed Leukocyte Reaction Assay

PBMCs were isolated from buffy coats via centrifugation of fresh whole blood over Lymphoprep using SepMate-50 tubes (both from STEMCELL Technologies) according to the manufacturer's instructions. Naïve $CD4^+$ T cells were isolated from the PBMCs using the Naïve $CD4^+$ T cell Isolation Kit II, human (Miltenyi Biotec) according to the manufacturer's instructions and cryopreserved in FBS with 10% DMSO until required. $CD14^+$ monocytes were also isolated from the PBMC samples using CD14 MicroBeads, human (MiltenyiBiotec) according to the manufacturer's instructions and used on the day of isolation.

Monocytes were resuspended in RPMI (Lonza) with 10% FBS and cultured in a humidified incubator at 37° C. with 5% $CO_2$ for 6 days in the presence of GM-CSF and IL-4 (R&D Systems), each at 50 ng/ml in 24 well plates. On day 3 of culture half of the medium was carefully removed and replaced with fresh medium containing 100 ng/ml of GM-CSF and IL-4.

On day 6 of culture monocyte-derived dendritic cells (MoDCs) were harvested and washed into X-VIVO15 medium containing 5% human male AB serum (Biowest) and 1 mM sodium pyruvate (Lonza). Naïve $CD4^+$ T cells from a different donor were thawed and CFSE-labelled as described above and washed into the same medium as the MoDCs. Finally, $1\times10^4$ MoDCs were cultured with $1\times10^5$ naïve $CD4^+$ T cells in the presence of ATP (Sigma-Aldrich), uridine or uracil in 96 round well bottom plates for 72 h in a humidified incubator at 37° C. with 5% $CO_2$.

Analysis of proliferation of CD4 T cells via CSFE dilution was performed by flow cytometry using a BD LSR Fortessa with data analysis on FlowJo (BD Biosciences). Cytokines were analysed by alphaLISA (Perkin Elmer) according to the manufacturer's instructions.

CMV Antigen Recall Assay

Figure 3:
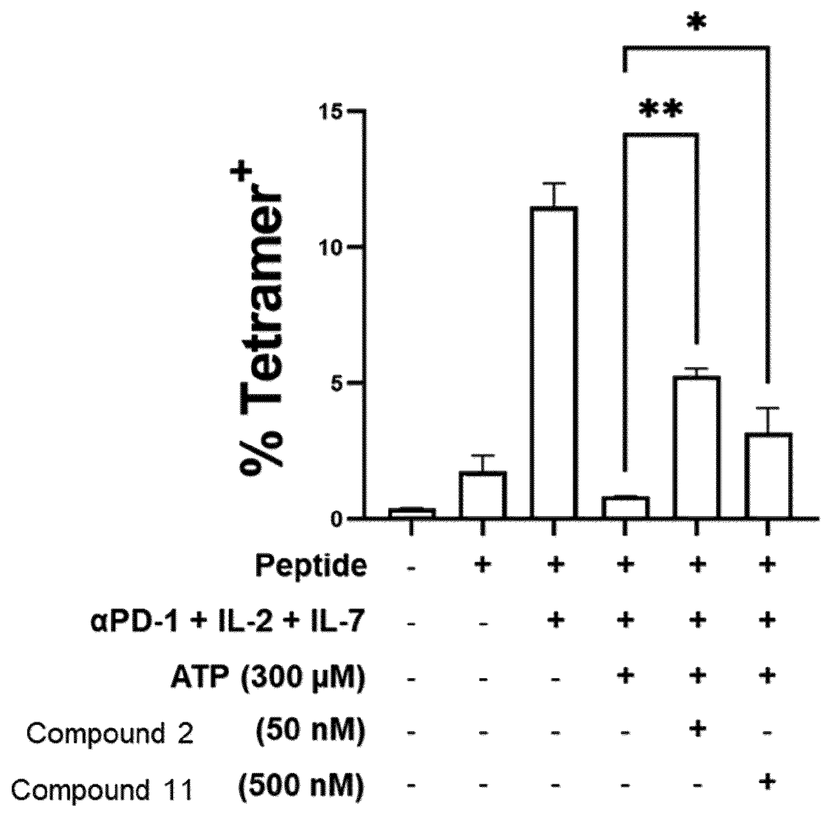
FIG. 3 depicts a bar graph of percent tetramer. PBMCs from a healthy volunteer donor with previous history of CMV infection and known HLA-A*02 subtype were cultured for 7 days with a peptide (NLVPMVATV) derived from the immunodominant CMV antigen pp65 alongside IL-2, IL-7 and the anti-PD1 antibody nivolumab. ATP was added to the cultures as a source of adenosine, alongside the ENT1 inhibitor molecules as indicated. Expansion of the peptide-specific $CD8^+$ T cell population was monitored via flow cytometry using NLVPMVATV-MHC-I tetramers linked with BV421. **=p<0.01; *=p<0.05; derived from one-way ANOVA with Tukey's multiple comparisons test from technical replicates in a single experiment.

Frozen vials of PBMCs from a healthy volunteer donor with history of CMV infection and known HLA-A*02 subtype were purchased from ImmuneXperts. Cells were thawed and washed into X-VIVO15 medium containing 5% human serum and 1 mM sodium pyruvate and plated in 96 U bottom plates ($1\times10^6$ cells per well). Cultures at time of plating contained combinations of CMV peptide (NLVPMVATV, 10 μg/ml, IBA Lifesciences), IL-7 (5 ng/ml, kind gift from ImmuneXperts), anti-PD1 (10 μg/ml, Nivolumab, Bristol Meyers Squibb), ATP (300 μM) and the various ENT1 inhibitors as indicated in FIG. 3. After one day of culture in a humidified incubator at 37° C. with 5% $CO_2$, half the medium was removed from each well and all reagents except the peptide replenished at their original concentrations and the plate returned to the incubator. This was repeated on day 4 of culture with the addition of IL-2 (20 U/ml, Proleukin, Novartis) to all wells. On day 7 of culture the cells were harvested and the frequency of CMV-peptide specific $CD8^+$ T cells was assessed via flow cytometry using NLVPMVATV-MHC-I tetramers (Tetramer Shop) by quantifying the frequency of tetramer$^+$ cells within the viable $CD8^+$ T cell gate.

Description of Data

Figure 1B:
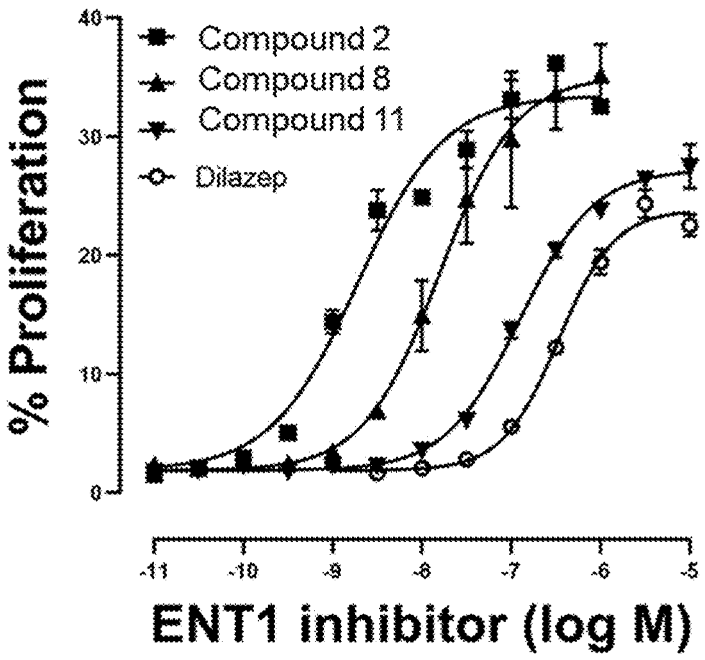
FIG. 1B depicts a graph of log concentration of ENT1 inhibitor (M) versus percent proliferation. Experiment performed as in FIG. A with the addition of HSA and AAG to the culture medium (final concentration 2 and 0.1%, respectively).

Proliferation of human T cells was significantly inhibited in the presence of 100 μM ATP as a source of adenosine. This suppression could however be dose-dependently restored with various macrocyclic ENT1 inhibitors as well as the parent molecule of this series, dilazep (FIG. 1A). The order of potency was Compound 2, Compound 8, Compound 11 and then dilazep, with $IC_{50}$ values of 0, 3, 2, 7 and 71 nM, respectively. Human serum albumin (HSA) and alpha-1-acid glycoprotein (AAG) were added to the cultures at final concentrations of 2 and 0.1%, respectively, to determine the potency of the ENT1 inhibitor molecules under high protein binding conditions (FIG. 1B). Whilst this treatment did not change the order of potencies of the molecules, the $IC_{50}$ values for each was increased (2, 16, 125 and 337 nM, respectively).

Figure 2A:
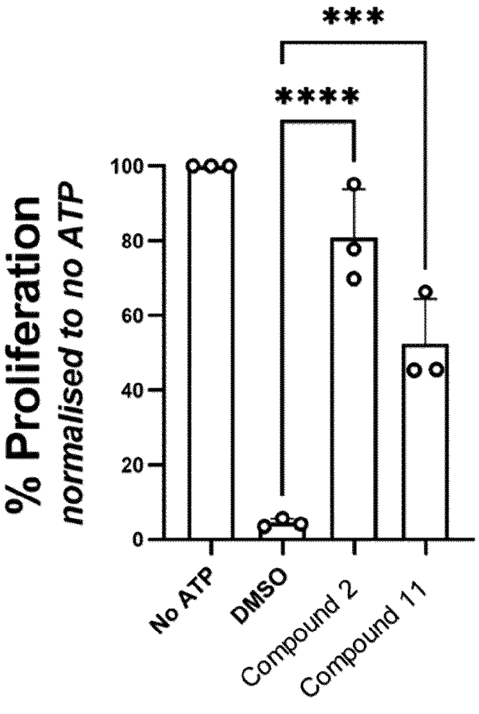
FIG. 2A depicts a bar graph of percent proliferation normalized to no ATP. Naïve $CD4^+$ T cells were cultured with allogeneic monocyte-derived dendritic cells at a ratio of 10:1 for 96 h in the presence of 300 μM ATP as a source of adenosine and the molecules Compound 2 (50 nM), Compound 11 (500 nM) or concentration-matched DMSO. Proliferation of T cells was assessed by CFSE dilution and normalized to the level observed in T cells activated in the absence of ATP.
Figure 2B:
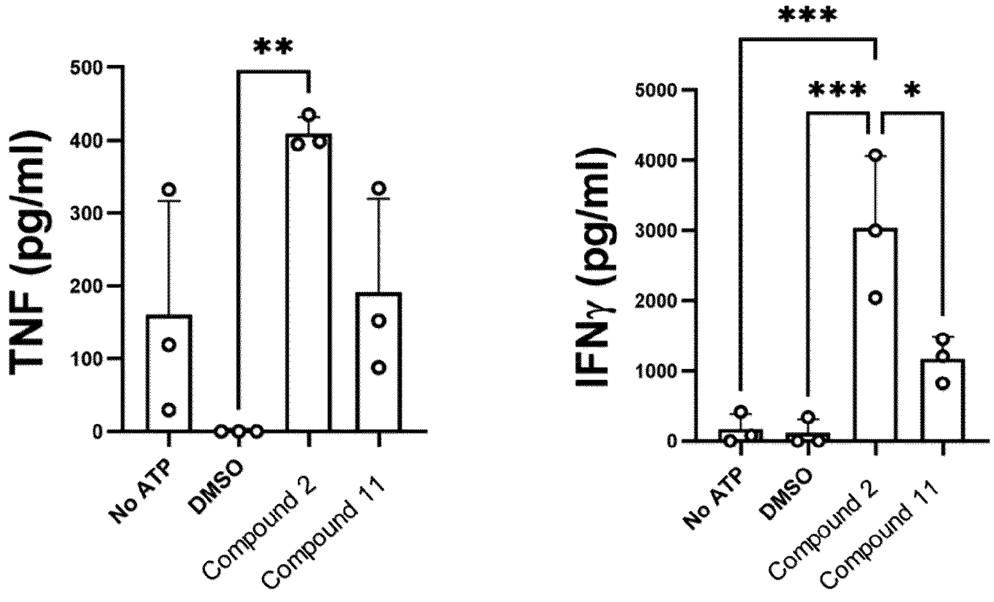
FIG. 2B depicts two bar graphs, one showing TNF concentration (pg/mL), and the other showing IFNγ (pg/mL). Experiment performed as described in FIG. 2A and supernatant sampled for analysis of cytokines by alphaLISA. **=p<0,0001; *=p<0,001; **=p<0.01 and *=p<0.05; derived from one-way ANOVA with Tukey's multiple comparisons test.

Proliferation of naïve CD4 T cells during MLR experiments was significantly inhibited by 300 μM ATP as a source of adenosine during the culture (FIG. 2). A near complete rescue of this proliferation was observed in the presence of Compound 2, with weaker restoration induced by Compound 11 (FIG. 2). Production of TNF followed a similar trend to the proliferation data, with production inhibited by ATP and clear restoration with Compound 2, even beyond the control level (FIG. 2B). Interestingly, IFNγ production followed a different pattern with low production observed in the presence or absence of ATP. There was however a significant and consistent increase in IFNγ production induced by Compound 2, with a smaller effect for Compound 11 (FIG. 2B). This suggests an unexpected synergy between ATP or adenosine and high potency ENT1 inhibition by macrocyclic ENT1 inhibitors.

Finally, proliferation of $CD8^+$ T cells with TCR specificity for the NLVPMVATV peptide derived from the immunodominant CMV antigen pp65 was significantly inhibited in the presence of ATP (300 μM, added at various stages during the culture) as a source of adenosine in the CMV antigen recall assay (FIG. 3). A significant rescue of proliferation of these cells was observed when Compound 2 or Compound 11 were included in the culture. These data are consistent with adenosine suppressing the proliferation of these CMV peptide-specific $CD8^+$ T cells and the highly potent macrocyclic ENT1 inhibitors acting to restrict the uptake of adenosine and thus restore proliferation.

Example IV

To assess the anti-tumor efficacy of compound Compound 8 in syngeneic fibrosarcoma model, C57BL/6 (n=8) were subcutaneously inoculated with $200\times10^5$ MCA205 cells in the right flank. At day 8 after inoculation the mice were randomized according tumor size and received oral treatment of Compound 8 at 10 mg/kg or its vehicle. The mice were monitored 3 times a week for tumor measurements, and the data plotted below. (FIG. 4A) The median tumor growth kinetics show a slight change in tumor size between Compound 8 treated mice and vehicle. (FIG. 4B and FIG. 4C) At day 21 after inoculation, 57% of the mice treated with 10 mg/kg of Compound 8 were responsive to Compound 8 treatment and at day 31 15% of the mice presented significant tumor growth delay with tumors below 1000 $mm^3$. The statistical analysis was performed in JMP software using linear fixed model.

INCORPORATION BY REFERENCE

The entire disclosures of all patent and non-patent publications cited herein are each incorporated by reference in their entireties for all purposes.

OTHER EMBODIMENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

What is claimed is:

1. A compound of formula IIa1:

(IIa1)

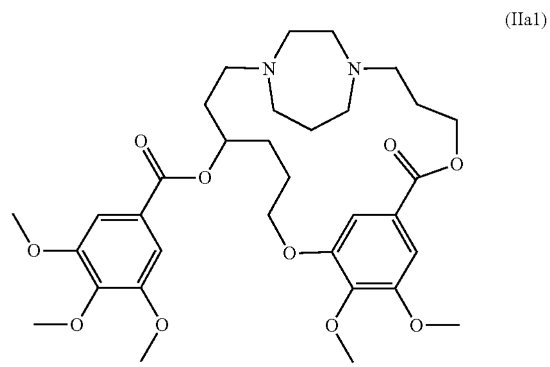

or a pharmaceutically acceptable salt or solvate thereof.

2. A pharmaceutical composition comprising a compound of claim 1 and at least one pharmaceutically acceptable excipient.

3. A compound having the structure:

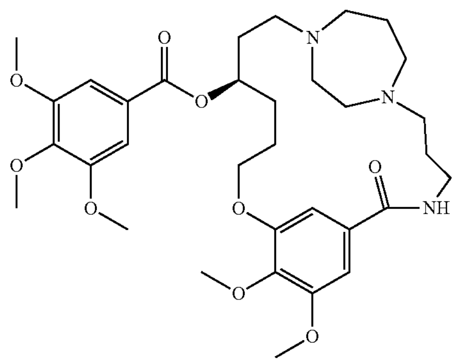 [SMILES: COc1cc(C(=O)O[C@@H]2CCCOc3cc(cc(OC)c3OC)C(=O)NCCCN3CCCN(CC2)CC3)cc(OC)c1OC]

or a pharmaceutically acceptable salt or solvate thereof.

4. A pharmaceutical composition comprising a compound of claim 3 and at least one pharmaceutically acceptable excipient.

5. A compound selected from the group consisting of:

(12S)-$7^4$,$7^5$-dimethoxy-6-oxo-5,8-dioxa-1(1,4)-diazepana-7(1,3)-benzenacyclotetradecaphane-12-yl 3,4,5-trimethoxybenzoate;

(12R)-$7^4$,$7^5$-dimethoxy-6-oxo-5,8-dioxa-1(1,4)-diazepana-7(1,3)-benzenacyclotetradecaphane-12-yl 3,4,5-trimethoxybenzoate;

16,16-difluoro-$7^4$,$7^5$-dimethoxy-6-oxo-5,8-dioxa-1(1,4)-diazepana-7(1,3)-benzenacyclotetradecaphane-12-yl 3,4,5-trimethoxybenzoate;

(12S)-16,16-difluoro-$7^4$,$7^5$-dimethoxy-6-oxo-5,8-dioxa-1(1,4)-diazepana-7(1,3)-benzenacyclotetradecaphane-12-yl 3,4,5-trimethoxybenzoate;

(12R)-16,16-difluoro-$7^4$,$7^5$-dimethoxy-6-oxo-5,8-dioxa-1(1,4)-diazepana-7(1,3)-benzenacyclotetradecaphane-12-yl 3,4,5-trimethoxybenzoate;

N-($7^4$,$7^5$-dimethoxy-6-oxo-5,8-dioxa-1(1,4)-diazepana-7(1,3)-benzenacyclotetradecaphane-12-yl)-3,4,5-trimethoxybenzamide;

$7^4$,$7^5$-dimethoxy-6-oxo-8-oxa-5-aza-1(1,4)-diazepana-7(1,3)-benzenacyclotetradecaphane-12-yl 3,4,5-trimethoxybenzoate;

(12S)-$7^4$,$7^5$-dimethoxy-6-oxo-8-oxa-5-aza-1(1,4)-diazepana-7(1,3)-benzenacyclotetradecaphane-12-yl 3,4,5-trimethoxybenzoate;

(12R)-$7^4$,$7^5$-dimethoxy-6-oxo-8-oxa-5-aza-1(1,4)-diazepana-7(1,3)-benzenacyclotetradecaphane-12-yl 3,4,5-trimethoxybenzoate;

$7^4$,$7^5$-dimethoxy-5-methyl-6-oxo-8-oxa-5-aza-1(1,4)-diazepana-7(1,3)-benzenacyclotetradecaphane-12-yl 3,4,5-trimethoxybenzoate;

(12S)-$7^4$,$7^5$-dimethoxy-5-methyl-6-oxo-8-oxa-5-aza-1(1,4)-diazepana-7(1,3)-benzenacyclotetradecaphane-12-yl 3,4,5-trimethoxybenzoate;

(12R)-$7^4$,$7^5$-dimethoxy-5-methyl-6-oxo-8-oxa-5-aza-1(1,4)-diazepana-7(1,3)-benzenacyclotetradecaphane-12-yl 3,4,5-trimethoxybenzoate;

(11R)-$7^4$,$7^5$-dimethoxy-6-oxo-5-aza-1(1,4)-diazepana-7(1,3)-benzenacyclotridecaphane-11-yl 3,4,5-trimethoxybenzoate;

(10S)-14-chloro-2-oxo-11H-3-aza-1(6,1)-indazola-7(1,4)-diazepanacyclotridecaphane-O-yl 3,4,5-trimethoxybenzoate;

(10R)-14-chloro-2-oxo-11H-3-aza-1(6,1)-indazola-7(1,4)-diazepanacyclotridecaphane-O-yl 3,4,5-trimethoxybenzoate;

(12S)-6-oxo-5,8-dioxa-1(1,4)-diazepana-7(1,3)-benzenacyclotetradecaphane-12-yl 3,4,5-trimethoxybenzoate;

(12R)-6-oxo-5,8-dioxa-1(1,4)-diazepana-7(1,3)-benzenacyclotetradecaphane-12-yl 3,4,5-trimethoxybenzoate;

(12S)-6-oxo-8-oxa-5-aza-1(1,4)-diazepana-7(1,3)-benzenacyclotetradecaphane-12-yl benzoate;

(12R)-6-oxo-8-oxa-5-aza-1(1,4)-diazepana-7(1,3)-benzenacyclotetradecaphane-12-yl benzoate;

$7^4$,$7^5$-dichloro-6-oxo-5,8-dioxa-1(1,4)-diazepana-7(1,3)-benzenacyclotetradecaphane-12-yl 3,4,5-trimethoxybenzoate;

(12S)-$7^4$,$7^5$-dichloro-6-oxo-5,8-dioxa-1(1,4)-diazepana-7(1,3)-benzenacyclotetradecaphane-12-yl 3,4,5-trimethoxybenzoate;

(12R)-$7^4$,$7^5$-dichloro-6-oxo-5,8-dioxa-1(1,4)-diazepana-7(1,3)-benzenacyclotetradecaphane-12-yl 3,4,5-trimethoxybenzoate;

$7^5$-carbamoyl-$7^4$-chloro-6-oxo-5,8-dioxa-1(1,4)-diazepana-7(1,3)-benzenacyclotetradecaphane-12-yl 3,4,5-trimethoxybenzoate;

(11Z,16E,10S)-14-chloro-2-oxo-12H-3-aza-1(6,2)-indazola-7(1,4)-diazepanacyclotridecaphane-10-yl 3,4,5-trimethoxybenzoate;

(11Z,16E,10R)-14-chloro-2-oxo-12H-3-aza-1(6,2)-indazola-7(1,4)-diazepanacyclotridecaphane-10-yl 3,4,5-trimethoxybenzoate;

(12S)-$7^4$-carbamoyl-$7^5$-chloro-6-oxo-8-oxa-5-aza-1(1,4)-diazepana-7(1,3)-benzenacyclotetradecaphane-12-yl 3,4,5-trimethoxybenzoate;

(12R)-$7^4$-carbamoyl-$7^5$-chloro-6-oxo-8-oxa-5-aza-1(1,4)-diazepana-7(1,3)-benzenacyclotetradecaphane-12-yl 3,4,5-trimethoxybenzoate;

$7^4$-bromo-$7^5$-chloro-6-oxo-8-oxa-5-aza-1(1,4)-diazepana-7(1,3)-benzenacyclotetradecaphane-12-yl 3,4,5-trimethoxybenzoate;

$7^5$-chloro-$7^4$-cyano-6-oxo-8-oxa-5-aza-1(1,4)-diazepana-7(1,3)-benzenacyclotetradecaphane-12-yl 3,4,5-trimethoxybenzoate;

(12R)-$7^4$,$7^5$-dimethoxy-6-oxo-5,8-dioxa-1(1,4)-diazepana-7(1,3)-benzenacyclotetradecaphane-12-yl benzoate;

(12S)-$7^4$,$7^5$-dimethoxy-6-oxo-5,8-dioxa-1(1,4)-diazepana-7(1,3)-benzenacyclotetradecaphane-12-yl benzoate;

(Z)-benzaldehyde O-($7^4$,$7^5$-dimethoxy-6-oxo-5,8-dioxa-1(1,4)-diazepana-7(1,3)-benzenacyclotetradecaphane-12-yl) oxime;

12-hydroxy-$7^4$,$7^5$-dimethoxy-5,8-dioxa-1(1,4)-diazepana-7(1,3)-benzenacyclotetradecaphan-6-one;

$7^4$,$7^5$-dimethoxy-6-oxo-5,8-dioxa-1(1,4)-diazepana-7(1,3)-benzenacyclotetradecaphane-12-yl 4-hydroxybenzoate;

$7^4$,$7^5$-dimethoxy-6-oxo-5,8-dioxa-1(1,4)-diazepana-7(1,3)-benzenacyclotetradecaphane-12-yl 4-fluorobenzoate;

$7^4$,$7^5$-dimethoxy-6-oxo-5,8-dioxa-1(1,4)-diazepana-7(1,3)-benzenacyclotetradecaphane-12-yl 4-isopropoxybenzoate;

$7^4$,$7^5$-dimethoxy-6-oxo-5,8-dioxa-1(1,4)-diazepana-7(1,3)-benzenacyclotetradecaphane-12-yl 3-(trifluoromethyl)benzoate;

$7^4$,$7^5$-dimethoxy-6-oxo-5,8-dioxa-1(1,4)-diazepana-7(1,3)-benzenacyclotetradecaphane-12-yl 3-(methylsulfonyl)benzoate;

$7^4$,$7^5$-dimethoxy-6-oxo-5,8-dioxa-1(1,4)-diazepana-7(1,3)-benzenacyclotetradecaphane-12-yl 3-phenoxybenzoate;

$7^4$,$7^5$-dimethoxy-6-oxo-5,8-dioxa-1(1,4)-diazepana-7(1,3)-benzenacyclotetradecaphane-12-yl 2-fluorobenzoate;

$7^4$,$7^5$-dimethoxy-6-oxo-5,8-dioxa-1(1,4)-diazepana-7(1,3)-benzenacyclotetradecaphane-12-yl 4-bromo-3-cyanobenzoate;

$7^4$,$7^5$-dimethoxy-6-oxo-5,8-dioxa-1(1,4)-diazepana-7(1,3)-benzenacyclotetradecaphane-12-yl 3-methyl-5-(trifluoromethyl)benzoate;

$7^4$,$7^5$-dimethoxy-6-oxo-5,8-dioxa-1(1,4)-diazepana-7(1,3)-benzenacyclotetradecaphane-12-yl 2-fluoro-4-methoxybenzoate;

$7^4$,$7^5$-dimethoxy-6-oxo-5,8-dioxa-1(1,4)-diazepana-7(1,3)-benzenacyclotetradecaphane-12-yl 4-methoxy-2-(trifluoromethoxy)benzoate;

$7^4$,$7^5$-dimethoxy-6-oxo-5,8-dioxa-1(1,4)-diazepana-7(1,3)-benzenacyclotetradecaphane-12-yl picolinate;

$7^4$,$7^5$-dimethoxy-6-oxo-5,8-dioxa-1(1,4)-diazepana-7(1,3)-benzenacyclotetradecaphane-12-yl nicotinate;

$7^4$,$7^5$-dimethoxy-6-oxo-5,8-dioxa-1(1,4)-diazepana-7(1,3)-benzenacyclotetradecaphane-12-yl pyrazine-2-carboxylate;

$7^4$,$7^5$-dimethoxy-6-oxo-5,8-dioxa-1(1,4)-diazepana-7(1,3)-benzenacyclotetradecaphane-12-yl 6-hydroxynicotinate;

$7^4$,$7^5$-dimethoxy-6-oxo-5,8-dioxa-1(1,4)-diazepana-7(1,3)-benzenacyclotetradecaphane-12-yl quinoline-5-carboxylate;

$7^4$,$7^5$-dimethoxy-6-oxo-5,8-dioxa-1(1,4)-diazepana-7(1,3)-benzenacyclotetradecaphane-12-yl oxazole-4-carboxylate;

$7^4$,$7^5$-dimethoxy-6-oxo-5,8-dioxa-1(1,4)-diazepana-7(1,3)-benzenacyclotetradecaphane-12-yl 1H-1,2,3-triazole-4-carboxylate;

$7^4$,$7^5$-dimethoxy-6-oxo-5,8-dioxa-1(1,4)-diazepana-7(1,3)-benzenacyclotetradecaphane-12-yl acetate;

$7^4$,$7^5$-dimethoxy-6-oxo-5,8-dioxa-1(1,4)-diazepana-7(1,3)-benzenacyclotetradecaphane-12-yl cyclopropanecarboxylate;

$7^4$,$7^5$-dimethoxy-6-oxo-5,8-dioxa-1(1,4)-diazepana-7(1,3)-benzenacyclotetradecaphane-12-yl 3-methylbutanoate;

$7^4$,$7^5$-dimethoxy-6-oxo-5,8-dioxa-1(1,4)-diazepana-7(1,3)-benzenacyclotetradecaphane-12-yl 4,4,4-trifluorobutanoate;

$7^4$,$7^5$-dimethoxy-6-oxo-5,8-dioxa-1(1,4)-diazepana-7(1,3)-benzenacyclotetradecaphane-12-yl cyclohexanecarboxylate;

$7^4$,$7^5$-dimethoxy-6-oxo-5,8-dioxa-1(1,4)-diazepana-7(1,3)-benzenacyclotetradecaphane-12-yl 1-methylpiperidine-4-carboxylate;

$7^4$,$7^5$-dimethoxy-6-oxo-5,8-dioxa-1(1,4)-diazepana-7(1,3)-benzenacyclotetradecaphane-12-yl 3,3-dimethylcyclobutane-1-carboxylate;

$7^4$,$7^5$-dimethoxy-6-oxo-5,8-dioxa-1(1,4)-diazepana-7(1,3)-benzenacyclotetradecaphane-12-yl 2-(oxetan-3-yl)acetate;

$7^4$,$7^5$-dimethoxy-6-oxo-5,8-dioxa-1(1,4)-diazepana-7(1,3)-benzenacyclotetradecaphane-12-yl (1R,5S,6R)-3-oxabicyclo[3.1.0]hexane-6-carboxylate;

$7^4$,$7^5$-dimethoxy-6-oxo-5,8-dioxa-1(1,4)-diazepana-7(1,3)-benzenacyclotetradecaphane-12-yl 5-oxopyrrolidine-3-carboxylate;

$7^4$,$7^5$-dimethoxy-6-oxo-5,8-dioxa-1(1,4)-diazepana-7(1,3)-benzenacyclotetradecaphane-12-yl 1-benzyl-5-oxopyrrolidine-3-carboxylate;

$7^4$,$7^5$-dimethoxy-6-oxo-5,8-dioxa-1(1,4)-diazepana-7(1,3)-benzenacyclotetradecaphane-12-yl 4-methoxycyclohexane-1-carboxylate;

$7^4$,$7^5$-dimethoxy-6-oxo-5,8-dioxa-1(1,4)-diazepana-7(1,3)-benzenacyclotetradecaphane-12-yl 2,6-difluorobenzoate;

$7^4$,$7^5$-dimethoxy-6-oxo-5,8-dioxa-1(1,4)-diazepana-7(1,3)-benzenacyclotetradecaphane-12-yl 4-(trifluoromethoxy)benzoate;

$7^4$,$7^5$-dimethoxy-6-oxo-5,8-dioxa-1(1,4)-diazepana-7(1,3)-benzenacyclotetradecaphane-12-yl 3-cyanobenzoate;

$7^4$,$7^5$-dimethoxy-6-oxo-5,8-dioxa-1(1,4)-diazepana-7(1,3)-benzenacyclotetradecaphane-12-yl 2-oxo-1,2,3,4-tetrahydroquinoline-6-carboxylate;

$7^4$,$7^5$-dimethoxy-6-oxo-5,8-dioxa-1(1,4)-diazepana-7(1,3)-benzenacyclotetradecaphane-12-yl 3-(difluoromethoxy)benzoate;

$7^4$,$7^5$-dimethoxy-6-oxo-5,8-dioxa-1(1,4)-diazepana-7(1,3)-benzenacyclotetradecaphane-12-yl 3,5-dichlorobenzoate;

$7^4$,$7^5$-dimethoxy-6-oxo-5,8-dioxa-1(1,4)-diazepana-7(1,3)-benzenacyclotetradecaphane-12-yl 3,4-dichlorobenzoate;

$7^4$,$7^5$-dimethoxy-6-oxo-5,8-dioxa-1(1,4)-diazepana-7(1,3)-benzenacyclotetradecaphane-12-yl 2,3-dichlorobenzoate;

$7^4$,$7^5$-dimethoxy-6-oxo-5,8-dioxa-1(1,4)-diazepana-7(1,3)-benzenacyclotetradecaphane-12-yl 2-chloro-6-fluoro-3-methylbenzoate;

$7^4$,$7^5$-dimethoxy-6-oxo-5,8-dioxa-1(1,4)-diazepana-7(1,3)-benzenacyclotetradecaphane-12-yl 3-fluoro-5-(trifluoromethyl)benzoate;

$7^4$,$7^5$-dimethoxy-6-oxo-5,8-dioxa-1(1,4)-diazepana-7(1,3)-benzenacyclotetradecaphane-12-yl 4-fluoro-3-(trifluoromethyl)benzoate;

$7^4$,$7^5$-dimethoxy-6-oxo-5,8-dioxa-1(1,4)-diazepana-7(1,3)-benzenacyclotetradecaphane-12-yl 4-cyano-3-fluorobenzoate;

$7^4$,$7^5$-dimethoxy-6-oxo-5,8-dioxa-1(1,4)-diazepana-7(1,3)-benzenacyclotetradecaphane-12-yl 4-(trifluoromethyl)benzoate;

$7^4$,$7^5$-dimethoxy-6-oxo-5,8-dioxa-1(1,4)-diazepana-7(1,3)-benzenacyclotetradecaphane-12-yl 3,5-difluorobenzoate;

$7^4$,$7^5$-dimethoxy-6-oxo-5,8-dioxa-1(1,4)-diazepana-7(1,3)-benzenacyclotetradecaphane-12-yl 3,4-difluorobenzoate;

$7^4$,$7^5$-dimethoxy-6-oxo-5,8-dioxa-1(1,4)-diazepana-7(1,3)-benzenacyclotetradecaphane-12-yl 3-cyano-4-fluorobenzoate;

$7^4$,$7^5$-dimethoxy-6-oxo-5,8-dioxa-1(1,4)-diazepana-7(1,3)-benzenacyclotetradecaphane-12-yl 4-cyanobenzoate;

$7^4$,$7^5$-dimethoxy-6-oxo-5,8-dioxa-1(1,4)-diazepana-7(1,3)-benzenacyclotetradecaphane-12-yl 3-chloro-4-fluorobenzoate;

$7^4$,$7^5$-dimethoxy-6-oxo-5,8-dioxa-1(1,4)-diazepana-7(1,3)-benzenacyclotetradecaphane-12-yl 1-methyl-1H-benzo[d]imidazole-5-carboxylate;

$7^4$,$7^5$-dimethoxy-6-oxo-5,8-dioxa-1(1,4)-diazepana-7(1,3)-benzenacyclotetradecaphane-12-yl 4-(oxazol-5-yl)benzoate;

$7^4$,$7^5$-dimethoxy-6-oxo-5,8-dioxa-1(1,4)-diazepana-7(1,3)-benzenacyclotetradecaphane-12-yl 4,5-dichloro-2-fluorobenzoate;

$7^4$,$7^5$-dimethoxy-6-oxo-5,8-dioxa-1(1,4)-diazepana-7(1,3)-benzenacyclotetradecaphane-12-yl 3,4,5-triethoxybenzoate;

$7^4$,$7^5$-dimethoxy-6-oxo-5,8-dioxa-1(1,4)-diazepana-7(1,3)-benzenacyclotetradecaphane-12-yl 3-methoxypropanoate;

$7^4$,$7^5$-dimethoxy-6-oxo-5,8-dioxa-1(1,4)-diazepana-7(1,3)-benzenacyclotetradecaphane-12-yl 3-(1H-pyrazol-1-yl)propanoate;

$7^4$,$7^5$-dimethoxy-6-oxo-5,8-dioxa-1(1,4)-diazepana-7(1,3)-benzenacyclotetradecaphane-12-yl 3-cyanopropanoate;

$7^4$,$7^5$-dimethoxy-6-oxo-5,8-dioxa-1(1,4)-diazepana-7(1,3)-benzenacyclotetradecaphane-12-yl 4-cyanobutanoate;

$7^4$,$7^5$-dimethoxy-6-oxo-5,8-dioxa-1(1,4)-diazepana-7(1,3)-benzenacyclotetradecaphane-12-yl 4-acetamidobutanoate;

$7^4$,$7^5$-dimethoxy-6-oxo-5,8-dioxa-1(1,4)-diazepana-7(1,3)-benzenacyclotetradecaphane-12-yl 3-(1H-tetrazol-1-yl)propanoate;

$7^4$,$7^5$-dimethoxy-6-oxo-5,8-dioxa-1(1,4)-diazepana-7(1,3)-benzenacyclotetradecaphane-12-yl 4-(dimethylamino)-4-oxobutanoate;

$7^4$,$7^5$-dimethoxy-6-oxo-5,8-dioxa-1(1,4)-diazepana-7(1,3)-benzenacyclotetradecaphane-12-yl 3-acetamidopropanoate;

$7^4$,$7^5$-dimethoxy-6-oxo-5,8-dioxa-1(1,4)-diazepana-7(1,3)-benzenacyclotetradecaphane-12-yl 4-(methylamino)-4-oxobutanoate;

$7^4$,$7^5$-dimethoxy-6-oxo-5,8-dioxa-1(1,4)-diazepana-7(1,3)-benzenacyclotetradecaphane-12-yl 3-(1H-1,2,4-triazol-1-yl)propanoate;

$7^4$,$7^5$-dimethoxy-6-oxo-5,8-dioxa-1(1,4)-diazepana-7(1,3)-benzenacyclotetradecaphane-12-yl 4-morpholino-4-oxobutanoate;

$7^4$,$7^5$-dimethoxy-6-oxo-5,8-dioxa-1(1,4)-diazepana-7(1,3)-benzenacyclotetradecaphane-12-yl 3-(4-fluorophenoxy)propanoate;

$7^4$,$7^5$-dimethoxy-6-oxo-5,8-dioxa-1(1,4)-diazepana-7(1,3)-benzenacyclotetradecaphane-12-yl 4,4-difluorocyclohexane-1-carboxylate;

$7^4$,$7^5$-dimethoxy-6-oxo-5,8-dioxa-1(1,4)-diazepana-7(1,3)-benzenacyclotetradecaphane-12-yl 4-(trifluoromethyl)cyclohexane-1-carboxylate;

$7^4$,$7^5$-dimethoxy-6-oxo-5,8-dioxa-1(1,4)-diazepana-7(1,3)-benzenacyclotetradecaphane-12-yl 3-(2,5-dioxopyrrolidin-1-yl)propanoate;

$7^4$,$7^5$-dimethoxy-6-oxo-5,8-dioxa-1(1,4)-diazepana-7(1,3)-benzenacyclotetradecaphane-12-yl 3-methoxycyclohexane-1-carboxylate;

$7^4$,$7^5$-dimethoxy-6-oxo-8-oxa-5-aza-1(1,4)-diazepana-7(1,3)-benzenacyclotetradecaphane-12-yl benzoate;

(E)-benzaldehyde O-($7^4$,$7^5$-dimethoxy-6-oxo-8-oxa-5-aza-1(1,4)-diazepana-7(1,3)-benzenacyclotetradecaphane-12-yl) oxime;

(E)-benzaldehyde O—((12R) $7^4$,$7^5$-dimethoxy-6-oxo-8-oxa-5-aza-1(1,4)-diazepana-7(1,3)-benzenacyclotetradecaphane-12-yl) oxime;

(E)-benzaldehyde O—((12S)-$7^4$,$7^5$-dimethoxy-6-oxo-8-oxa-5-aza-1(1,4)-diazepana-7(1,3)-benzenacyclotetradecaphane-12-yl) oxime;

12-hydroxy-$7^4$,$7^5$-dimethoxy-8-oxa-5-aza-1(1,4)-diazepana-7(1,3)-benzenacyclotetradecaphan-6-one;

(12R)-12-hydroxy-$7^4$,$7^5$-dimethoxy-5,8-dioxa-1(1,4)-diazepana-7(1,3)-benzenacyclotetradecaphan-6-one;

(12S)-12-hydroxy-$7^4$,$7^5$-dimethoxy-5,8-dioxa-1(1,4)-diazepana-7(1,3)-benzenacyclotetradecaphan-6-one;

$7^4$,$7^5$-dimethoxy-12-(5-phenyl-2H-tetrazol-2-yl)-5,8-dioxa-1(1,4)-diazepana-7(1,3)-benzenacyclotetradecaphan-6-one;

$7^4$,$7^5$-dimethoxy-12-(4-phenyl-1H-1,2,3-triazol-1-yl)-5,8-dioxa-1(1,4)-diazepana-7(1,3)-benzenacyclotetradecaphan-6-one;

$7^4$,$7^5$-dimethoxy-12-(5-phenyl-1H-tetrazol-1-yl)-5,8-dioxa-1(1,4)-diazepana-7(1,3)-benzenacyclotetradecaphan-6-one;

and pharmaceutically acceptable salts or solvates thereof.

6. A pharmaceutical composition comprising a compound of claim 5 and at least one pharmaceutically acceptable excipient.

* * * * *